United States Patent
Niyaz et al.

(10) Patent No.: US 9,655,365 B2
(45) Date of Patent: *May 23, 2017

(54) PESTICIDAL COMPOSITIONS AND PROCESSES RELATED THERETO

(71) Applicant: Dow AgroSciences LLC, Indianapolis, IN (US)

(72) Inventors: Noormohamed M. Niyaz, Indianapolis, IN (US); Negar Garizi, Westfield, IN (US); Yu Zhang, Carmel, IN (US); Tony K. Trullinger, Westfield, IN (US); Ricky Hunter, Westfield, IN (US); Ann M. Buysse, Carmel, IN (US); Asako Kubota, Indianapolis, IN (US); Paul R. LePlae, Jr., Brownsburg, IN (US); Daniel Knueppel, Zionsville, IN (US); Christian T. Lowe, Westfield, IN (US); Dan Pernich, Indianapolis, IN (US); David A. Demeter, Fishers, IN (US); Timothy C. Johnson, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 23 days.

This patent is subject to a terminal disclaimer.

(21) Appl. No.: 14/547,188

(22) Filed: Nov. 19, 2014

(65) Prior Publication Data

US 2015/0072859 A1    Mar. 12, 2015

Related U.S. Application Data

(63) Continuation of application No. 13/658,846, filed on Oct. 24, 2012, now Pat. No. 8,937,083.

(60) Provisional application No. 61/551,585, filed on Oct. 26, 2011.

(51) Int. Cl.
| | | |
|---|---|---|
| *A01N 43/78* | (2006.01) | |
| *A01N 43/56* | (2006.01) | |
| *C07D 405/14* | (2006.01) | |
| *C07D 409/14* | (2006.01) | |
| *C07D 413/14* | (2006.01) | |
| *A01N 43/76* | (2006.01) | |
| *C07D 401/14* | (2006.01) | |
| *C07D 401/04* | (2006.01) | |
| *C07D 417/14* | (2006.01) | |
| *A01N 43/653* | (2006.01) | |
| *A01N 43/80* | (2006.01) | |
| *A61K 31/4439* | (2006.01) | |
| *A61K 31/444* | (2006.01) | |
| *A01N 47/18* | (2006.01) | |

(52) U.S. Cl.
CPC ............. *A01N 43/78* (2013.01); *A01N 43/56* (2013.01); *A01N 43/653* (2013.01); *A01N 43/76* (2013.01); *A01N 43/80* (2013.01); *A01N 47/18* (2013.01); *A61K 31/444* (2013.01); *A61K 31/4439* (2013.01); *C07D 401/04* (2013.01); *C07D 401/14* (2013.01); *C07D 405/14* (2013.01); *C07D 409/14* (2013.01); *C07D 413/14* (2013.01); *C07D 417/14* (2013.01)

(58) Field of Classification Search
CPC ........ A01N 43/56; A01N 47/18; A01N 43/78; A01N 43/653; A01N 43/76; A01N 43/80; A61K 31/4439; A61K 31/444; C07D 401/04; C07D 401/14; C07D 405/14; C07D 409/14; C07D 413/13; C07D 417/14
See application file for complete search history.

(56) References Cited

U.S. PATENT DOCUMENTS

| | | | |
|---|---|---|---|
| 4,080,457 A | 3/1978 | Harrison et al. | |
| 4,260,765 A | 4/1981 | Harrison et al. | |
| 4,536,506 A | 8/1985 | Marcoux et al. | |
| 4,747,870 A | 5/1988 | Wexler et al. | |
| 5,556,873 A * | 9/1996 | Huang | A01N 43/56 514/407 |
| 5,625,074 A | 4/1997 | Daum et al. | |
| 5,631,380 A | 5/1997 | Haas et al. | |
| 5,652,372 A | 7/1997 | Muller et al. | |
| 5,693,657 A | 12/1997 | Lee et al. | |
| 5,750,718 A | 5/1998 | Muller et al. | |

(Continued)

FOREIGN PATENT DOCUMENTS

| | | |
|---|---|---|
| EP | 0097323 A2 | 1/1984 |
| EP | 0205024 A2 | 12/1986 |

(Continued)

OTHER PUBLICATIONS

Friedman, Michael et al. "Structure activity optimization of 6H-pyrollo[2,3-e][1,2,4]triazolo[4,3-a]pyrazines as Jak1 kinase inhibitors" Bioorganic & Medicinal Chemistry Letters 25, 4399-4404 (2015).

(Continued)

*Primary Examiner* — Sue Liu
*Assistant Examiner* — Erin Hirt
(74) *Attorney, Agent, or Firm* — Carl D. Corvin

(57) ABSTRACT

This document discloses molecules having the following formula ("Formula One"):

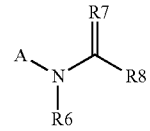

and processes related thereto.

52 Claims, No Drawings

(56) References Cited

U.S. PATENT DOCUMENTS

| | | |
|---|---|---|
| 5,817,677 A | 10/1998 | Linz et al. |
| 5,854,264 A | 12/1998 | Anthony et al. |
| 5,854,265 A | 12/1998 | Anthony |
| 5,869,681 A | 2/1999 | Muller et al. |
| 5,972,363 A | 10/1999 | Clikeman et al. |
| 6,218,418 B1 | 4/2001 | Pevarello et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 7,192,906 B2 | 3/2007 | Hirohara et al. |
| 7,196,104 B2 | 3/2007 | Askew, Jr. et al. |
| 7,319,108 B2 | 1/2008 | Schwink et al. |
| 7,514,561 B2 | 4/2009 | Schnatterer et al. |
| 7,774,978 B2 | 8/2010 | Ding et al. |
| 7,803,832 B2 | 9/2010 | Critcher et al. |
| 7,910,606 B2 | 3/2011 | Nazare et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,536,204 B2 * | 9/2013 | Bretschneider ...... C07D 401/04 514/341 |
| 8,815,271 B2 * | 8/2014 | Yap ........................ A61K 45/06 514/341 |
| 8,937,083 B2 * | 1/2015 | Niyaz ...................... A01N 43/56 514/277 |
| 9,282,739 B2 * | 3/2016 | Buysse ................... A01N 47/36 |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0160857 A1 | 7/2006 | Buettelmann et al. |
| 2006/0160875 A1 | 7/2006 | Gaines et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0069244 A1 | 3/2010 | Breuninger et al. |
| 2010/0075956 A1 | 3/2010 | Critcher et al. |
| 2010/0130474 A1 | 5/2010 | Bothmann et al. |
| 2010/0204164 A1 | 8/2010 | Crouse et al. |
| 2010/0292253 A1 | 11/2010 | Trullinger et al. |
| 2010/0305200 A1 | 12/2010 | Veliclebi et al. |
| 2011/0021771 A1 | 1/2011 | Mallais et al. |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0220453 A1 | 8/2012 | Lowe et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324735 A1 | 12/2013 | Ross, Jr. et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0057785 A1 | 2/2014 | Parker et al. |
| 2014/0213448 A1 | 7/2014 | Buysse et al. |
| 2015/0111734 A1 * | 4/2015 | Zhang ..................... A01N 43/50 504/100 |
| 2015/0335022 A1 * | 11/2015 | Buysse ................... A01N 47/18 504/100 |
| 2016/0060245 A1 * | 3/2016 | Buysse ................ C07D 401/04 504/100 |

FOREIGN PATENT DOCUMENTS

| | | |
|---|---|---|
| EP | 0248315 A2 | 12/1987 |
| EP | 0425948 A2 | 5/1991 |
| EP | 1273582 A1 | 1/2003 |
| EP | 1321463 A1 | 6/2003 |
| EP | 1329160 A2 | 7/2003 |
| JP | 1987-153273 A | 7/1987 |
| JP | 1988-174905 A | 7/1988 |
| JP | 1989-226815 A | 9/1989 |
| JP | 2003-212864 A | 7/2003 |
| JP | 2003-313103 A | 11/2003 |
| JP | 2004-051628 A | 2/2004 |
| JP | 2004-292703 A | 10/2004 |
| JP | 2012-188418 A | 10/2012 |
| JP | 2013-075871 A | 4/2013 |
| JP | 2013-082699 A | 5/2013 |
| JP | 2013-082704 A | 5/2013 |
| JP | 2013-107867 A | 6/2013 |
| JP | 2013-129651 A | 7/2013 |
| JP | 2013-129653 A | 7/2013 |
| WO | WO 94/13644 A1 | 6/1994 |
| WO | WO 97/36897 A1 | 10/1997 |
| WO | WO 98/49166 A1 | 11/1998 |
| WO | WO 00/35919 A2 | 6/2000 |
| WO | WO 01/34127 A1 | 5/2001 |
| WO | WO 01/90078 A1 | 11/2001 |
| WO | WO 02/083111 A2 | 10/2002 |
| WO | WO 03/008405 A1 | 1/2003 |
| WO | WO 03/072102 A1 | 9/2003 |
| WO | WO 2004/041813 A1 | 5/2004 |
| WO | WO 2005/070925 A1 | 8/2005 |
| WO | WO 2005/074875 A2 | 8/2005 |
| WO | WO 2006/023462 A1 | 3/2006 |
| WO | WO 2006/033005 A1 | 3/2006 |
| WO | WO 2006/046593 A1 | 5/2006 |
| WO | WO 2006/103045 A1 | 10/2006 |
| WO | WO 2007/005838 A2 | 1/2007 |
| WO | WO 2007/087427 A2 | 8/2007 |
| WO | WO 2007/098826 A2 | 9/2007 |
| WO | WO 2008/005457 A2 | 1/2008 |
| WO | WO 2008/079277 A1 | 7/2008 |
| WO | WO 2008/090382 A1 | 7/2008 |
| WO | WO 2009/149858 A1 | 12/2009 |
| WO | WO 2010/006713 A2 | 1/2010 |
| WO | WO 2010/009290 A1 | 1/2010 |
| WO | WO 2010/012442 A2 | 2/2010 |
| WO | WO 2010/048207 A2 | 4/2010 |
| WO | WO 2010/060379 A1 | 6/2010 |
| WO | WO 2010/075376 A2 | 7/2010 |
| WO | WO 2010/129497 A1 | 11/2010 |
| WO | WO 2010/133336 A1 | 11/2010 |
| WO | WO 2010/146236 A1 | 12/2010 |
| WO | WO 2011/003065 A2 | 1/2011 |
| WO | WO 2011/043371 A1 | 4/2011 |
| WO | WO 2011/045224 A1 | 4/2011 |
| WO | WO 2011/045240 A1 | 4/2011 |
| WO | WO 2011/091153 A1 | 7/2011 |
| WO | WO 2011/101229 A1 | 8/2011 |
| WO | WO 2011/126903 A2 | 10/2011 |
| WO | WO 2011/128304 A1 | 10/2011 |
| WO | WO 2011/134964 | 11/2011 |
| WO | WO 2011/138285 | 11/2011 |
| WO | WO 2011/163518 | 12/2011 |
| WO | WO 2012/000896 | 1/2012 |
| WO | WO 2012/004217 | 1/2012 |
| WO | WO 2012/007500 | 1/2012 |
| WO | WO 2010/033360 A1 | 3/2012 |
| WO | WO 2012/035011 | 3/2012 |
| WO | PCT-US2011-058578 | 4/2012 |

(56) References Cited

FOREIGN PATENT DOCUMENTS

| WO | WO 2012/052412 | 4/2012 |
|---|---|---|
| WO | WO 2012/061290 | 5/2012 |
| WO | WO 2012/070114 | 5/2012 |
| WO | WO 2012/102387 | 8/2012 |
| WO | WO 2012/108511 A1 | 8/2012 |
| WO | PCT-US2011-058578 | 12/2012 |
| WO | PCT/US2012/061508 | 12/2012 |
| WO | WO 2012/168361 A1 | 12/2012 |
| WO | WO 2013/000931 A1 | 1/2013 |
| WO | WO 2013/010946 A2 | 1/2013 |
| WO | WO 2013/010947 A1 | 1/2013 |
| WO | PCT-US2013-029615 | 5/2013 |
| WO | WO 2013/062980 A1 | 5/2013 |
| WO | WO 2013/156431 A1 | 10/2013 |
| WO | WO 2013/156433 A1 | 10/2013 |

OTHER PUBLICATIONS

Stellwagen, J.C. and Uehling, D.E et al. "Development of potent B-RafV600E inhibitors containing an arylsulfonamide headgroup" Bioorganic & Medicinal Chemistry Letters 21, 4436-4440 (2011).
Nordhoff, S. et al. "Discovery of β-homophenylalanine based pyrrolidin-2-ylmethyl amides and sulfonamides as highly potent and selective inhibitors of dipeptidyl peptidase IV" Bioorganic & Medicinal Chemistry Letters 19, 4201-4203 (2009).

* cited by examiner

PESTICIDAL COMPOSITIONS AND PROCESSES RELATED THERETO

CROSS-REFERENCE TO RELATED APPLICATIONS

This application is a continuation of, and claims the benefit of, U.S. patent application Ser. No. 13/658,846, which was filed Oct. 24, 2012, and which claims priority from U.S. provisional application 61/551,585, which was filed on Oct. 26, 2011. The entire content of these applications are hereby incorporated by reference into this Application.

FIELD OF THE DISCLOSURE

This disclosure is related to the field of processes to produce molecules that are useful as pesticides (e.g., acaricides, insecticides, molluscicides, and nematicides), such molecules, and processes of using such molecules to control pests.

BACKGROUND

Pests cause millions of human deaths around the world each year. Furthermore, there are more than ten thousand species of pests that cause losses in agriculture. The world-wide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, ($C_3$)alkyl which represents n-propyl and isopropyl), ($C_4$)alkyl which represents n-butyl, sec-butyl, isobutyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"($C_x$-$C_y$)" where the subscripts "x" and "y" are integers such as 1, 2, or 3, means the range of carbon atoms for a substituent—for example, ($C_1$-$C_4$)alkyl means methyl, ethyl, n-propyl, isopropyl, n-butyl, sec-butyl, isobutyl, and tert-butyl, each individually.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following

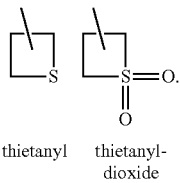

thietanyl    thietanyl-
             dioxide

DETAILED DESCRIPTION

This document discloses molecules having the following formula ("Formula One"):

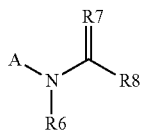

wherein
(a) A is either

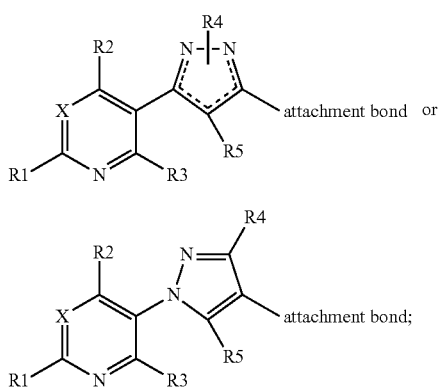

(b) R1 is H, F, Cl, Br, I, CN, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, OR9, C(=X1)R9, C(=X1)OR9, C(=X1)N(R9)$_2$, N(R9)$_2$, N(R9)C(=X1)R9, S(O)$_n$R9, S(O)$_n$OR9, S(O)$_n$N(R9)$_2$, or R9S(O)$_n$R9,
wherein each said R1, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, C$_6$-C$_{20}$ aryl, or C$_1$-C$_{20}$ heterocyclyl, (each of which that can be substituted, may optionally be substituted with R9);

(c) R2 is H, F, Cl, Br, I, CN, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R2, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, C$_6$-C$_{20}$ aryl, or C$_1$-C$_{20}$ heterocyclyl, (each of which that can be substituted, may optionally be substituted with R9);

(d) R3 is H, F, Cl, Br, I, CN, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R3, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, C$_6$-C$_{20}$ aryl, or C$_1$-C$_{20}$ heterocyclyl, (each of which that can be substituted, may optionally be substituted with R9);

(e) when A is
(1) A1 then A1 is either
  (a) A11

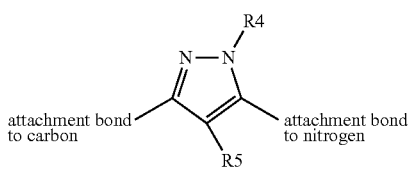

where R4 is H, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, C(=X1)R9, C(=X1)OR9, C(=X1)N(R9)$_2$, N(R9)$_2$, N(R9)C(=X1)R9, S(O)$_n$OR9, or R9S(O)$_n$R9,
wherein each said R4, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, C$_6$-C$_{20}$ aryl, or C$_1$-C$_{20}$ heterocyclyl, (each of which that can be substituted, may optionally be substituted with R9), or (b) A12

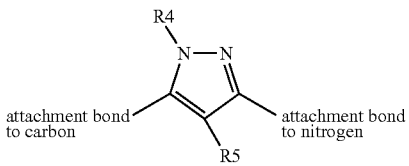

where R4 is a $C_1$-$C_6$ alkyl, (2) A2 then R4 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(f) R5 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R5, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);

(g)

(1) when A is A1 then R6 is R11, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl) S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9, wherein each said R6 (except R11), which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, R9aryl, (each of which that can be substituted, may optionally be substituted with R9), optionally R6 (except R11) and R8 can be connected in a cyclic arrangement, where optionally such arrangement can have one or more heteroatoms selected from O, S, or, N, in the cyclic structure connecting R6 and R8, and (2) when A is A2 then R6 is R11, H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl) S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9, wherein each said R6 (except R11), which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, R9aryl, (each of which that can be substituted, may optionally be substituted with R9), optionally R6 (except R11) and R8 can be connected in a cyclic arrangement, where optionally such arrangement can have one or more heteroatoms selected from O, S, or N, in the cyclic structure connecting R6 and R8;

(h) R7 is O, S, NR9, or NOR9;

(i) R8 is substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl OR9, OR9S(O)$_n$R9, C(=X1)R9, C(=X1)OR9, R9C(=X1)OR9, R9X2C(=X1)R9X2R9, C(=X1)N(R9)$_2$, N(R9)$_2$, N(R9)(R9S(O)$_n$R9), N(R9)C(=X1)R9, SR9, S(O)$_n$OR9, R9S(O)$_n$R9, or R9S(O)$_n$(NZ)R9, wherein each said R8, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $N(R9)S(O)_nR9$, oxo, OR9, $S(O)_nOR9$, $R9S(O)_nR9$, $S(O)_nR9$, $C_6$-$C_{20}$ aryl, or $C_1$-$C_{20}$ heterocyclyl, (each of which that can be substituted, may optionally be substituted with R9);

(j) R9 is (each independently) H, CN, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted $S(O)_nC_1$-$C_6$ alkyl, substituted or unsubstituted $N(C_1$-$C_6alkyl)_2$, wherein each said R9, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nC_1$-$C_6alkyl$, $S(O)_nOC_1$-$C_6$ alkyl, $C_6$-$C_{20}$ aryl, or $C_1$-$C_{20}$ heterocyclyl;

(k) n is 0, 1, or 2;

(l) X is N or $CR_{n1}$ where $R_{n1}$ is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, $S(O)_nR9$, $S(O)_nOR9$, or $R9S(O)_nR9$, wherein each said $R_{n1}$ which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, $S(O)_nOR9$, $C_6$-$C_{20}$ aryl, or $C_1$-$C_{20}$ heterocyclyl, (each of which that can be substituted, may optionally be substituted with R9);

(m) X1 is (each independently) O or S;

(n) X2 is (each independently) O, S, =NR9, or =NOR9;

(o) Z is CN, $NO_2$, $C_1$-$C_6$ alkyl(R9), C(=X1)N(R9)$_2$;

(p) R11 is $Q_1$(C≡C)R12, wherein $Q_1$ is a bond, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, substituted or unsubstituted $C_2$-$C_{10}$ cycloalkoxy, substituted or unsubstituted $C_1$-$C_6$ alkylOR9, substituted or unsubstituted $C_1$-$C_6$ alkylS(O)$_n$R9, substituted or unsubstituted $C_1$-$C_6$ alkylS(O)$_n$(=NR), substituted or unsubstituted $C_1$-$C_6$ alkylN(R9) (where (C≡C) is attached directly to the N by a bond), substituted or unsubstituted $C_1$-$C_6$ alkylN(R9)$_2$, substituted or unsubstituted $C_2$-$C_6$ alkenyloxy, substituted or unsubstituted $C_3$-$C_{10}$ cycloalkenyl, substituted or unsubstituted $C_0$-$C_6$ alkylC(=R7)$C_0$-$C_6$ alkylR9, substituted or unsubstituted $C_0$-$C_6$ alkylC(=R7)OR9, substituted or unsubstituted $C_1$-$C_6$ alkylOC$_0$-$C_6$ alkylC(=R7)R9, substituted or unsubstituted $C_1$-$C_6$ alkylN(R9)(C(=R7)R9), substituted or unsubstituted $C_1$-$C_6$ alkylN(R9)(C(=R7)OR9), substituted or unsubstituted $C_0$-$C_6$ alkyl C(=R7)$C_0$-$C_6$ alkylN(R9) (where (C≡C) is attached directly to the N by a bond), substituted or unsubstituted $C_0$-$C_6$alkylC(=R7)$C_0$-$C_6$ alkylN(R9)$_2$, OR9, $S(O)_nR9$, N(R9)R9, substituted or unsubstituted $C_6$-$C_{20}$ aryl, substituted or unsubstituted $C_1$-$C_{20}$ heterocyclyl, wherein each said $Q_1$, which is substituted, has one or more substituents selected from F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, SR9, $S(O)_nR9$, $S(O)_nOR9$, $C_6$-$C_{20}$ aryl, or $C_1$-$C_{20}$ heterocyclyl, R9aryl, $C_1$-$C_6$alkylOR9, $C_1$-$C_6$alkylS(O)$_n$R9, (each of which that can be substituted, may optionally be substituted with R9)

optionally $Q_1$ and R8 can be connected in a cyclic arrangement, where optionally such arrangement can have one or more heteroatoms selected from O, S, or N, in the cyclic structure connecting $Q_1$ and R8;

(q) R12 is $Q_1$ (except where $Q_1$ is a bond), F, Cl, Br, I, Si(R9)$_3$ (where each R9 is independently selected), or R9; and (r) with the following provisos
(1) that R6 and R8 cannot both be C(=O)CH$_3$,
(2) that when A1 is A11 then R6 and R8 together do not form fused ring systems,
(3) that R6 and R8 are not linked in a cyclic arrangement with only —CH$_2$—,
(4) that when A is A2 then R5 is not C(=O)OH,
(5) that when A is A2 and R6 is H then R8 is not a —(C$_1$-C$_6$ alkyl)-O-(substituted aryl), and
(6) that when A is A2 then R6 is not —(C$_1$alkyl)(substituted aryl).

In another embodiment of this invention A is A1.
In another embodiment of this invention A is A2.
In another embodiment of this invention R1 is H.
In another embodiment of this invention R2 is H.
In another embodiment of this invention R3 is selected from H, or substituted or unsubstituted $C_1$-$C_6$ alkyl.
In another embodiment of this invention R3 is selected from H or CH$_3$.
In another embodiment of the invention when A is A1 then A1 is A11.
In another embodiment of the invention when A is A1, and A1 is A11, then R4 is selected from H, or substituted or unsubstituted $C_1$-$C_6$ alkyl, or substituted or unsubstituted $C_6$-$C_{20}$ aryl.
In another embodiment of the invention when A is A1, and A1 is A11 then R4 is selected from CH$_3$, CH(CH$_3$)$_2$, or phenyl.
In another embodiment of the invention when A is A1, and A1 is A12, then R4 is CH$_3$.
In another embodiment of this invention when A is A2 then R4 is selected from H, or substituted or unsubstituted $C_1$-$C_6$ alkyl, substituted or unsubstituted $C_2$-$C_6$ alkenyl, substituted or unsubstituted $C_3$-$C_{10}$ cycloalkyl, substituted or unsubstituted $C_6$-$C_{20}$ aryl, wherein each said R4, which is substituted, has one or more substituents selected from F, Cl, Br, or I.
In another embodiment of this invention when A is A2 then R4 is H or $C_1$-$C_6$ alkyl.
In another embodiment of this invention when A is A2 then R4 is H, CH$_3$, CH$_2$CH$_3$, CH=CH$_2$, cyclopropyl, CH$_2$Cl, CF$_3$, or phenyl.
In another embodiment of this invention when A is A2 then R4 is Cl.
In another embodiment of this invention R5 is H, F, Cl, Br, I, or substituted or unsubstituted $C_1$-$C_6$ alkyl, substituted or unsubstituted $C_1$-$C_6$ alkoxy.

In another embodiment of this invention R5 is H, OCH$_2$CH$_3$, F, Cl, Br, or CH$_3$.

In another embodiment of this invention, when A is A1 then R6 is substituted or unsubstituted C$_1$-C$_6$ alkyl.

In another embodiment of this invention when A is A2 then R6 is selected from is substituted or unsubstituted C$_1$-C$_6$ alkyl, substituted or unsubstituted C$_2$-C$_6$ alkenyl, substituted or unsubstituted C$_3$-C$_{10}$ cycloalkyl, C(=X1)R9, C(=X1)X2R9, R9X2R9, C(=O)(C$_1$-C$_6$ alkyl)S(O)$_n$(C$_1$-C$_6$ alkyl), (C$_1$-C$_6$ alkyl)OC(=O)(C$_6$-C$_{20}$ aryl), (C$_1$-C$_6$ alkyl)OC(=O)(C$_1$-C$_6$ alkyl), or R9X2C(=X1)X2R9.

In another embodiment of this invention when A is A2 then R6 and R8 are connected in a cyclic arrangement, where optionally such arrangement can have one or more heteroatoms selected from O, S, or, N, in the cyclic structure connecting R6 and R8.

In another embodiment of this invention R6 is C$_1$-C$_6$ alkyl, or C$_1$-C$_6$ alkyl-phenyl.

In another embodiment of this invention R6 is H, CH$_3$, CH$_2$CH$_3$, CH$_2$CH$_2$CH$_3$, CH(CH$_3$)$_2$, CH$_2$-phenyl, CH$_2$CH(CH$_3$)$_2$, CH$_2$cyclopropyl, C(=O)CH$_2$CH$_2$SCH$_3$, C(=O)OC(CH$_3$)$_3$, CH$_2$CH=CH$_2$, C(=O)OCH$_2$CH$_3$, C(=O)CH(CH$_3$)CH$_2$SCH$_3$, cyclopropyl, CD$_3$, CH$_2$OC(=O)phenyl, C(=O)CH$_3$, C(=O)CH(CH$_3$)$_2$, CH$_2$C(=O)CH(CH$_3$)$_2$, CH$_2$C(=O)CH$_3$, C(=O)phenyl, CH$_2$OCH$_3$, CH$_2$C(=O)CH$_2$OCH$_2$CH$_3$, CH$_2$CH$_2$OCH$_3$, CH$_2$C(=O)OCH(CH$_3$)$_2$, CH$_2$CH$_2$OCH$_2$OCH$_3$, CH$_2$CH$_2$OCH$_3$, CH$_2$CH$_2$C(=O)CH$_3$, CH$_2$CN.

In another embodiment of this invention R6 is methyl or ethyl.

In another embodiment of this invention R7 is O or S.

In another embodiment of this invention R8 is selected from substituted or unsubstituted C$_1$-C$_6$ alkyl, substituted or unsubstituted C$_2$-C$_6$ alkenyl, substituted or unsubstituted C$_3$-C$_{10}$ cycloalkyl, substituted or unsubstituted C$_6$-C$_{20}$ aryl, substituted or unsubstituted C$_1$-C$_{20}$ heterocyclyl, R9C(=X1)OR9, SR9, S(O)$_n$OR9, R9S(O)$_n$R9, or R9S(O)$_n$(NZ)R9.

In another embodiment of this invention R8 is CH(CH$_3$)CH$_2$SCH$_3$, CH(CH$_3$)$_2$, C(CH$_3$)$_2$CH$_2$SCH$_3$, CH$_2$CH$_2$SCH$_3$, CH$_2$CF$_3$, CH$_2$CH$_2$C(=O)OCH$_3$, N(H)(CH$_2$CH$_2$SCH$_3$), OCH$_2$CH$_2$SCH$_3$, CH(CH$_2$SCH$_3$)(CH$_2$-phenyl), thiazolyl, oxazolyl, isothiazolyl, substituted-furanyl, CH$_3$, C(CH$_3$)$_3$, phenyl, CH$_2$CH$_2$OCH$_3$, pyridyl, CH$_2$CH(CH$_3$)SCH$_3$, OC(CH$_3$)$_3$, C(CH$_3$)$_2$CH$_2$SCH$_3$, CH(CH$_3$)CH(CH$_3$)SCH$_3$, CH(CH$_3$)CF$_3$, CH$_2$CH$_2$-thienyl, CH(CH$_3$)SCF$_3$, CH$_2$CH$_2$Cl, CH$_2$CH$_2$CH$_2$CF$_3$, CH$_2$CH$_2$S(=O)CH$_3$, CH(CH$_3$)CH$_2$S(=O)CH$_3$, CH$_2$CH$_2$S(=O)$_2$CH$_3$, CH(CH$_3$)CH$_2$S(=O)$_2$CH$_3$, NCH$_2$CH$_3$, N(H)(CH$_2$CH$_2$CH$_3$), C(CH$_3$)=C(H)(CH$_3$), N(H)(CH$_2$CH=CH$_2$), CH$_2$CH(CF$_3$)SCH$_3$, CH(CF$_3$)CH$_2$SCH$_3$, thietanyl, CH$_2$CH(CF$_3$)$_2$, CH$_2$CH$_2$CF(OCF$_3$)CF$_3$, CH$_2$CH$_2$CF(CF$_3$)CF$_3$, CF(CH$_3$)$_2$, CH(CH$_3$)phenyl-Cl, CH(CH$_3$)phenyl-F, CH(CH$_3$)phenyl-OCF$_3$, CH$_2$N(CH$_3$)(S(=O)$_2$N(CH$_3$)$_2$, CH(CH$_3$)OCH$_2$CH$_2$SCH$_3$, CH(CH$_3$)OCH$_2$CH$_2$OCH$_3$, OCH$_3$, CH(CH$_3$)SCH$_3$, CH$_2$SCH$_3$, N(H)CH$_3$, CH(Br)CH$_2$Br, CH$_2$CH$_2$SCH$_2$CH$_2$CF$_3$, CH$_2$CH$_2$SH, CH$_2$CH$_2$SC(phenyl)$_3$, CH$_2$N(CH$_3$)S(O)$_2$CH$_3$, CH(SCH$_3$)(C(=O)CH$_2$SCH$_3$), CH$_2$S(O)CH$_3$, CH$_2$CH(cyclopropyl)SCH$_3$, or CH(CH$_3$)CH$_2$SCD$_3$.

In another embodiment of this invention R8 is selected from (substituted or unsubstituted C$_1$-C$_6$ alkyl)-S(O)$_n$-(substituted or unsubstituted C$_1$-C$_6$ alkyl) wherein said substituents on said substituted alkyls are selected from F, Cl, Br, I, CN, NO$_2$, N(R9)S(O)$_n$R9, OR9, S(O)$_n$OR9, R9S(O)$_n$R9, S(O)$_n$R9, C$_6$-C$_{20}$ aryl, or C$_1$-C$_{20}$ heterocyclyl, (each of which that can be substituted, may optionally be substituted with R$_9$).

In another embodiment of this invention X is CR$_{n1}$ where R$_{n1}$ is H or halo.

In another embodiment of this invention X is CR$_{n1}$ where R$_{n1}$ is H or F.

In another embodiment of this invention X1 is O.

In another embodiment of this invention X2 is O.

In another embodiment of this invention R11 is substituted or unsubstituted C$_1$-C$_6$ alkylC=CR12.

In another embodiment of this invention R11 is CH$_2$C=CH.

In another embodiment R11 is preferably CH$_2$C=CH and R8 is preferably (substituted or unsubstituted C$_1$-C$_6$ alkyl)-S(O)$_n$-(substituted or unsubstituted C$_1$-C$_6$ alkyl) wherein said substituents on said substituted alkyls are selected from F, Cl, Br, I.

In another embodiment R11 is preferably CH$_2$C=CH and R8 is preferably (unsubstituted C$_1$-C$_6$ alkyl)-S(O)$_n$-(substituted C$_1$-C$_6$ alkyl) wherein said substituents on said substituted alkyls are selected from F, Cl, Br, I.

In another embodiment R11 is preferably CH$_2$C=CH and R8 is preferably (unsubstituted C$_1$-C$_2$ alkyl)-S(O)$_n$-(substituted C$_1$-C$_3$ alkyl) wherein said substituents on said substituted alkyls are F.

The molecules of Formula One will generally have a molecular mass of about 100 Daltons to about 1200 Daltons. However, it is generally preferred if the molecular mass is from about 120 Daltons to about 900 Daltons, and it is even more generally preferred if the molecular mass is from about 140 Daltons to about 600 Daltons.

The following schemes illustrate approaches to generating aminopyrazoles. In step a of Scheme I, treatment of a 3-acetopyridine or a 5-acetopyrimidine of Formula II, wherein R1, R2, R3 and X are as previously defined, with carbon disulfide and iodomethane in the presence of a base such as sodium hydride and in a solvent such as dimethyl sulfoxide provides the compound of Formula III. In step b of Scheme I, the compound of Formula III can be treated with an amine or amine hydrochloride, in the presence of a base, such as triethylamine, in a solvent such as ethyl alcohol to afford the compound of Formula IV, wherein R1, R2, R3, R6 and X are as previously defined. The compound of Formula IV can be transformed into the aminopyrazole of Formula Va where R5=H as in step c of Scheme I and as in Peruncheralathan, S. et al. *J. Org. Chem.* 2005, 70, 9644-9647, by reaction with a hydrazine, such as methylhydrazine, in a polar protic solvent such as ethyl alcohol.

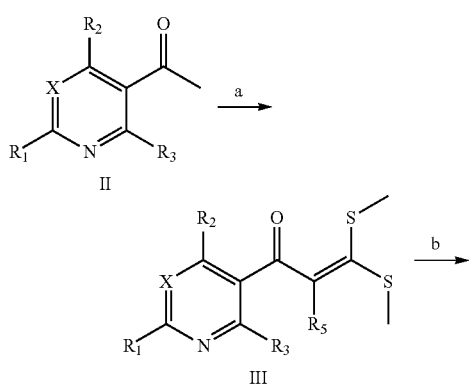

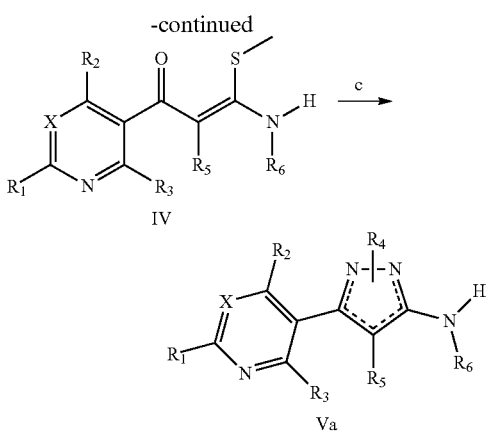

Another approach to aminopyrazoles is illustrated in Scheme II. In step a, the nitrile of Formula VI wherein X, R1, R2 and R3 are as previously defined and R5 is hydrogen, is condensed as in Dhananjay, B. Kendre et al. *J. Het Chem* 2008, 45, (5), 1281-86 with hydrazine of Formula VII, such as methylhydrazine to give a mixture of aminopyrazoles of Formula Vb, wherein R5 and R6=H, both of whose components were isolated.

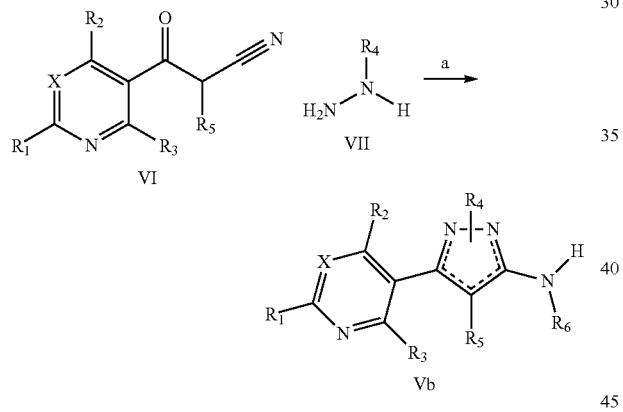

Preparation of aminopyrazoles such as those of Formula XIIa is demonstrated in Scheme III. The compound of Formula X in step a and as in Cristau, Henri-Jean et al. *Eur. J. Org. Chem.* 2004, 695-709 can be prepared through the N-arylation of a pyrazole of Formula IX with an appropriate aryl halide of Formula VIIIa where Q is bromo in the presence of a base such as cesium carbonate, a copper catalyst such as copper (II) oxide and a ligand such as salicylaldoxime in a polar aprotic solvent such as acetonitrile. Compounds of Formula IX, as shown in Scheme III, wherein R4=Cl and R5=H, can be prepared as in Pelcman, B. et al WO 2007/045868 A1. Nitration of the pyridylpyrazole of Formula X as in step b of Scheme III and as in Khan, Misbanul Ain et al. *J. Heterocyclic Chem.* 1981, 18, 9-14 by reaction with nitric acid and sulfuric acid gave compounds of Formula XIa. Reduction of the nitro functionality of compounds of Formula XIa in the presence of hydrogen with a catalyst such as 5% Pd/C in a polar aprotic solvent such as tetrahydrofuran gave the amine of Formula XIIa, as shown in step c in Scheme III. Reduction of the nitro functionality of compounds of Formula XIa, wherein R1, R2, R3, R4 and X are as previously defined and R5=H, in the presence of hydrogen with a catalyst such as 10% Pd/C in a polar protic solvent such as ethanol gave the amine of Formula XIIa, wherein R5=H, as well as the amine of Formula XIIa, wherein R5=OEt, as shown in step d of Scheme III. Compounds of Formula XIa, wherein R1, R2, R3, R5 and X are as previously defined and R4=Cl, can be reduced in the presence of a reducing agent such as iron in a mixture of polar protic solvents such as acetic acid, water, and ethanol to give amines of Formula XIIa, wherein R1, R2, R3, R5 and X are as previously defined R4=Cl, as shown in step e of Scheme III. Compounds of Formula XIa, wherein R1, R2, R3, R5 and X are as previously defined and R4=Cl, can be allowed to react under Suzuki coupling conditions with a boronic acid such as phenylboronic acid in the presence of a catalyst such as palladium tetrakis, a base such as 2M aqueous potassium carbonate, and in a mixed solvent system such as ethanol and toluene to provide cross-coupled pyrazoles of Formula XIb, as shown in step f of Scheme III.

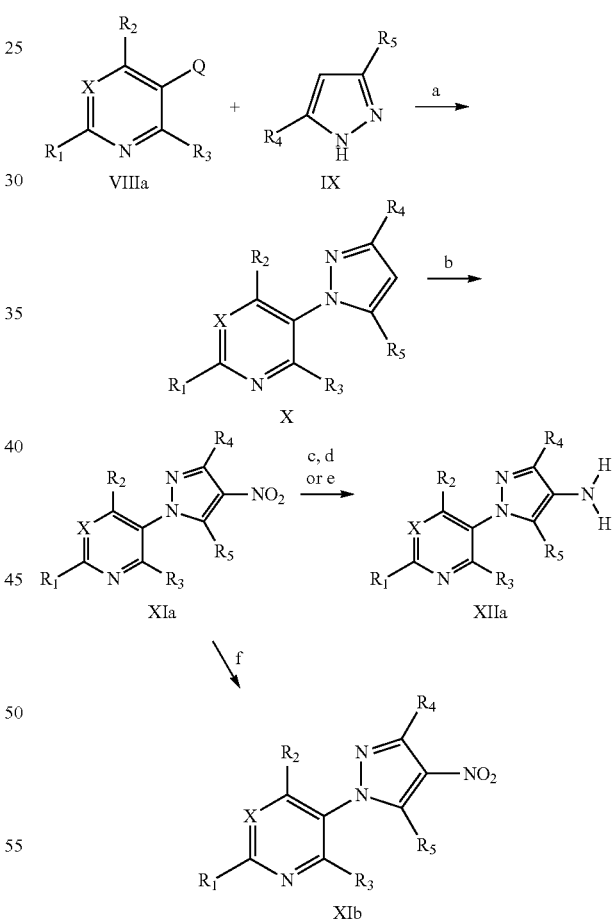

In step a of Scheme IV, the compounds of Formula XIIb can be treated with triethylorthoformate and an acid such as trifluoroacetic acid. Subsequent addition of a reducing agent such as sodium borohydride in a polar protic solvent such as ethanol gave a compound of Formula XIIIa, wherein R6=methyl.

In step b of Scheme IV, the compound of Formula XIIb can be treated with acetone in a solvent such as isopropyl acetate, an acid such as trifluoroacetic acid and sodium triacetoxyborohydride to give compounds of Formula XIIIa, wherein R6=isopropyl.

In step c of Scheme IV, the compounds of Formula XIIb can be acylated with an acid chloride such as acetyl chloride in a polar aprotic solvent such as dichloromethane using the conditions described in Scheme V. Reduction of the amide with a reducing agent such as lithium aluminum hydride in a polar aprotic solvent such tetrahydrofuran gives compounds of Formula XIIIa, wherein R6=ethyl.

Alternatively, in step d of Scheme IV, the compounds of Formula XIIb can be treated with benzotriazole and an aldehyde in ethanol followed by reduction using, for example, sodium borohydride, to afford compounds of Formula XIIIa. In step e of Scheme IV, the compounds of Formula XIIb can be treated with an aldehyde such as propionaldehyde and sodium triacetoxyborohydride in a polar aprotic solvent such as dichloromethane to give compounds of Formula XIIIa, wherein R6=propyl. As in step f acylation of compounds of Formula XIIIa in Scheme IV using the conditions described in Scheme IX affords compounds of Formula Ia, wherein R1, R2, R3, R4, R5, R6, R8 and X are as previously defined.

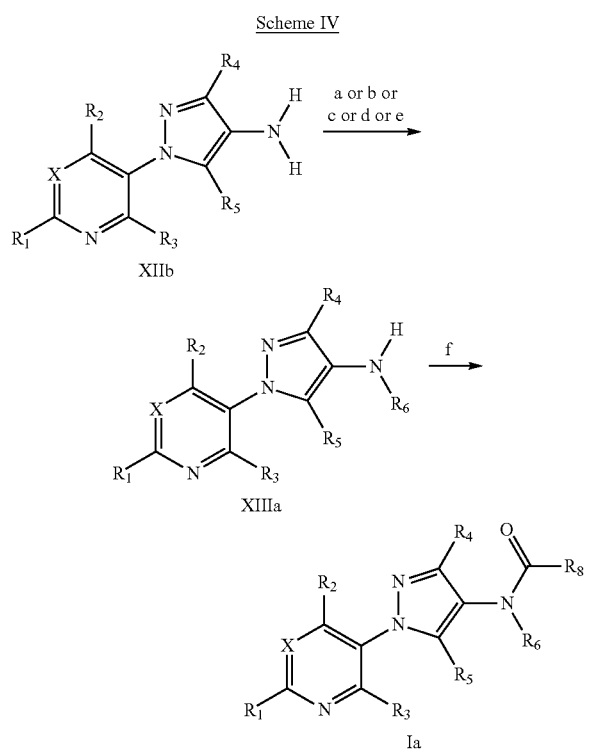

In step a of Scheme V, the compounds of Formula Vc, wherein R1, R2, R3, R4, R5 and R6 and X are as previously defined, can be treated with an acid chloride of Formula XIV, in the presence of a base such as triethylamine or N,N-dimethylaminopyridine in a polar aprotic solvent such as dichloroethane (DCE) to yield compounds of Formula Ib, wherein R8 is as previously defined. Additionally, when R6=H the 2° amide may be subsequently alkylated in step b of Scheme V with an alkyl halide such as iodoethane, in the presence of a base such as sodium hydride and a polar aprotic solvent such as N,N-dimethylformamide (DMF) to yield the desired compounds of Formula Ib. The acid chlorides used in the acylation reactions herein are either commercially available or can be synthesized by those skilled in the art.

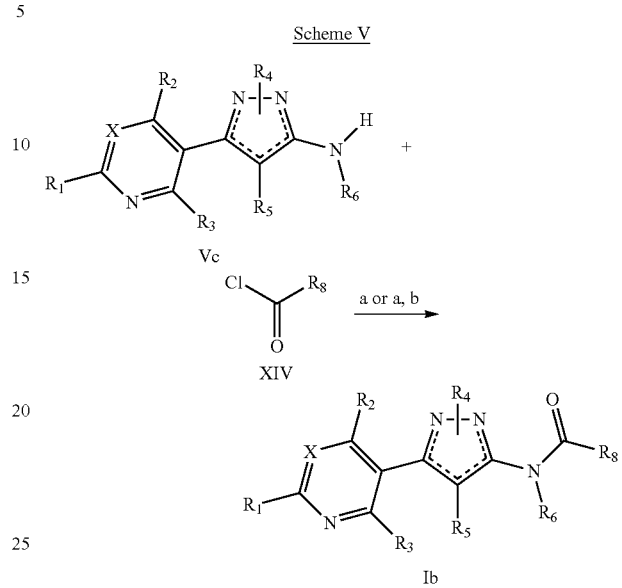

In step a of Scheme VI and as in Sammelson et al. *Bioorg. Med. Chem.* 2004, 12, 3345-3355, the aminopyrazoles of Formula Vd, wherein R1, R2, R3, R4, R6 and X are as previously defined and R5=H, can be halogenated with a halogen source such as N-chlorosuccinimide or N-bromosuccinimide in a polar aprotic solvent such as acetonitrile to provide the R5-substituted pyrazole. In step b, acylation of this compound using the conditions described in Scheme V affords the compound of Formula Ic, wherein R1, R2, R3, R4, R5, R6, R8 and X are as previously defined.

In step a of Scheme VII, ureas and carbamates are made from the aminopyrazoles of Formula Ve. Compounds of Formula Ve, wherein X, R1, R2, R3, R4, R5 and R6 are as previously defined are allowed to react with phosgene to provide the intermediate carbamoyl chloride which is subsequently treated with an amine, as shown in step b, or alcohol, as shown in step c, respectively, to generate a urea of Formula Id or a carbamate of Formula Ie, respectively, wherein R9 is as previously defined.

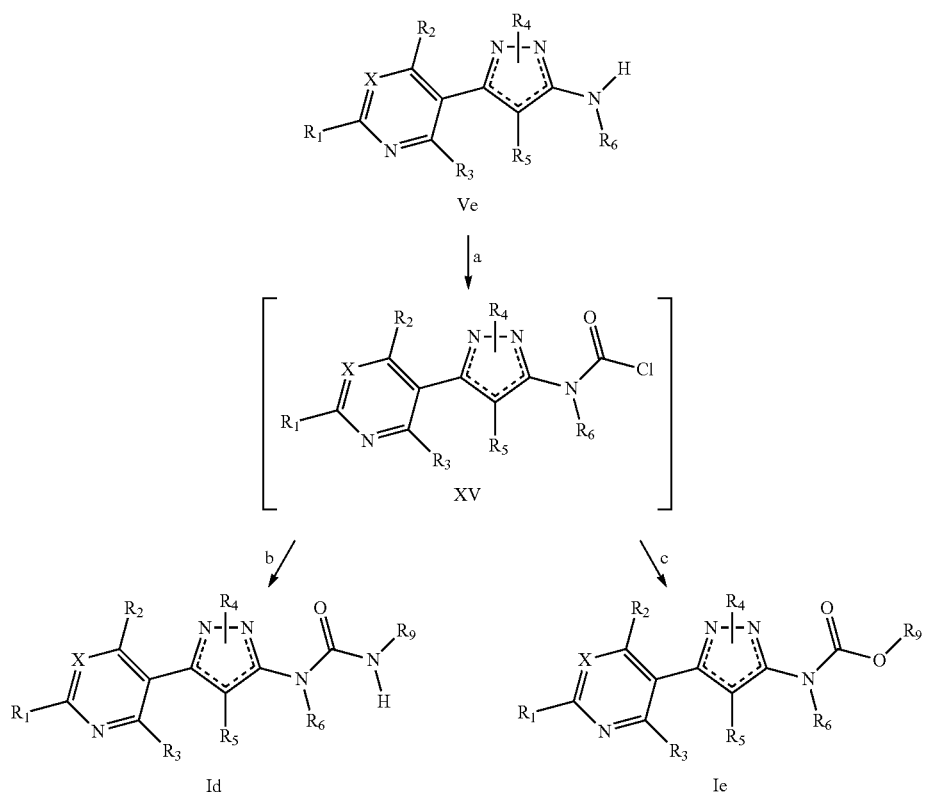

In step a of Scheme VIII, compounds of Formula XIIc, wherein X, R1, R2, R3, R4 and R5 are as previously defined, can be treated with di-tert-butyl dicarbonate (Boc₂O) and a base such as triethylamine in a polar aprotic solvent such as dichloromethane (DCM) to yield compounds of Formula XVIa. Treatment of the carbamate functionality with an alkyl halide such as iodomethane or Boc-anhydride in the presence of a base such as sodium hydride and in a polar aprotic solvent such as DMF yields carbamates of Formula XVII, as shown in step b of Scheme VIII, wherein R6 is as previously defined, except where R6 is hydrogen. The Boc-group can be removed under conditions that are well-known in the art, such as under acidic conditions such as trifluoroacetic acid (TFA) in a polar aprotic solvent like dichloromethane to give compounds of Formula XIIIb as in step c.

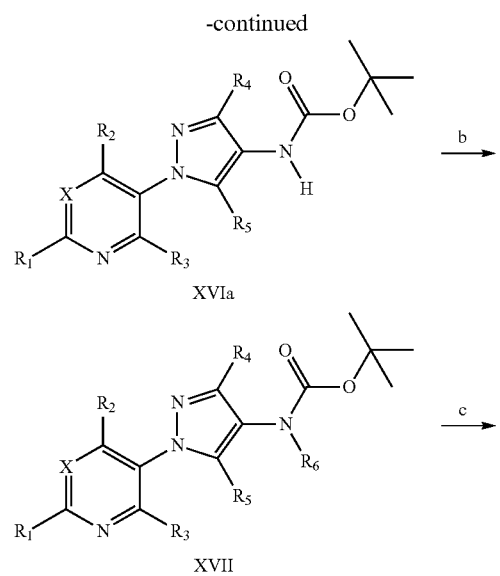

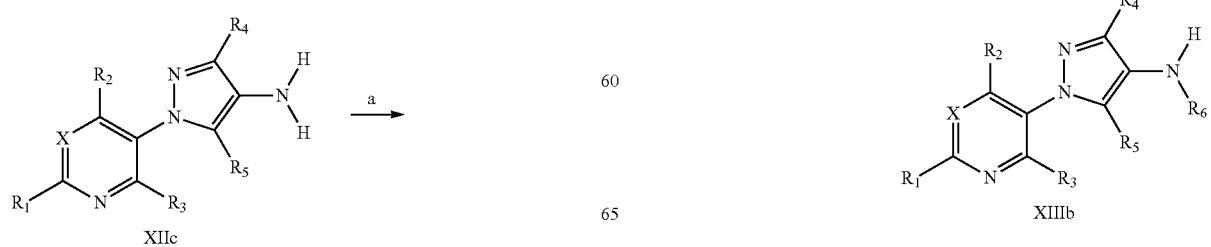

In steps a, b and c of Scheme IX, compounds of Formula XIIIc, wherein X, R1, R2, R3, R4, R5 and R6 are as previously defined, can be treated with a compound of Formula XVIII, wherein R8 is as previously defined and R10 is either OH, OR9 or O(C=O)OR9, to yield compounds of Formula Id. When R10=OH, compounds of Formula XIIIc can be converted to compounds of Formula Id in the presence of a coupling reagent such as 1-(3-dimethylaminopropyl)-3-ethylcarbodiimide hydrochloride (EDC.HCl) and a base such as N,N-dimethylaminopyridine (DMAP) in a polar aprotic solvent such as dichloroethane (DCE), as shown in step a. When R10=OR9, compounds of Formula XIIIc can be converted to compounds of Formula Id in the presence of 2,3,4,6,7,8-hexahydro-1H-pyrimido[1,2-a]pyrimidine in a polar aprotic solvent such as 1,4-dioxane under elevated temperature, as shown in step b. When R10=O(C=O)OR9, compounds of Formula XIIIc can be converted to compounds of Formula Id in a polar aprotic solvent such as dichloromethane (DCM), as shown in step c. Acylation of amides of Formula Id, when R6=H, with an acid chloride in the presence of a base such as diisopropyl ethylamine in a polar aprotic solvent such as dichloroethane (DCE) yields imides of Formula Ie, as shown in step d. Furthermore, alkylation of amides of Formula Id, when R6=H, with an alkyl halide in the presence of a base such as sodium hydride in a polar aprotic solvent such as N,N-dimethylformamide (DMF) yields alkylated amides of Formula Ie, as shown in step e. Halogenation of compounds of Formula Id, wherein R1, R2, R3, R4, R6, R8 and X are as previously defined and R5=H, with a halogen source such as N-bromosuccinimide in a polar aprotic solvent such as DCE or a halogen source such as N-chlorosuccinimide in a polar aprotic solvent such as DCE or acetonitrile or a halogen source such as Selectfluor® in a mixture of polar aprotic solvents such as acetonitrile and DMF give halogenated pyrazoles of Formula Ie, wherein R5=halogen, as shown in step f of Scheme IX. Amides of Formula Id can be converted to thioamides of Formula If in the presence of a thionating agent such as Lawesson's reagent in a polar aprotic solvent such as dichloroethane (DCE), as shown in step g.

In step a of Scheme X, compounds of Formula XIIId, wherein X, R1, R2, R3, R4, R5 and R6 are as previously defined, can be treated with compounds of Formula XIX, wherein R8 is as previously defined, in a polar aprotic solvent such as dichloroethane (DCE) to yield compounds of Formula XX. Additionally, when R6=H and R8 contains a halogen, compounds of Formula XX can be treated with a base, such as sodium hydride, in a polar aprotic solvent, such as THF, to yield compounds of Formula XXI, where m is an integer selected from 1, 2, 3, 4, 5, or 6, as shown in step b of Scheme X.

Scheme X

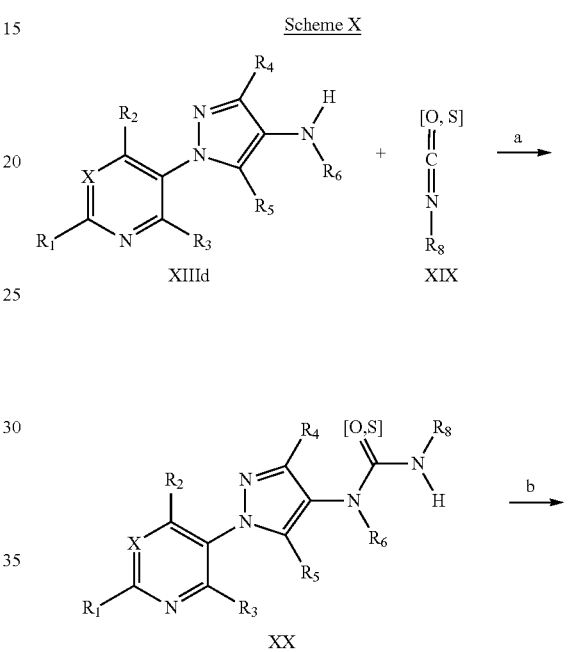

Scheme IX

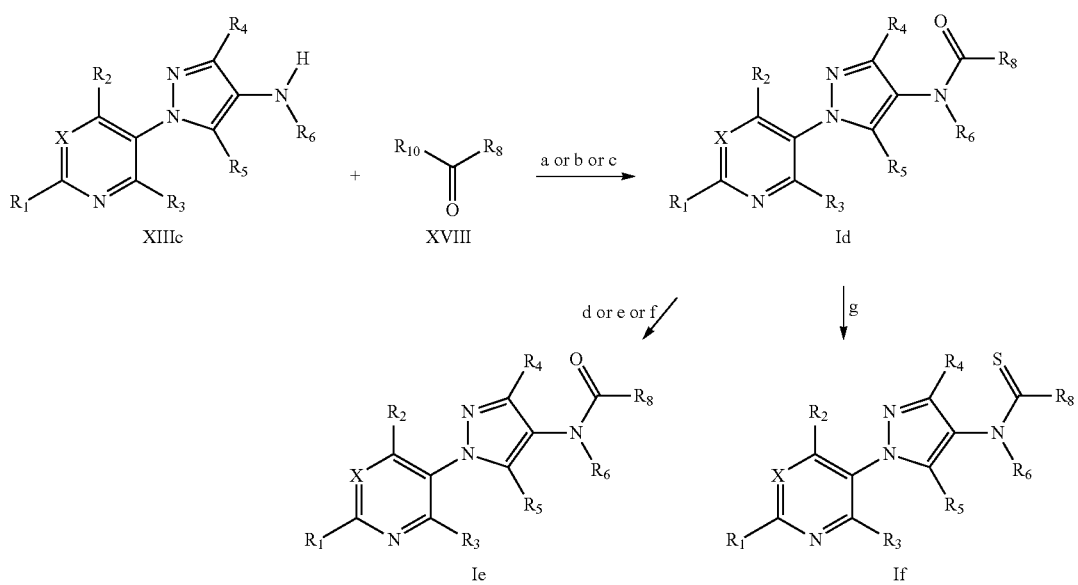

-continued

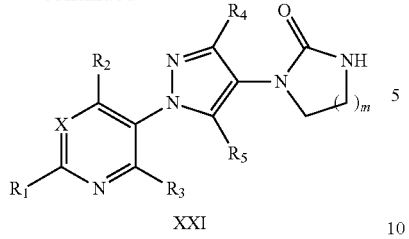

XXI

Oxidation of the sulfide to the sulfoxide or sulfone is accomplished as in Scheme XI where (~S~) can be any sulfide previously defined within the scope of R8 of this invention. The sulfide of Formula XXIIa, wherein X, R1, R2, R3, R4, R5 and R6 are as previously defined, is treated with an oxidant such as sodium perborate tetrahydrate in a polar protic solvent such as glacial acetic acid to give the sulfoxide of Formula XXIII as in step a of Scheme XI. Alternatively, the sulfide of Formula XXIIa can be oxidized with an oxidant such as hydrogen peroxide in a polar protic solvent such as hexafluoroisopropanol to give the sulfoxide of Formula XXIII as in step d of Scheme XI. The sulfoxide of Formula XXIII can be further oxidized to the sulfone of Formula XXIV by sodium perborate tetrahydrate in a polar protic solvent such as glacial acetic acid as in step c of Scheme XI. Alternatively, the sulfone of Formula XXIV can be generated in a one-step procedure from the sulfide of Formula XXIIa by using the aforementioned conditions with >2 equivalents of sodium perborate tetrahydrate, as in step b of Scheme XI.

such as potassium carbonate in a protic polar solvent system such as ethanol and water as in step b of Scheme XII.

Scheme XII

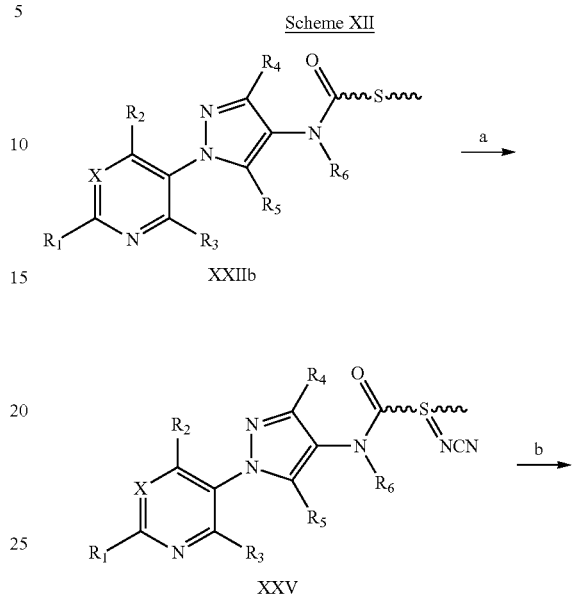

Scheme XI

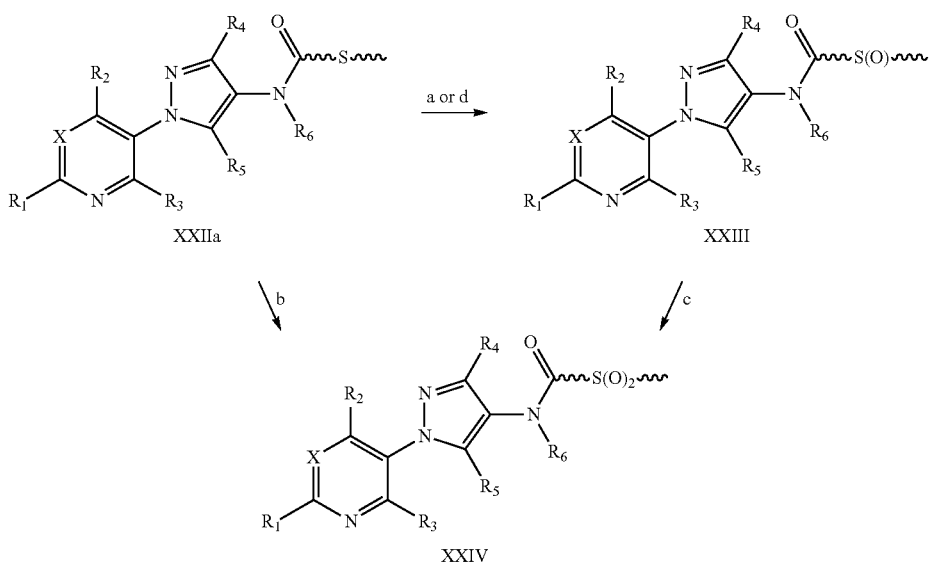

Oxidation of the sulfide to the sulfoximine is accomplished as in Scheme XII where (~S~) can be any sulfide previously defined within the scope of R8 of this invention. The sulfide of Formula XXIIb, wherein X, R1, R2, R3, R4, R5 and R6 are as previously defined, is oxidized as in step a with iodobenzene diacetate in the presence of cyanamide in a polar aprotic solvent such as methylene chloride (DCM) to give the sulfilimine of the Formula XXV. The sulfilimine of Formula XXV may be further oxidized to the sulfoximine of Formula XXVI with an oxidant such as meta-Chloroperoxybenzoic acid ("mCPBA") in the presence of a base -continued

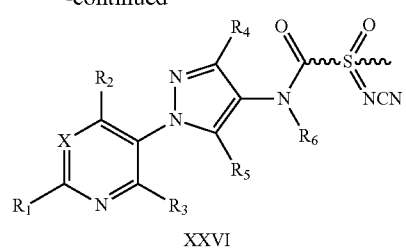

XXVI

Iodination of the pyrazole of Formula Xb as in step a of Scheme XIII and as in Potapov, A. et al. *Russ. J. Org. Chem.* 2006, 42, 1368-1373 was accomplished by reaction with an iodinating agent such as iodine in the presence of acids such as iodic acid and sulfuric acid in a polar protic solvent such as acetic acid gives compounds of Formula XXVII. In step b of Scheme XIII and as in Wang, D. et al. *Adv. Synth. Catal.* 2009, 351, 1722-1726, aminopyrazoles of Formula XIIIe can be prepared from iodopyrazoles of Formula XXVII through cross coupling reactions with an appropriate amine in the presence of a base such as cesium carbonate, a copper catalyst such as copper (I) bromide, and a ligand such as 1-(5,6,7,8-tetrahydroquinolin-8-yl)ethanone in a polar aprotic solvent such as DMSO.

In step a of the Scheme XIV, compounds of the formula XXIX, wherein R4 is Cl, R5 is H and $X^-$ represents $Cl^-$, can be prepared according to the methods described in *Acta. Pharm. Suec.* 22, 147-156 (1985) by Tolf, Bo-Ragnar and Dahlbom, R. In a similar manner, compounds of the Formula XXIX, wherein R4 is $Br^-$, $X^-$ represents $Br^-$ and R5 is as defined previously, can be prepared by treating compounds of the Formula XXVIII with hydrogen gas in the presence of a metal catalyst such as 5% Pd on alumina and a solution of 50% aqueous HBr in a solvent such as ethanol. Alternatively, in step a of Scheme XIV, compounds of the Formula XXIX, wherein R4 is Cl or Br, $X^-$ represents $Cl^-$ or $Br^-$ and R5 is as defined previously, can be prepared by treating compounds of the Formula XXVIII, wherein R5 is as defined previously, with a hydrosilane such as triethyl silane in the presence of a metal catalyst such as 5% Pd on alumina and an acid such as HCl or HBr, respectively, in a solvent such as ethanol.

In step b of the Scheme XIV, compounds of the Formula XXX, wherein R4 is Cl or Br and R5 is as defined previously, can be prepared by treating the compounds of the Formula XXIX, wherein R4 is Cl or Br, $X^-$ represents $Cl^-$ or $Br^-$ and R5 is as defined previously, with di-tert-butyl dicarbonate ($Boc_2O$) in the presence of a mixture of solvents such as THF and water and a base such as sodium bicarbonate.

In step c of the Scheme XIV, compounds of the Formula XVIa, wherein X, R1, R2, R3 and R5 are as defined previously and R4 is Cl or Br can be obtained by treating compounds of the Formula XXX, wherein R4 is Cl or Br and R5 is as defined previously, with compounds of the Formula VIIIb, wherein X, R1, R2 and R3 are as defined previously and Q is bromo or iodo, in the presence of a catalytic amount of copper salt such as $CuCl_2$, an ethane-1,2-diamine derivative such as $N^1,N^2$-dimethylethane-1,2-diamine and a base such as $K_3PO_4$ in a polar aprotic solvent such as acetonitrile at a suitable temperature.

The Boc-group of compounds of Formula XVIa can be removed under conditions that are well-known in the art such as under acidic conditions such as TFA in a polar aprotic solvent such as dichloromethane to give compounds of Formula XIId, as shown in step d of Scheme XIV.

Scheme XIII

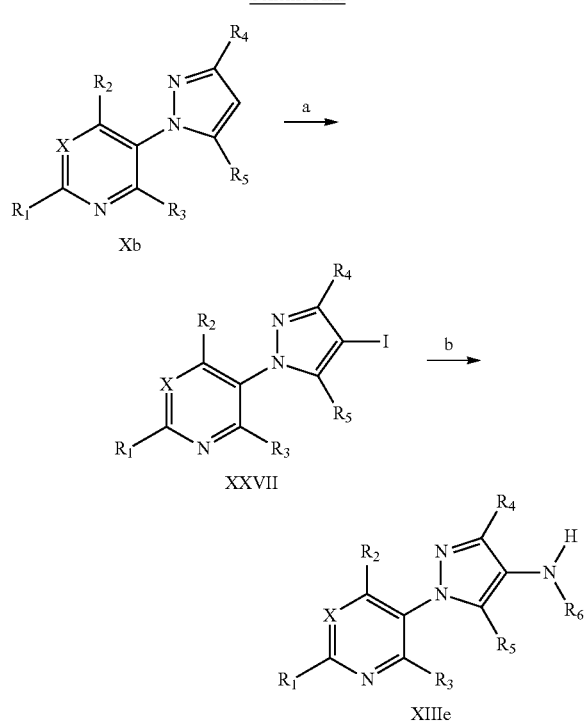

Scheme XIV

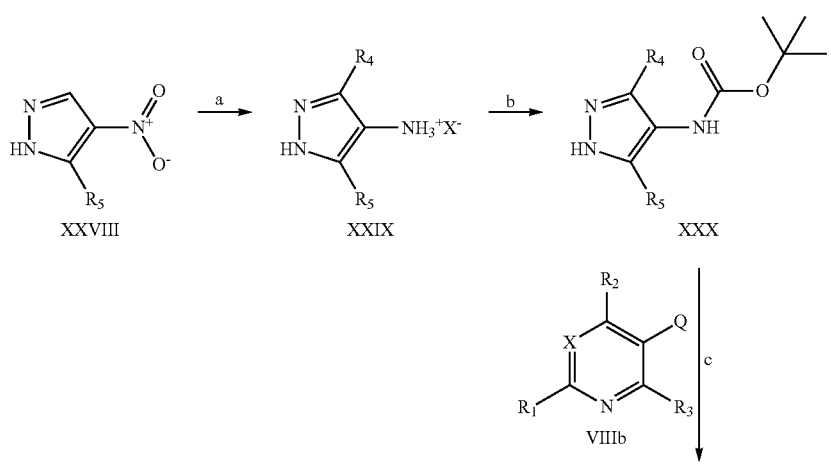

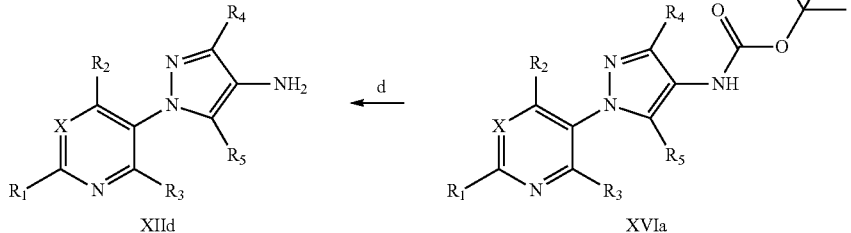

Bromopyrazoles of Formula XXXI, wherein R1, R2, R3, R5, R8 and X are as previously defined, can be allowed to react under Suzuki coupling conditions with a boronic ester such as vinylboronic acid pinacol ester or cyclopropylboronic acid pinacol ester in the presence of a catalyst such as palladium tetrakis, a base such as 2 M aqueous potassium carbonate, and in a mixed solvent system such as ethanol and toluene to provide compounds of Formula XXXII, as shown in step a of Scheme XV.

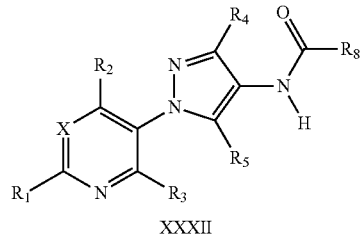

The vinyl group of compounds of Formula XXXIII, wherein R1, R2, R3, R5, R6, R8 and X are as previously defined, can be reduced in the presence of hydrogen with a catalyst such as 10% Pd/C in a polar protic solvent such methanol to give compounds of Formula XXXIV, as shown in step a of Scheme XVI. Oxidation of the vinyl group of compounds of Formula XXXIII using an oxidant such as osmium tetroxide in the presence of sodium periodate in mixture of a polar protic solvent such as water and a polar aprotic solvent such as THF gave compounds of Formula XXXV, as shown in step b of Scheme XVI. Reduction of the aldehyde of compounds of Formula XXXV, as shown in step c of Scheme XVI, with a reducing agent such as sodium borohydride in a polar protic solvent such as methanol gave the corresponding alcohol of Formula XXXVI. Treatment of compounds of Formula XXXVI with a chlorinating agent such as thionyl chloride in a polar aprotic solvent such as dichloromethane gave compounds of Formula XXXVII, as shown in step d of Scheme XVI.

Scheme XV

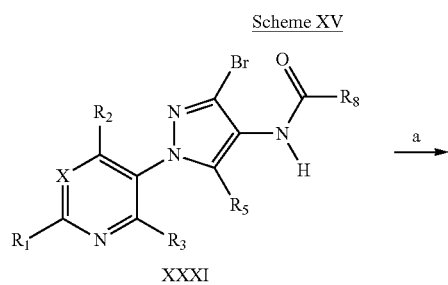

Scheme XVI

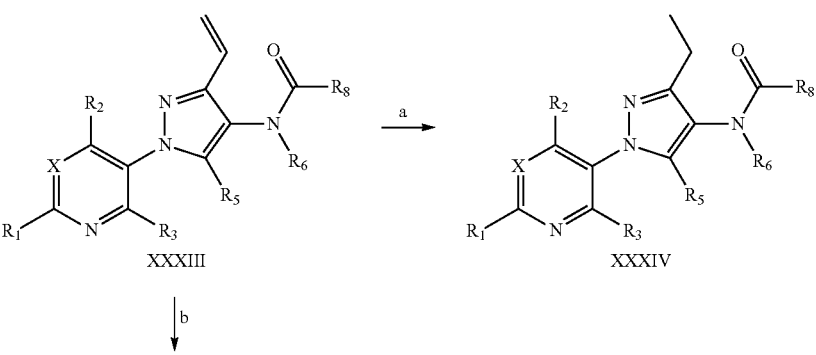

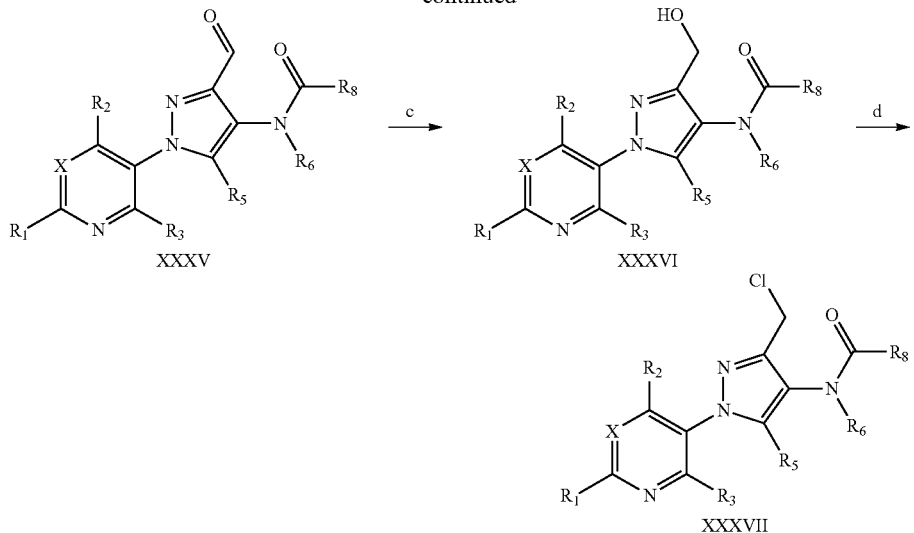

In step a of Scheme XVII, an α,β-unsaturated acid XXXVIII can be treated with a nucleophile such as sodium thiomethoxide in a polar protic solvent such as methanol to give acid XXXIX.

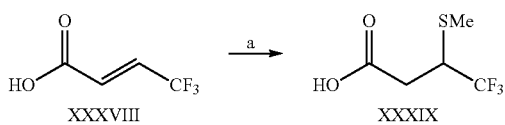

In Step a of the Scheme XVIII, treatment of the compounds of Formula Ig, where A is A2, R7 is O and R8 is tert-butoxy with a reagent such as propargyl bromide in the presence of a base such as sodium hydride and in a polar aprotic solvent such as DMF yields compounds of Formula Ih, wherein R6=R11.

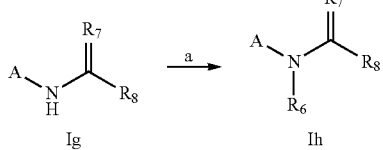

Sulfonamide compounds of Formula II, wherein (~N) can be any amine defined within the scope of R8 of this invention, can be prepared through steps a, b, and c illustrated in Scheme XIX. In step a, acylation of compounds of Formula XIIIf according to methods described in Scheme IX affords compounds of Formula XXXX, wherein R1, R2, R3, R4, R5, R9, X, and where R6=R11 are as previously defined. Removal of the Boc group of compounds of Formula XXXX, depicted in step b, can be achieved using the conditions described in Scheme XIV to give compounds of Formula XXXXI, wherein R1, R2, R3, R4, R5, R9, X, and where R6=R11 are as previously defined. Compounds of Formula XXXXI can be treated with sulfonyl chlorides of Formula XXXXII such as methanesulfonyl chloride in the presence of a base such as diisopropylethylamine in a polar aprotic solvent such as dichloromethane to give compounds of Formula II, as shown in step c of Scheme XIX

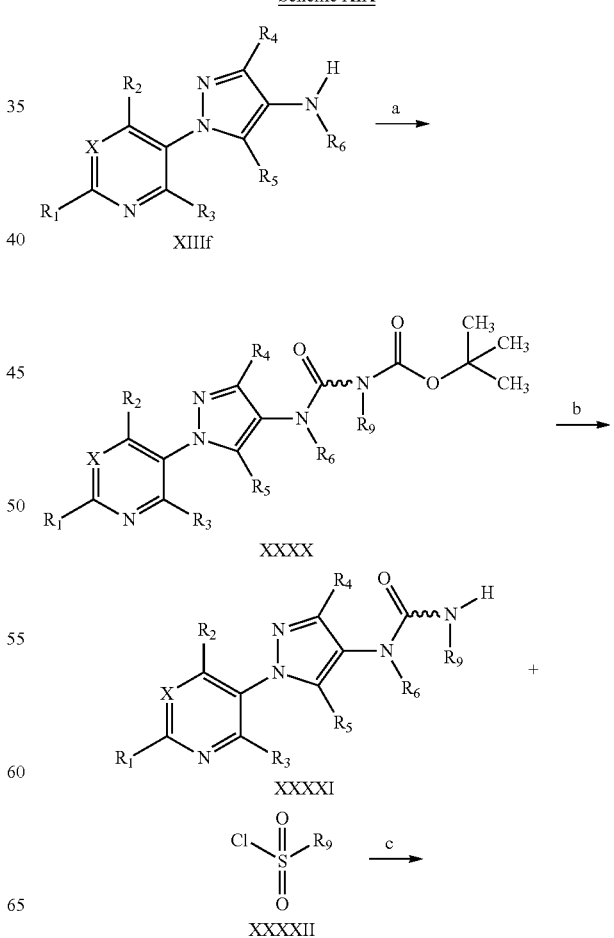

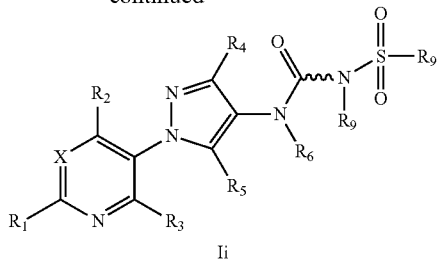

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. All NMR shifts are in ppm (δ) and were recorded at 300, 400 or 600 MHz unless otherwise stated.

Example 1

Step 1: Preparation of 3,3-bis-methylsulfanyl-1-pyridin-3-yl-propenone

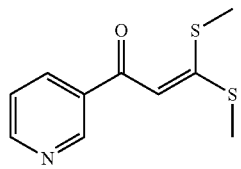

To a room-temperature suspension of sodium hydride (NaH, 60% suspension in mineral oil; 4.13 g, 86 mmol) in dry dimethyl sulfoxide (DMSO, 60 mL) under an atmosphere of nitrogen (N$_2$) was added 3-acetylpyridine (5.00 g, 41.3 mmol) dropwise over 30 minutes (min). The mixture was stirred for an additional 30 minutes at the same temperature. Carbon disulfide (CS$_2$; 3.27 g, 43 mmol) was added dropwise with vigorous stirring followed by iodomethane (12.21 g, 86 mmol) dropwise over a period of 45 min. Stirring was continued for an additional 18 hours (h) under N$_2$. The reaction was quenched with cold water (H$_2$O, 50 mL). The dark solid was filtered and washed with ice-cold ethyl alcohol (EtOH) until the washings were colorless. The off-white solid product was dried under vacuum at 60° C. to provide 3,3-bis-methylsulfanyl-1-pyridin-3-yl-propenone as a brown solid (4.8 g, 51%): $^1$H NMR (300 MHz, CDCl$_3$) δ 9.13 (d, J=1.8 Hz, 1H), 8.72 (dd, J=4.8, 1.6 Hz, 1H), 8.23 (ddd, J=7.9, 2, 2 Hz, 1H), 7.40 (dd, J=7.9, 4.8 Hz, 1H), 6.73 (s, 1H), 2.58 (d, J=9.4 Hz, 6H); MS m/z 226.2 (M+1).

1-(5-fluoropyridin-3-yl)-3,3-bis(methylthio)prop-2-en-1-one was prepared as described in Example 1, Step 1: mp 150-152° C.; $^1$H NMR (400 MHz, CDCl$_3$) δ 8.93 (t, J=1.6 Hz, 1H), 8.58 (d, J=2.8 Hz, 1H), 7.94 (ddd, J=8.9, 2.8, 1.7 Hz, 1H), 6.69 (s, 1H), 2.60 (s, 3H), 2.57 (s, 3H).

Example 1

Step 2: Preparation of (Z)-3-methylamino-3-methylsulfanyl-1-pyridin-3-yl-propenone

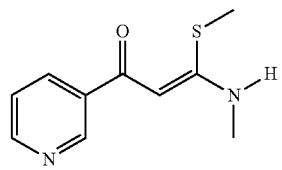

A solution of 3,3-bis-methylsulfanyl-1-pyridin-3-yl-propenone (18.6 g, 82.5 mmol) in absolute alcohol (400 mL) under N$_2$ was treated with methylamine hydrochloride (27.86 g, 412 mmol) followed by triethylamine (Et$_3$N, 58.5 mL, 412 mmol). The mixture was heated to reflux for 3 h, cooled to room temperature and concentrated under reduced pressure. The solid residue was dissolved in ethyl acetate (EtOAc; 150 mL). The solution was washed with H$_2$O (2×50 mL) and brine (50 mL), dried over Na$_2$SO$_4$, concentrated under reduced pressure and purified by silica gel chromatography eluting with 10% EtOAc in petroleum ether to yield (Z)-3-methylamino-3-methylsulfanyl-1-pyridin-3-yl-propenone as a pale yellow solid (8.6 g, 50%): $^1$H NMR (300 MHz, CDCl$_3$) δ 11.8 (br s, 1H), 9.06 (s, 1H); 8.67 (d, J=3.9 Hz, 1H), 8.26 (d, J=8.0 Hz 1H), 7.46 (dd, J=7.6, 4.9 Hz 1H), 5.62 (s, 1H), 3.10 (d, J=5.2 Hz, 3H), 2.52 (s, 3H); MS (m/z) 209.2 [M+1].

(Z)-3-(ethylamino)-3(methylthio)-1-(pyridin-3-yl)prop-2-en-1-one was prepared as described in Example 1, Step 2: $^1$H NMR (400 MHz, CDCl$_3$) δ 11.81 (bs, 1H), 9.04 (dd, J=2.2, 0.7 Hz, 1H), 8.64 (dd, J=4.8, 1.7 Hz, 1H), 8.29-7.98 (m, 1H), 7.35 (ddd, J=7.9, 4.8, 0.9 Hz, 1H), 3.45 (q, J=7.2, 5.6 Hz, 2H), 2.50 (s, 3H), 1.35 (t, J=7.2 Hz, 3H).

(Z)-3-(cyclopropylmethyl)amino-3(methylthio)-1-(pyridin-3-yl)prop-2-en-1-one was prepared as described in Example 1, Step 2: $^1$H NMR (400 MHz, CDCl$_3$) δ 9.00 (s, 1H), 9.05 (dd, J=2.2, 0.7 Hz, 1H), 8.64 (dd, J=4.8, 1.7 Hz, 1H), 8.16 (dt, J=7.9, 2.0 Hz, 1H), 7.35 (ddd, J=7.9, 4.8, 0.8 Hz, 1H), 5.62 (s, 1H), 3.27 (dd, J=7.0, 5.5 Hz, 2H), 2.50 (s, 3H), 1.20-1.07 (m, 1H), 0.73-0.49 (m, 2H), 0.41-0.17 (m, 2H).

Example 1

Step 3: Preparation of methyl-(2-methyl-5-pyridin-3-pyrazol-3-yl)-amine

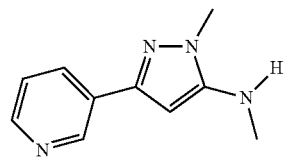

A solution of (Z)-3-methylamino-3-methylsulfanyl-1-pyridin-3-yl-propenone (3.00 g, 14 mmol) and methylhydrazine (729 mg, 15.4 mmol) in absolute EtOH (64 mL) was stirred at reflux for 18 h under N$_2$, cooled to room temperature and evaporated under reduced pressure. The residue was dissolved in EtOAc (50 mL), and the organic layer was washed with H$_2$O (2×30 mL) and brine (30 mL), dried over Na$_2$SO$_4$, concentrated under reduced pressure and purified using silica gel chromatography eluting with a gradient of 0-1% EtOH in EtOAc to yield two regioisomers in a 1:2 ratio, with the major regioisomer as a brown solid (1.0 g, 27%): $^1$H NMR (300 MHz, CDCl$_3$) δ 8.97 (d, J=1.3 Hz, 1H), 8.51 (dd, J=3.6, 1.0 Hz, 1H), 8.07 (ddd, J=5.9, 1.4, 1.4 Hz, 1H), 7.30 (dd, J=5.9, 3.6 Hz, 1H), 5.82 (s, 1H), 3.69 (s, 3H), 2.93 (s, 3H); MS (m/z) 188.6 [M+1].

1-Ethyl-N-methyl-3-(pyridin-3-yl)-1H-pyrazol-5-amine was prepared as described in Example 1, Step 3: ESIMS m/z 204 ([M+2H]).

N-ethyl-1-methyl-3-(pyridin-3-yl)-1H-pyrazol-5-amine was prepared as described in Example 1, Step 3: ESIMS m/z 203 ([M+H]).

N-methyl-1-phenyl-3-(pyridin-3-yl)-1H-pyrazol-5-amine was prepared as described in Example 1, Step 3: ESIMS m/z 252 ([M+2H]).

N-(cyclopropylmethyl)-1-methyl-3-(pyridin-3-yl)-1H-pyrazol-5-amine was prepared as described in Example 1, Step 3: ESIMS m/z 230 ([M+2H]).

1-Isopropyl-N-methyl-3-pyridin-3-yl)-1H-pyrazol-5-amine was prepared as described in Example 1, Step 3: $^1$H NMR (300 MHz, CDCl$_3$) δ 8.53 (s, 1H), 8.06-7.90 (m, J=7.2 Hz, 2H), 7.13 (dd, J=7.9, 5.6 Hz, 1H), 5.33 (s, 1H), 3.70 (bs, 1H), 3.65 (dt, J=13.2, 6.6 Hz, 1H), 2.31 (s, 3H), 0.88 (d, J=6.6 Hz, 6H); ESIMS m/z 217 ([M+H]).

3-(5-Fluoropyridin-3-yl)-N, 1-dimethyl-1H-pyrazol-5-amine was prepared as described in Example 1, Step 3: $^1$H NMR (300 MHz, CDCl$_3$) δ 8.28 (s, 1H), 7.87 (t, J=1.3 Hz, 1H), 7.60 (m, 1H), 6.66 (s, 1H), 5.28 (bs, 2H), 3.12 (s, 3H), 2.34 (s, 3H); ESIMS m/z 206 ([M+H])

Example 2

Preparation of (4-chloro-2-methyl-5-pyridin-3-yl-2H-pyrazol-3-yl)-methyl-amine

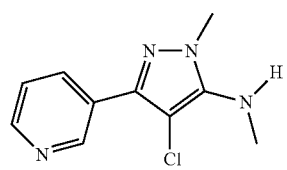

A mixture of methyl-(2-methyl-5-pyridin-3-yl-2H-pyrazol-3-yl)-amine (0.35 g, 1.8 mmol) and N-chlorosuccinimide (0.273 g, 2 mmol) was combined in acetonitrile (3 mL), stirred at room temperature for 30 minutes, concentrated under reduced pressure and purified using silica gel chromatography eluting with a gradient of EtOAc in hexanes to yield the title compound as a yellow oil (0.096 g, 23%): IR (thin film) 1581.6 cm$^{-1}$; $^1$H NMR (400 MHz, CDCl$_3$) δ 9.12 (d, J=1.5 Hz, 1H), 8.57 (dd, J=4.8, 1.3 Hz, 1H), 8.15 (ddd, J=7.8, 2.0, 2.0 Hz, 1H), 7.33 (dd, J=8.1, 5.1 Hz, 1H), 3.80 (s, 3H), 2.91 (d, J=5.8 Hz, 3H); ESIMS (m/z) 225.6 [M+2].

The reaction also gave 4-chloro-2-methyl-5-pyridin-3-yl-2H-pyrazol-3-ylamine as a green gum (0.046 g, 13%): IR (thin film) 1720.5 cm$^{-1}$; $^1$H NMR (CDCl$_3$, 400 MHz) δ 9.13 (br s, 1H), 8.57 (br s, 1H), 8.16 (dt, J=8.0, 2.0 Hz, 1H), 7.33 (dd, J=7.8, 4.8 Hz, 1H), 3.76 (s, 3H); ESIMS (m/z) 207.0 [M−1].

Example 3

Preparation of 2,N-dimethyl-N-(2-methyl-5-pyridin-3-yl-2H-pyrazol-3-yl)-3-methylsulfanyl-propionamide (Compound 1)

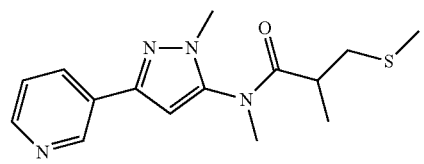 [SMILES: CSCC(C)C(=O)N(C)c1cc(-c2cccnc2)nn1C]

To a solution of methyl-(2-methyl-5-pyridin-3-yl-2H-pyrazol-3-yl)-amine (150 mg, 0.8 mmol) under N$_2$ in ice-cold dichloroethane (DCE; 2 mL) was added dropwise via pipette a solution of 2-methyl-3-methylsulfanyl-propionyl-chloride (146 mg, 0.9 mmol) in DCE (1.5 mL). After stirring for 10 minutes (min), a solution of 4-N,N-dimethylaminopyridine (DMAP; 107 mg, 0.9 mmol) in DCE (2 mL) was added dropwise. The ice bath was removed after 30 min, and the mixture was stirred at room temperature for 90 min and then at reflux for 14 h. The mixture was concentrated under reduced pressure and was purified by silica gel chromatography eluting with a gradient of EtOAc in hexane. The product, 2,N-dimethyl-N-(2-methyl-5-pyridin-3-yl-2H-pyrazol-3-yl)-3-methylsulfanyl-propionamide, was isolated as a yellow semi-solid (44 mg, 24%): $^1$H NMR (400 MHz, CDCl$_3$) δ 9.00 (s, 1H), 8.58 (s, 1H), 8.08 (br d, J=7.0 Hz, 1H), 7.35 (br dd, J=7.3, 4.8 Hz, 1H), 6.58 (br s, 0.5H), 6.49 (br s, 0.5H), 3.89-3.79 (m, 3H), 3.25 (s, 3H), 2.96-2.80 (m, 1H), 2.42-2.40 (m, 1H), 2.02-1.99 (m, 3H), 2.62 (m, 1H), 1.15 (d, J=6.0 Hz, 3H); MS (m/z) 305.0 [M+1].

Compounds 2-6, 9-10, 12, 18-21, 24-33, 477, 487, 509, 520, 556-557, 562-568 were made from the appropriate amines in accordance with the procedures disclosed in Example 3.

Example 4

Preparation of 1-methyl-1-(2-methyl-5-pyridin-3-yl-2H-pyrazol-3-yl)-3-(2-methylsulfanyl-ethyl)-urea (Compound 7)

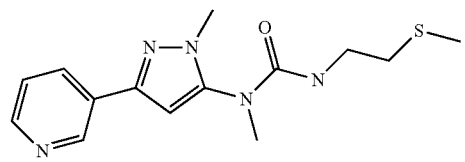 [SMILES: CSCCNC(=O)N(C)c1cc(-c2cccnc2)nn1C]

To a solution of methyl-(2-methyl-5-pyridin-3-yl-2H-pyrazol-3-yl)-amine (150 mg, 0.8 mmol) in ice-cold DCE (2 mL) under N$_2$ was added a solution of phosgene in toluene (20%, 0.43 mL, 0.88 mmol). The ice bath was removed after 30 min, and the mixture was stirred at room temperature for 1 h and at reflux for 2 h. The mixture was cooled to room temperature and then more phosgene (0.86 mL, 1.76 mmol) was added. The mixture was stirred at reflux for 90 min and then cooled in an ice bath. To this was added a solution of 2-methylthioethylamine (80 mg, 0.88 mmol) in DCE (2 mL). The ice bath was removed after 10 min, and the reaction mixture was stirred at reflux for 14 h, cooled, and diluted with DCE (30 mL). The diluted reaction mixture was washed with saturated NaHCO$_3$ (20 mL), dried over MgSO$_4$, adsorbed onto silica gel and purified using silica gel chromatography eluting with a gradient of methanol in dichloromethane to afford 1-methyl-1-(2-methyl-5-pyridin-3-yl-2H-pyrazol-3-yl)-3-(2-methylsulfanyl-ethyl)-urea as a yellow gum (14 mg, 6%): $^1$H NMR (400 MHz, CDCl$_3$) δ 8.99 (d, J=1.5 Hz, 1H), 8.57 (dd, J=4.8, 1.5 Hz, 1H), 8.08 (ddd, J=8.1, 2.1, 2.1 Hz, 1H), 7.34 (dd, J=7.9, 4.8 Hz, 1H), 6.52 (s, 1H), 4.88 (br t, J=5.5 Hz, 1H), 3.80 (s, 3H), 3.41 (q, J=6.3 Hz, 2H), 3.24 (s, 3H), 2.61 (t, J=6.3 Hz, 2H), 2.06 (s, 3H); ESIMS (m/z) 292.2 [M+2].

Compound 8 was made in accordance with the procedures disclosed in Example 4 using 2-(methylthio)ethanol in place of 2-methylthioethylamine.

Example 5

Preparation of 1-methyl-5-(pyridin-3-yl)-1H-pyrazol-3-amine and 1-methyl-3-(pyridin-3-yl)-1H-pyrazol-5-amine

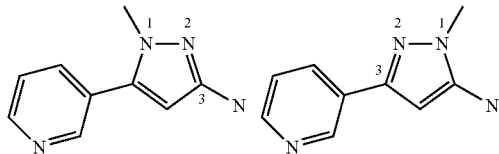

To ethanol (8.53 ml) was added 3-oxo-3-(pyridin-3-yl) propanenitrile (0.82 g, 5.61 mmol) and methylhydrazine (0.25 g, 5.61 mmol) and stirred at reflux for 2 hours. The reaction was cooled to room temperature and concentrated to dryness. The crude material was purified by silica gel chromatography by eluting with 0-20% MeOH/dichloromethane to yield two products—1-methyl-5-(pyridin-3-yl)-1H-pyrazol-3-amine (0.060 g; 6.14%): $^1$H NMR (300 MHz, CDCl$_3$) δ 8.72 (s, 1H), 8.53 (d, 1H), 7.76-7.63 (m, 1H), 7.43-7.33 (m, 1H), 5.75 (s, 1H), 3.76-3.57 (m, 5H) and 1-methyl-3-(pyridin-3-yl)-1H-pyrazol-5-amine (0.150 g, 15.35%): $^1$H NMR (300 MHz, CDCl$_3$) δ 8.88 (s, 1H), 8.48 (d, 1H), 7.99 (d, 1H), 7.38-7.07 (m, 1H), 585 (s, 1H), 3.80-3.59 (m, 5H).

Example 6

Step 1: Preparation of 3-pyrazol-1-yl-pyridine

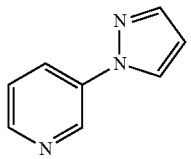 [SMILES: c1cncc(-n2cccn2)c1]

To a solution of 3-bromopyridine (5 g, 0.031 mol) in 50 ml of acetonitrile were added pyrazole (2.6 g, 0.038 mol), Cs$_2$CO$_3$ (16.5 g, 0.050 mol), Cu$_2$O (0.226 g, 0.0016 mol), and salicylaldoxime (0.867 g, 0.006 mol) under N$_2$ atmosphere. The reaction mass was refluxed for 24 hrs at 80° C. The reaction mass was concentrated and the crude was purified by column chromatography using ethyl acetate and hexane (1:1) to afford the pyrazolyl pyridine as a dark brown liquid (2 g, 43%): $^1$H NMR (400 MHz, CDCl$_3$) δ 8.99 (d, J=2.8 Hz, 1H), 8.48 (dd, J=4.8, 1.2 Hz, 1H), 8.11-8.08 (m, 1H), 7.99 (d, J=1.2 Hz, 1H), 7.78 (d, J=1.2 Hz, 1H), 7.38-7.35 (m, 1H), 6.53 (t, J=1.2 Hz, 1H); MS (m/z) 146 [M+1].

3-(3-chloro-1H-pyrazol-1-yl)pyridine was prepared as in Example 6, Step 1: mp 98-106° C.; $^1$H NMR (400 MHz, CDCl$_3$) δ 8.93 (d, J=2.6 Hz, 1H), 8.57 (dd, J=4.8, 1.4 Hz, 1H), 8.03 (ddd, J=8.3, 2.7, 1.5 Hz, 1H), 7.90 (d, J=2.5 Hz, 1H), 7.42 (ddd, J=8.3, 4.8, 0.7 Hz, 1H), 6.46 (d, J=2.5 Hz, 1H); $^{13}$C (DMSO-d$_6$) 148, 142, 140, 136, 131, 126, 125, 108.

2-methyl-3-(3-methyl-1H-pyrazol-1-yl)pyridine was prepared as in Example 6, Step 1: $^1$H NMR (400 MHz, CDCl$_3$) δ 8.53 (d, J=4.7 Hz, 1H), 7.67 (d, J=7.9 Hz, 1H), 7.54 (t, J=8.0 Hz, 1H), 7.27-7.19 (m, 1H), 6.27 (d, J=1.4 Hz, 1H), 2.53 (s, 3H), 2.38 (s, 3H).

3-(3-(Trifluoromethyl)-1H-pyrazol-1-yl)pyridine was prepared from the appropriate starting materials as described in Example 6, Step 1: mp 59.0-61.0° C.; $^1$H NMR (400 MHz, CDCl$_3$) δ 9.00 (s, 1H), 8.70-8.59 (m, 1H), 8.11 (ddd, J=8.3, 2.7, 1.5 Hz, 1H), 8.05-7.98 (m, 1H), 7.46 (dd, J=8.3, 4.8 Hz, 1H), 6.79 (d, J=2.4 Hz, 1H); EIMS m/z 213.

3-Fluoro-5-(3-methyl-1H-pyrazol-1-yl)pyridine was prepared from the appropriate starting materials as described in Example 6, Step 1: mp 70.0-72.0° C.; $^1$H NMR (400 MHz, CDCl$_3$) δ 8.76-8.73 (m, 1H), 8.37-8.33 (m, 1H), 7.88-7.85 (m, 1H), 7.84-7.79 (m, 1H), 6.34-6.29 (m, 1H), 2.37 (s, 3H); EIMS m/z 177.

3-(3-Chloro-1H-pyrazol-1-yl)-5-fluoropyridine was prepared from the appropriate starting materials as described in Example 6, Step 1: mp 77.0-82.0° C.; $^1$H NMR (400 MHz, CDCl$_3$) δ 8.75 (d, J=1.8 Hz, 1H), 8.43 (d, J=2.3 Hz, 1H), 7.92 (d, J=2.6 Hz, 1H), 7.84 (dt, J=9.3, 2.4 Hz, 1H), 6.48 (d, J=2.6 Hz, 1H); EIMS m/z 198.

3-(3-methyl-1H-pyrazol-1-yl)pyridine was prepared as described in Example 6, Step 1: $^1$H NMR (400 MHz, CDCl$_3$) δ 8.94 (bs, 1H), 8.51 (d, J=3.9 Hz, 1H), 8.02 (ddd, J=8.3, 2.6, 1.5 Hz, 1H), 7.90-7.79 (m, 1H), 7.39 (dd, J=8.2, 5.1 Hz, 1H), 6.30 (d, J=2.4 Hz, 1H), 2.39 (s, 3H).

3-(5-methyl-1H-pyrazol-1-yl)pyridine was prepared as in Example 6, Step 1: $^1$H NMR (400 MHz, CDCl$_3$) δ 8.77 (d, J=2.5 Hz, 1H), 8.65 (dd, J=4.8, 1.5 Hz, 1H), 7.84 (ddd, J=8.2, 2.5, 1.5 Hz, 1H), 7.63 (d, J=1.6 Hz, 1H), 7.44 (ddd, J=8.2, 4.8, 0.7 Hz, 1H), 6.225 (dd, J=1.6, 0.7 Hz, 1H), 2.40 (s, 3H).

Example 6

Step 2: Preparation of 3-(4-nitro-pyrazol-1-yl)-pyridine

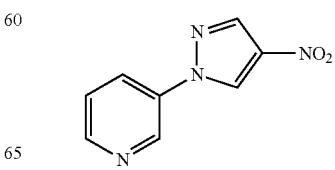

3-Pyrazol-1-yl-pyridine (2 g, 0.032 mol) was dissolved in concentrated $H_2SO_4$ (32 mL 0.598 mmol.) and cooled to $-5°$ C. using an ice bath. To the reaction mass, a 1:1 mixture of concentrated $HNO_3$ (30 mL, 0.673 mmol) and concentrated $H_2SO_4$ (30 ml, 15 Vol.) was added dropwise over a period of 30 min. Cooling was discontinued and the reaction mixture was stirred at room temperature overnight. After the reaction was complete, the mixture was poured over crushed ice and neutralized with saturated $NaHCO_3$, filtered, washed with water and dried to furnish the nitro pyrazole as pale yellow solid (1.8 g, 68%): $^1H$ NMR (400 MHz, DMSO-$d_6$) δ 9.03 (d, J=2.8 Hz, 1H); 8.70 (dd, J=4.8, 1.6 Hz, 1H), 8.69 (s, 1H), 8.33 (s, 1H), 8.11-8.08 (m, 1H), 7.51 (dd, J=8.4, 4.8 Hz, 1H); MS (m/z) 191 [M+1].

3-(3-chloro-4-nitro-1H-pyrazol-1-yl)pyridine was prepared as in Example 6, Step 2: mp 139-142° C., $^1H$ NMR (400 MHz, $CDCl_3$) δ 9.01 (d, J=2.0 Hz, 1H), 8.73 (d, J=4.9 Hz, 2H), 8.08 (ddd, J=8.3, 2.5, 1.3 Hz, 1H), 7.52 (dd, J=8.3, 4.8 Hz, 1H), EIMS m/z 224.

3-(5-methyl-4-nitro-1H-pyrazol-1-yl)pyridine was prepared as in Example 6, Step 2: $^1H$ NMR (400 MHz, $CDCl_3$) δ 8.81-8.71 (m, 2H), 8.32 (s, 1H), 7.83 (ddd, J=8.2, 2.5, 1.6 Hz, 1H), 7.54 (dd, J=8.2, 4.8 Hz, 1H), 2.72 (s, 3H).

2-methyl-3-(3-methyl-4-nitro-1H-pyrazol-1-yl)pyridine was prepared as in Example 6, Step 2: $^1H$ NMR (400 MHz, $d_6$-DMSO) δ 14.01 (s, 1H), 9.37 (d, J=4.0 Hz, 1H), 8.69 (t, J=17.3 Hz, 1H), 8.21 (dd, J=7.7, 4.8 Hz, 1H), 2.29 (s, 3H), 2.20 (s, 3H); $^{13}C$ 154, 150, 146, 135, 134.9, 134.8, 134.3, 122, 21, 14; EIMS m/z 218.

3-(3-methyl-4-nitro-1H-pyrazol-1-yl)pyridine was prepared as in Example 6, Step 2: mp 122-124° C.; $^1H$ NMR (400 MHz, $CDCl_3$) δ 9.01 (d, J=2.5 Hz, 1H), 8.77-8.56 (m, 2H), 8.07 (ddd, J=8.3, 2.7, 1.5 Hz, 1H), 7.56-7.37 (m, 1H), 2.66 (s, 3H); EIMS m/z 208.

3-Fluoro-5-(3-methyl-4-nitro-1H-pyrazol-1-yl)pyridine was prepared from the appropriate starting material as described in Example 6, Step 2: mp 90.0-92.0° C.; $^1H$ NMR (400 MHz, $CDCl_3$) δ 8.82 (d, J=2.0 Hz, 1H), 8.69 (s, 1H), 8.54 (d, J=2.5 Hz, 1H), 7.89 (dt, J=8.9, 2.4 Hz, 1H), 2.66 (s, 3H); EIMS m/z 222.

3-(4-Nitro-3-(trifluoromethyl)-1H-pyrazol-1-yl)pyridine was prepared from the appropriate starting material as described in Example 6, Step 2: mp 121.0-123.0° C.; $^1H$ NMR (400 MHz, $CDCl_3$) δ 9.04 (d, J=2.5 Hz, 1H), 8.79 (s, 1H), 8.77 (d, J=0.9 Hz, 1H), 8.13 (ddd, J=8.3, 2.7, 1.4 Hz, 1H), 7.55 (dt, J=10.8, 5.4 Hz, 1H); EIMS m/z 258.

3-(3-Chloro-4-nitro-1H-pyrazol-1-yl)-5-fluoropyridine was prepared from the appropriate starting material as described in Example 6, Step 2: mp 109.5-111.0° C.; $^1H$ NMR (400 MHz, $CDCl_3$) δ 8.83 (d, J=2.1 Hz, 1H), 8.75 (s, 1H), 8.60 (d, J=2.4 Hz, 1H), 7.89 (dt, J=8.6, 2.4 Hz, 1H); EIMS m/z 242.

3-(3-Bromo-4-nitro-1H-pyrazol-1-yl)pyridine was prepared from the appropriate starting material as described in Example 6, Step 2: mp 139.0-141.0° C.; $^1H$ NMR (400 MHz, $CDCl_3$) δ 9.01 (d, J=2.5 Hz, 1H), 8.73 (dd, J=4.7, 1.1 Hz, 1H), 8.71 (s, 1H), 8.15-8.00 (m, 1H), 7.52 (dd, J=8.3, 4.8 Hz, 1H); ESIMS m/z 271 ([M+2]$^+$).

Example 6

Step 3: Preparation of 1-pyridin-3-yl-1H-pyrazol-4-ylamine

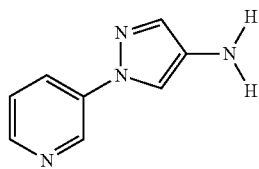 [SMILES: Nc1cnn(-c2cccnc2)c1]

To a solution of 3-(4-nitro-pyrazol-1-yl)-pyridine (1.8 g, 0.009 mol) in dry THF (18 ml) was added 5% Pd/C (180 mg) under nitrogen atmosphere. The mixture was then stirred under hydrogen atmosphere until the reaction was complete. The reaction mixture was filtered through a pad of celite, and concentrated to dryness to give an impure dark brown solid (1.76 g): $^1H$ NMR (400 MHz, DMSO-$d_6$) δ 8.89 (dd, J=2.8. 0.4 Hz, 1H); 8.48 (dd, J=4.8, 1.2 Hz, 1H), 7.99-7.96 (m, 1H), 7.54 (d, J=1.2 Hz, 1H), 7.45 (d, J=0.4 Hz, 1H), 7.38-7.35 (m, 1H), 4.81 (bs 1H); ESIMS (m/z) 161 [M+1].

5-methyl-1-(pyridin-3-yl)-1H-pyrazol-4-amine was prepared as in Example 6, Step 3: $^1H$ NMR (400 MHz, $CDCl_3$) δ 8.74 (d, J=2.3 Hz, 1H), 8.63-8.50 (m, 1H), 7.81 (ddd, J=8.2, 2.5, 1.5 Hz, 1H), 7.46-7.33 (m, 2H), 2.64 (bs, 1H), 2.29 (s, 3H); $^{13}C$ (DMSO-$d_6$) 147, 144, 137, 133, 130, 129, 124, 123, 10; EIMS m/z 174

3-methyl-1-(pyrimidin-5-yl)-1H-pyrazol-4-amine was prepared as in Example 6, Step 3: mp 211-215° C.; $^1H$ NMR (400 MHz, $CDCl_3$) δ 9.10-8.87 (m, 3H), 7.51 (s, 1H), 3.24 (bs, 2H), 2.29 (s, 3H); ESIMS m/z 176 ([M+H]).

3-chloro-1-(pyrimidin-5-yl)-1H-pyrazol-4-amine was prepared as in Example 6, Step 3: mp 146-148° C.; $^1H$ NMR (400 MHz, $CDCl_3$) δ 9.07 (s, 1H), 9.02 (s, 2H), 7.52 (s, 1H), 3.45 (s, 2H); ESIMS m/z 196 ([M+H]).

Example 7

Preparation of methyl-(1-pyridin-3-yl-1H-pyrazol-4-yl)-amine

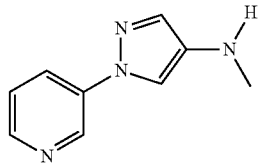

Method A:
To a 25 ml round bottom flask containing 1-pyridin-3-yl-1H-pyrazol-4-ylamine (1.76 g, 0.011 mol) in ethanol (26.4 ml) was added benzotriazole (1.31 g, 0.011 mol). The reaction was cooled to 0° C.-10° C. and formaldehyde (0.36 mL, 0.0121 mol) was added slowly and kept for 30 min at this temperature. The reaction was filtered and concentrated to dryness. The crude material (2.56 g, 0.009 mol) was dissolved in dry tetrahydrofuran (25.6 mL), cooled to 0° C. and sodium borohydride (0.326 g, 0.00882 mol.) was added over 15 min. The reaction was warmed to room temperature and stirred for 2 hours. The reaction was poured into water and extracted using dichloromethane, the organic layer was dried over anhydrous Na$_2$SO$_4$ and concentrated to dryness. Purified the crude material by silica gel chromatography eluting with 20% methanol/chloroform to afford the desired product as a brown solid (0.610 g, 32%): $^1$H NMR (400 MHz, d$_6$-DMSO) δ 8.92 (d, J=2.4 Hz, 1H), 8.47 (dd, J=4.8, 1.6 Hz, 1H), 8.01-7.98 (m, 1H), 7.45 (s, 1H), 7.30 (s, 1H), 7.37 (dd, J=8.0, 4.4 Hz, 1H), 2.84 (s, 3H); ESIMS m/z 175 ([M+1]).

Method B:

1-pyridin-3-yl-1H-pyrazol-4-ylamine (1.0 g, 6.2 mmol) was dissolved in triethyl orthoformate (5 ml, 30 mmol) and to that was added trifluoroacetic acid (3-4 drops). The reaction mixture was refluxed at 120° C. for 3 hours and was then concentrated. The crude was dissolved in ethanol (5 ml), cooled to 0° C. and treated with sodium borohydride (0.6 g, 15.7 mmol). After warming to room temperature, the mixture was refluxed for 3 hours. The mixture was concentrated and the residue was suspended between water and diethyl ether. The diethyl ether layer was separated and concentrated to dryness. The crude material was purified by silica gel chromatography, eluting with 5% methanol/chloroform to afford the desired product as a pale yellow solid (0.3 g, 27%): mp 65-67° C.; $^1$H NMR (300 MHz, CDCl$_3$) δ 8.91 (bs, 1H), 8.46 (d, J=4.5 Hz, 1H), 7.99 (d, J=8.3 Hz, 1H), 7.43 (s, 1H), 7.41 (s, 1H), 7.36 (dd, J=8.3, 4.7 Hz, 1H), 2.86 (d, J=12.4 Hz, 3H); ESIMS m/z 175 ([M+1]).

Example 8

Preparation of ethyl-(1-pyridin-3-yl-1H-pyrazol-4-yl)-amine

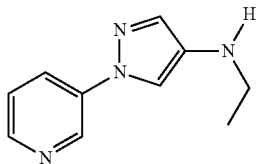

Method A:

To 1-pyridin-3-yl-1H-pyrazol-4-ylamine (0.5 g, 3.12 mmol) in dichloromethane (5 ml) was added acetyl chloride (0.28 g, 3.75 mmol) followed by DMAP (0.57 g, 4.68 mmol) and stirred at room temperature for 3 hours. The reaction mixture was concentrated and purified by silica gel column chromatography. The recovered material was dissolved in tetrahydrofuran (5 ml) and lithium aluminum hydride (0.23 g, 6.25 mmol) was added and stirred at room temperature for 12 hours. The reaction was quenched with saturated Na$_2$SO$_4$ and filtered through celite. The filtrate was collected and concentrated to dryness. The crude material was purified by silica gel column chromatography eluting with 0-5% methanol/chloroform and resubjected to silica gel chromatography, eluting with 0-100% ethyl acetate/hexanes) to give the desired product (0.080 g, 14%): $^1$H NMR (400 MHz, CDCl$_3$) δ 8.90 (d, J=2.7 Hz, 1H), 8.46 (dd, J=4.7, 1.3 Hz, 1H), 7.98 (ddd, J=8.3, 2.6, 1.5 Hz, 1H), 7.41 (dt, J=13.3, 6.6 Hz, 2H), 7.36 (ddd, J=8.3, 4.7, 0.7 Hz, 1H), 3.10 (q, J=7.1 Hz, 2H), 1.27 (t, 3H).

Method B:

To a solution of tert-butyl ethyl(1-(pyridin-3-yl)-1H-pyrazol-4-yl)carbamate (3.4 g, 11.79 mmol) in dichloromethane (4.54 ml) was added trifluoroacetic acid (9 ml), and the reaction mixture was stirred for 1 hour at room temperature. Toluene was added and the reaction was concentrated to near dryness. The reaction was poured into a separatory funnel and carefully quenched with saturated aqueous NaHCO$_3$ and extracted with dichloroethane. The organic layer was dried (MgSO$_4$), filtered and concentrated to dryness. The crude product was purified by silica gel chromatography (0-10% MeOH/dichloromethane) to give the desired product as a pale yellow oil (2.10 g, 95%): $^1$H NMR (400 MHz, CDCl$_3$) δ 8.90 (dd, J=1.8, 0.8 Hz, 1H), 8.51-8.39 (m, 1H), 7.97 (ddt, J=8.3, 2.7, 1.3 Hz, 1H), 7.41 (d, J=0.8 Hz, 2H), 7.38-7.30 (m, 1H), 3.21-2.93 (m, 2H), 1.34-1.19 (m, 3H).

3-chloro-N-ethyl-1-(pyridin-3-yl)-1H-pyrazol-4-amine was prepared as described in Example 8, Method B: $^1$H NMR (400 MHz, CDCl$_3$) δ 8.87 (d, J=2.5 Hz, 1H), 8.47 (dd, J=4.7, 1.2 Hz, 1H), 7.96 (ddd, J=8.4, 2.6, 1.4 Hz, 1H), 7.38-7.32 (m, 2H), 3.11 (q, J=7.1 Hz, 2H), 2.97 (bs, 1H), 1.31 (t, J=7.1 Hz, 3H).

3-chloro-N-methyl-1-(pyridin-3-yl)-1H-pyrazol-4-amine was prepared as in Example 8, Method B: mp 108-118 C; $^1$H NMR (400 MHz, CDCl$_3$) δ 8.88 (d, J=2.4 Hz, 1H), 8.48 (dd, J=4.7, 1.4 Hz, 1H), 7.96 (ddd, J=8.3, 2.7, 1.4 Hz, 1H), 7.41-7.29 (m, 2H), 2.87 (s, 3H); EIMS m/z 208.

N,3-dimethyl-1-(pyridin-3-yl)-1H-pyrazol-4-amine was prepared as in Example 8, Method B: $^1$H NMR (400 MHz, CDCl$_3$) δ 9.03-8.73 (m, 1H), 8.41 (dd, J=4.7, 1.4 Hz, 1H), 7.95 (ddd, J=8.4, 2.7, 1.4 Hz, 1H), 7.42-7.27 (m, 2H), 2.85 (s, 4H), 2.25 (s, 3H); EIMS m/z 189

3-chloro-N-(cylopropylmethyl)-1-(pyridin-3-yl)-1H-pyrazol-4-amine was prepared as in Example 8, Method B: $^1$H NMR (400 MHz, CDCl$_3$) δ 8.86 (d, J=2.5 Hz, 1H), 8.47 (dd, J=4.7, 1.4 Hz, 1H), 8.03-7.89 (m, 1H), 7.40-7.29 (m, 2H), 3.21 (s, 1H), 2.91 (d, J=4.4 Hz, 2H), 1.18-1.02 (m, 1H), 0.65-0.45 (m, 2H), 0.41-0.12 (m, 2H).

3-chloro-N-propyl-1-(pyridin-3-yl)-1H-pyrazol-4-amine was prepared as in Example 8, Method B: $^1$H NMR (400 MHz, CDCl$_3$) δ 8.86 (d, J=2.6 Hz, 1H), 8.47 (dd, J=4.7, 1.4 Hz, 1H), 8.01-7.89 (m, 1H), 7.42-7.27 (m, 2H), 3.23-2.84 (m, 3H), 1.77-1.59 (m, 2H), 1.03 (t, J=7.4 Hz, 3H).

1-(5-Fluoropyridin-3-yl)-N,3-dimethyl-1H-pyrazol-4-amine was prepared from the appropriate Boc-amine as described in Example 8, Method B: mp 142.0-143.5° C.; $^1$H NMR (400 MHz, CDCl$_3$) δ 8.67 (s, 1H), 8.26 (d, J=2.3 Hz, 1H), 7.73 (dt, J=10.0, 2.4 Hz, 1H), 7.27 (s, 1H), 2.92-2.81 (m, 4H), 2.24 (s, 3H); ESIMS m/z 207 ([M+H]$^+$).

N-ethyl-1-(5-fluoropyridin-3-yl)-3-methyl-1H-pyrazol-4-amine was prepared from the appropriate Boc-amine as described in Example 8, Method B: mp 85.0-86.0° C.; $^1$H NMR (400 MHz, CDCl$_3$) δ 8.66 (s, 1H), 8.25 (d, J=2.5 Hz, 1H), 7.72 (dt, J=10.0, 2.3 Hz, 1H), 7.27 (s, 1H), 3.07 (q, J=7.1 Hz, 2H), 2.71 (s, 1H), 2.25 (s, 3H), 1.30 (t, J=7.1 Hz, 3H); ESIMS m/z 221 ([M+H]$^+$).

3-Methyl-N-propyl-1-(pyridin-3-yl)-1H-pyrazol-4-amine was prepared from the appropriate Boc-amine as described in Example 8, Method B: mp 65.0-67.0° C.; $^1$H NMR (400 MHz, CDCl$_3$) δ 8.86 (d, J=2.4 Hz, 1H), 8.40 (dd, J=4.7, 1.4 Hz, 1H), 7.94 (ddd, J=8.3, 2.7, 1.5 Hz, 1H), 7.35-7.28 (m, 2H), 3.00 (t, J=7.1 Hz, 2H), 2.26 (s, 3H), 1.76-1.58 (m, 2H), 1.03 (t, J=7.4 Hz, 3H); ESIMS m/z 217 ([M+H]$^+$).

N-(cyclopropylmethyl)-3-methyl-1-(pyridin-3-yl)-1H-pyrazol-4-amine was prepared from the appropriate Boc-amine as described in Example 8, Method B: mp 73.0-75.0° C.; $^1$H NMR (400 MHz, CDCl$_3$) δ 8.86 (d, J=2.4 Hz, 1H), 8.40 (dd, J=4.7, 1.3 Hz, 1H), 7.94 (ddd, J=8.3, 2.6, 1.5 Hz, 1H), 7.35-7.28 (m, 2H), 2.87 (d, J=6.9 Hz, 2H), 2.75 (s, 1H), 2.28 (s, 3H), 1.22-1.05 (m, 1H), 0.63-0.56 (m, 2H), 0.26 (q, J=4.7 Hz, 2H); ESIMS m/z 229 ([M+H]$^+$). N-isopropyl-3-methyl-1-(pyridin-3-yl)-1H-pyrazol-4-amine was prepared from the appropriate Boc-amine as described in Example 8, Method B: IR (thin film) 3303 cm$^{-1}$; $^1$H NMR (400 MHz, CDCl$_3$) δ 8.86 (d, J=2.3 Hz, 1H), 8.41 (dd, J=4.7, 1.4 Hz, 1H), 7.94 (ddd, J=8.3, 2.7, 1.5 Hz, 1H), 7.36-7.28 (m, 2H), 3.30 (hept, J=6.3 Hz, 1H), 2.25 (s, 3H), 1.24 (d, J=6.3 Hz, 6H); EIMS m/z 216.

5-Ethoxy-1-(5-fluoropyridin-3-yl)-N,3-dimethyl-1H-pyrazol-4-amine was prepared from the appropriate Boc-amine as described in Example 8, Method B: IR (thin film) 3340 cm$^{-1}$; $^1$H NMR (400 MHz, CDCl$_3$) δ 8.91 (s, 1H), 8.31 (d, J=2.5 Hz, 1H), 7.88-7.80 (m, 1H), 4.24 (q, J=7.1 Hz, 2H), 2.79 (s, 3H), 2.24 (s, 3H), 1.36 (t, J=7.1 Hz, 3H); EIMS m/z 250.

5-Bromo-N-methyl-1-(pyridin-3-yl)-1H-pyrazol-4-amine was prepared from the appropriate Boc-amine as described in Example 8, Method B: mp 77.0-79.0° C.; $^1$H NMR (400 MHz, CDCl$_3$) δ 8.90 (d, J=2.0 Hz, 1H), 8.63 (d, J=3.9 Hz, 1H), 7.93 (ddd, J=8.2, 2.4, 1.5 Hz, 1H), 7.51 (s, 1H), 7.43 (dd, J=8.2, 4.8 Hz, 1H), 4.49 (s, 1H), 2.91 (s, 3H); ESIMS m/z 255 ([M+2]$^+$).

5-Fluoro-N,3-dimethyl-1-(pyridin-3-yl)-1H-pyrazol-4-amine was prepared from the appropriate Boc-amine as described in Example 8, Method B: $^1$H NMR (400 MHz, CDCl$_3$) δ 8.91 (t, J=2.1 Hz, 1H), 8.50 (dd, J=4.8, 1.5 Hz, 1H), 7.93 (ddt, J=8.3, 2.8, 1.5 Hz, 1H), 7.37 (ddd, J=8.3, 4.8, 0.7 Hz, 1H), 2.86 (d, J=1.6 Hz, 3H), 2.43 (s, 2H), 2.24 (s, 3H); EIMS m/z 206.

5-Bromo-N,3-dimethyl-1-(pyridin-3-yl)-1H-pyrazol-4-amine was prepared from the appropriate Boc-amine as described in Example 8, Method B: $^1$H NMR (400 MHz, CDCl$_3$) δ 8.86 (dd, J=2.5, 0.5 Hz, 1H), 8.59 (dd, J=4.8, 1.5 Hz, 1H), 7.88 (ddd, J=8.2, 2.6, 1.5 Hz, 1H), 7.40 (ddd, J=8.2, 4.8, 0.7 Hz, 1H), 2.85 (s, 3H), 2.69 (s, 1H), 2.35 (s, 3H); ESIMS m/z 268 ([M+H]$^+$).

5-Chloro-N,3-dimethyl-1-(pyridin-3-yl)-1H-pyrazol-4-amine was prepared from the appropriate Boc-amine as described in Example 8, Method B: $^1$H NMR (400 MHz, CDCl$_3$) δ 8.87 (d, J=2.3 Hz, 1H), 8.59 (dd, J=4.8, 1.3 Hz, 1H), 7.90 (ddd, J=8.2, 2.6, 1.5 Hz, 1H), 7.40 (ddd, J=8.2, 4.8, 0.6 Hz, 1H), 2.87 (s, 3H), 2.45-2.19 (m, 4H); EIMS m/z 223.

3-Chloro-1-(5-fluoropyridin-3-yl)-N-methyl-1H-pyrazol-4-amine was prepared from the appropriate Boc-amine as described in Example 8, Method B: mp 117.5-119.0° C.; $^1$H NMR (400 MHz, CDCl$_3$) δ 8.68 (d, J=1.1 Hz, 1H), 8.33 (d, J=2.5 Hz, 1H), 7.75 (dt, J=9.6, 2.4 Hz, 1H), 7.31 (s, 1H), 3.14 (s, 1H), 2.87 (s, 3H); ESIMS m/z 227 ([M]$^+$).

3-Chloro-N-ethyl-1-(5-fluoropyridin-3-yl)-1H-pyrazol-4-amine amine was prepared from the appropriate Boc-amine as described in Example 8, Method B: $^1$H NMR (400 MHz, CDCl$_3$) δ 8.70-8.63 (m, 1H), 8.32 (d, J=2.4 Hz, 1H), 7.74 (dt, J=9.7, 2.4 Hz, 1H), 7.31 (s, 1H), 3.11 (q, J=7.2 Hz, 2H), 1.31 (t, J=7.1 Hz, 3H).

1-(5-Fluoropyridin-3-yl)-N-methyl-3-vinyl-1H-pyrazol-4-amine was prepared from the appropriate Boc-amine as described in Example 8, Method B: 105.0-107.0° C.; $^1$H NMR (400 MHz, CDCl$_3$) δ 8.72 (s, 1H), 8.31 (d, J=2.5 Hz, 1H), 7.81 (dt, J=9.8, 2.4 Hz, 1H), 7.33 (s, 1H), 6.75 (dd, J=18.0, 11.6 Hz, 1H), 5.83 (dd, J=18.0, 1.1 Hz, 1H), 5.46 (dd, J=11.6, 1.1 Hz, 1H), 2.86 (s, 3H); ESIMS m/z 219 ([M+H]$^+$).

3-Cyclopropyl-1-(5-fluoropyridin-3-yl)-N-methyl-1H-pyrazol-4-amine was prepared from the appropriate Boc-amine as described in Example 8, Method B: mp 118.0-119.5° C.; $^1$H NMR (400 MHz, CDCl$_3$) δ 8.66-8.58 (m, 1H), 8.23 (d, J=2.5 Hz, 1H), 7.75-7.68 (m, 1H), 7.25 (s, 1H), 3.09 (s, 1H), 2.86 (s, 3H), 1.78-1.63 (m, 1H), 0.99-0.90 (m, 4H); ESIMS m/z 233 ([M+H]$^+$).

3-Chloro-1-(pyridin-3-yl)-1H-pyrazol-4-amine was prepared from the appropriate Boc-amine as described in Example 8, Method B: mp 137.9-139.9 C; $^1$H NMR (400 MHz, CDCl$_3$) δ 8.84 (d, J=2.4 Hz, 1H), 8.50 (dd, J=4.7, 1.4 Hz, 1H), 7.95 (ddd, J=8.3, 2.7, 1.5 Hz, 1H), 7.52 (s, 1H), 7.37 (ddd, J=8.4, 4.7, 0.7 Hz, 1H), 3.18 (s, 2H); ESIMS m/z 196 ([M+H]$^+$).

2-((3-Chloro-1-(pyridin-3-yl)-1H-pyrazol-4-yl)amino)acetonitrile was prepared from tert-butyl (3-chloro-1-(pyridin-3-yl)-1H-pyrazol-4-yl)(cyanomethyl)carbamate as in Example 8, Method B: mp 141-143° C.; $^1$H NMR (300 MHz, CDCl$_3$) δ 8.91 (d, J=2.7 Hz, 1H), 8.54 (dd, J=5.1, 1.8 Hz, 1H), 7.97 (m, 1H), 7.62 (s, 1H), 7.38 (dd, J=12.0, 7.5 Hz, 1H), 4.97 (d, J=6.9 Hz, 2H), 3.52 (m, 1H); EIMS m/z 235 ([M+1]$^+$).

N-3-dimethyl-1-(pyrimidin-5-yl)-1H-pyrazol-4-amine was prepared as in Example 8, Method B: mp 139-143° C.; $^1$H NMR (400 MHz, CDCl$_3$) δ 9.02 (s, 2H), 9.00 (s, 1H), 7.30 (s, 1H), 2.87 (d, J=11.5 Hz, 3H), 2.27 (s, 3H); ESIMS m/z 190 ([M+H]).

3-chloro-N-methyl-1-(pyrimidin-5-yl)1-1H-pyrazol-4-amine was prepared as in Example 8, Method B: mp 111-114° C.; $^1$H NMR (400 MHz, CDCl$_3$) δ 9.09-9.04 (m, 1H), 9.02 (s, 2H), 7.30 (s, 1H), 3.14 (bs, 1H), 2.88 (s, 3H); ESIMS m/z 196 ([M+H]).

1-(5-Fluoro-3-pyridyl)-3-methyl-N-(trideuteriomethyl)pyrazol-4-amine was prepared from compound 380 using the procedure as described in Example 8, method B: mp 146-148° C.; $^1$H NMR (400 MHz, CDCl$_3$) δ 8.67 (s, 1H), 8.25 (d, J=2.5 Hz, 1H), 7.73 (dt, J=10.0, 2.3 Hz, 1H), 7.27 (s, 1H), 2.87 (s, 1H), 2.24 (s, 3H); ESIMS m/z 210 ([M+H]$^+$); IR (Thin film) 1599 cm$^{-1}$.

3-Chloro-1-(3-pyridyl)-N-(trideuteriomethyl)pyrazol-4-amine was prepared from compound 381 using the procedure as described in Example 8, method B: mp 104-106° C.; $^1$H NMR (400 MHz, CDCl$_3$) δ 8.87 (d, J=1.9 Hz, 1H), 8.47 (d, J=4.7 Hz, 1H), 8.00-7.90 (m, 1H), 7.40-7.30 (m, 2H), 3.10 (s, 1H); ESIMS m/z 212 ([M+H]$^+$); IR (Thin film) 1579 cm$^{-1}$.

3-Chloro-N-(cyclopropylmethyl)-1-(pyridin-3-yl)-1H-pyrazol-4-amine was prepared from compound 361 using the procedure as described in Example 8, method B: mp 82-83° C.; $^1$H NMR (400 MHz, CDCl$_3$) δ 8.86 (d, J=2.5 Hz, 1H), 8.47 (dd, J=4.7, 1.3 Hz, 1H), 7.95 (ddd, J=8.4, 2.7, 1.5 Hz, 1H), 7.38-7.32 (m, 2H), 3.22 (s, 1H), 2.90 (d, J=6.9 Hz, 2H), 1.23-1.06 (m, 1H), 0.65-0.53 (m, 2H), 0.31-0.19 (m, 2H); ESIMS m/z 249 ([M+H]$^+$);

3-Chloro-N-propyl-1-(pyridin-3-yl)-1H-pyrazol-4-amine was prepared from compound 360 using the procedure as described in Example 8, method B: mp 92-94° C.; $^1$H NMR (400 MHz, CDCl$_3$) δ 8.86 (d, J=2.6 Hz, 1H), 8.47 (dd, J=4.7, 1.4 Hz, 1H), 7.95 (ddd, J=8.3, 2.7, 1.5 Hz, 1H), 7.35 (ddd, J=8.4, 4.7, 0.6 Hz, 1H), 7.33 (s, 1H), 3.22-2.94 (m, 3H), 1.75-1.52 (m, 2H), 1.02 (t, J=7.4 Hz, 3H); ESIMS m/z 237 ([M+H]$^+$).

Example 9

Preparation of isopropyl-(1-pyridin-3-yl-1H-pyrazol-4-yl)-amine

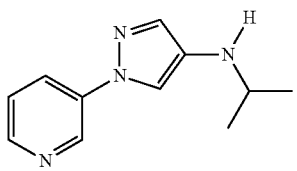

1-pyridin-3-yl-1H-pyrazol-4-ylamine (0.6 g, 3.7 mmol) was dissolved in isopropyl acetate (8.5 ml). To the mixture, acetone (0.261 g, 4.5 mmol), trifluoroacetic acid (0.855 g, 7.5 mmol) and sodium triacetoxyborohydride (0.945 g, 4.5 mmol) were added. The reaction was stirred under nitrogen at room temperature for 4.5 hours and then quenched with 10% sodium hydroxide solution until the pH reached ~9. The layers were separated, and the aqueous phase was extracted with ethyl acetate. The organic extracts were combined, dried over sodium sulfate and concentrated to dryness. The crude material was purified by silica gel chromatography (gradient elution of 5% methanol/dichloromethane) to give the title compound as an off white solid (0.35 g, 46%): mp 105-107° C.; $^1$H NMR (300 MHz, CDCl$_3$) δ 8.82 (d, J=2.2 Hz, 1H), 8.63 (dd, J=4.8, 1.5 Hz, 1H), 8.13 (d, J=1.8 Hz, 1H), 8.03 (d, J=2.7 Hz, 1H), 7.94-7.77 (m, 1H), 7.38 (dt, J=15.2, 7.6 Hz, 1H), 6.99 (t, 1H), 3.72 (m, 1H), 1.30 (t, J=10.0 Hz, 6H). ESIMS 214 m/z (M+1).

Example 10

Preparation of propyl-(1-pyridin-3-yl-1H-pyrazol-4-yl-amine

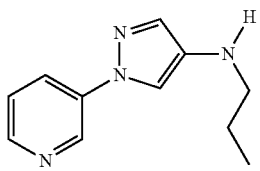

To 1-pyridin-3-yl-1H-pyrazol-4-ylamine (0.5 g, 3.12 mmol) in dichloromethane (5 ml) was added propionaldehyde (0.18 g, 3.12 mmol) and sodium triacetoxy borohydride (0.99 g, 4.68 mmol) and stirred at room temperature for 16 hours. The reaction was taken up in dichloromethane and was washed with water and brine. The organic layer was dried (MgSO$_4$), filtered and concentrated to dryness. The crude material was purified by silica gel chromatography eluting with 0-5% MeOH/Dichloromethane and resubjected in 0-100% ethylacetate/hexanes) to give the title compound as a dark oil (0.05 g, 7%): $^1$H NMR (300 MHz, CDCl$_3$) δ 8.92 (d, J=2.6 Hz, 1H), 8.48 (dd, J=4.7, 1.4 Hz, 1H), 8.00 (ddd, J=8.3, 2.7, 1.5 Hz, 1H), 7.47-7.40 (m, 2H), 7.37 (dd, J=8.3, 4.7 Hz, 1H), 3.04 (t, J=7.1 Hz, 3H), 1.92-1.46 (m, 2H), 1.03 (t, J=7.4 Hz, 3H).

Example 11

Preparation of N-methyl-N-(1-pyridin-3-yl-1H-pyrazol-4-yl)-isobutyramide (Compound 42)

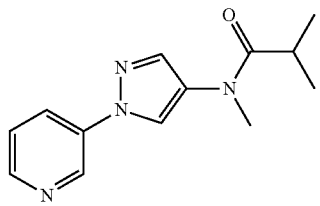 [SMILES: CC(C)C(=O)N(C)c1cnn(-c2cccnc2)c1]

A solution of isobutyryl chloride (0.138 g, 1.3 mmol) in dichloroethane (1 mL) was pipetted at a dropwise rate into an ice-cold suspension of methyl-(1-pyridin-3-yl-1H-pyrazol-4-yl)-amine (0.15 g, 0.86 mmol) in dichloroethane (5 mL), stirred for 10 minutes and then treated at a dropwise rate with a solution of 4-N,N-dimethylaminopyridine (0.11 g, 0.9 mmol) in dichloroethane (1.5 mL). The cooling bath was removed after 30 minutes, stirred under nitrogen at room temperature for 14 hours, diluted with dichloroethane (40 mL), washed with water (30 mL), brine (10 mL), dried over MgSO$_4$ and purified by reversed phase column chromatography to give a yellowish gum (0.114 g, 54%) $^1$H NMR (300 MHz, CDCl$_3$) δ 9.01-8.93 (m, 1H), 8.67 (s, 0.4H), 8.61 (d, J=4.2 Hz, 0.6H), 8.54 (d, 0.4H), 8.08-8.02 (m, 1H), 7.96 (s, 0.6H), 7.80 (s, 0.4H), 7.70 (s, 0.6H), 7.47-7.37 (m, 1H), 3.49 (s, 1.2H), 3.26 (s, 2.8H), 3.06-2.98 (m, 0.4H), 2.86-2.70 (m, 0.6H), 1.25 (d, J=6.1 Hz, 2.4H), 1.09 (d, J=6.6 Hz, 3.6H). ESIMS m/z 245 ([M+1]).

Compounds 32-41, 43-52, 54-56, 59-61, 66, 73-75, 77-79, 82-85, 93-100, 113, 117-129, 131-134, 139-140, 142-144, 148, 160, 163, 173-175, 184-186, 197-198, 202, 208, 215-217, 252-253, 277, 282-285, 287-290, 314-316, 347, 350-351, 353-355, 365-367, 370, 388, 395, 399-403, 407, 409, 415-418, 444-449, 452-454, 462-463, 465, 467-469, 496-498, 506-507, 512, 525-527, 569, 577, 581, 591 and 592 were made from the appropriate amines in accordance with the procedures disclosed in Example 11.

Example 12

Preparation of 4,4,4-trifluoro-2-methyl-N-(1-(pyridin-3-yl)-1H-pyrazol-4-yl)butanamide (Compound 65)

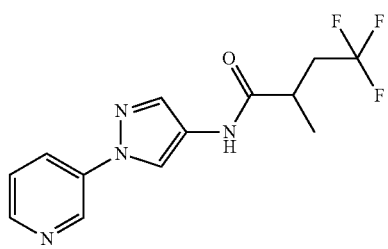 [SMILES: CC(CC(F)(F)F)C(=O)Nc1cnn(-c2cccnc2)c1]

To a solution of 1-(pyridin-3-yl)-1H-pyrazol-4-amine (0.150 g, 0.93 mmol) in dichloroethane (1.8 ml) was added 4,4,4-trifluoro-2-methylbutanoic acid (0.14 g, 0.93 mmol) and 4-N,N-dimethylaminopyridine (0.23 g, 1.87 mmol) followed by 1-(3-dimethylaminopropyl)-3-ethylcarbodiimide hydrochloride (0.36 g, 1.87 mmol). The reaction stirred at room temperature overnight. The reaction mixture was concentrated and the crude product was purified by silica gel chromatography eluting with 0-5% MeOH/dichloromethane to give a white solid (0.15 g, 55%); mp 140-145° C.; $^1$H NMR (400 MHz, CDCl$_3$) δ 9.00 (d, J=2.4 Hz, 1H), 8.62-8.47 (m, 2H), 8.01 (ddd, J=8.3, 2.7, 1.5 Hz, 1H), 7.68 (s, 1H), 7.53 (bs, 1H), 7.40 (ddd, J=8.3, 4.8, 0.6 Hz, 1H), 2.92-2.61 (m, 2H), 2.32-2.05 (m, 1H), 1.38 (d, J=6.6 Hz, 3H); ESIMS m/z 300 ([M+2]).

Compounds 53, 58, 62-63, 72, 76, 80-81, 107-108, 136-138, 147, 151-159, 164-168, 176-179, 187-196, 201, 203-207, 209-214, 220, 224-249, 251, 259-275, 286, 292-296, 303-313, 323-326, 341-344, 356-359, 371, 378-379, 382, 384, 419-426, 439-443, 455, 458-461, 464, 466, 476, 486, 490-493, 505, 508, 517, 528-529, 536-537, 539-541, 544-545, 549-554, 572-577, 578, 579 and 580 were prepared from the appropriate amines in accordance with the procedures disclosed in Example 12.

Example 13

Preparation of tert-butyl 1-(pyridin-3-yl)-1H-pyrazol-4-ylcarbamate (Compound 57)

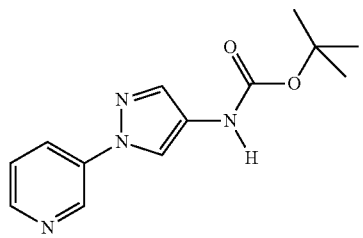 [SMILES: CC(C)(C)OC(=O)Nc1cnn(-c2cccnc2)c1]

Method A:

To a solution of 1-(pyridin-3-yl)-1H-pyrazol-4-amine (3 g, 18.73 mmol) in dichloromethane (33.4 ml) was added triethylamine (3.13 ml, 7.68 mmol) and BOC-anhydride (4.5 g, 20.60 mmol). The resulting solution was stirred at room temperature overnight. The reaction mixture was partitioned between ethyl acetate and water. The organic portion was dried (MgSO$_4$), filtered and concentrated to dryness. The crude product was purified by silica gel chromatography eluting with 0-100% ethyl acetate/hexanes to yield a white solid (2.0 g, 41%); mp 108-112° C.; $^1$H NMR (400 MHz, CDCl$_3$) δ 9.02 (d, J=2.2 Hz, 1H), 8.51 (t, J=8.7 Hz, 1H), 8.37 (s, 1H), 8.30 (s, 1H), 7.98 (ddd, J=8.3, 2.4, 1.3 Hz, 1H), 7.68 (s, 1H), 7.36 (dd, J=8.2, 4.8 Hz, 1H), 1.52 (s, 9H); ESIMS m/z 261 ([M+1]).

Compounds 64 and 130 were prepared in accordance with the procedures disclosed in Example 13, Method A.

Method B:

To a solution of 1-(pyridin-3-yl)-1H-pyrazol-4-amine (0.1 g, 0.624 mmol) and di-tert-butyl dicarbonate (0.161 ml, 0.693 mmol) in tetrahydrofuran (1.890 ml) and water (0.568 ml) was added dropwise saturated aqueous sodium bicarbonate (0.572 ml, 0.687 mmol). The reaction was stirred at room temperature overnight. The reaction was diluted with water and extracted with ethyl acetate. The combined organic phases were concentrate to give tert-butyl 1-(pyridin-3-yl)-1H-pyrazol-4-ylcarbamate (135 mg, 0.519 mmol, 83%), for which the analytical data was consistent with that reported in Example 13, Method A.

Compounds 150, 172, 223, and 317 were prepared in accordance with the procedures disclosed in Example 13, Method B. Compounds 172 and 317 were also prepared in accordance with the procedures disclosed in Example 17. These compounds, as well as, certain other compounds, were made by alternative methods further illustrating certain embodiments.

Example 14

Preparation of tert-butyl methyl(1-(pyridin-3-yl)-1H-pyrazol-4-yl)carbamate (Compound 67)

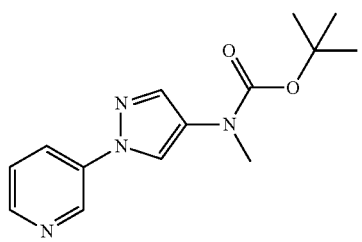 [SMILES: CN(C(=O)OC(C)(C)C)c1cnn(-c2cccnc2)c1]

To a solution of tert-butyl 1-(pyridin-3-yl)-1H-pyrazol-4-ylcarbamate (1.6 g, 6.15 mmol) in DMF (30.7 ml) at 0° C. was added sodium hydride (0.34 g, 8.61 mmol, 60% dispersion in mineral oil) in one portion and the suspension was stirred for 30 minutes. The ice bath was removed and stirred for an additional 30 minutes. Iodomethane (0.46 ml, 7.38 mmol) was added in one portion and stirred overnight at room temperature. Water and ethyl acetate were added and the resulting biphasic mixture was separated. The aqueous layer was extracted one time with ethyl acetate. The combined organic extracts were washed with brine, dried (MgSO$_4$), filtered and concentrated to dryness. The crude product was purified by silica gel chromatography eluting with 0-35% ethyl acetate/hexanes to yield a light yellow semi-solid (0.85 g, 50%): IR (KBr) 1703 cm$^{-1}$; $^1$H NMR (400 MHz, CDCl$_3$) δ 8.98 (s, 1H), 8.52 (d, J=3.8 Hz, 1H), 8.32 (s, 0.5H), 8.13-7.97 (m, 1H), 7.84 (s, 0.5H), 7.74 (s, 1H), 7.39 (dd, J=8.0, 4.8 Hz, 1H), 3.30 (s, 3H), 1.56 (s, 9H); ESIMS m/z 275 ([M+H]).

Compounds 68, 86-92, 105-106, 114-116, 141, 149, 161-162, 199-200, 254, 258, 291, 332, 352, 360-361, 380-381, 414, 430-431, 450, 457, 474-475, 485, 488, 510-511, 515, 523, and 590 were prepared from the appropriate amides in accordance with the procedures disclosed in Example 14.

Tert-butyl methyl(3-methyl-1-(pyridin-3-yl)-1H-pyrazol-4-yl)carbamate was prepared as in Example 14: $^1$H NMR (400 MHz, CDCl$_3$) δ 8.91 (d, J=2.5 Hz, 1H), 8.51 (dd, J=4.7, 1.3 Hz, 1H), 8.00 (ddd, J=8.3, 2.4, 1.4 Hz, 1H), 7.83 (s, 1H), 7.38 (dd, J=8.3, 4.7 Hz, 1H), 3.20 (s, 3H), 2.22 (s, 3H), 1.60-1.30 (m, 9H).

Example 15

Preparation of N-ethyl-N-(1-methyl-3-(pyridin-3-yl)-1H-pyrazol-5-yl)isobutyramide (Compound 23)

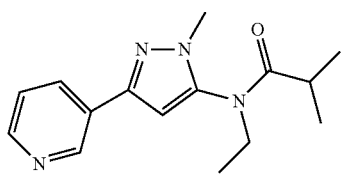 [SMILES: CCN(C(=O)C(C)C)c1cc(-c2cccnc2)nn1C]

To a solution of N-(1-methyl-3-(pyridine-3-yl)-1H-pyrazol-5-yl)isobutyramide (0.08 g, 0.33 mmol) in DMF (0.66 ml) at 0° C. was added sodium hydride (0.016 g, 0.39 mmol, 60% dispersion in mineral oil) in one portion and the suspension was stirred for 30 minutes. The ice bath was removed and stirred for an additional 30 minutes. Iodoethane (0.06 g, 0.39 mmol) was added in one portion and stirred overnight at room temperature. Water and ethyl acetate were added and the resulting biphasic mixture was separated. The aqueous layer was extracted one time with ethyl acetate. The combined organic extracts were washed with brine, dried (MgSO$_4$), filtered and concentrated to dryness. The crude product was purified by silica gel chromatography to give the title compound as a clear oil (27.5 mg, 30%): $^1$H NMR (300 MHz, CDCl$_3$) δ 9.00 (bs, 1H), 8.57 (s, 1H), 8.09 (dd, J=7.9 Hz, 1H), 7.34 (dd, 1H), 6.48 (s, 1H), 4.00 (m, 1H), 3.76 (s, 3H), 3.36 (m, 1H), 2.33 (m, 1H), 1.17 (t, J=7.1 Hz, 3H), 1.08 (t, J=6.7 Hz, 6H); ESIMS m/z 273 (M+H).

Compound 22 was prepared in accordance with the procedures disclosed in Example 15.

Example 16

Preparation of 5-bromo-1H-pyrazol-4-amine, HBr

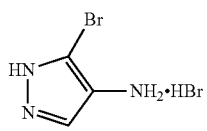

A mixture of 4-nitro-1H-pyrazole (10 g, 88 mmol) and 5% palladium on Al$_2$O$_3$ (1 g) in a mixture of ethanol (150 mL) and 50% aqueous HBr (50 mL) was shaken in a Par apparatus under hydrogen (10 psi) for 36 h. The mixture was filtered and the catalyst washed with ethanol. The filtrate was concentrated in vacuo to give a white solid. This solid was suspended in 10 mL of ethanol. After swirling the flask for 5 min, ether was added to complete the crystallization. The solid was filtered, was washed with ether and dried under high vacuum to afford 5-bromo-1H-pyrazol-4-amine, HBr (18.1 g, 84% yield) as a white solid: mp 248° C. dec; $^1$H NMR (400 MHz, DMSO-d$_6$) δ 11.47 (s, 1H), 10.00 (s, 1H), 7.79 (s, 1H).

Example 17

Preparation of tert-butyl (3-chloro-1-(pyridin-3-yl)-1H-pyrazol-4-yl)carbamate (Compound 172)

Example 17

Step 1: Preparation of 3-chloro-1H-pyrazol-4-amine hydrochloride

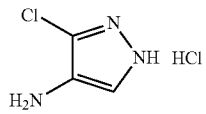

Into a 2 L three-necked round bottom flask affixed with an overhead stirrer, a temperature probe, an addition funnel, and a nitrogen inlet were added ethanol (600 mL) and 4-nitro-1H-pyrazole (50.6 g, 447 mmol). To this solution was added, in one portion, conc. HCl (368 mL) (note: rapid exotherm from 15° C. to 39° C.) and the resulting mixture was purged with nitrogen for 5 minutes. Palladium on alumina (5% w/w) (2.6 g, Alfa, black solid) was added to the mixture and stirred at room temperature while triethylsilane (208 g, 1789 mmol) was added drop-wise over 4 h. The reaction, which started to slowly exotherm from 35° C. to 55° C. over 2.0 h, was stirred for a total of 16 h and vacuum filtered through a plug of Celite® to give a biphasic mixture. The mixture was transferred to a separatory funnel, the bottom aqueous layer was collected and rotary evaporated (60° C., 50 mmHg) to dryness with the aid of acetonitrile (3×350 mL). The resulting yellow solid was suspended in acetonitrile (150 mL) and allowed to stand for 2 h at room temperature followed by 1 h at 0° C. in the refrigerator. The solids were filtered and washed with acetonitrile (100 mL) to afford the titled compound 3-chloro-1H-pyrazol-4-amine hydrochloride (84 g, 97% yield, 80% purity) as a white solid: mp 190-193° C.; $^1$H NMR (400 MHz, DMSO-d$_6$) δ 10.46-10.24 (bs, 2H), 8.03 (s, 0.54H), 7.75 (s, 0.46H), 5.95 (bs, 1H)); $^{13}$C-NMR (101 MHz, DMSO) δ 128.24, 125.97, 116.71.

Example 17

Step 2: Preparation of tert-butyl (3-chloro-1H-pyrazol-4-yl)carbamate

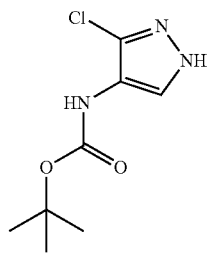

Into a 2 L round bottom flask was added 3-chloro-1H-pyrazol-4-amine hydrochloride (100 g, 649 mmol) and THF (500 mL). To this mixture were added di-tert-butyldicarbonate (156 g, 714 mmol) followed by sodium bicarbonate (120 g, 1429 mmol) and water (50.0 ml). The mixture was stirred for 16 h, diluted with water (500 mL) and ethyl acetate (500 mL) and transferred to a separatory funnel. This gave three layers; bottom—a white gelatinous precipitate, middle—light yellow aqueous, top—auburn organic. The phases were separated collecting the white gelatinous precipitate and the aqueous layer together. The aqueous was extracted with ethyl acetate (2×200 mL) and the ethyl acetate extracts were combined, washed with brine (200 mL), dried over anhydrous sodium sulfate, filtered and rotary evaporated to give an auburn thick oil (160 g.). The thick oil was suspended in hexane (1000 mL) and stirred at 55° C. for 2 h. This gave a light brown suspension. The mixture was cooled to 0° C. and the solid collected by vacuum filtration and rinsed with hexane (2×10 mL). The sample was air dried to constant mass to afford (3-chloro-1H-pyrazol-4-yl)carbamate (102.97 g, 72% yield, 80% purity) as a light brown solid: mp 137-138° C.; $^1$H NMR (400 MHz, CDCl$_3$) δ 10.69 (s, 1H), 7.91 (s, 1H), 1.52 (s, 9H).

Example 17

Step 3: Preparation of tert-butyl (3-chloro-1-(pyridin-3-yl)-1H-pyrazol-4-yl)carbamate (Compound 172)

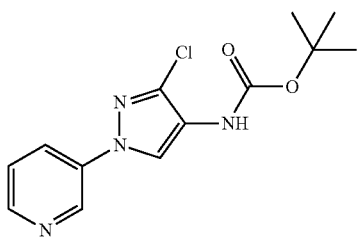 [SMILES: CC(C)(C)OC(=O)Nc1cn(-c2cccnc2)nc1Cl]

To a dry 2 L round bottom flask equipped with mechanical stirrer, nitrogen inlet, thermometer, and reflux condenser was charged the 3-iodopyridine (113.0 g, 551 mmol), (3-chloro-1H-pyrazol-4-yl)-carbamate (100 g, 459 mmol), potassium phosphate (powdered in a mortar and pestle) (195 g, 919 mmol), and copper chloride (3.09, 22.97 mmol). Acetonitrile (1 L) followed by N$^1$,N$^2$-dimethylethane-1,2-diamine were added and the mixture was heated to 81° C. for 4 hours. The mixture was cooled to room temperature and filtered through a bed of Celite®. The filtrate was transferred to a 4 L Erlenmeyer flask equipped with mechanical stirrer and diluted with water until the total volume was about 4 L. The mixture was stirred for 30 minutes at room temperature and the resulting solid was collected by vacuum filtration. The solid was washed with water and washed with water and oven dried for several days in vacuo at 40° C. to a constant weight to give tert-butyl (3-chloro-1-(pyridin-3-yl)-1H-pyrazol-4-yl)carbamate (117.8 g, 87% yield, 80% purity) as a tan solid: mp 140-143° C.; $^1$H NMR (400 MHz, CDCl$_3$) δ 8.96 (s, 1H), 8.53 (dd, J=4.7, 1.2 Hz, 1H), 8.36 (s, 1H), 7.98 (ddd, J=8.3, 2.7, 1.4 Hz, 1H), 7.38 (dd, J=8.3, 4.8 Hz, 1H), 6.37 (s, 1H), 1.54 (s, 9H); ESIMS (m/z) 338 [M-t-Bu]$^+$), 220 ([M-O-t-Bu]).

Compound 172 was also prepared in accordance with the procedures disclosed in Example 13. Compound 317 was prepared in accordance with the procedures disclosed in Example 17 from tert-butyl (3-bromo-1H-pyrazol-4-yl)carbamate and also in accordance with the procedures disclosed in Example 13.

Example 18

Preparation of 3-(3-methyl-1H-pyrazol-1-yl)pyridine and 3-(5-methyl-1H-pyrazol-1-yl)pyridine

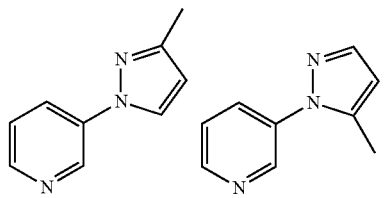

To a solution of 3-methyl-1H-pyrazole (10.99 g, 134 mmol) in N,N-dimethylformamide (100 ml) at 0° C. was added sodium hydride (3.71 g, 154 mmol, 60% dispersion). The reaction was stirred at 0° C. for 2 hours. 3-Fluoropyridine (10.0 g, 103 mmol) was added, and the reaction was stirred at 100° C. overnight. The reaction was cooled to room temperature and water was added slowly. The mixture was extracted with dichloromethane and the combined organic phases were washed with brine, concentrated and chromatographed (0-100% ethyl acetate/hexanes) to afford 3-(3-methyl-1H-pyrazol-1-yl)pyridine (8.4 g, 52.77 mmol, 51.2%) and 3-(5-methyl-1H-pyrazol-1-yl)pyridine (1.0 g, 6%). Analytical data of both products is consistent with that reported under Example 6, Step 1.

3-(3-Bromo-1H-pyrazol-1-yl)pyridine was prepared from 3-fluoropyridine and 3-bromopyrazole, which was made as in WO2008130021, as described Example 18: mp 89.5-92.5° C.; $^1$H NMR (400 MHz, CDCl$_3$) δ 8.94 (d, J=2.4 Hz, 1H), 8.62-8.49 (m, 1H), 8.03 (ddd, J=8.3, 2.7, 1.4 Hz, 1H), 7.87 (d, J=2.5 Hz, 1H), 7.42 (dd, J=8.2, 4.7 Hz, 1H), 6.54 (d, J=2.5 Hz, 1H); ESIMS m/z 224 ([M]$^+$).

Example 19

Preparation of 3-chloro-1-(5-fluoropyridin-3-yl)-1H-pyrazol-4-amine

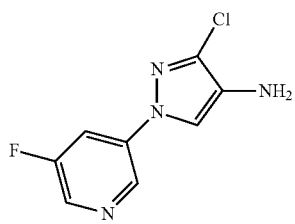 [SMILES: Nc1cn(-c2cncc(F)c2)nc1Cl]

To a stirred solution of 5-chloro-1H-pyrazol-4-amine, HCl (2 g, 12.99 mmol) and cesium carbonate (8.89 g, 27.3 mmol) in DMF (13 mL) was added 3,5-difluoropyridine (1.794 g, 15.58 mmol) and the mixture heated at 70° C. for 12 h. The mixture was cooled to room temperature and filtered. The solids were washed with copious amount of ethyl acetate. The filtrates was washed with brine, dried over anhydrous MgSO$_4$ and concentrated in vacuo to give a brown solid. This solid was dissolved in ethyl acetate and the resulting solution was saturated with hexanes to precipitate 3-chloro-1-(5-fluoropyridin-3-yl)-1H-pyrazol-4-amine (2.31 g, 10.32 mmol, 79% yield) as a brown solid: $^1$H NMR (400 MHz, DMSO-d$_6$) δ 8.89-8.82 (m, 1H), 8.45 (d, J=2.5 Hz, 1H), 8.07 (d, J=10.4 Hz, 1H), 7.94 (s, 1H), 4.51 (s, 2H); EIMS (m/z) 213 ([M+1]+).

3-Bromo-1-(5-fluoropyridin-3-yl)-1H-pyrazol-4-amine was prepared from the corresponding pyrazole as described in Example 19: mp 164-165° C.; $^1$H NMR (400 MHz, CDCl$_3$) δ 8.65 (d, J=1.7 Hz, 1H), 8.36 (d, J=2.5 Hz, 1H), 7.76 (dd, J=5.9, 3.6 Hz, 1H), 7.48 (s, 1H), 3.22 (s, 2H). $^{13}$C NMR (101 MHz, CDCl$_3$) δ 160.87, 158.30, 135.36, 135.13, 134.39, 134.35, 131.16, 123.31, 114.02, 112.77, 112.54; EIMS (m/z) 258 ([M+1]+).

Example 20

Preparation of 1-(5-fluoropyridin-3-yl)-3-methyl-1H-pyrazol-4-amine

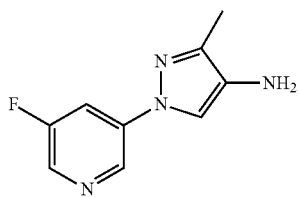

To a solution of 3-fluoro-5-(3-methyl-4-nitro-1H-pyrazol-1-yl)pyridine (3.133 g, 14.10 mmol) in ethanol (28.2 ml) was added ethyl acetate until all of the starting material went into solution. The solution was degassed and 10% palladium on carbon (0.750 g, 0.705 mmol) was added and the reaction was stirred in a parr hydrogenator at 40 psi for 3 hours. The solution was filtered through celite with ethyl acetate and concentrated to give 1-(5-fluoropyridin-3-yl)-3-methyl-1H-pyrazol-4-amine (2.000 g, 10.41 mmol, 73.8%) as a brown solid: mp 136.0-138.0° C.; $^1$H NMR (400 MHz, CDCl$_3$) δ 8.67-8.59 (m, 1H), 8.27 (d, J=2.5 Hz, 1H), 7.73 (dt, J=9.9, 2.3 Hz, 1H), 7.45 (s, 1H), 3.01 (s, 2H), 2.28 (s, 3H); EIMS m/z 192.

1-(Pyridin-3-yl)-3-(trifluoromethyl)-1H-pyrazol-4-amine was prepared from the appropriate nitropyrazole as described in Example 20: mp 112.5-115.0° C.; $^1$H NMR (400 MHz, CDCl$_3$) δ 8.89 (d, J=2.4 Hz, 1H), 8.57 (dd, J=4.7, 1.4 Hz, 1H), 8.03 (ddd, J=8.3, 2.7, 1.5 Hz, 1H), 7.56 (d, J=0.7 Hz, 1H), 7.41 (ddd, J=8.3, 4.8, 0.7 Hz, 1H), 3.47-3.31 (m, 2H); EIMS m/z 228.

Example 21

Preparation of 3-chloro-1-(pyridin-3-yl)-1H-pyrazol-4-amine

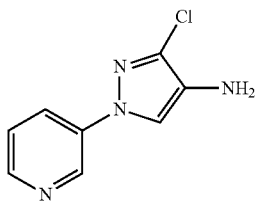 [SMILES: Nc1cn(-c2cccnc2)nc1Cl]

To 3-(3-chloro-4-nitro-1H-pyrazol-1-yl)pyridine (0.95 g, 4.23 mmol) in acetic acid (8.46 mL), ethanol (8.46 mL) and water (4.23 mL) was added iron powder (1.18 g, 21.15 mmol) and the reaction was stirred at room temperature for 30 minutes. To this was added carefully 2 M KOH and extracted with ethyl acetate. The ethyl acetate layers were combined, dried (MgSO$_4$), filtered and concentrated to dryness. The crude material was purified by silica gel chromatography (0-10% methanol/dichloromethane) to give the desired product as a white solid (0.66 g, 80%): $^1$H NMR (400 MHz, CDCl$_3$) δ 8.84 (d, J=2.6 Hz, 1H), 8.49 (dd, J=4.7, 1.4 Hz, 1H), 7.95 (ddd, J=8.3, 2.7, 1.5 Hz, 1H), 7.53 (s, 1H), 7.37 (ddd, J=8.4, 4.7, 0.6 Hz, 1H), 3.17 (bs, 2H).

3-methyl-1-(2-methylpyridin-3-yl)-1H-pyrazol-4-amine was prepared as described in Example 21: $^1$H NMR (400 MHz, CDCl$_3$) δ 8.48 (dd, J=4.8, 1.6 Hz, 1H), 7.62 (dd, J=8.0, 1.6 Hz, 1H), 7.23-7.18 (m, 2H), 2.91 (bs, 2H), 2.55 (s, 3H), 2.28 (s, 3H); EIMS m/z 188.

3-Phenyl-1-(pyridin-3-yl)-1H-pyrazol-4-amine was prepared from the appropriate nitropyrazole as described in Example 21: IR (thin film) 3324 cm$^{-1}$; $^1$H NMR (400 MHz, CDCl$_3$) δ 8.94 (d, J=2.2 Hz, 1H), 8.47 (dd, J=4.7, 1.4 Hz, 1H), 8.07 (ddd, J=8.3, 2.7, 1.5 Hz, 1H), 7.87-7.80 (m, 2H), 7.60 (s, 1H), 7.50-7.44 (m, 2H), 7.40-7.34 (m, 2H), 3.86 (s, 2H); EIMS m/z 236.

3-Chloro-1-(5-fluoropyridin-3-yl)-1H-pyrazol-4-amine was prepared from the appropriate nitropyrazole as described in Example 21: mp 149.0-151.0° C.; $^1$H NMR (400 MHz, CDCl$_3$) δ 8.65 (d, J=1.6 Hz, 1H), 8.35 (d, J=2.4 Hz, 1H), 7.75 (dt, J=9.5, 2.4 Hz, 1H), 7.51 (s, 1H), 3.21 (s, 2H); ESIMS m/z 213 ([M]$^+$).

3-Bromo-1-(pyridin-3-yl)-1H-pyrazol-4-amine was prepared from the appropriate nitropyrazole as described in Example 21: mp 143.0-146.0° C.; $^1$H NMR (400 MHz, CDCl$_3$) δ 8.85 (d, J=2.4 Hz, 1H), 8.50 (dd, J=4.7, 1.4 Hz, 1H), 7.96 (ddd, J=8.3, 2.7, 1.5 Hz, 1H), 7.49 (s, 1H), 7.37 (ddd, J=8.4, 4.7, 0.7 Hz, 1H), 3.21 (s, 2H); ESIMS m/z 241 ([M+2]$^+$).

Example 22

Preparation of tert-butyl (5-methyl-1-(pyridin-3-yl)-1H-pyrazol-4-yl)carbamate (Compound 281)

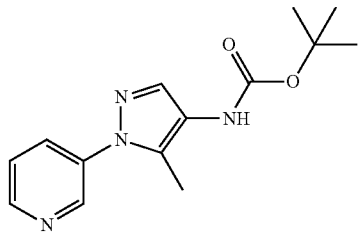 [SMILES: Cc1c(NC(=O)OC(C)(C)C)cnn1-c1cccnc1]

To a solution of (E)-tert-butyl 1-(dimethylamino)-3-oxobut-1-en-2-ylcarbamate (0.59 g, 2.58 mmol) in ethanol (2.5 mL) was added 3-hydrazinylpyridine, 2HCl (0.470 g, 2.58 mmol). The reaction mixture was stirred at ambient temperature for 16 hours. The reaction mixture was concentrated and purified using silica gel chromatography (0-100% ethyl acetate/hexanes) to yield the title compound as an orange foam (0.235 g, 30%): IR (thin film) 3268, 2978 and 1698 cm$^{-1}$; $^1$H NMR (400 MHz, CDCl$_3$) δ 8.75 (dd, J=2.5, 0.5 Hz, 1H), 8.62 (dd, J=4.8, 1.5 Hz, 1H), 7.82 (ddd, J=8.2, 2.6, 1.5 Hz, 1H), 7.78 (s, 1H), 7.43 (ddd, J=8.1, 4.8, 0.6 Hz, 1H), 6.04 (s, 1H), 2.29 (s, 3H), 1.52 (s, 9H); ESIMS m/z 275 ([M+H]$^+$), 273 ([M−H]$^-$).

Example 23

Preparation of tert-butyl 1-(5-fluoropyridin-3-yl)-3-methyl-1H-pyrazol-4-ylcarbamate (Compound III) and tert-butyl 5-ethoxy-1-(5-fluoropyridin-3-yl)-3-methyl-1H-pyrazol-4-ylcarbamate (Compound 112)

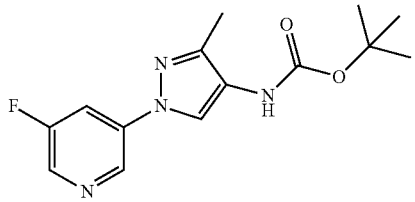

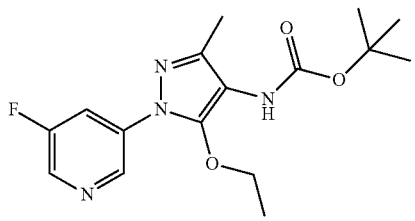

To a solution of 3-fluoro-5-(3-methyl-4-nitro-1H-pyrazol-1-yl)pyridine (3.133 g, 14.10 mmol) in ethanol (28.2 ml) was added ethyl acetate until all of the starting material went into solution. The solution was degassed and 10% palladium on carbon (0.750 g, 0.705 mmol) was added and the reaction was stirred in a parr hydrogenator at 40 psi for 3 hours. The solution was filtered through celite with ethyl acetate and the solvent was removed under reduced pressure. The residue was dissolved in tetrahydrofuran (32.0 ml) and water (9.61 ml). Di-tert-butyl dicarbonate (2.52 g, 11.55 mmol) was added followed by saturated aqueous sodium bicarbonate (9.54 ml, 11.45 mmol). The reaction was stirred at room temperature overnight, diluted with water and extracted with ethyl acetate. The combined organic phases were concentrated and chromatographed (0-100% ethyl acetate/hexanes) to give tert-butyl 1-(5-fluoropyridin-3-yl)-3-methyl-1H-pyrazol-4-ylcarbamate (1.673 g, 5.72 mmol, 41.0%) as a yellow solid and the tert-butyl 5-ethoxy-1-(5-fluoropyridin-3-yl)-3-methyl-1H-pyrazol-4-ylcarbamate (0.250 g, 0.74 mmol, 5.2%) as a brown oil:

tert-Butyl 1-(5-fluoropyridin-3-yl)-3-methyl-1H-pyrazol-4-ylcarbamate (Compound III): mp 131.5-133.0° C.; $^1$H NMR (400 MHz, CDCl$_3$) δ 8.75 (s, 1H), 8.32 (d, J=2.5 Hz, 1H), 8.28 (s, 1H), 7.77 (dt, J=9.7, 2.4 Hz, 1H), 6.15 (s, 1H), 2.29 (s, 3H), 1.54 (s, 9H); ESIMS m/z 293 ([M+H]$^+$).

tert-Butyl 5-ethoxy-1-(5-fluoropyridin-3-yl)-3-methyl-1H-pyrazol-4-ylcarbamate (Compound 112): IR (thin film) 1698 cm$^{-1}$; $^1$H NMR (400 MHz, CDCl$_3$) δ 8.88 (s, 1H), 8.34 (d, J=2.5 Hz, 1H), 7.83 (d, J=9.9 Hz, 1H), 5.99 (s, 1H), 4.37 (q, J=7.0 Hz, 2H), 2.17 (s, 3H), 1.50 (s, 9H), 1.37 (t, J=7.1 Hz, 3H); ESIMS m/z 337 ([M+H]$^+$).

Example 24

Preparation of Bis tert-t-butyl (1-(pyridin-3-yl)-1H-pyrazol-4-yl)carbamate (Compound 595)

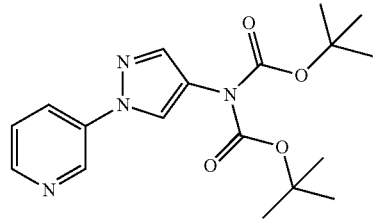 [SMILES: CC(C)(C)OC(=O)N(C(=O)OC(C)(C)C)c1cnn(-c2cccnc2)c1]

To a solution of tert-butyl (1-(pyridin-3-yl)-1H-pyrazol-4-yl)carbamate (2.00 g, 7.68 mmol) in dry THF (21.95 mL) at 0° C. was added 60% sodium hydride (0.33 g, 8.45 mmol) in one portion and stirred at that temperature for 30 minutes. To this was then added Boc-Anhydride (1.84 g, 8.45 mmol) in one portion and stirred for 5 minutes at 0° C. The water bath was removed and the reaction was warmed to room temperature and stirred at additional 30 minutes. The reaction was quenched with water and extracted with ethyl acetate. The ethyl acetate layers were combined, dried (MgSO$_4$), filtered and concentrated to dryness. The crude material was purified by silica gel chromatography (0-100% ethyl acetate/hexanes) to give the desired product as a white solid (2.0 g, 72%): $^1$H NMR (400 MHz, CDCl$_3$) δ 9.12-8.86 (m, 1H), 8.55 (dd, J=4.7, 1.4 Hz, 1H), 8.04 (ddd, J=8.3, 2.7, 1.5 Hz, 1H), 8.01 (d, J=0.5 Hz, 1H), 7.84-7.65 (m, 1H), 7.41 (ddd, J=8.3, 4.8, 0.7 Hz, 1H), 1.51 (s, 18H).

Example 25

Preparation of 3-chloro-1-(pyridin-3-yl)-1H-pyrazol-4-amine (Compound 516)

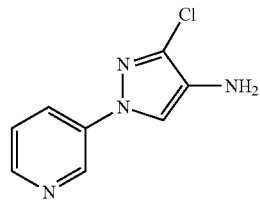 [SMILES: Nc1cn(-c2cccnc2)nc1Cl]

To tert-butyl (3-chloro-1-(pyridin-3-yl)-1H-pyrazol-4-yl)carbamate (2 g, 6.79 mmol) in dichloromethane (6.79 ml) was added trifluoroacetic acid (6.79 ml) and the mixture was left stirring at room temperature for 2 hours. Toluene (12 mL) was added and the reaction was concentrated to near dryness. The mixture was poured into a separatory funnel containing saturated aqueous sodium bicarbonated and was extracted with dichloromethane. The combined organic layers were concentrated to give 3-chloro-1-(pyridin-3-yl)-1H-pyrazol-4-amine (0.954 g, 4.90 mmol, 72.2%) as a white solid: mp 137.9-139.9° C.; $^1$H NMR (400 MHz, CDCl$_3$) δ 8.84 (d, J=2.4 Hz, 1H), 8.50 (dd, J=4.7, 1.4 Hz, 1H), 7.95 (ddd, J=8.3, 2.7, 1.5 Hz, 1H), 7.52 (s, 1H), 7.37 (ddd, J=8.4, 4.7, 0.7 Hz, 1H), 3.18 (s, 2H); ESIMS m/z 196 ([M+H]$^+$).

Example 26

Preparation of N-allyl-1-(5-fluoropyridin-3-yl)-3-methyl-1H-pyrazol-4-amine hydrochloride

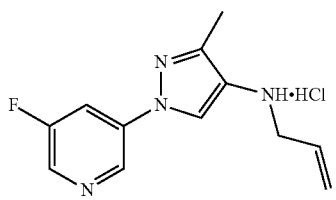

To a solution of tert-butyl allyl(1-(5-fluoropyridin-3-yl)-3-methyl-1H-pyrazol-4-yl)carbamate (908 mg, 2.73 mmol) in dioxane (5 mL) was added HCl (1M in ether) (13.65 mL, 13.65 mmol) and the mixture stirred at room temperature for 48 h. The resulting white solid was filtered, washed with ether and dried under vacuum to give N-allyl-1-(5-fluoropyridin-3-yl)-3-methyl-1H-pyrazol-4-amine, HCl (688 mg, 94% yield) as a white solid: mp 189-190° C.; $^1$H NMR (400 MHz, CDCl$_3$) δ 8.79-8.68 (m, 1H), 8.32-8.26 (m, 1H), 8.23 (s, 1H), 7.98-7.86 (m, 1H), 5.86-5.68 (m, 1H), 5.28-5.17 (m, 1H), 5.17-5.03 (m, 1H), 3.59 (d, J=6.2 Hz, 2H), 2.11 (s, 3H); EIMS (m/z) 233 ([M+1]+).

N-Allyl-3-chloro-1-(pyridin-3-yl)-1H-pyrazol-4-amine, HCl was prepared as described in Example 26 from tert-butyl allyl(3-chloro-1-(pyridin-3-yl)-1H-pyrazol-4-yl)carbamate: mp 172-174° C.; $^1$H NMR (400 MHz, CDCl$_3$) δ 9.20 (d, J=2.5 Hz, 1H), 8.65 (dd, J=5.3, 1.1 Hz, 1H), 8.61 (ddd, J=8.6, 2.5, 1.1 Hz, 1H), 8.24 (s, 1H), 7.93 (dd, J=8.6, 5.3 Hz, 1H), 3.66 (dt, J=5.5, 1.3 Hz, 2H); EIMS (m/z) 235 ([M+1]+).

N-Allyl-3-methyl-1-(pyridin-3-yl)-1H-pyrazol-4-amine, HCl was prepared as described in Example 26 from tert-butyl allyl(3-methyl-1-(pyridin-3-yl)-1H-pyrazol-4-yl): mp 195-197° C.; $^1$H NMR (400 MHz, DMSO-d$_6$) δ 9.12 (d, J=2.4 Hz, 1H), 8.58 (dd, J=5.0, 1.2 Hz, 1H), 8.48 (s, 1H), 8.43 (d, J=9.7 Hz, 1H), 7.77 (dd, J=8.4, 5.0 Hz, 1H), 6.04-5.92 (m, 1H), 5.44 (dd, J=17.2, 1.4 Hz, 1H), 5.32 (d, J=9.4 Hz, 1H), 3.81 (d, J=6.2 Hz, 2H); EIMS (m/z) 249 ([M-1]+).

3-Bromo-1-(5-fluoropyridin-3-yl)-N-methyl-1H-pyrazol-4-amine, HCl was prepared as described in Example 26 from tert-butyl 3-bromo-1-(5-fluoropyridin-3-yl)-1H-pyrazol-4-yl(methyl)carbamate: mp 167-168° C.; $^1$H NMR (400 MHz, CDCl$_3$) δ 8.93 (s, 1H), 8.50 (d, J=2.5 Hz, 1H), 8.23 (s, 1H), 8.14 (dt, J=10.4, 2.3 Hz, 1H), 2.73 (s, 3H).

3-Bromo-N-methyl-1-(pyridin-3-yl)-1H-pyrazol-4-amine, HCl was prepared as described in Example 26 from tert-butyl (3-bromo-1-(pyridin-3-yl)-1H-pyrazol-4-yl)(methyl)carbamate (160 mg, 0.45 mmol) in dioxane (1 mL) was added 4M HCl: mp. 226-228° C.; $^1$H NMR (400 MHz, DMSO-d$_6$) δ 9.26-9.06 (d, J=2.6 Hz, 1H), 8.69-8.54 (m, 1H), 8.54-8.39 (d, J=8.0 Hz, 1H), 8.33-8.14 (s, 1H), 7.90-7.72 (m, 1H), 2.82-2.67 (s, 3H); EIMS (m/z) 253 ([M+1]+), 255 ([M+2H]+).

3-Bromo-N-ethyl-1-(pyridin-3-yl)-1H-pyrazol-4-amine, HCl was prepared as described in Example 26 from 3-bromo-N-ethyl-1-(pyridin-3-yl)-1H-pyrazol-4-amine, HCl: mp 216-217° C.; $^1$H NMR (400 MHz, DMSO-d$_6$) δ 10.66-10.05 (s, 3H), 9.28-9.20 (d, J=2.5 Hz, 1H), 8.74-8.67 (m, 1H), 8.67-8.56 (m, 3H), 7.96-7.84 (m, 1H), 3.21-3.14 (m, 2H), 1.29-1.22 (m, 3H); EIMS (m/z) 267 ([M+1]+).

3-Chloro-N-(2-methoxyethyl)-1-(pyridin-3-yl)-1H-pyrazol-4-amine, HCl was prepared as described in Example 26 from tert-butyl (3-chloro-1-(pyridin-3-yl)-1H-pyrazol-4-yl)(2-methoxyethyl)carbamate, HCl: mp 157-158° C.; $^1$H NMR (400 MHz, DMSO) δ 9.22-9.14 (d, J=2.5 Hz, 1H), 8.70-8.65 (s, 1H), 8.65-8.59 (m, 1H), 8.38-8.33 (m, 1H), 8.00-7.89 (m, 1H), 3.59-3.50 (t, J=5.8 Hz, 2H), 3.32-3.27 (s, 3H), 3.22-3.14 (m, 2H); EIMS (m/z) 253 ([M+1]+).

Example 27

Preparation of 3-chloro-N-ethyl-1-(pyridin-3-yl)-1H-pyrazol-4-amine hydrochloride

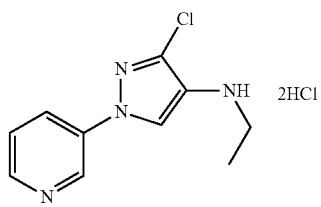

Into a 500 mL three-necked round bottom flask equipped with a magnetic stir bar was added a solution of tert-butyl (3-chloro-1-(pyridin-3-yl)-1H-pyrazol-4-yl)(ethyl)carbamate (21 g, 65.1 mmol) in 1,4-dioxane (35 mL). This pale yellow solution was placed into an ice bath and cooled to 1° C. A solution of 4M HCl in dioxane (65 mL, 260 mmol) was added in one portion. After stirring for 20 minutes, the ice bath was removed and the suspension was stirred further at ambient temperature for 16 hours. The reaction was diluted with 200 mL of ethyl ether and the solid was filtered and washed with ether and placed in a vacuum oven at 40° C. for 18 hours. The title compound was isolated as a pale yellow solid (18.2 g, 95%): $^1$H NMR (400 MHz, MeOD) δ 9.52 (d, J=2.5 Hz, 1H), 9.17 (s, 1H), 9.14 (ddd, J=8.7, 2.5, 1.1 Hz, 1H), 8.93 (ddd, J=5.7, 1.1, 0.6 Hz, 1H), 8.31 (ddd, J=8.7, 5.7, 0.5 Hz, 1H), 3.58 (q, J=7.3 Hz, 2H), 1.48 (t, J=7.3 Hz, 3H); ESIMS m/z 223 ([M+H]$^+$).

3-Chloro-N-methyl-1-(pyridin-3-yl)-1H-pyrazole-4-amine, 2HCl was prepared as described in Example 27: $^1$H NMR (400 MHz, MeOD) δ 9.28 (d, J=2.5 Hz, 1H), 8.86 (ddd, J=8.7, 2.5, 1.2 Hz, 1H), 8.79-8.75 (m, 1H), 8.62 (s, 1H), 8.19 (ddd, J=8.7, 5.6, 0.5 Hz, 1H), 3.06 (s, 3H); $^{13}$C NMR (101 MHz, MeOD) δ 141.42, 139.58, 137.76, 134.58, 134.11, 129.33, 127.55, 122.14, 35.62); ESIMS m/z 209 ([M+H]$^+$).

Example 28

Preparation of 3-(4-nitro-3-phenyl-1H-pyrazol-1-yl)pyridine

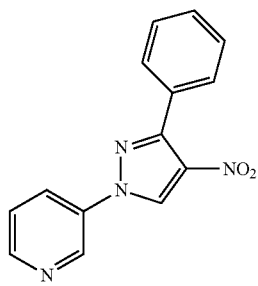 [SMILES: O=[N+]([O-])c1cn(-c2cccnc2)nc1-c1ccccc1]

To a suspension of phenylboronic acid (0.546 g, 4.47 mmol) in toluene (6.63 ml) was added 3-(3-chloro-4-nitro-1H-pyrazol-1-yl)pyridine (0.335 g, 1.492 mmol) followed by ethanol (3.31 ml) and 2 M aqueous potassium carbonate (1.492 ml, 2.98 mmol). The solution was degassed by applying vacuum and then purging with nitrogen (3 times). To the reaction mixture was added palladium tetrakis (0.086 g, 0.075 mmol) and the flask was heated at 110° C. under nitrogen for 16 hours. The aqueous layer was removed and the organic layer was concentrated. The crude product was purified via silica gel chromatography (0-100% ethyl acetate/hexanes) to give 3-(4-nitro-3-phenyl-1H-pyrazol-1-yl)pyridine (499 mg, 1.874 mmol, 80%) as a yellow solid: mp 144.0-146.0° C.; $^1$H NMR (400 MHz, CDCl$_3$) δ 9.09 (d, J=2.3 Hz, 1H), 8.82 (s, 1H), 8.71 (dd, J=4.8, 1.4 Hz, 1H), 8.16 (ddd, J=8.3, 2.7, 1.5 Hz, 1H), 7.82-7.74 (m, 2H), 7.55-7.48 (m, 4H); EIMS m/z 266.

Example 29

Preparation of 5-bromo-1-(pyridin-3-yl)-1H-pyrazol-4-ylmethyl)carbamate (Compound 110)

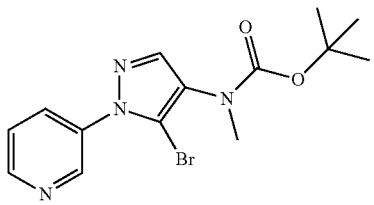 [SMILES: CN(C(=O)OC(C)(C)C)c1cnn(-c2cccnc2)c1Br]

To tert-butyl methyl(1-(pyridin-3-yl)-1H-pyrazol-4-yl) carbamate (0.200 g, 0.729 mmol) in dichloroethane (3.65 ml) was added 1-bromopyrrolidine-2,5-dione (0.260 g, 1.458 mmol) and the reaction was stirred overnight at 50° C. The reaction was concentrated, diluted with dichloromethane, and washed with water and saturated aqueous sodium thiosulfate. The organic phase was concentrated to give tert-butyl 5-bromo-1-(pyridin-3-yl)-1H-pyrazol-4-yl (methyl)carbamate (256 mg, 0.725 mmol, 99%) as a brown oil: IR (thin film) 1697 cm$^{-1}$; $^1$H NMR (400 MHz, CDCl$_3$) δ 8.89 (s, 1H), 8.68 (d, J=4.1 Hz, 1H), 7.93 (ddd, J=8.2, 2.5, 1.5 Hz, 1H), 7.69 (s, 1H), 7.46 (dd, J=8.1, 4.8 Hz, 1H), 3.22 (s, 3H), 1.44 (s, 9H); ESIMS m/z 352 ([M−H]$^-$).

Example 30

Preparation of Bis tert-t-butyl (5-chloro-1-(pyridin-3-yl)-1H-pyrazol-4-yl)carbamate (Compound 109)

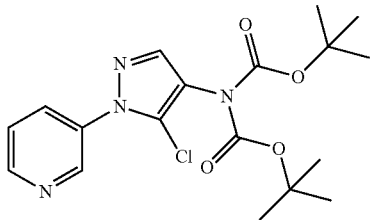 [SMILES: CC(C)(C)OC(=O)N(C(=O)OC(C)(C)C)c1cnn(-c2cccnc2)c1Cl]

To bis t-butyl (1-(pyridin-3-yl)-1H-pyrazol-4-yl)carbamate (1.30 g, 3.61 mmol) in acetonitrile (21.22 mL) was added N-chlorosuccinimide (0.96 g, 7.21 mmol) and the reaction was stirred at 45° C. for 48 hours. The reaction was cooled to room temperature and poured into water and extracted with dichloromethane. The dichloromethane layers were combined, poured through a phase separator to remove water and concentrated to dryness. The crude material was purified by silica gel chromatography (0-60% ethyl acetate/hexanes) to give the desired product as a yellow solid (0.90 g, 63%): mp 109-115° C.; $^1$H NMR (400 MHz, CDCl$_3$) δ 8.90 (d, J=2.3 Hz, 1H), 8.68 (dd, J=4.8, 1.5 Hz, 1H), 7.94 (ddd, J=8.2, 2.5, 1.5 Hz, 1H), 7.70 (s, 1H), 7.47 (dtd, J=11.0, 5.6, 5.5, 4.8 Hz, 1H), 1.49 (s, 18H); ESIMS m/z 395 ([M+H]$^+$).

tert-Butyl (5-chloro-3-methyl-1-(pyridin-3-yl)-1H-pyrazol-4-yl)(methyl)carbamate was prepared from the appropriate pyrazole in dichloroethane as the solvent as described in Example 30. ESIMS m/z 324 ([M+H]$^+$).

Compounds 110 (see also procedure in Example 29) and 146 were prepared from the appropriate pyrazoles using N-bromosuccinimide in accordance with the procedures disclosed in Example 30.

tert-Butyl 5-bromo-3-methyl-1-(pyridin-3-yl)-1H-pyrazol-4-yl(methyl)carbamate was prepared from the appropriate pyrazole in dichloroethane as described in Example 30: $^1$H NMR (400 MHz, CDCl$_3$) δ 8.88 (d, J=2.3 Hz, 1H), 8.69-8.60 (m, 1H), 7.96-7.86 (m, 1H), 7.48-7.39 (m, 1H), 3.18 (s, 3H), 2.26 (s, 3H), 1.60-1.36 (m, 9H); ESIMS m/z 368 ([M+H]$^+$).

Example 31

Preparation of bis tert-butyl (5-fluoro-1-(pyridin-3-yl)-1H-pyrazol-4-yl)carbamate (Compound 135)

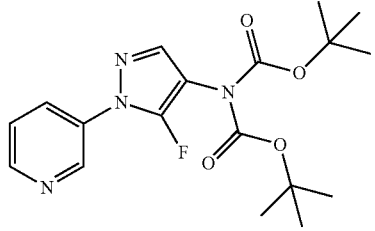 [SMILES: CC(C)(C)OC(=O)N(C(=O)OC(C)(C)C)c1cnn(-c2cccnc2)c1F]

To a solution of bis tert-t-butyl (1-(pyridin-3-yl)-1H-pyrazol-4-yl)carbamate (0.075 g, 0.208 mmol) in DMF (0.416 ml) and acetonitrile (0.416 ml) was added Selectfluor® (0.184 g, 0.520 mmol). The reaction was stirred at room temperature for one week. The reaction was concentrated, saturated aqueous ammonium chloride was added and the mixture was extracted with ethyl acetate. The combined organic phases were concentrated and chromatographed (0-100% ethyl acetate/hexanes) to give bis tert-butyl (5-fluoro-1-(pyridin-3-yl)-1H-pyrazol-4-yl)carbamate (16 mg, 0.042 mmol, 20.32%) as an off-white solid: $^1$H NMR (400 MHz, CDCl$_3$) δ 8.97 (t, J=2.0 Hz, 1H), 8.61 (dd, J=4.8, 1.4 Hz, 1H), 7.99 (ddt, J=8.3, 2.6, 1.3 Hz, 1H), 7.57 (d, J=2.5 Hz, 1H), 7.44 (ddd, J=8.3, 4.8, 0.6 Hz, 1H), 1.50 (s, 18H); ESIMS m/z 379 ([M+H]$^+$).

tert-Butyl (5-fluoro-3-methyl-1-(pyridin-3-yl)-1H-pyrazol-4-yl)(methyl)carbamate was prepared as described in Example 31: $^1$H NMR (400 MHz, CDCl$_3$) δ 8.94 (s, 1H), 8.57 (d, J=4.2 Hz, 1H), 7.96 (d, J=7.7 Hz, 1H), 7.41 (dd, J=7.9, 4.7 Hz, 1H), 3.17 (s, 3H), 2.23 (s, 3H), 1.58-1.40 (m, 9H); ESIMS m/z 307 ([M+H]+).

Example 32

Preparation of N-cyclopropyl-3-methyl-1-(pyridin-3-yl)-1H-pyrazol-4-amine

Example 32

Step 1: Preparation of 3-(4-iodo-3-methyl-1H-pyrazol-1-yl)pyridine

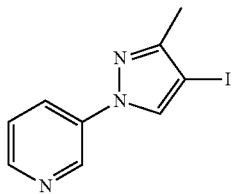

To a mixture of 3-(3-methyl-1H-pyrazol-1-yl)pyridine (6.7 g, 42.1 mmol), iodic acid (2.96 g, 16.84 mmol), and diiodine (8.55 g, 33.7 mmol) in acetic acid (60.1 ml) was added concentrated sulfur acid (3.74 ml, 21.04 mmol). The reaction mixture heated to 70° C. for 30 minutes. The reaction mixture was poured onto ice with sodium thiosulfate and was extracted with diethyl ether. The combined organic phases were washed with saturated aqueous sodium bicarbonate. The organic phases were then dried with magnesium sulfate, filtered and concentrated in vacuo. The solid residue was dissolved in dichloromethane, applied to a 80 g silica gel column, and eluted with 0-80% acetone in hexanes to afford 3-(4-iodo-3-methyl-1H-pyrazol-1-yl)pyridine (11.3 g, 35.7 mmol, 85%) as a white solid: mp 131° C.; $^1$H NMR (400 MHz, CDCl$_3$) δ 8.95-8.85 (m, 1H), 8.52 (dd, J=4.8, 1.4 Hz, 1H), 8.00-7.94 (m, 1H), 7.91 (s, 1H), 7.38 (ddd, J=8.3, 4.8, 0.7 Hz, 1H), 2.34 (s, 3H); EIMS m/z 285.

Example 32

Step 2: Preparation of N-cyclopropyl-3-methyl-1-(pyridin-3-yl)-1H-pyrazol-4-amine

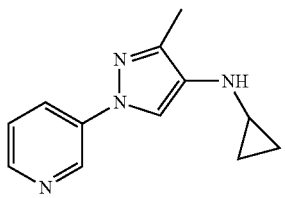 [SMILES: Cc1nn(-c2cccnc2)cc1NC1CC1]

To a solution of 3-(4-iodo-3-methyl-1H-pyrazol-1-yl)pyridine (2.0 g, 7.02 mmol) in dimethylsulfoxide (7.02 ml) was added 1-(5,6,7,8-tetrahydroquinolin-8-yl)ethanone (0.246 g, 1.403 mmol), cyclopropanamine (0.486 ml, 7.02 mmol), cesium carbonate (6.86 g, 21.05 mmol) and copper (I) bromide (0.101 g, 0.702 mmol). The reaction mixture was stirred at 35° C. for 2 days. The reaction mixture was diluted with water and extracted with dichloromethane. The combined organics were washed with brine, concentrated and chromatographed (0-100% ethyl acetate/hexanes) to give N-cyclopropyl-3-methyl-1-(pyridin-3-yl)-1H-pyrazol-4-amine (269 mg, 1.255 mmol, 17.90%) as a yellow solid: mp 104.0-107.0° C.; $^1$H NMR (400 MHz, CDCl$_3$) δ 8.89 (dd, J=2.7, 0.5 Hz, 1H), 8.41 (dd, J=4.7, 1.4 Hz, 1H), 7.96 (ddd, J=8.3, 2.7, 1.5 Hz, 1H), 7.51 (s, 1H), 7.33 (ddd, J=8.3, 4.7, 0.7 Hz, 1H), 3.42 (s, 1H), 2.53-2.42 (m, 1H), 2.22 (s, 3H), 0.72-0.65 (m, 2H), 0.60-0.53 (m, 2H); ESIMS m/z 215 ([M+H]+).

3-Methyl-N-(3-(methylthio)propyl)-1-(pyridin-3-yl)-1H-pyrazol-4-amine was prepared as described in Example 32: IR (thin film) 3298 cm$^{-1}$; $^1$H NMR (400 MHz, CDCl$_3$) δ 8.87 (d, J=2.3 Hz, 1H), 8.40 (dd, J=4.7, 1.4 Hz, 1H), 7.93 (ddd, J=8.3, 2.7, 1.5 Hz, 1H), 7.35 (s, 1H), 7.34-7.29 (m, 1H), 3.16 (t, J=6.8 Hz, 2H), 2.89 (s, 1H), 2.64 (t, J=7.0 Hz, 2H), 2.25 (s, 3H), 2.13 (s, 3H), 1.95 (p, J=6.9 Hz, 2H); ESIMS m/z 263 ([M+H]+).

3-Methyl-N-(2-methyl-3-(methylthio)propyl)-1-(pyridin-3-yl)-1H-pyrazol-4-amine was prepared as described in Example 32: IR (thin film) 3325 cm$^{-1}$; $^1$H NMR (400 MHz, CDCl$_3$) δ 8.86 (d, J=2.5 Hz, 1H), 8.40 (dd, J=4.7, 1.2 Hz, 1H), 7.93 (ddd, J=8.3, 2.7, 1.5 Hz, 1H), 7.35 (s, 1H), 7.32 (ddd, J=8.3, 4.7, 0.5 Hz, 1H), 3.12 (dd, J=11.5, 6.1 Hz, 1H), 2.94 (dd, J=11.9, 6.6 Hz, 1H), 2.62 (dd, J=12.9, 6.9 Hz, 1H), 2.52 (dd, J=12.9, 6.2 Hz, 1H), 2.26 (s, 3H), 2.14 (s, 3H), 2.12-2.02 (m, 1H), 1.11 (d, J=6.8 Hz, 3H); EIMS m/z 276.

Example 33

Preparation of tert-butyl (3-cyclopropyl-1-(5-fluoropyridin-3-yl)-1H-pyrazol-4-yl)carbamate (Compound 434) and tert-butyl (1-(5-fluoropyridin-3-yl)-1H-pyrazol-4-yl)carbamate (Compound 489)

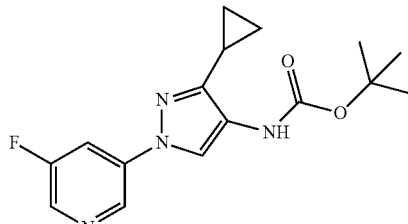

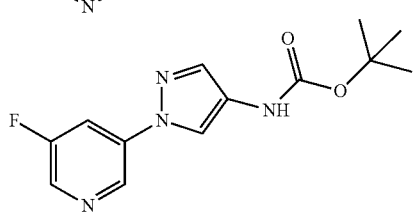

To a suspension of 2-cyclopropyl-4,4,5,5-tetramethyl-1,3,2-dioxaborolane (1.087 g, 6.47 mmol) in toluene (13.69 ml) was added tert-butyl (3-bromo-1-(5-fluoropyridin-3-yl)-1H-pyrazol-4-yl)carbamate (1.1 g, 3.08 mmol) followed by ethanol (6.84 ml) and 2 M aqueous potassium carbonate (3.08 mL, 6.16 mmol). The solution was degassed by applying vacuum and then purging with nitrogen (3 times). To the reaction mixture was added palladium tetrakis (0.178 g, 0.154 mmol) and the flask was heated at 100° C. under nitrogen for 36 hours. Water (5 mL) was added and the mixture was extracted with ethyl acetate. The combined organics were concentrated and chromatographed (0-100% ethyl acetate/hexanes) to give tert-butyl (3-cyclopropyl-1-

(5-fluoropyridin-3-yl)-1H-pyrazol-4-yl)carbamate (705 mg, 2.215 mmol, 71.9% yield) as a yellow solid and tert-butyl (1-(5-fluoropyridin-3-yl)-1H-pyrazol-4-yl)carbamate (242 mg, 0.870 mmol, 28.2% yield) as a yellow solid. tert-Butyl (3-cyclopropyl-1-(5-fluoropyridin-3-yl)-1H-pyrazol-4-yl) carbamate: mp 156.5-158.0; $^1$H NMR (400 MHz, CDCl$_3$) δ 8.73 (s, 1H), 8.30 (d, J=2.5 Hz, 1H), 8.27 (s, 1H), 7.76 (dt, J=9.8, 2.4 Hz, 1H), 6.43 (s, 1H), 1.55 (s, 9H), 1.01-0.91 (m, 4H); ESIMS m/z 319 ([M+H]$^+$).

(1-(5-Fluoropyridin-3-yl)-1H-pyrazol-4-yl)carbamate: mp 121.0-123.0° C.; $^1$H NMR (300 MHz, CDCl3) δ 8.78 (s, 1H), 8.37 (s, 1H), 8.28 (s, 1H), 7.81 (d, J=9.6 Hz, 1H), 7.59 (s, 1H), 6.44 (s, 1H), 1.53 (s, 9H). ESIMS m/z 278 ([M]$^+$).

Compounds 340 and 404 were prepared as described in Example 33.

Example 34

Preparation of tert-butyl (3-ethyl-1-(5-fluoropyridin-3-yl)-1H-pyrazol-4-yl)(methyl)carbamate (Compound 408)

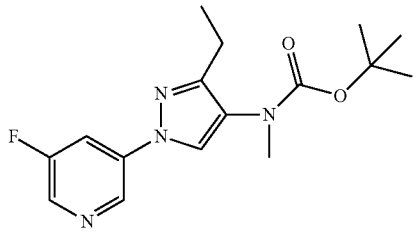 [SMILES: CCc1nn(-c2cncc(F)c2)cc1N(C)C(=O)OC(C)(C)C]

To a N$_2$-purged solution of tert-butyl (1-(5-fluoropyridin-3-yl)-3-vinyl-1H-pyrazol-4-yl)(methyl)carbamate (0.730 g, 2.293 mmol) in methanol (15.29 ml) was added 10% palladium on carbon (0.036 g, 0.339 mmol). The reaction was purged with hydrogen and run under 80 psi of hydrogen at room temperature for 60 hours. The reaction gave less than 20% conversion. The reaction mixture was filtered through celite, concentrated, and redissolved in ethyl acetate (4 mL) and transferred to a bomb. The reaction was heated at 50° C. at 600 psi of hydrogen for 20 hours. The reaction was only 50% complete. Methanol (1 mL) and 10% palladium on carbon (36 mg) were added, and the reaction was heated at 80° C. at 650 psi of hydrogen for 20 hours. The reaction was filtered through celite and concentrated to give tert-butyl (3-ethyl-1-(5-fluoropyridin-3-yl)-1H-pyrazol-4-yl)(methyl)carbamate (616 mg, 1.923 mmol, 84% yield) as yellow oil: IR (thin film) 1692 cm$^{-1}$; $^1$H NMR (300 MHz, CDCl$_3$) δ 8.71 (t, J=1.4 Hz, 1H), 8.35 (d, J=2.6 Hz, 1H), 7.83 (dt, J=9.5, 2.3 Hz, 2H), 3.18 (s, 3H), 2.65 (q, J=7.5 Hz, 2H), 1.44 (s, 9H), 1.25 (t, J=7.1 Hz, 3H); EIMS m/z 320.

Example 35

Preparation of N-(1-(5-fluoropyridin-3-yl)-3-formyl-1H-pyrazol-4-yl)isobutyramide (Compound 560)

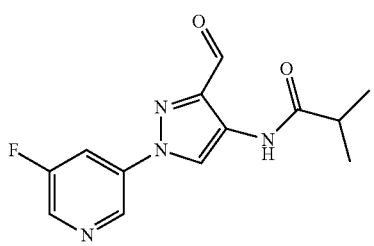 [SMILES: CC(C)C(=O)Nc1cn(-c2cncc(F)c2)nc1C=O]

To a solution of N-(1-(5-fluoropyridin-3-yl)-3-vinyl-1H-pyrazol-4-yl)isobutyramide (0.706 g, 2.57 mmol) in tetrahydrofuran (12.87 ml) and water (12.87 ml) was added osmium tetroxide (0.164 ml, 0.026 mmol). After 10 minutes at room temperature, sodium periodate (1.101 g, 5.15 mmol) was added in portions over 3 minutes and the resulting solution was stirred at room temperature. After 18 hours, the solution was poured into 10 mL water and was extracted with 3×10 mL dichloromethane. The combined organic layers were dried, concentrated and chromatographed (0-100% ethyl acetate/hexanes) to give N-(1-(5-fluoropyridin-3-yl)-3-formyl-1H-pyrazol-4-yl)isobutyramide (626 mg, 2.266 mmol, 88% yield) as a yellow solid: mp 140.0-142.0° C.; $^1$H NMR (300 MHz, CDCl$_3$) δ 10.12 (s, 1H), 9.14 (s, 1H), 8.90 (d, J=2.0 Hz, 1H), 8.82 (s, 1H), 8.51 (d, J=2.5 Hz, 1H), 7.92 (dt, J=9.2, 2.4 Hz, 1H), 2.65 (dt, J=13.8, 6.9 Hz, 1H), 1.31 (d, J=6.9 Hz, 6H); ESIMS m/z 277 ([M+H]$^+$).

Compound 369 was prepared in accordance with the procedures disclosed in Example 35.

Example 36

Preparation of N-(1-(5-fluoropyridin-3-yl)-3-(hydroxymethyl)-1H-pyrazol-4-yl)isobutyramide (Compound 435) and N-(1-(5-fluoropyridin-3-yl)-1H-pyrazol-4-yl)isobutyramide (Compound 436)

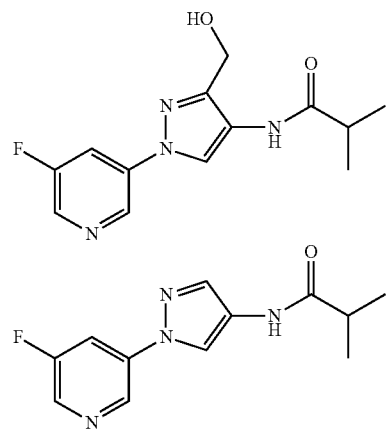

To a solution of N-(1-(5-fluoropyridin-3-yl)-3-formyl-1H-pyrazol-4-yl)isobutyramide (0.315 g, 1.140 mmol) in methanol (5.70 ml) at 0° C. was added sodium borohydride (0.086 g, 2.280 mmol). The reaction was stirred at 0° C. for 2 hours, and room temperature for 20 hours. 0.5 M HCl was added, the reaction was neutralized with saturated aqueous sodium bicarbonate, and the mixture was extracted with dichloromethane. The organic phases were concentrated and chromatographed (0-100% ethyl acetate/hexanes) to give N-(1-(5-fluoropyridin-3-yl)-3-(hydroxymethyl)-1H-pyrazol-4-yl)isobutyramide (180 mg, 0.647 mmol, 56.7%) as a white solid and N-(1-(5-fluoropyridin-3-yl)-1H-pyrazol-4-yl)isobutyramide (9 mg, 0.036 mmol, 3.18%) as a white solid.

N-(1-(5-Fluoropyridin-3-yl)-3-(hydroxymethyl)-1H-pyrazol-4-yl)isobutyramide: mp 144.0-146.0° C.; $^1$H NMR (400 MHz, CDCl$_3$) δ 8.74 (d, J=1.1 Hz, 1H), 8.64 (s, 1H), 8.37-8.29 (m, 2H), 7.74 (dt, J=9.5, 2.3 Hz, 1H), 4.95 (d, J=3.0 Hz, 2H), 3.21-3.06 (m, 1H), 2.63-2.48 (m, 1H), 1.26 (d, J=6.9 Hz, 6H); ESIMS m/z 279 ([M+H]$^+$).

N-(1-(5-Fluoropyridin-3-yl)-1H-pyrazol-4-yl)isobutyramide: IR (thin film) 1659 cm$^{-1}$; $^1$H NMR (400 MHz, CDCl$_3$) δ 8.79 (d, J=1.2 Hz, 1H), 8.60 (s, 1H), 8.38 (d, J=2.5 Hz, 1H), 7.81 (dt, J=9.5, 2.3 Hz, 1H), 7.68 (s, 1H), 7.54 (s, 1H), 2.63-2.51 (m, 1H), 1.28 (d, J=6.9 Hz, 6H); ESIMS m/z 249 ([M+H]$^+$).

Example 37

Preparation of N-(3-(chloromethyl)-1-(5-fluoropyridin-3-yl)-1H-pyrazol-4-yl)isobutyramide (Compound 561)

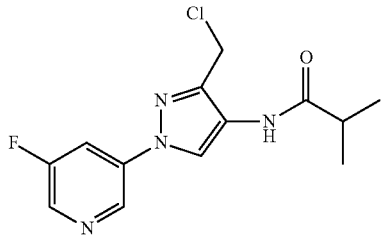 [SMILES: CC(C)C(=O)Nc1cn(-c2cncc(F)c2)nc1CCl]

To a solution of N-(1-(5-fluoropyridin-3-yl)-3-(hydroxymethyl)-1H-pyrazol-4-yl)isobutyramide (0.100 g, 0.359 mmol) in dichloromethane (3.59 ml) was added thionyl chloride (0.157 ml, 2.151 mmol). The reaction was stirred at room temperature for 2 hours. Saturated aqueous sodium bicarbonate was added, and the mixture was extracted with dichloromethane. The combined organic phases were washed with brine and concentrated to give N-(3-(chloromethyl)-1-(5-fluoropyridin-3-yl)-1H-pyrazol-4-yl)isobutyramide (100 mg, 0.337 mmol, 94% yield) as a white solid: mp 172.0-177.0° C.; $^1$H NMR (400 MHz, CDCl$_3$) δ 8.79 (s, 1H), 8.67 (s, 1H), 8.40 (s, 1H), 7.80 (dt, J=9.4, 2.3 Hz, 1H), 7.42 (s, 1H), 4.77 (s, 2H), 2.63 (hept, J=6.9 Hz, 1H), 1.30 (d, J=6.9 Hz, 6H); ESIMS m/z 298 ([M+H]$^+$).

Example 38

Preparation of N-(3-chloro-1-(pyridin-3-yl)-1H-pyrazol-4-yl)-N-ethyl-2-methoxyacetamide (Compound 512) (see also Example 11)

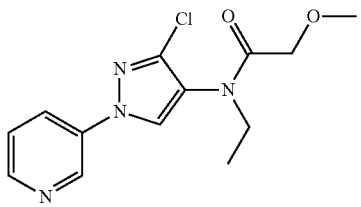 [SMILES: CCN(C(=O)COC)c1cn(-c2cccnc2)nc1Cl]

To a solution of 3-chloro-N-ethyl-1-(pyridin-3-yl)-1H-pyrazol-4-amine, 2HCl (0.130 g, 0.502 mmol) and in DCM (2.508 ml) was added N-ethyl-N-isopropylpropan-2-amine (0.257 ml, 1.505 mmol) followed by 2-methoxyacetyl chloride (0.109 g, 1.003 mmol) and the reaction mixture was stirred at ambient temperature for 16 hours. The reaction was quenched by the addition of saturated sodium bicarbonate. The organic layer was extracted with DCM. The organic layer was dried over sodium sulfate, filtered, concentrated and purified using silica gel chromatography (0-100% ethyl acetate/hexanes) to yield the title compound as a pale yellow oil (0.12 g, 77%): IR (thin film) 3514, 3091, 2978, 1676 cm$^{-1}$; $^1$H NMR (400 MHz, CDCl$_3$) δ 8.96 (d, J=2.4 Hz, 1H), 8.63 (d, J=3.8 Hz, 1H), 8.09-8.03 (m, 1H), 7.99 (s, 1H), 7.47 (dd, J=8.3, 4.8 Hz, 1H), 3.88 (s, 2H), 3.77-3.65 (m, 2H), 3.40 (s, 3H), 1.18 (t, J=7.2 Hz, 3H); ESIMS m/z 295 ([M+H]$^+$).

Compounds 71, 478, 481, 483-484, and 543 were prepared in accordance with the procedures disclosed in Example 38.

Example 39

Preparation of N-(3-chloro-1-(5-fluoropyridin-3-yl)-1H-pyrazol-4-yl)-N-ethyl-2-methyl-3-(methylthio)butanamide (Compound 182) and (Z)—N-(3-chloro-1-(5-fluoropyridin-3-yl)-1H-pyrazol-4-yl)-N-ethyl-2-methylbut-2-enamide (Compound 183)

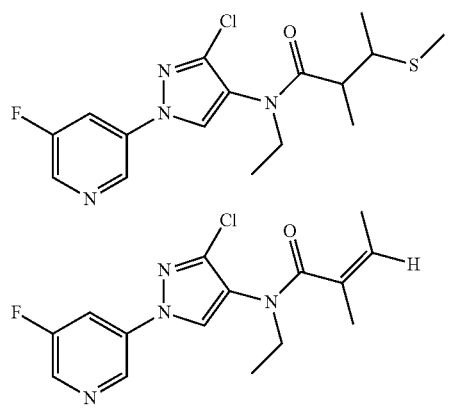

To a solution 2-methyl-3-(methylthio)butanoic acid (0.154 g, 1.039 mmol) in dichloromethane (1 mL) at room temperature was added 1 drop of dimethylformamide. Oxalyl dichloride (0.178 ml, 2.078 mmol) was added dropwise and the reaction was stirred at room temperature overnight. The solvent was removed under reduced pressure. The residue was redissolved in dichloromethane (1 mL) and the solvent was removed under reduced pressure. The residue was redissolved in dichloromethane (0.5 mL) and the solution was added to a solution of 3-chloro-N-ethyl-1-(5-fluoropyridin-3-yl)-1H-pyrazol-4-amine (0.100 g, 0.416 mmol) and 4-dimethylaminopyridine (0.254 g, 2.078 mmol) in dichloromethane (1.5 mL) and stirred at room temperature overnight. The solvent was removed under reduced pressure and the residue was purify by chromatography (0-100% ethyl acetate/hexanes) to give N-(3-chloro-1-(5-fluoropyridin-3-yl)-1H-pyrazol-4-yl)-N-ethyl-2-methyl-3-(methylthio)butanamide (34 mg, 0.092 mmol, 22.06%) as a faint yellow oil and (Z)—N-(3-chloro-1-(5-fluoropyridin-3-yl)-1H-pyrazol-4-yl)-N-ethyl-2-methylbut-2-enamide (38 mg, 0.118 mmol, 28.3% yield) as a yellow oil.

N-(3-Chloro-1-(5-fluoropyridin-3-yl)-1H-pyrazol-4-yl)-N-ethyl-2-methyl-3-(methylthio)butanamide: IR (thin film) 1633 cm$^{-1}$; $^1$H NMR (400 MHz, CDCl$_3$) δ 8.79 (d, J=2.0 Hz, 0.66H), 8.77 (d, J=2.0 Hz, 0.33H), 8.50 (d, J=2.6 Hz, 0.33H), 8.49 (d, J=2.5 Hz, 0.66H), 8.08 (s, 0.66H), 7.95 (s, 0.33H), 7.92-7.81 (m, 1H), 4.03-3.46 (m, 2H), 3.03-2.78 (m, 1H), 2.59-2.33 (m, 1H), 2.04 (s, 2H), 2.02 (s, 1H), 1.32 (d, J=6.7 Hz, 1H), 1.27 (d, J=6.2 Hz, 1H), 1.23 (d, J=6.9 Hz, 2H), 1.18-1.12 (m, 5H); ESIMS m/z 371 ([M]⁺).

(Z)—N-(3-Chloro-1-(5-fluoropyridin-3-yl)-1H-pyrazol-4-yl)-N-ethyl-2-methylbut-2-enamide: ¹H NMR (400 MHz, CDCl₃) δ 8.73 (d, J=2.0 Hz, 1H), 8.46 (d, J=2.4 Hz, 1H), 7.87 (d, J=4.9 Hz, 1H), 7.84 (dt, J=9.2, 2.4 Hz, 1H), 5.93-5.76 (m, 1H), 3.73 (q, J=7.1 Hz, 2H), 1.72 (s, 3H), 1.58 (dd, J=6.9, 0.9 Hz, 3H), 1.17 (t, J=7.1 Hz, 3H); ESIMS m/z 323 ([M]⁺).

Compounds 70, 180-181, 389-392, 397-398, 405-406, 427-429, 432, 456, 482, 521-522, 532-534, 555, and 589 were prepared from the corresponding intermediates and starting materials in accordance with the procedures disclosed in Example 39.

Example 40

Preparation of N-(3-chloro-1-(pyridin-3-yl)-1H-pyrazol-4-yl)-N-methyl-2-(methylthio)acetamide (Compound 337)

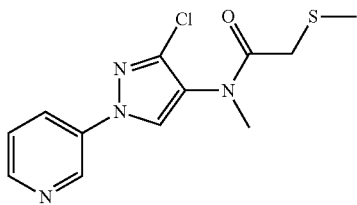 [SMILES: CSCC(=O)N(C)c1cn(-c2cccnc2)nc1Cl]

To an ice cold solution of 2-(methylthio)acetic acid (0.092 g, 0.863 mmol) in DCM (2 mL) was added N-ethyl-N-isopropylpropan-2-amine (0.111 g, 0.863 mmol) followed by isobutyl chloroformate (0.099 ml, 0.767 mmol). Stirring was continued for 10 minutes. Next, the mixed anhydride was added to a solution of 3-chloro-N-methyl-1-(pyridin-3-yl)-1H-pyrazol-4-amine (0.08 g, 0.383 mmol) in DCM (0.66 mL) and the reaction mixture was stirred at ambient temperature for 2 hours. The reaction mixture was concentrated and purified using reverse phase C-18 column chromatography (0-100% CH₃CN/H₂O) to yield the title compound as a pale yellow oil (0.075 g, 66%): ¹H NMR (400 MHz, CDCl₃) δ 8.95 (d, J=2.5 Hz, 1H), 8.62 (dd, J=4.8, 1.4 Hz, 1H), 8.13 (s, 1H), 8.04 (ddd, J=8.3, 2.7, 1.4 Hz, 1H), 7.50-7.43 (m, 1H), 3.26 (s, 3H), 3.12 (s, 2H), 2.24 (s, 3H); ¹³C NMR (101 MHz, CDCl₃) δ 170.00, 148.61, 140.15, 140.03, 135.68, 126.56, 126.42, 125.33, 124.15, 37.16, 34.94, 16.22; ESIMS m/z 297 ([M+H]⁺).

Compounds 335, 336, and 542 were prepared in accordance with the procedures disclosed in Example 40.

Example 41

Preparation of N-(3-chloro-1-(pyridin-3-yl)-1H-pyrazol-4-yl)-N-ethyl-2-methyl-3-oxobutanamide (Compound 499)

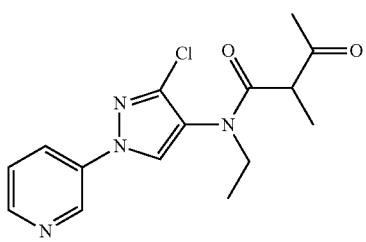 [SMILES: CCN(C(=O)C(C)C(C)=O)c1cn(-c2cccnc2)nc1Cl]

To a solution of 3-chloro-N-ethyl-1-(pyridin-3-yl)-1H-pyrazol-4-amine, HCl (259 mg, 1 mmol) and ethyl 2-methyl-3-oxobutanoate (144 mg, 1.000 mmol) in dioxane (1 mL) was added 2,3,4,6,7,8-hexahydro-1H-pyrimido[1,2-a]pyrimidine (181 mg, 1.30 mmol) and the mixture was heated in a microwave (CEM Discover) at 150° C. for 1.5 h, with external IR-sensor temperature monitoring from the bottom of the vessel. LCMS (ELSD) indicated a 40% conversion to the desired product. The mixture was diluted with ethyl acetate (50 ML) and saturated aqueous NH₄Cl (15 mL), and the organic phase was separated. The aqueous phase was extracted with ethyl acetate (20 mL) and the combined organic phase was washed with brine, dried over MgSO₄ and concentrated in vacuo to give an oily residue. This residue was purified on silica gel eluting with mixtures of ethyl acetate and hexanes to give N-(3-chloro-1-(pyridin-3-yl)-1H-pyrazol-4-yl)-N-ethyl-2-methyl-3-oxobutanamide (37 mg, 11% yield, 96% purity) as a colorless oil: ¹H NMR (400 MHz, CDCl₃) δ 9.02-8.92 (dd, J=2.6, 0.8 Hz, 1H), 8.68-8.60 (dd, J=4.8, 1.5 Hz, 1H), 8.09-7.98 (m, 1H), 7.96-7.87 (s, 1H), 3.87-3.58 (d, J=3.0 Hz, 2H), 3.49-3.38 (m, 1H), 2.16-2.08 (s, 3H), 1.39-1.32 (d, J=7.0 Hz, 3H), 1.22-1.13 (m, 3H); EIMS (m/z) 321 ([M+1]⁺), 319 ([M−1]⁻).

Example 42

Preparation of N-(3-chloro-1-(pyridin-3-yl)-1H-pyrazol-4-yl)-N-ethylcyclopropanecarboxamide (Compound 538)

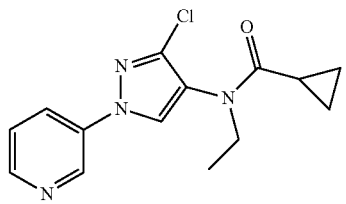 [SMILES: CCN(C(=O)C1CC1)c1cn(-c2cccnc2)nc1Cl]

To a solution of 3-chloro-N-ethyl-1-(pyridin-3-yl)-1H-pyrazol-4-amine monohydrochloride (0.10 g, 0.0.38 mmol) in dichloroethane (0.75 ml) was added cyclopropanecarboxylic acid (0.03 g, 0.38 mmol) and 4-N,N-dimethylaminopyridine (0.14 g, 1.15 mmol) followed by 1-(3-dimethylaminopropyl)-3-ethylcarbodiimide hydrochloride (0.14 g, 0.77 mmol). The reaction was stirred at room temperature overnight. The reaction mixture was concentrated to dryness and the crude product was purified by reverse phase silica gel chromatography eluting with 0-50% acetonitrile/water to give a white solid (0.03 g, 25%); mp 111-119° C.; ¹H NMR (400 MHz, CDCl₃) δ 8.96 (d, J=2.5 Hz, 1H), 8.63-8.59 (m, 1H), 8.06 (ddd, J=8.3, 2.6, 1.4 Hz, 1H), 8.01 (s, 1H), 7.46 (dd, J=8.3, 4.7 Hz, 1H), 3.73 (q, J=7.2 Hz, 2H), 1.46 (ddd, J=12.6, 8.1, 4.7 Hz, 1H), 1.16 (t, J=7.2 Hz, 3H), 1.04 (t, J=3.7 Hz, 2H), 0.71 (dd, J=7.7, 3.0 Hz, 2H); ESIMS m/z 291 ([M+H]).

Compounds 69, 516, 524, 546, 558-559, 582-588, 593, and 594 were prepared from the appropriate acids in accordance with the procedures disclosed in Example 42.

Example 43

Preparation of N-(3-chloro-1-(pyridin-3-yl)-1H-pyrazol-4-yl)-2-methyl-3-(methylthio)-N-(3-(methylthio)propanoyl)propanamide (Compound 407)

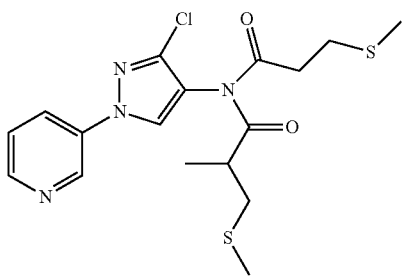 [SMILES: CSCCC(=O)N(C(=O)C(C)CSC)c1cn(-c2cccnc2)nc1Cl]

To a solution of N-(3-chloro-1-(pyridin-3-yl)-1H-pyrazol-4-yl)-3-(methylthio)propanamide (0.216 g, 0.728 mmol) in DCE (2.91 ml) in a 10 mL vial was added 2-methyl-3-(methylthio)propanoyl chloride (0.244 g, 1.601 mmol). The vial was capped and placed in a Biotage Initiator microwave reactor for 3 hours at 100° C., with external IR-sensor temperature monitoring from the side of the vessel. The crude mixture was concentrated and purified using reverse phase C-18 column chromatography (0-100% acetonitrile/water) to yield the title compound as a pale yellow oil (67 mg, 22%): IR (thin film) 2916 and 1714 cm$^{-1}$; $^1$H NMR (300 MHz, CDCl$_3$) δ 8.96-8.92 (d, J=2.7 Hz, 1H), 8.64-8.59 (dd, J=4.9, 1.4 Hz, 1H), 8.07-7.99 (m, 2H), 7.50-7.40 (dd, J=8.4, 4.8 Hz, 1H), 3.39-3.28 (m, 1H), 3.10-2.99 (td, J=7.2, 3.9 Hz, 2H), 2.96-2.86 (dd, J=13.2, 8.7 Hz, 1H), 2.86-2.79 (t, J=7.3 Hz, 2H), 2.58-2.48 (dd, J=13.1, 5.8 Hz, 1H), 2.14-2.12 (s, 3H), 2.09-2.06 (s, 3H), 1.30-1.26 (d, J=6.9 Hz, 3H); ESIMS m/z 413 ([M+H]$^+$).

Compounds 383, 410, 433, 437, 451, 470, 530 and 531 were prepared in accordance with the procedures disclosed in Example 43.

Example 44

Preparation of N-[3-chloro-1-(3-pyridyl)pyrazol-4-yl]-2,2-dideuterio-N-ethyl-3-methylsulfanyl-propanamide (Compound 393)

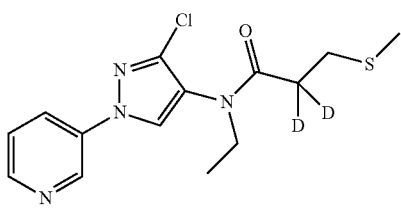 [SMILES: [2H]C([2H])(CSC)C(=O)N(CC)c1cn(-c2cccnc2)nc1Cl]

To a 7 mL vial was added 3-chloro-N-ethyl-1-(pyridin-3-yl)-1H-pyrazol-4-amine (111 mg, 0.5 mmol), 2,2-dideuterio-3-methylsulfanyl-propanoic acid (58.0 mg, 0.475 mmol) and followed by DCM (Volume: 2 mL). The solution was stirred at 0° C. Then the solution of DCC (0.500 mL, 0.500 mmol, 1.0M in DCM) was added. The solution was allowed to warm up to 25° C. slowly and stirred at 25° C. overnight. White precipitate formed during the reaction. The crude reaction mixture was filtered through a cotton plug and purified by silica gel chromatography (0-100% EtOAc/hexane) to give N-[3-chloro-1-(3-pyridyl)pyrazol-4-yl]-2,2-dideuterio-N-ethyl-3-methylsulfanyl-propanamide (97 mg, 0.297 mmol, 59.4% yield) as a colorless oil: $^1$H NMR (400 MHz, CDCl$_3$) δ 8.96 (d, J=2.4 Hz, 1H), 8.63 (dd, J=4.6, 0.9 Hz, 1H), 8.06 (ddd, J=8.4, 2.7, 1.4 Hz, 1H), 7.98 (s, 1H), 7.52-7.40 (m, 1H), 3.72 (q, J=7.2 Hz, 2H), 2.78 (s, 2H), 2.06 (s, 3H), 1.17 (t, J=7.2 Hz, 3H); ESIMS m/z 327 ([M+H]$^+$); IR (Thin film) 1652 cm$^{-1}$.

Compounds 394, 396, and 471-473 were prepared from the corresponding intermediates and starting materials in accordance with the procedures disclosed in Example 44.

Example 45

Preparation of 1-ethyl-3-(3-methyl-1-(pyridin-3-yl)-1H-pyrazol-4-yl)urea (Compound 145)

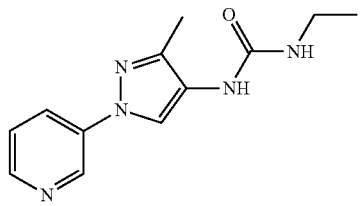 [SMILES: CCNC(=O)Nc1cn(-c2cccnc2)nc1C]

To a solution of 3-methyl-1-(pyridin-3-yl)-1H-pyrazol-4-amine (0.1 g, 0.574 mmol) in DCM (5.74 ml) was added ethyl isocyanate (0.041 g, 0.574 mmol) and the reaction mixture was stirred at ambient temperature for 40 minutes. The reaction mixture had turned from a clear solution to a suspension with white solid material. The reaction mixture was concentrated and purified using silica gel chromatography (0-20% MeOH/DCM) to yield the title compound as a white solid (0.135 g, 95%): mp 197-200° C.; $^1$H NMR (400 MHz, CDCl$_3$) δ 8.94 (d, J=2.3 Hz, 1H), 8.48-8.37 (m, 1H), 8.32 (s, 1H), 7.94 (d, J=8.3 Hz, 1H), 7.52 (br s, 1H), 7.41-7.25 (m, 1H), 5.79 (br s, 1H), 3.33-3.23 (m, 2H), 2.29 (d, J=2.9 Hz, 3H), 1.16 (dd, J=8.7, 5.7 Hz, 3H); ESIMS m/z 246 ([M+H]$^+$), 244 ([M−H]$^-$).

Compounds 169-171, 221-222, 255-257, 278-280, 297-302, 318-322, 334, 345, 348, 375-377, 385-387, and 411-413 were prepared in accordance with the procedures disclosed in Example 45.

Example 46

Preparation of 3-butyl-1-(3-chloro-1-(pyridin-3-yl)-1H-pyrazol-4-yl)-1-ethylurea (Compound 500)

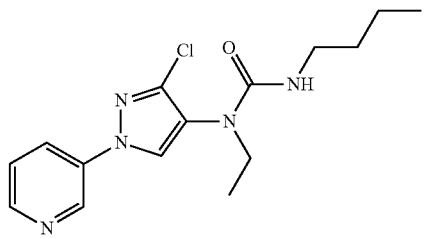 [SMILES: CCCCNC(=O)N(CC)c1cn(-c2cccnc2)nc1Cl]

To a solution of 3-chloro-N-ethyl-1-(pyridin-3-yl)-1H-pyrazol-4-amine, 2HCl (0.130 g, 0.502 mmol) in DCE (1.25 ml) was added N-ethyl-N-isopropylpropane-2-amine (0.21 mL, 1.255 mmol) followed by 1-isocyanatobutane (0.109 g, 1.104 mmol) and the reaction mixture was stirred at ambient temperature for 16 hours. The reaction mixture was concentrated and purified using silica gel chromatography (0-20% MeOH/DCM) to yield the title compound as a beige solid (0.131 g, 77%): IR (thin film) 3326, 2959, 2931, 1648 cm$^{-1}$; $^1$H NMR (400 MHz, CDCl$_3$) δ 8.95 (s, 1H), 8.62 (d, J=4.0 Hz, 1H), 8.08-8.01 (m, 1H), 7.97 (s, 1H), 7.46 (dd, J=8.3, 4.7 Hz, 1H), 4.42-4.32 (m, 1H), 3.74-3.61 (m, 2H), 3.27-3.15 (m, 2H), 1.49-1.37 (m, 2H), 1.37-1.22 (m, 2H), 1.19-1.12 (m, 3H), 0.94-0.84 (m, 3H); ESIMS m/z 322 ([M+H]$^+$).

Compounds 479-480, 501-504, 513, 518 and 519 were prepared according to Example 46.

Example 47

Preparation of 1-(3-chloro-1-(pyridin-3-yl)-1H-pyrazol-4-yl)imidazolidin-2-one (Compound 374)

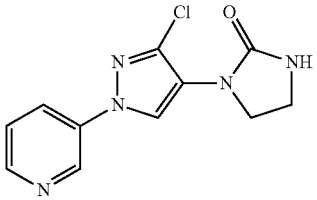 [SMILES: O=C1NCCN1c1cn(-c2cccnc2)nc1Cl]

To a solution of 1-(3-chloro-1-(pyridin-3-yl)-1H-pyrazol-4-yl)-3-(2-chloroethyl)urea (0.1 g, 0.333 mmol) in THF (6.66 ml) was added sodium hydride (8.00 mg, 0.333 mmol) and the reaction mixture was stirred at ambient temperature for 30 minutes. The reaction was quenched by the addition of a solution of saturated ammonium chloride and the product was extracted with ethyl acetate (2×). The combined organic layers were dried over sodium sulfate, filtered and concentrated. The product was a beige solid which was pure and did not need any further purification (63 mg, 72%): mp 167-170° C.; $^1$H NMR (400 MHz, CDCl$_3$) δ 8.96 (d, J=2.2 Hz, 1H), 8.56 (dd, J=4.7, 1.4 Hz, 1H), 8.33 (s, 1H), 7.99 (ddd, J=8.3, 2.7, 1.4 Hz, 1H), 7.40 (ddd, J=8.3, 4.8, 0.7 Hz, 1H), 5.00 (s, 1H), 4.14-4.07 (m, 2H), 3.68-3.58 (m, 2H); ESIMS m/z 264 ([M+H]$^+$).

Compound 349 was prepared in accordance with the procedures disclosed in Example 47.

Example 48

Preparation of S-tert-butyl (3-chloro-1-(pyridin-3-yl)-1H-pyrazol-4-yl)(ethyl)carbamothioate (Compound 514)

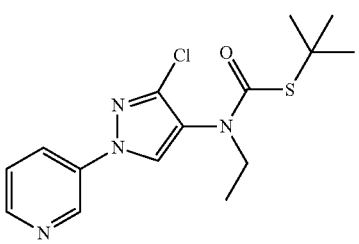 [SMILES: CCN(C(=O)SC(C)(C)C)c1cn(-c2cccnc2)nc1Cl]

To a solution of 3-chloro-N-ethyl-1-(pyridin-3-yl)-1H-pyrazol-4-amine, 2HCl (0.13 g, 0.502 mmol) in DCM (2.508 ml) was added N-ethyl-N-isopropylpropan-2-amine (0.257 ml, 1.505 mmol) followed by S-tert-butyl carbonochloridothioate (0.153 g, 1.003 mmol). The reaction mixture was stirred at ambient temperature for 16 hours. The reaction was quenched by the addition of saturated sodium bicarbonate. The organic layer was extracted with DCM. The organic layer was dried over sodium sulfate, filtered, concentrated and purified using silica gel column chromatography (0-100% ethyl acetate/hexanes) to yield the title compound as a white solid (132 mg, 78%): mp 91-93° C.; $^1$H NMR (400 MHz, CDCl$_3$) δ 8.96 (d, J=2.5 Hz, 1H), 8.60 (dd, J=4.7, 1.4 Hz, 1H), 8.08-8.03 (m, 1H), 7.97 (s, 1H), 7.47-7.41 (m, 1H), 3.69 (q, J=7.2 Hz, 2H), 1.47 (s, 9H), 1.21-1.13 (m, 3H); ESIMS m/z 339 ([M+H]$^+$).

Compounds 333, 338, 339, 346, 368 and 373 were prepared in accordance with the procedures disclosed in Example 48.

Example 49

Preparation of N-(3-chloro-1-(pyridin-3-yl)-1H-pyrazol-4-yl)-N-ethyl-2-methyl-3-(methio)propanethioamide (Compound 364)

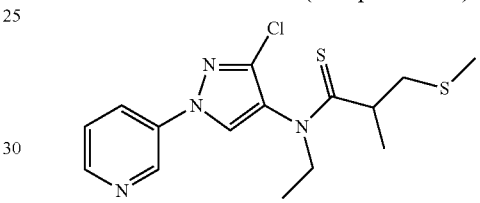

To a microwave reaction vessel was added N-(3-chloro-1-(pyridin-3-yl)-1H-pyrazol-4-yl)-N-ethyl-2-methyl-3-(methio)propanamide (0.07 g, 0.22 mmol) in dichloroethane (1.87 mL) and Lawesson's reagent (0.05 g, 0.12 mmol). The vessel was capped and heated in a Biotage Initiator microwave reactor for 15 minutes at 130° C., with external IR-sensor temperature monitoring from the side of the vessel. The reaction was concentrated to dryness and the crude material was purified by silica gel chromatography (0-80% acetonitrile/water) to give the desired product as a yellow oil (0.33 g, 44%): IR (thin film) 1436 cm$^{-1}$; $^1$H NMR (400 MHz, CDCl$_3$) δ 8.97 (d, J=2.5 Hz, 1H), 8.77-8.52 (m, 1H), 8.11-7.89 (m, 2H), 7.60-7.38 (m, 1H), 4.62 (bs, 1H), 4.02 (bs, 1H), 3.21-2.46 (m, 3H), 2.01 (s, 3H), 1.35-1.15 (m, 6H); ESIMS m/z 355 ([M+H]$^+$).

Compounds 372, 438 and 548 were prepared in accordance with the procedures disclosed in Example 49.

Example 50

Preparation of N-(3-chloro-1-(pyridin-3-yl)-1H-pyrazol-4-yl)-N-ethyl-4,4,4-trifluoro-3-(methylsulfinyl)butanamide (Compound 570)

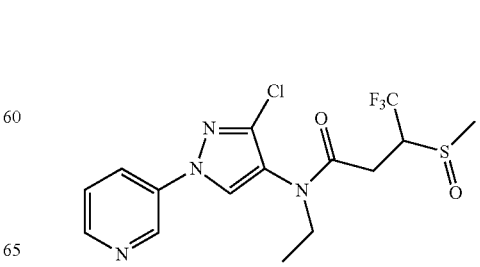

To a 20 mL vial was added N-(3-chloro-1-(pyridin-3-yl)-1H-pyrazol-4-yl)-N-ethyl-4,4,4-trifluoro-3-(methylthio)butanamide (82 mg, 0.209 mmol) and hexafluoroisopropanol (1.5 mL). Hydrogen peroxide (0.054 mL, 0.626 mmol, 35% solution in water) was added in one portion and the solution was stirred at room temperature. After 3 hours the reaction was quenched with saturated sodium sulfite solution and extracted with EtOAc (3×20 mL). The combined organic layers were dried over sodium sulfate, concentrated and purified by chromatography (0-10% MeOH/DCM) to give N-(3-chloro-1-(pyridin-3-yl)-1H-pyrazol-4-yl)-N-ethyl-4,4,4-trifluoro-3-(methylsulfinyl) butanamide (76 mg, 0.186 mmol, 89% yield) as white semi-solid: $^1$H NMR (400 MHz, CDCl$_3$) δ 8.98 (d, J=2.3 Hz, 1H), 8.63 (td, J=4.8, 2.4 Hz, 1H), 8.14-8.01 (m, 2H), 7.46 (ddd, J=8.3, 4.8, 0.7 Hz, 1H), 4.26 (dd, J=17.2, 8.4 Hz, 1H), 3.89-3.61 (m, 2H), 3.01 (dd, J=17.6, 8.2 Hz, 1H), 2.77 (s, 2H), 2.48 (dd, J=17.7, 3.3 Hz, 1H), 1.19 (t, J=7.2 Hz, 3H) (only one isomer shown); ESIMS m/z 409 ([M+H]$^+$); IR (Thin film) 1652 cm$^{-1}$.

Compound 571 was prepared from the corresponding intermediates and starting materials in accordance with the procedures disclosed in Example 50.

Example 51

Preparation of N-(3-chloro-1-(pyridin-3-yl)-1H-pyrazol-4-yl)-N-ethyl-3-(methylsulfinyl)propanamide (Compound 362)

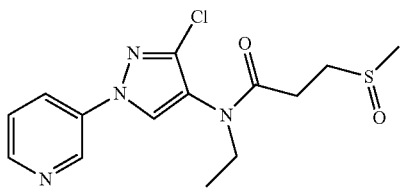 [SMILES: CCN(C(=O)CCS(C)=O)c1cn(-c2cccnc2)nc1Cl]

To N-(3-chloro-1-(pyridin-3-yl)-1H-pyrazol-4-yl)-N-ethyl-3-(methylthio)propanamide (0.08 g, 0.24 mmol) in glacial acetic acid (0.82 mL) was added sodium perborate tetrahydrate (0.05 g, 0.25 mmol), and the mixture was heated at 60° C. for 1 hour. The reaction mixture was carefully poured into a separatory funnel containing saturated aqueous NaHCO$_3$ resulting in gas evolution. When the gas evolution had ceased, ethyl acetate was added and the layers were separated. The aqueous layer was extracted twice with ethyl acetate, and all the organic layers were combined, dried over MgSO$_4$, filtered and concentrated under reduced pressure. The crude material was purified by silica gel chromatography (0-10% methanol/dichloromethane) to give the desired product as a clear oil (0.03 g, 40%): IR (thin film) 1655 cm$^{-1}$; $^1$H NMR (400 MHz, CDCl$_3$) δ 8.95 (t, J=9.2 Hz, 1H), 8.63 (dd, J=4.7, 1.4 Hz, 1H), 8.20-7.86 (m, 2H), 7.59-7.33 (m, 1H), 3.73 (ddt, J=20.5, 13.4, 6.8 Hz, 2H), 3.23-3.06 (m, 1H), 2.94-2.81 (m, 1H), 2.74-2.62 (m, 2H), 2.59 (s, 3H), 1.25-1.07 (m, 3H); ESIMS m/z 341 ([M+H]$^+$).

Compounds 101-102, 218, 328, 330, and 494 were prepared from the appropriate sulfides in accordance with the procedures disclosed in Example 51.

Example 52

Preparation of N-(3-chloro-1-(pyridin-3-yl)-1H-pyrazol-4-yl)-N-ethyl-3-(methylsulfonyl)propanamide (Compound 363)

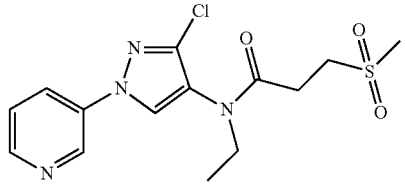 [SMILES: CCN(C(=O)CCS(C)(=O)=O)c1cn(-c2cccnc2)nc1Cl]

To N-(3-chloro-1-(pyridin-3-yl)-1H-pyrazol-4-yl)-N-ethyl-3-(methylthio)propanamide (0.08 g, 0.25 mmol) in glacial acetic acid (0.85 mL) was added sodium perborate tetrahydrate (0.11 g, 0.52 mmol), and the mixture was heated at 60° C. for 1 hour. The reaction mixture was carefully poured into a separatory funnel containing saturated aqueous NaHCO$_3$ resulting in gas evolution. When the gas evolution had ceased, ethyl acetate was added and the layers were separated. The aqueous layer was extracted twice with ethyl acetate, and all the organic layers were combined, dried over MgSO$_4$, filtered and concentrated under reduced pressure. The crude product was purified by silica gel column chromatography (0 to 10% methanol/dichloromethane) to give the desired product as a clear oil (0.04, 47%): (thin film) 1661 cm$^{-1}$; $^1$H NMR (400 MHz, CDCl$_3$) δ 8.95 (t, J=11.5 Hz, 1H), 8.64 (dd, J=4.8, 1.4 Hz, 1H), 8.17-7.96 (m, 2H), 7.59-7.39 (m, 1H), 3.73 (d, J=7.0 Hz, 2H), 3.44 (dd, J=22.5, 15.7 Hz, 2H), 2.96 (s, 3H), 2.71 (t, J=6.9 Hz, 2H), 1.18 (dd, J=8.8, 5.5 Hz, 3H); ESIMS m/z 357 ([M+H]$^+$).

Compounds 103, 104, 219, 329, 331 and 495 were prepared from the appropriate sulfides in accordance with the procedures disclosed in Example 52.

Example 53

Preparation of N-(3-methyl-1-(3-fluoropyridin-5-yl)-1H-pyrazol-4-yl)N-ethyl-2-methyl-(3-oxido-λ$^4$-sulfanylidenecyanamide)(methyl)propanamide (Compound 250)

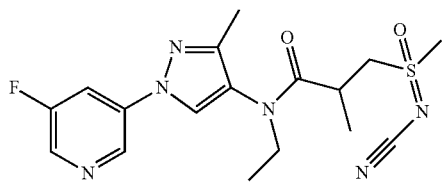 [SMILES: CCN(C(=O)C(C)CS(C)(=O)=NC#N)c1cn(-c2cncc(F)c2)nc1C]

To a solution of N-ethyl-N-(1-(5-fluoropyridin-3-yl)-3-methyl-1H-pyrazol-4-yl)-2-methyl-3-(methylthio)propanamide (0.30 g, 0.89 mmol) in dichloromethane (3.57 mL) at 0° C. was added cyanamide (0.07 g, 1.78 mmol) and iodobenzenediacetate (0.31 g, 0.98 mmol) and subsequently stirred at room temperature for 1 hour. The reaction was concentrated to dryness and the crude material was purified by silica gel column chromatography (10% methanol/ethyl acetate) to give the desired sulfilamine as a light yellow solid (0.28 g, 85%). To a solution of 70% mCPBA (0.25 g, 1.13 mmol) in ethanol (4.19 mL) at 0° C. was added a solution of potassium carbonate (0.31 g, 2.26 mmol) in water (4.19 mL) and stirred for 20 minutes after which a solution of sulfilamine (0.28 g, 0.75 mmol) in ethanol (4.19 mL) was added in one portion. The reaction was stirred for 1 hour at 0° C.

The excess mCPBA was quenched with 10% sodium thiosulfite and the reaction was concentrated to dryness. The residue was purified by silica gel chromatography (0-10% methanol/dichloromethane) to give the desired product as a clear oil (0.16 g, 56%): IR (thin film) 1649 cm$^{-1}$; $^1$H NMR (400 MHz, CDCl$_3$) δ 8.80 (dd, J=43.8, 10.1 Hz, 1H), 8.51-8.36 (m, 1H), 8.11 (d, J=38.7 Hz, 1H), 7.96-7.77 (m, 1H), 4.32-3.92 (m, 2H), 3.49-3.11 (m, 6H), 2.32 (s, 3H), 1.27-1.05 (m, 6H); ESIMS m/z 393 ([M+H]$^+$).

Example 54

Preparation of N-ethyl-4,4,4-trifluoro-3-methoxy-N-(3-methyl-1-(pyridin-3-yl)-1H-pyrazol-4-yl)-3-(trifluoromethyl)butanamide (Compound 276)

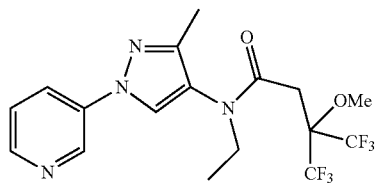 [SMILES: CCN(C(=O)CC(OC)(C(F)(F)F)C(F)(F)F)c1cn(-c2cccnc2)nc1C]

To a solution of N-ethyl-4,4,4-trifluoro-3-hydroxy-N-(3-methyl-1-(pyridin-3-yl)-1H-pyrazol-4-yl)-3-(trifluoromethyl)butanamide (184 mg, 0.448 mmol) in DMF (3 mL) stirring at 0° C. was added sodium hydride (26.9 mg, 0.673 mmol). The solution was stirred at 0° C. for 0.5 hour. Then iodomethane (0.034 mL, 0.538 mmol) was added and ice bath was removed and the mixture was stirred at 25° C. overnight. Reaction was worked up by slow addition of water and further diluted with 20 mL of water, then extracted with 4×20 mL of EtOAc. The combined organic layers were washed with water, dried over Na$_2$SO$_4$ and concentrated. Silica Gel chromatography (0-100% EtOAc/hexane) gave N-ethyl-4,4,4-trifluoro-3-methoxy-N-(3-methyl-1-(pyridin-3-yl)-1H-pyrazol-4-yl)-3-(trifluoromethyl)butanamide (52 mg, 0.123 mmol, 27.3% yield) as a white solid: mp=83-86° C.; $^1$H NMR (400 MHz, CDCl$_3$) δ 8.94 (d, J=2.5 Hz, 1H), 8.59 (dd, J=4.7, 1.3 Hz, 1H), 8.01 (ddd, J=8.3, 2.7, 1.5 Hz, 1H), 7.85 (s, 1H), 7.44 (ddd, J=8.3, 4.8, 0.6 Hz, 1H), 4.00 (brs, 1H), 3.73 (s, 3H), 3.39 (brs, 1H), 2.86 (s, 2H), 2.26 (s, 3H), 1.16 (t, J=7.1 Hz, 3H); ESIMS m/z 425 ([M+H]$^+$); IR (Thin film) 1664 cm$^{-1}$.

Compound 327 was prepared from the corresponding intermediates and starting materials in accordance with the procedures disclosed in Example 54.

Example 55

Step 1: Preparation of N-(2-((tert-butyldimethylsilyl)oxy)ethyl)-N-(3-chloro-1-(pyridin-3-yl)-1H-pyrazol-4-yl)-2-methyl-3-(methylthio)propanamide

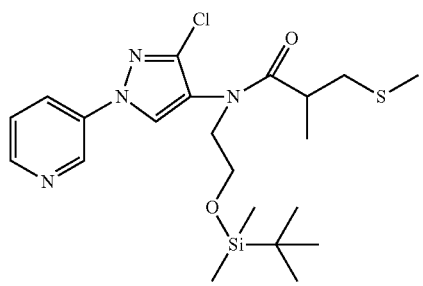 [SMILES: CSCC(C)C(=O)N(CCO[Si](C)(C)C(C)(C)C)c1cn(-c2cccnc2)nc1Cl]

A solution of N-(3-chloro-1-(pyridin-3-yl)-1H-pyrazol-4-yl)-2-methyl-3-(methylthio)propanamide (0.150 g, 0.483 mmol) in N,N-dimethylformamide (2.413 ml) was cooled to 0° C. Sodium hydride (0.039 g, 0.965 mmol, 60% dispersion) was added at and the reaction was stirred at 0° C. for 30 minutes. (2-Bromoethoxy)(tert-butyl)dimethylsilane (0.231 g, 0.965 mmol) was added, the ice bath was removed, and the reaction was stirred at room temperature for 2 hours. The reaction was heated at 65° C. for 1.5 hours and then cooled to room temperature. Brine was added and the mixture was extracted with dichloromethane. The combined organic phases were concentrated and chromatographed (0-100% ethyl acetate/hexanes) to give N-(2-((tert-butyldimethylsilyl)oxy)ethyl)-N-(3-chloro-1-(pyridin-3-yl)-1H-pyrazol-4-yl)-2-methyl-3-(methylthio)propanamide (0.120 g, 0.243 mmol, 50.4%) as an orange oil: IR (thin film) 1669 cm$^{-1}$; $^1$H NMR (400 MHz, CDCl$_3$) δ 8.88 (d, J=2.5 Hz, 1H), 8.55 (dd, J=4.7, 1.4 Hz, 1H), 8.05 (s, 1H), 7.98 (ddd, J=8.3, 2.6, 1.4 Hz, 1H), 7.41 (ddd, J=8.4, 4.8, 0.5 Hz, 1H), 4.35-3.06 (m, 4H), 2.86-2.73 (m, 1H), 2.73-2.59 (m, 1H), 2.41 (dd, J=12.8, 5.7 Hz, 1H), 1.94 (s, 3H), 1.11 (d, J=6.7 Hz, 3H), 0.80 (s, 9H), 0.00 (s, 3H), −0.01 (s, 3H); ESIMS m/z 470 ([M+H]$^+$).

Example 55

Step 2: Preparation of N-(3-chloro-1-(pyridin-3-yl)-1H-pyrazol-4-yl)-N-(2-hydroxyethyl)-2-methyl-3-(methylthio)propanamide (Compound 535)

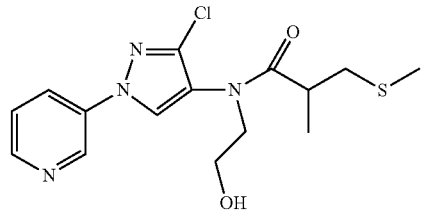

To a solution of N-(2-((tert-butyldimethylsilyl)oxy)ethyl)-N-(3-chloro-1-(pyridin-3-yl)-1H-pyrazol-4-yl)-2-methyl-3-(methylthio)propanamide (0.180 g, 0.384 mmol) in tetrahydrofuran (1.54 ml) was added tetrabutylammonium fluoride (0.201 g, 0.767 mmol) and the reaction was stirred at room temperature for 2 hours. Brine was added and the mixture was extracted with ethyl acetate. The combined organic phases were concentrated and chromatographed (0-100% water/acetonitrile) to give N-(3-chloro-1-(pyridin-3-yl)-1H-pyrazol-4-yl)-N-(2-hydroxyethyl)-2-methyl-3-(methylthio)propanamide as a white oil (0.081 g, 0.217 mmol, 56.5%): IR (thin film) 3423, 1654 cm$^{-1}$; $^1$H NMR (400 MHz, CDCl$_3$) δ 9.00 (d, J=2.5 Hz, 1H), 8.62 (dd, J=4.7, 1.2 Hz, 1H), 8.25 (s, 1H), 8.07 (ddd, J=8.3, 2.4, 1.3 Hz, 1H), 7.47 (dd, J=8.3, 4.7 Hz, 1H), 4.47-3.70 (m, 3H), 3.65-3.09 (m, 2H), 2.91-2.68 (m, 2H), 2.48 (dd, J=12.4, 5.0 Hz, 1H), 2.01 (s, 3H), 1.18 (d, J=6.5 Hz, 3H); ESIMS m/z 356 ([M+H]$^+$).

Example 56

Preparation of 2-(N-(3-chloro-1-(pyridin-3-yl)-1H-pyrazol-4-yl)-2-methyl-3-(methylthio)propanamido) ethyl acetate (Compound 547)

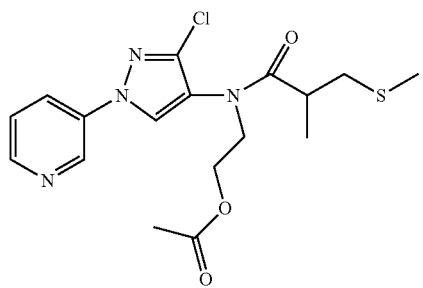 [SMILES: CSCC(C)C(=O)N(CCOC(C)=O)c1cn(-c2cccnc2)nc1Cl]

To a solution of N-(3-chloro-1-(pyridin-3-yl)-1H-pyrazol-4-yl)-N-(2-hydroxyethyl)-2-methyl-3-(methylthio)propanamide (0.045 g, 0.127 mmol) in dichloromethane (1.27 ml) was added N,N-dimethylpyridin-4-amine (0.023 g, 0.190 mmol) and triethylamine (0.019 g, 0.190 mmol) followed by acetyl chloride (0.015 g, 0.190 mmol). The reaction was stirred at room temperature overnight. Water was added and the mixture was extracted with dichloromethane. The combined organic phases were concentrated and chromatographed (0-100% ethyl acetate/hexanes) to give 2-(N-(3-chloro-1-(pyridin-3-yl)-1H-pyrazol-4-yl)-2-methyl-3-(methylthio)propanamido)ethyl acetate as a yellow oil (0.015 g, 0.034 mmol, 26.8%): IR (thin film) 1739, 1669 cm$^{-1}$; $^1$H NMR (400 MHz, CDCl$_3$) δ 8.97 (d, J=2.3 Hz, 1H), 8.64 (dd, J=4.7, 1.4 Hz, 1H), 8.15 (s, 1H), 8.04 (ddd, J=8.3, 2.7, 1.4 Hz, 1H), 7.47 (ddd, J=8.3, 4.8, 0.7 Hz, 1H), 4.50-3.40 (m, 4H), 2.84 (dd, J=12.7, 8.9 Hz, 1H), 2.78-2.63 (m, 1H), 2.46 (dd, J=12.7, 5.4 Hz, 1H), 2.03 (s, 3H), 2.01 (s, 3H), 1.16 (d, J=6.6 Hz, 3H); ESIMS m/z 398 ([M+H]$^+$).

Example 57

Preparation of 2,2-dideuterio-3-methylsulfanyl-propanoic acid

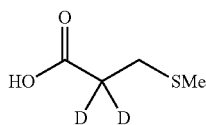

To a 100 mL round bottom flask was added 3-(methylthio)propanoic acid (3 g, 24.96 mmol), followed by D$_2$O (23 mL) and KOD (8.53 mL, 100 mmol) (40% wt solution in D$_2$O), the solution was heated to reflux overnight. NMR showed ca. 95% D at alpha-position. The reaction was cooled down and quenched with concentrated HCl until pH<2. White precipitate appeared in aqueous layer upon acidifying. Reaction mixture was extracted with 3×50 mL EtOAc, the combined organic layers were dried over Na$_2$SO$_4$, concentrated in vacuo to almost dryness. 100 mL hexane was added and the solution was concentrated again to give 2,2-dideuterio-3-methylsulfanyl-propanoic acid as a colorless oil (2.539 g, 20.78 mmol, 83%): IR (Thin film) 3430, 1704 cm$^{-1}$; $^1$H NMR (400 MHz, CDCl$_3$) δ 2.76 (s, 2H), 2.14 (s, 3H); $^{13}$C NMR (101 MHz, CDCl$_3$) δ 178.28, 38.14-28.55 (m), 28.55, 15.51; EIMS m/z 122.

2-Deuterio-2-methyl-3-methylsulfanyl-propanoic acid was prepared as described in Example 57 to afford a colorless oil (3.62 g, 26.8 mmol, 60.9%): IR (Thin film) 2975, 1701 cm$^{-1}$; $^1$H NMR (400 MHz, CDCl$_3$) δ 11.39-10.41 (brs, 1H), 2.88-2.79 (d, J=13.3 Hz, 1H), 2.61-2.53 (d, J=13.3 Hz, 1H), 2.16-2.09 (s, 3H), 1.32-1.25 (s, 3H); $^{13}$C NMR (101 MHz, CDCl$_3$) δ 181.74, 39.74-39.02 (m), 37.16, 16.50, 16.03; EIMS m/z 135.

Example 58

Preparation of 2-methyl-3-(trideuteriomethylsulfanyl)propanoic acid

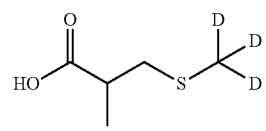

To a 50 mL round bottom flask was added 3-mercapto-2-methylpropanoic acid (5 g, 41.6 mmol), followed by MeOH (15 mL), the solution was stirred at 25° C. Potassium hydroxide (5.14 g, 92 mmol) was added slowly as the reaction is exothermic. Iodomethane-d$_3$ (6.63 g, 45.8 mmol) was added slowly and then the reaction mixture was heated at 65° C. overnight. The reaction was worked up by addition of 2 N HCl until the mixture was acidic. It was then extracted with EtOAc (4×50 mL) and the combined organic layers were dried over Na$_2$SO$_4$, concentrated and purified with flash chromatography, eluted with 0-80% EtOAc/hexane to give 2-methyl-3-(trideuteriomethylsulfanyl)propanoic acid (4.534 g, 33.0 mmol, 79%) as colorless oil: IR (Thin film) 3446, 1704 cm$^{-1}$; $^1$H NMR (400 MHz, CDCl$_3$) δ 2.84 (dd, J=13.0, 7.1 Hz, 1H), 2.80-2.66 (m, 1H), 2.57 (dd, J=13.0, 6.6 Hz, 1H), 1.30 (d, J=7.0 Hz, 3H); EIMS m/z 137.

Example 59

Preparation of 2-hydroxy-3-(methylthio)propanoic acid

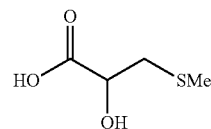

Sodium methanethiolate (4.50 g, 64.2 mmol) was added at 25° C. to a solution of 3-chloro-2-hydroxypropanoic acid (2 g, 16.06 mmol) in MeOH (120 mL). The reaction mixture was heated at reflux for 8 hours, then cooled to 25° C. The precipitate was removed by filtration and the filtrate was evaporated. The residue was acidified to pH 2 with 2 N HCl, extracted with EtOAc (3×30 mL), combined organic layers were dried with Na$_2$SO$_4$, concentrated to give 2-hydroxy-3-(methylthio)propanoic acid as a white solid, (1.898 g, 13.94 mmol, 87% yield): mp 55-59° C.; IR (Thin film) 2927, 1698 cm$^{-1}$; $^1$H NMR (400 MHz, CDCl$_3$) δ 6.33 (s, 3H), 4.48

(dd, J=6.3, 4.2 Hz, 1H), 3.02 (dd, J=14.2, 4.2 Hz, 1H), 2.90 (dd, J=14.2, 6.3 Hz, 1H), 2.20 (s, 3H); EIMS m/z 136.

Example 60

Preparation of 2-methoxy-3-(methylthio)propanoic acid

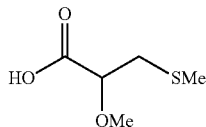

To a stirred solution of sodium hydride (0.176 g, 4.41 mmol) in DMF (5 mL) was added a solution of 2-hydroxy-3-(methylthio)propanoic acid (0.25 g, 1.836 mmol) in 1 mL DMF at 25° C. and stirred for 10 min. Vigorous bubbling was observed upon addition of NaH. Then iodomethane (0.126 mL, 2.020 mmol) was added and the solution was stirred at 25° C. overnight. The reaction was quenched by addition of 2 N HCl, extracted with 3×10 mL of EtOAc, the combined organic layers were washed with water (2×20 mL), concentrated and purified by column chromatography, eluted with 0-100% EtOAc/hexane, gave 2-methoxy-3-(methylthio)propanoic acid (126 mg, 0.839 mmol, 45.7% yield) as colorless oil: $^1$H NMR (400 MHz, CDCl$_3$) δ 9.10 (s, 1H), 4.03 (dd, J=6.9, 4.4 Hz, 1H), 3.51 (s, 3H), 2.98-2.93 (m, 1H), 2.86 (dd, J=14.1, 6.9 Hz, 1H), 2.21 (s, 3H); EIMS m/z 150.

Example 61

Preparation of 2-(acetylthiomethyl)-3,3,3-trifluoropropanoic acid

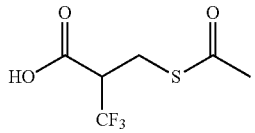

To a 50 mL round bottom flask was added 2-(trifluoromethyl)acrylic acid (6 g, 42.8 mmol), followed by thioacetic acid (4.59 ml, 64.3 mmol). The reaction was slightly exothermic. The mixture was then stirred at 25° C. overnight. NMR showed some starting material (~30%). One more equiv of thioacetic acid was added and the mixture was heated at 95° C. for 1 hour, then allowed to cool to room temperature. Mixture was purified by vacuum distillation at 2.1-2.5 mm Hg, fraction distilled at 80-85° C. was mostly thioacetic acid, fraction distilled at 100-110° C. was almost pure product, contaminated by a nonpolar impurity (by TLC). It was again purified by flash chromatography (0-20% MeOH/DCM), to give 2-(acetylthiomethyl)-3,3,3-trifluoropropanoic acid (7.78 g, 36.0 mmol, 84% yield) as colorless oil, which solidified under high vacuum to give a white solid: mp 28-30° C.; $^1$H NMR (400 MHz, CDCl$_3$) δ 7.52 (brs, 1H), 3.44 (dt, J=7.5, 3.5 Hz, 2H), 3.20 (dd, J=14.9, 11.1 Hz, 1H), 2.38 (s, 3H); $^{13}$C NMR (101 MHz, CDCl$_3$) δ 194.79, 171.14, 123.44 (q, J=281.6 Hz), 50.47 (q, J=27.9 Hz), 30.44, 24.69 (q, J=2.6 Hz); $^{19}$F NMR (376 MHz, CDCl$_3$) δ -67.82.

Example 62

Preparation of 3,3,3-trifluoro-2-(methylthiomethyl)propanoic acid

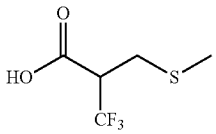

To a solution of 2-(acetylthiomethyl)-3,3,3-trifluoropropanoic acid (649 mg, 3 mmol) in MeOH (5 mL) stirring at 25° C. was added pellets of potassium hydroxide (421 mg, 7.50 mmol) in four portions over 5 minutes. Reaction was exothermic. Then MeI was added in once, the reaction mixture was then heated at 65° C. for 18 hours. The reaction was then cooled down and quenched with 2N HCl until acidic, and the aqueous layer extracted with chloroform (4×20 mL). Combined organic layer was dried, concentrated in vacuo, purified with flash chromatography (0-20% MeOH/DCM), to give 3,3,3-trifluoro-2-(methylthiomethyl)propanoic acid (410 mg, 2.179 mmol, 72.6% yield) as a light yellow oil: $^1$H NMR (400 MHz, CDCl$_3$) δ 10.95 (s, 1H), 3.49-3.37 (m, 1H), 3.02 (dd, J=13.8, 10.8 Hz, 1H), 2.90 (dd, J=13.8, 4.0 Hz, 1H), 2.18 (s, 3H); $^{13}$C NMR (101 MHz, CDCl$_3$) δ 172.04 (q, J=2.8 Hz), 123.55 (q, J=281.2 Hz), 50.89 (q, J=27.5 Hz), 29.62 (q, J=2.3 Hz), 15.85; $^{19}$F NMR (376 MHz, CDCl$_3$) δ -67.98.

Example 63

Preparation of 3-(methylthio)pentanoic acid

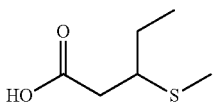

S,S-dimethyl carbonodithioate (1.467 g, 12.00 mmol) was added with vigorous stirring to a solution of (E)-pent-2-enoic acid (2.002 g, 20 mmol) in 30% KOH solution (prepared from potassium hydroxide (3.87 g, 69 mmol) and Water (10 mL)). The reaction mixture was slowly heated to 90° C. over a period of 20-30 min. Heating was continued for 3 hours before the reaction was cooled down to 25° C. and quenched slowly with HCl. The mixture was then extracted with DCM (3×30 mL), combined organic layer dried and concentrated to give 3-(methylthio)pentanoic acid (2.7 g, 18.22 mmol, 91% yield) as light orange oil: IR (Thin film) 2975, 1701 cm$^{-1}$; $^1$H NMR (400 MHz, CDCl$_3$) δ 2.92 (qd, J=7.3, 5.6 Hz, 1H), 2.63 (d, J=7.2 Hz, 2H), 2.08 (s, 3H), 1.75-1.51 (m, 2H), 1.03 (t, J=7.4 Hz, 3H); $^{13}$C NMR (101 MHz, CDCl$_3$) δ 178.14, 43.95, 39.78, 27.04, 12.95, 11.29; EIMS m/z 148.

4-methyl-3-(methylthio)pentanoic acid was prepared as described in Example 63 and isolated as a colorless oil: IR (Thin film) 2960, 1704 cm$^{-1}$; $^1$H NMR (400 MHz, CDCl$_3$)

δ 2.88 (ddd, J=9.1, 5.4, 4.7 Hz, 1H), 2.68 (dd, J=16.0, 5.5 Hz, 1H), 2.55 (dd, J=16.0, 9.1 Hz, 1H), 2.13 (s, 3H), 2.01-1.90 (m, 1H), 1.03 (d, J=6.8 Hz, 3H), 0.99 (d, J=6.8 Hz, 3H); EIMS m/z 162.

Example 64

Preparation of ethyl 1-(hydroxymethyl)cyclopropanecarboxylate

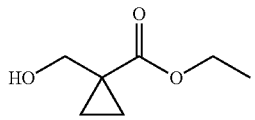

A 1M solution of lithium aluminum tri-tert-butoxyhydride in tetrahydrofuran (70.90 mL, 70.90 mmol) was added to a stirred solution of diethyl cyclopropane-1,1'-dicarboxylate (6 g, 32.20 mmol) in tetrahydrofuran (129 mL) at 23° C. The resulting solution was heated to 65° C. and stirred for 24 h. The cooled reaction mixture was diluted with a 10% solution of sodium bisulfate (275 mL) and extracted with ethyl acetate. The combined organic layers were dried (MgSO$_4$), filtered, and concentrated to dryness to give the desired product as a pale yellow oil (4.60, 91%): $^1$H NMR (300 MHz, CDCl$_3$) δ 4.16 (q, J=7 Hz, 2H), 3.62 (s, 2H), 2.60 (br s, 1H), 1.22-1.30 (m, 5H), 0.87 (dd, J=7, 4 Hz, 2H).

Example 65

Preparation of ethyl 1-((methylsulfonyloxy)methyl)cyclopropanecarboxylate

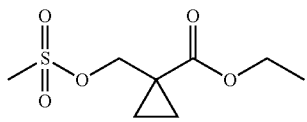

Triethylamine (5.57 mL, 40.00 mmol) and methanesulfonyl chloride (2.85 mL, 36.60 mmol) were sequentially added to a stirred solution of ethyl 1-(hydroxymethyl)cyclopropanecarboxylate (4.80 g, 33.30 mmol) in dichloromethane (83 mL) at 23° C. The resulting bright yellow solution was stirred at 23° C. for 20 h. The reaction mixture was diluted with water and extracted with dichloromethane. The combined organic layers were dried (MgSO$_4$), filtered, and concentrated to dryness to give the desired product as a brown oil (6.92 g, 94%): $^1$H NMR (300 MHz, CDCl$_3$) δ 4.33 (s, 2H), 4.16 (q, J=7 Hz, 2H), 3.08 (s, 3H), 1.43 (dd, J=7, 4 Hz, 2H), 1.26 (t, J=7 Hz, 3H), 1.04 (dd, J=7, 4 Hz, 2H).

Example 66

Preparation of ethyl 1-(methylthiomethyl)cyclopropanecarboxylate

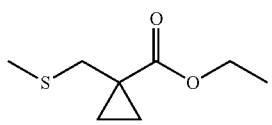

Sodium methanethiolate (4.36 g, 62.30 mmol) was added to a stirred solution of ethyl 1-((methylsulfonyloxy)methyl)cyclopropanecarboxylate (6.92 g, 31.10 mmol) in N,N-dimethylformamide (62.30 mL) at 23° C. The resulting brown suspension was stirred at 23° C. for 18 h. The reaction mixture was diluted with water and extracted with diethyl ether. The combined organic layers were dried (MgSO$_4$), filtered, and concentrated by rotary evaporation to afford the title compound as a brown oil (5.43 g, 100%): $^1$H NMR (300 MHz, CDCl$_3$) δ 4.14 (q, J=7 Hz, 2H), 2.83 (s, 2H), 2.16 (s, 3H), 1.31 (dd, J=7, 4 Hz, 2H), 1.25 (t, J=7 Hz, 3H), 0.89 (dd, J=7, 4 Hz, 2H).

Example 67

Preparation of 1-(methylthiomethyl)cyclopropanecarboxylic acid

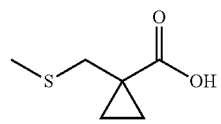

A 50% solution of sodium hydroxide (12.63 mL, 243 mmol) was added to a stirred solution of ethyl 1-(methylthiomethyl)cyclopropanecarboxylate (5.43 g, 31.20 mmol) in absolute ethanol (62.30 mL) at 23° C. The resulting solution was stirred at 23° C. for 20 h. The reaction mixture was diluted with a 0.5 M solution of sodium hydroxide and washed with dichloromethane. The aqueous layer was acidified to pH≈1 with concentrated hydrochloric acid and extracted with dichloromethane. The combined organic layers were dried (Na$_2$SO$_4$), filtered, and concentrated and concentrated to dryness to give the desired product as a light brown oil (2.10 g, 46%): $^1$H NMR (300 MHz, CDCl$_3$) δ 2.82 (s, 2H), 2.17 (s, 3H), 1.41 (dd, J=7, 4 Hz, 2H), 0.99 (dd, J=7, 4 Hz, 2H).

Example 68

Preparation of 2,2-dimethyl-3-(methylthio)propanoic acid

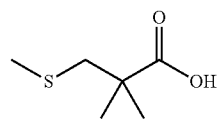

2,2-Dimethyl-3-(methylthio)propanoic acid can be prepared as demonstrated in the literature (reference Musker, W. K.; et al. *J. Org. Chem.* 1996, 51, 1026-1029). Sodium methanethiolate (1.0 g, 14 mmol, 2.0 equiv) was added to a stirred solution of 3-chloro-2,2-dimethylpropanoic acid (1.0 g, 7.2 mmol, 1.0 equiv) in N,N-dimethylformamide (3.7 mL) at 0° C. The resulting brown suspension was allowed to warm to 23° C. and stirred for 24 h. The reaction mixture was diluted with a saturated solution of sodium bicarbonate (300 mL) and washed with diethyl ether (3×75 mL). The aqueous layer was acidified to pH≈1 with concentrated hydrochloric acid and extracted with diethyl ether (3×75 mL). The combined organic layers were dried (sodium sulfate), gravity filtered, and concentrated to afford a colorless oil (1.2 g, 99% crude yield). $^1$H NMR (300 MHz, CDCl$_3$) δ 2.76 (s, 2H), 2.16 (s, 3H), 1.30 (s, 6H).

Example 69

Preparation of 4,4,4-trifluoro-3-(methylthio)butanoic acid

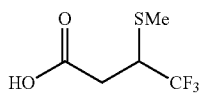

To a 100 mL round bottom flask was added (E)-4,4,4-trifluorobut-2-enoic acid (8 g, 57.1 mmol) and Methanol (24 mL), the solution was stirred in a water bath, then sodium methanethiolate (10.01 g, 143 mmol) was added in three portions. Vigorous bubbling was observed, the mixture was stirred at 25° C. overnight, NMR showed no more starting material. To the reaction mixture was added 2 N HCl until acidic. The mixture was extracted with chloroform (5×50 mL), combined organic layer was dried over Na$_2$SO$_4$, concentrated in vacuo and further dried under high vacuum until there was no weight loss to give 4,4,4-trifluoro-3-(methylthio)butanoic acid (10.68 g, 56.8 mmol, 99% yield) as a colorless oil: $^1$H NMR (400 MHz, CDCl$_3$) δ 10.88 (s, 1H), 3.53 (dqd, J=10.5, 8.3, 4.0 Hz, 1H), 2.96 (dd, J=16.9, 4.0 Hz, 1H), 2.65 (dd, J=16.9, 10.4 Hz, 1H), 2.29 (s, 3H); $^{13}$C NMR (101 MHz, CDCl$_3$) δ 175.78 (s), 126.61 (q, J$_{C-F}$=278.8 Hz), 44.99 (q, J$_{C-F}$=30.3 Hz), 34.12 (d, J$_{C-F}$=1.7 Hz), 15.95 (s); EIMS m/z 162.

Example 70

Preparation of 3-methyl-3-methylsulfanyl-butyric acid

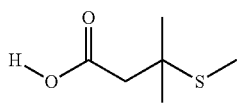

3-methyl-3-methylsulfanyl-butyric acid was made using the procedures disclosed in *J. Chem Soc Perkin* 1, 1992, 10, 1215-21.

Example 71

Preparation of 3-methylsulfanyl-butyric acid

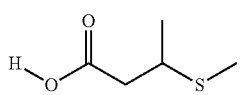

3-Methylsulfanyl-butyric acid was made using the procedures disclosed in *Synthetic Comm.*, 1985, 15 (7), 623-32.

Example 72

Preparation of tetrahydro-thiophene-3-carboxylic acid

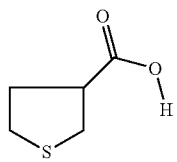

Tetrahydro-thiophene-3-carboxylic acid was made using the procedures disclosed in *Heterocycles*, 2007, 74, 397-409.

Example 73

Preparation of 2-methyl-3-methylsulfanyl-butyric acid

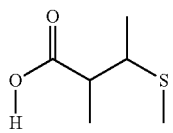

2-Methyl-3-methylsulfanyl-butyric acid was made as described in *J. Chem Soc Perkin* 1, 1992, 10, 1215-21.

Example 74

Preparation of (1S,2S)-2-(methylthio)cyclopropanecarboxylic acid

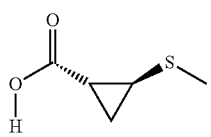

(1S,2S)-2-(Methylthio)cyclopropanecarboxylic acid was made using the procedures disclosed in *Synthetic Comm.*, 2003, 33 (5); 801-807.

Example 75

Preparation of 2-(2-(methylthio)ethoxy)propanoic acid

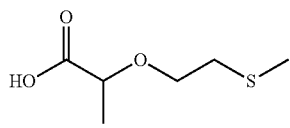

2-(2-(Methylthio)ethoxy)propanoic acid was made as described in WO 2007/064316 A1

Example 76

Preparation of 2-((tetrahydrofuran-3-yl)oxy)propanoic acid

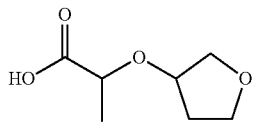

2-((Tetrahydrofuran-3-yl)oxy)propanoic acid was made as described in WO 2007/064316 A1.

Example 77

Preparation of tert-butyl 1-(5-fluoropyridin-3-yl)-3-methyl-1H-pyrazol-4-yl)prop-2-ynyl)carbamate (Compound 601)

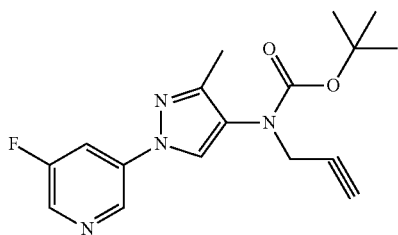 [SMILES: C#CCN(C(=O)OC(C)(C)C)c1cn(-c2cncc(F)c2)nc1C]

To an ice cold solution of tert-butyl 1-(5-fluoropyridin-3-yl)-3-methyl-1H-pyrazol-4-ylcarbamate (1200 mg, 4.11 mmol) in dry N,N-dimethylformamide (DMF; 4 mL) under nitrogen was added 60% wt sodium hydride (197 mg, 4.93 mmol) and the mixture stirred for 10 minutes (min). 3-Bromoprop-1-yne (733 mg, 6.16 mmol) was then added and the mixture was stirred for additional 0.5 hour (h) at 0-5° C. The mixture was allowed to warm to ambient temperature and then stirred for additional 3 h. The brown reaction mixture was poured into saturated aqueous ammonium chloride (NH$_4$Cl; 20 mL), and diluted with ethyl acetate (EtOAc; 50 mL). The organic phase was separated and the aqueous phase extracted with EtOAc (20 mL). The combined organic phase was washed with brine, dried over anhydrous magnesium sulfate (MgSO$_4$), filtered, and concentrated in vacuo to give a brown oil. This oil was purified on silica gel eluting with mixtures of hexanes and EtOAc to give the title compound as a light yellow solid (1103 mg, 81%): mp 81-82° C.; $^1$H NMR (400 MHz, CDCl$_3$) δ 8.73 (s, 1H), 8.37 (d, J=2.5 Hz, 1H), 7.99 (s, 1H), 7.83 (dt, J=9.5, 2.2 Hz, 1H), 4.31 (s, 2H), 2.29 (t, J=2.4 Hz, 1H), 2.27 (s, 3H), 1.45 (s, 9H); ESIMS m/z 229.84 ([M]$^+$).

Compounds 596 and 606 were prepared in accordance with the procedure disclosed in Example 77 from the corresponding amine.

Example 78

Preparation of 1-(5-fluoropyridin-3-yl)-3-methyl-N-(prop-2-ynyl)-1H-pyrazol-4-amine, hydrochloride

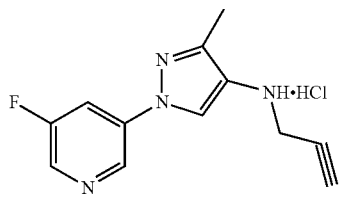

To a solution of tert-butyl 1-(5-fluoropyridin-3-yl)-3-methyl-1H-pyrazol-4-yl(prop-2-ynyl)carbamate (1.03 g, 3.11 mmol) in dioxane (5 mL) was added 4 molar (M) hydrogen chloride (HCl; 3.9 mL, 15.5 mmol) in diethyl ether (Et$_2$O). The mixture was stirred at room temperature for 48 h and the resulting white solid was filtered, washed with Et$_2$O and dried under vacuum to give the title compound as a white solid (741 mg, 89%): mp 167-168° C.; $^1$H NMR (400 MHz, DMSO d$_6$) δ 8.92-8.85 (m, 1H), 8.42 (d, J=2.5 Hz, 1H), 8.15 (s, 1H), 8.12-8.02 (m, 1H), 3.85 (d, J=2.5 Hz, 2H), 3.27-3.19 (m, 1H), 2.22 (s, 3H); ESIMS m/z 230.4 ([M]$^+$).

3-Chloro-N-(prop-2-ynyl)-1-(pyridin-3-yl)-1H-pyrazol-4-amine, hydrochloride was prepared in accordance with the procedure disclosed in Example 78 from Compound 606: mp 180-182° C.; $^1$H NMR (400 MHz, CDCl$_3$) δ 9.22 (d, J=2.5 Hz, 1H), 8.67 (dd, J=5.3, 1.0 Hz, 1H), 8.64 (ddd, J=8.6, 2.6, 1.2 Hz, 1H), 8.32 (s, 1H), 7.96 (dd, J=8.6, 5.3 Hz, 1H), 3.81 (d, J=2.4 Hz, 2H), 3.15 (t, J=2.4 Hz, 1H); ESIMS m/z 234 ([M+2]$^+$).

3-Methyl-N-(prop-2-yn-1-yl)-1-(pyridin-3-yl)-1H-pyrazol-4-amine, hydrochloride was prepared in accordance with the procedure disclosed in Example 78 from Compound 596: mp 161-163° C.; $^1$H NMR (400 MHz, DMSO-d$_6$) δ 8.46 (s, 1H), 8.05 (s, 1H), 7.83 (d, J=5.9 Hz, 1H), 7.57 (s, 1H), 7.29 (dd, J=8.8, 5.6 Hz, 1H), 3.27 (d, J=2.5 Hz, 2H), 3.21 (t, J=1.2 Hz, 1H), 1.52 (s, 3H); EIMS m/z 213.1 ([M]+).

Example 79

Preparation of N-(1-(5-fluoropyridin-3-yl)-3-methyl-1H-pyrazol-4-yl)-3-(methylthio)-N-(prop-2-ynyl)propanamide (Compound 605)

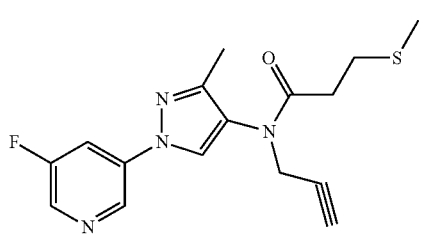 [SMILES: C#CCN(C(=O)CCSC)c1cn(-c2cncc(F)c2)nc1C]

To a stirred solution of 1-(5-fluoropyridin-3-yl)-3-methyl-N-(prop-2-yn-1-yl)-1H-pyrazol-4-amine, HCl (100 mg, 0.38 mmol) and N,N-dimethylpyridin-4-amine (DMAP; 115 mg, 0.94 mmol) in CH$_2$Cl$_2$ (DCM; 2 mL) was added 2-methyl-3-(methylthio)propanoyl chloride (69 mg, 0.45 mmol), and the mixture stirred at room temperature for 24 h. The mixture was concentrated in vacuo to give a brown oil which was purified on silica gel eluting with mixtures of EtOAc and hexanes to give the title compound as a colorless oil (80 mg, 61%): $^1$H NMR (400 MHz, CDCl$_3$) δ 8.76 (d, J=1.6 Hz, 1H), 8.44 (d, J=2.5 Hz, 1H), 8.05 (s, 1H), 7.86 (dt, J=9.3, 2.3 Hz, 1H), 4.45 (s, 2H), 2.79 (t, J=7.3 Hz, 2H), 2.43 (t, J=7.3 Hz, 2H), 2.30 (s, 3H), 2.25 (t, J=2.5 Hz, 1H), 2.06 (s, 3H); ESIMS m/z 333.6 ([M+H]$^+$).

Compounds 598, 599, 600, 602, 603, 607, 608 and 610 were prepared in accordance with the procedure disclosed in Example 79 from the corresponding amines.

Example 80

Preparation of N-(3-chloro-1-(pyridin-3-yl)-1H-pyrazol-4-yl)-4,4,4-trifluoro-3-(methylthio)-N-(prop-2-yn-1-yl)butanamide (Compound 613)

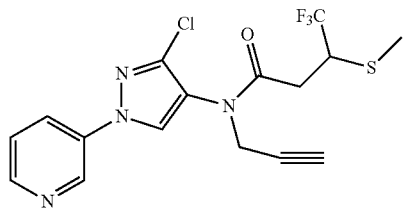 [SMILES: C#CCN(C(=O)CC(SC)C(F)(F)F)c1cn(-c2cccnc2)nc1Cl]

To a 7 mL vial was added 3-chloro-N-(prop-2-yn-1-yl)-1-(pyridin-3-yl)-1H-pyrazol-4-amine (140 mg, 0.6 mmol), N,N-dimethylpyridin-4-amine (249 mg, 2.040 mmol), N1-((ethylimino)methylene)-N3,N3-dimethylpropane-1,3-diamine hydrochloride (276 mg, 1.440 mmol) followed by 4,4,4-trifluoro-3-(methylthio)butanoic acid (158 mg, 0.840 mmol) and DCE (1.2 mL). The solution was stirred at 25° C. for 18 hours, the crude reaction mixture was concentrated and purified with silica gel chromatography (0-100% EtOAc/hexane) to give the title compound as a brown oil (237 mg, 0.588 mmol, 98%): (IR thin film) 1674 cm$^{-1}$; $^1$H NMR (400 MHz, CDCl$_3$) δ 8.97 (d, J=2.6 Hz, 1H), 8.64 (dd, J=4.7, 1.3 Hz, 1H), 8.13 (s, 1H), 8.07 (ddd, J=8.3, 2.7, 1.5 Hz, 1H), 7.48 (ddd, J=8.3, 4.8, 0.5 Hz, 1H), 4.39 (s, 2H), 3.76 (dqd, J=17.2, 8.6, 3.6 Hz, 1H), 2.67 (dd, J=16.6, 3.6 Hz, 1H), 2.46 (dd, J=16.5, 9.9 Hz, 1H), 2.29 (d, J=2.5 Hz, 4H); ESIMS m/z 403 ([M+H]$^+$).

tert-Butyl (2-((3-chloro-1-(pyridin-3-yl)-1H-pyrazol-4-yl)(prop-2-yn-1-yl)amino)-2-oxoethyl)(methyl)carbamate was prepared as described in Example 80: IR (thin film) 1696 cm$^{-1}$; $^1$H NMR (400 MHz, CDCl$_3$) δ 8.96 (bs, 1H), 8.63 (dd, J=4.9 Hz, 1H), 8.21-7.86 (m, 2H), 7.46 (dd, J=8.3, 4.8 Hz, 1H), 4.65-4.30 (m, 2H). 4.02-3.70 (bs, 2H), 3.06-2.79 (m, 3H), 2.25 (bs, 1H), 1.44 (s, 9H); ESIMS m/z 404 ([M+H]$^+$).

Compounds 597, 604, 609, 614-616, 619, 624, 626, and 627 were prepared in accordance with the procedure disclosed in Example 80. Compound 625 was prepared from Compound 624 using the methodology described in US 20120053146 A1.

Example 81

Preparation of 3-chloro-N-(prop-2-ynyl)-1-(pyridin-3-yl)-1H-pyrazol-4-amine

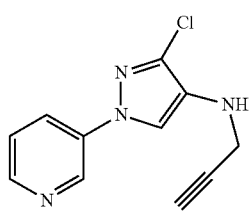 [SMILES: C#CCNc1cn(-c2cccnc2)nc1Cl]

To a solution of tert-butyl (3-chloro-1-(pyridin-3-yl)-1H-pyrazol-4-yl)(prop-2-yn-1-yl)carbamate (2.2 g, 6.61 mmol) in dichloromethane (DCM; 8.3 ml) was added 2,2,2-trifluoroacetic acid (12.06 g, 106 mmol) and the reaction mixture was stirred at ambient temperature for 1 h. The reaction was quenched by the addition of saturated sodium bicarbonate (NaHCO$_3$). The organic layer was extracted with DCM (2×20 mL). The organic layers were combined and dried over sodium sulfate (Na$_2$SO$_4$), filtered and concentrated to afford the title compound as a beige solid (1.5 g, 6.12 mmol, 93%): $^1$H NMR (400 MHz, CDCl$_3$) δ 8.89 (d, J=2.3 Hz, 1H), 8.50 (dd, J=4.7, 1.4 Hz, 1H), 8.01-7.93 (m, 1H), 7.54 (s, 1H), 7.37 (ddd, J=8.3, 4.8, 0.7 Hz, 1H), 3.90 (s, 2H), 3.38 (s, 1H), 2.44-2.09 (m, 1H); ESIMS m/z 233 ([M+H]$^+$).

Example 82

Preparation of N-(3-chloro-1-(pyridin-3-yl)-1H-pyrazol-4-yl)-2-(methylthio)-N-(prop-2-yn-1-yl)propanamide (Compound 611)

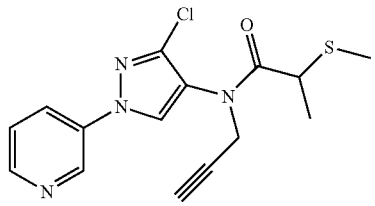 [SMILES: C#CCN(C(=O)C(C)SC)c1cn(-c2cccnc2)nc1Cl]

To a solution of 2-(methylthio)propanoic acid (0.36 g, 3.00 mmol) in DCM (3 mL) was added oxalyl dichloride (0.29 ml, 3.31 mmol) followed by one drop of DMF. The reaction mixture was stirred for 30 min before all of the solvent was evaporated. The resulting residue was dissolved in DCM (2 mL) and the solution was added to a pre-stirred solution of 3-chloro-N-(prop-2-yn-1-yl)-1-(pyridin-3-yl)-1H-pyrazol-4-amine (0.35 g, 1.50 mmol) and N-ethyl-N-isopropylpropan-2-amine (0.57 ml, 3.31 mmol) in DCM (5.5 mL). The reaction mixture was stirred at ambient temperature for 16 h. The reaction mixture was concentrated and the residue was purified using silica gel chromatography (0-100% EtOAc/hexanes) to afford the title compound as a yellow oil (432 mg, 1.23 mmol, 85%): $^1$H NMR (400 MHz, CDCl$_3$) δ 8.97 (d, J=2.5 Hz, 1H), 8.66-8.60 (m, 1H), 8.25 (s, 1H), 8.08-8.01 (m, 1H), 7.49-7.42 (m, 1H), 4.86 (s, 1H), 4.29-3.97 (m, 1H), 3.31 (d, J=6.5 Hz, 1H), 2.30-2.24 (m, 1H), 2.09 (s, 3H), 1.46 (d, J=6.9 Hz, 3H); $^{13}$C NMR (101 MHz, CDCl$_3$) δ 171.30, 148.66, 140.71, 140.18, 135.71, 127.87, 126.35, 124.11, 122.12, 78.53, 72.92, 53.39, 37.97, 16.42, 11.07; ESIMS m/z 335 ([M+H]$^+$).

Compounds 612 and 622 were prepared in accordance with the procedure disclosed in Example 82.

Example 83

Preparation of N-(3-chloro-1-(pyridin-3-yl)-1H-pyrazol-4-yl)-2-(methylsulfinyl)-N-(prop-2-yn-1-yl) propanamide (Compound 617)

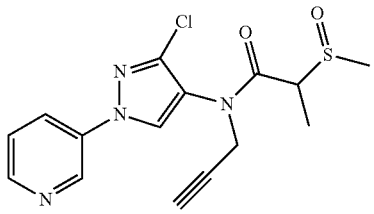 [SMILES: C#CCN(C(=O)C(C)S(C)=O)c1cn(-c2cccnc2)nc1Cl]

To a solution of N-(3-chloro-1-(pyridin-3-yl)-1H-pyrazol-4-yl)-2-(methylthio)-N-(prop-2-yn-1-yl)propanamide (0.1 g, 0.30 mmol) in hexafluoroisoproanol (2.0 ml) was added hydrogen peroxide (35 wt %, 0.08 ml, 0.90 mmol) and the reaction mixture was stirred vigorously at ambient temperature. The reaction was complete after 1 h. The reaction was quenched with saturated sodium sulfite solution and the organic layer was extracted with EtOAc (3×20 mL). The combined organic layers were dried over Na$_2$SO$_4$, filtered and concentrated. The residue was purified using silica gel chromatography (0-20% methanol (MeOH)/DCM) to afford the title compound as an off-white foam (82 mg, 0.21 mmol, 78%): $^1$H NMR (400 MHz, CDCl$_3$) δ 8.98 (s, 1H), 8.65 (d, J=4.6 Hz, 1H), 8.23 (s, 1H), 8.11-7.97 (m, 1H), 7.51-7.41 (m, 1H), 4.88 (br s, 1H), 4.14 (br s, 1H), 2.64 (s, 1.2H), 2.55 (s, 1.8H), 2.33-2.27 (m, 1H), 1.47 (d, J=6.8 Hz, 3H), 1.42 (br s, 1H); $^{13}$C NMR (101 MHz, CDCl$_3$) δ 168.11, 148.95, 148.78, 140.45, 140.33, 140.20, 135.56, 126.54, 124.10, 121.68, 121.58, 121.48, 77.69, 73.49, 38.60; ESIMS m/z 351 ([M+H]$^+$).

Example 84

Preparation of N-(3-chloro-1-(pyridin-3-yl)-1H-pyrazol-4-yl)-2-(methylsulfonyl)-N-(prop-2-yn-1-yl) propanamide (Compound 618)

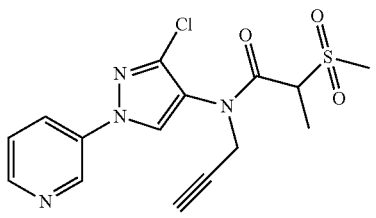 [SMILES: C#CCN(C(=O)C(C)S(C)(=O)=O)c1cn(-c2cccnc2)nc1Cl]

To a solution of N-(3-chloro-1-(pyridin-3-yl)-1H-pyrazol-4-yl)-2-(methylthio)-N-(prop-2-yn-1-yl)propanamide (0.10 g, 0.30 mmol) and acetic acid (2.0 ml) was added sodium perborate tetrahydrate (0.11 g, 0.74 mmol) and the vial was heated to 65° C. for 2 h. The reaction mixture was cooled to ambient temperature and neutralized with saturated NaHCO$_3$. The aqueous layer was extracted with EtOAc (3×). The organic layers were combined, dried over Na$_2$SO$_4$, filtered and concentrated. The residue was purified using silica gel chromatography (0-20% MeOH/DCM) to afford the title compound as a yellow foam (84 mg, 0.21 mmol, 73%): $^1$H NMR (400 MHz, CDCl$_3$) δ 9.00 (s, 1H), 8.65 (s, 1H), 8.29 (s, 1H), 8.03 (d, J=8.0 Hz, 1H), 7.54-7.39 (m, 1H), 4.89 (d, J=16.9 Hz, 1H), 4.20-4.08 (m, 1H), 4.07-3.92 (m, 1H), 3.01 (s, 3H), 2.34-2.29 (m, 1H), 1.67 (d, J=7.0 Hz, 3H); $^{13}$C NMR (101 MHz, CDCl$_3$) δ 166.97, 166.90, 148.77, 140.43, 140.24, 135.58, 129.36, 126.64, 124.14, 121.34, 73.80, 60.91, 38.78, 36.29, 13.97; ESIMS m/z 367 ([M+H]$^+$).

Compounds 620 and 621 were prepared in accordance with the procedure disclosed in Example 84.

Example 85

Preparation of N-(3-chloro-1-(pyridin-3-yl)-1H-pyrazol-4-yl)-2-(methylamino)-N-(prop-2-yn-1-yl) acetamide

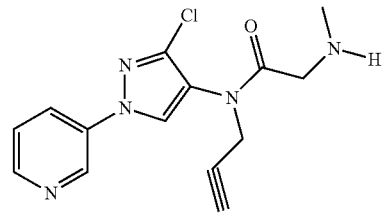 [SMILES: C#CCN(C(=O)CNC)c1cn(-c2cccnc2)nc1Cl]

To a solution of tert-butyl (2-((3-chloro-1-(pyridin-3-yl)-1H-pyrazol-4-yl)(prop-2-yn-1-yl)amino)-2-oxoethyl) (methyl)carbamate (0.47 g, 1.16 mmol) in DCM (1.16 ml) was added 2,2,2-trifluoroacetic acid (1.16 ml) and the reaction mixture was stirred at ambient temperature for 1 h. To the mixture was added toluene and then the reaction was concentrated to dryness. The oil was redissolved in DCM and saturated NaHCO$_3$ solution was added. The phases were separated and the aqueous phase was extracted with DCM. The organic layers were combined, the solvent evaporated, and the residue purified using silica gel chromatography (0-15% MeOH/DCM) to afford the title compound as yellow oil (0.258 g, 0.849 mmol, 73%): IR (thin film) 1696 cm$^{-1}$; $^1$H NMR (400 MHz, CDCl$_3$) δ 8.98 (d, J=2.6 Hz, 1H), 8.64 (dd, J=4.7, 1.3 Hz, 1H), 8.19 (s, 1H), 8.06 (ddd, J=8.3, 2.6, 1.4 Hz, 1H), 7.47 (dd, J=8.3, 4.7 Hz, 1H), 4.48 (s, 2H), 3.49 (s, 2H), 2.49 (s, 3H), 2.28 (t, J=2.5 Hz, 1H); ESIMS m/z 304 ([M+H]$^+$).

Example 86

Preparation of N-(3-chloro-1-(pyridin-3-yl)-1H-pyrazol-4-yl)-2-(N-methylmethylsulfonamido)-N-(prop-2-yn-1-yl)acetamide (Compound 623)

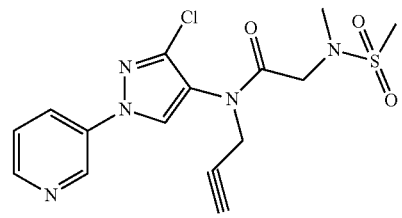 [SMILES: C#CCN(C(=O)CN(C)S(C)(=O)=O)c1cn(-c2cccnc2)nc1Cl]

To a solution of N-(3-chloro-1-(pyridin-3-yl)-1H-pyrazol-4-yl)-2-(methylamino)-N-(prop-2-yn-1-yl)acetamide (0.100 g, 0.329 mmol) in DCM (0.65 ml) was added methanesulfonyl chloride (0.057 g, 0.494 mmol) followed by diisopropylethylamine (0.11 ml, 0.658 mmol) and the reaction was stirred at room temperature for 24 h. The reaction mixture was poured into a solution of saturated NaHCO$_3$ and subsequently extracted with DCM. The organic layers were combined and concentrated, and the residue was purified using silica gel chromatography (50-100% EtOAc/hexanes) to afford the title compound as a yellow solid (0.091 g, 0.238 mmol, 72%): (IR thin film) 1678 cm$^{-1}$; $^1$H NMR (400 MHz, CDCl$_3$) δ 8.97 (d, J=2.6 Hz, 1H), 8.65 (dd, J=4.8, 1.3 Hz, 1H), 8.15 (s, 1H), 8.04 (ddd, J=8.3, 2.7, 1.4 Hz, 1H), 7.48 (dd, J=8.4, 4.7 Hz, 1H), 3.77 (hept, J=6.9 Hz, 2H), 3.05 (s, 2H), 3.01 (s, 3H), 2.87 (s, 3H), 2.31 (t, J=2.5 Hz, 1H); ESIMS m/z 382 ([M+H]$^+$).

Example 87

Preparation of 3-((3,3,3-trifluoropropyl)thio)propanoic acid

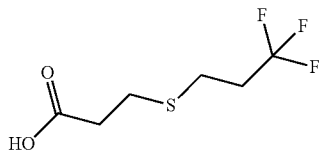 [SMILES: O=C(O)CCSCCC(F)(F)F]

3-Mercaptopropanoic acid (3.2 g, 30.1 mmol) was dissolved in MeOH (20 mL) and stirred at RT. Powdered potassium hydroxide (3.72 g, 66.3 mmol) was added to the solution, followed by 3-bromo-1,1,1-trifluoropropane (6.14 g, 34.7 mmol). The solution was then stirred at 65° C. for 3 h and then it was quenched with 1N HCl until the pH of the solution was acidic. The mixture was extracted with DCM (3×30 mL), the combined organic phases were dried, concentrated and purified by silica gel chromatography (0-50% EtOAc/hexane) to give 3-((3,3,3-trifluoropropyl)thio)propanoic acid (5.5 g, 27.2 mmol, 90% yield) as colorless oil mixed with some white suspension: IR (Thin film) 2936, 1708 cm$^{-1}$; $^1$H NMR (300 MHz, CDCl$_3$) δ 2.86-2.78 (m, 2H), 2.78-2.58 (m, 4H), 2.52-2.25 (m, 2H); EIMS m/z 202.

Example 88

Preparation of N-(3-methyl-1-(pyridin-3-yl)-1H-pyrazol-4-yl)-N-(prop-2-yn-1-yl)-3-((3,3,3-trifluoropropyl)thio)propanamide (Compound 627)

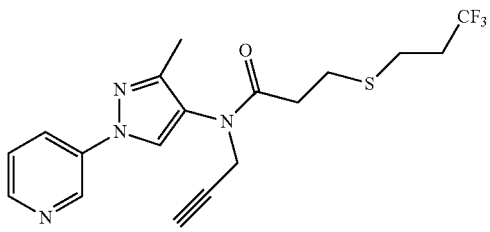 [SMILES: C#CCN(C(=O)CCSCCC(F)(F)F)c1cn(-c2cccnc2)nc1C]

In a 4 mL vial was added 3-methyl-N-(prop-2-yn-1-yl)-1-(pyridin-3-yl)-1H-pyrazol-4-amine hydrochloride (120 mg, 0.482 mmol) and DMAP (59 mg, 0.482 mmol) with dry Et$_2$O (1.6 mL). The solution was stirred at room temperature for 1 h. Then additional DMAP (200 mg, 1.639 mmol) was added. The solution was cooled to 0° C. under N$_2$ and dicyclohexylcarbodiimide (DCC; 239 mg, 1.158 mmol) was added. The solution was allowed to warm up to room temperature slowly and stirred overnight. White precipitate formed during the reaction. The crude reaction mixture was filtered and purified by silica gel chromatography (0-90% EtOAc/hexane) to give N-(3-methyl-1-(pyridin-3-yl)-1H-pyrazol-4-yl)-N-(prop-2-yn-1-yl)-3-((3,3,3-trifluoropropyl)thio)propanamide (113 mg, 0.269 mmol, 55.7% yield) as a yellow viscous oil: IR (Thin film) 3293, 1663 cm$^{-1}$; $^1$H NMR (400 MHz, CDCl$_3$) δ 8.96 (d, J=2.6 Hz, 1H), 8.58 (dd, J=4.8, 1.5 Hz, 1H), 8.04 (ddd, J=8.3, 2.7, 1.5 Hz, 1H), 8.01 (s, 1H), 7.44 (dd, J=8.3, 4.9 Hz, 1H), 4.45 (s, 2H), 2.84 (t, J=7.1 Hz, 2H), 2.72-2.60 (m, 2H), 2.44 (t, J=7.1 Hz, 2H), 2.41-2.32 (m, 2H), 2.31 (s, 3H), 2.26 (t, J=2.4 Hz, 1H); ESIMS m/z 397 ([M+H]$^+$).

Example A

Bioassays on Green Peach Aphid ("GPA") (*Myzus persicae*) (MYZUPE)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides.

Certain molecules disclosed in this document were tested against GPA using procedures described in the following example. In the reporting of the results, "Table 3: GPA (MYZUPE) and sweetpotato whitefly-crawler (BEMITA) Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in H$_2$O to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=100*(X−Y)/X where
X=No. of live aphids on solvent check plants and
Y=No. of live aphids on treated plants The results are indicated in the table entitled "Table 4. Biological Data for GPA (MYZUPE) and sweetpotato whitefly-crawler (BEMITA)" (See Table Section).

Example B

Insecticidal Test for Sweetpotato Whitefly-Crawler (*Bemisia tabaci*) (BEMITA) in Foliar Spray Assay Cotton plants grown in 3-inch pots, with 1 small (3-5 cm) true leaf, were used as test substrate. The plants were placed in a room with whitefly adults. Adults were allowed to deposit eggs for 2-3 days. After a 2-3 day egg-laying period, plants were taken from the adult whitefly room. Adults were blown off leaves using a hand-held Devilbiss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in $H_2O$ to obtain a test solution at 200 ppm. A hand-held Devilbiss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity was measured by using Abbott's correction formula and presented in "Table 4. Biological Data for GPA (MYZUPE) and sweetpotato whitefly-crawler (BEMITA)" (see column "BEMITA"):

$$\text{Corrected \% Control} = 100 * (X-Y)/X$$

where X=No. of live nymphs on solvent check plants
Y=No. of live nymphs on treated plants Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the invention disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

Molecules of Formula One may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, the molecules of Formula One may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with the Molecules of Formula One are—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DBdimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-5-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, bengodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluoron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlomidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenten, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfuram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujianxiaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, fluorochloridone, fluoroxypyr, fluoroxypyr-butomethyl, fluoroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexylure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nomicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluoron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluoron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfuram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluoron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluoron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood-.net/pesticides/index.html. Also consult "THE PESTICIDE MANUAL" 14th Edition, edited by C D S Tomlin, copyright 2006 by British Crop Production Council, or its prior or more recent editions.

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:
1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella granulovirus*).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:
1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N-1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Synergistic Mixtures

Molecules of Formula One may be used with certain active compounds to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of the molecules of Formula One in a synergistic mixture with another compound are from about 10:1 to about 1:10, in another embodiment from about 5:1 to about 1:5, and in another embodiment from about 3:1, and in another embodiment about 1:1.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n°2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana*.

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni*, and *Tapinoma sessile*.

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One may be used to control pest of the Order Symphyla. A non-exhaustive list of particular sp. includes, but is not limited to, *Scutigerella immaculata*.

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section

TABLE 1

Compound number, appearance, and structure

| Compound No. | Appearance | Structure |
|---|---|---|
| 1 | Yellow Gum | 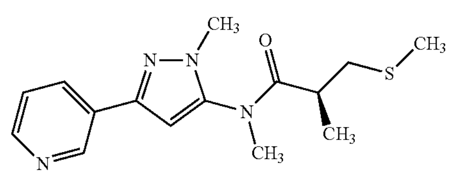 [SMILES: CSC[C@@H](C)C(=O)N(C)c1cc(-c2cccnc2)nn1C] |
| 2 | Yellow Solid | 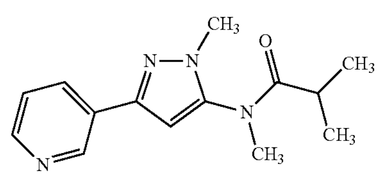 [SMILES: CC(C)C(=O)N(C)c1cc(-c2cccnc2)nn1C] |
| 3 | Yellow Gum | 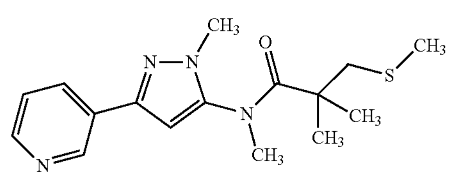 [SMILES: CSCC(C)(C)C(=O)N(C)c1cc(-c2cccnc2)nn1C] |
| 4 | Yellow Oil | 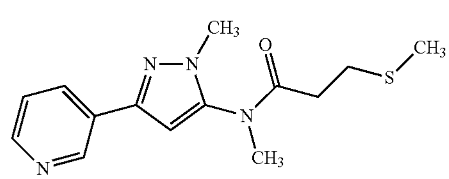 [SMILES: CSCCC(=O)N(C)c1cc(-c2cccnc2)nn1C] |

TABLE 1-continued

| Compound No. | Appearance | Structure |
|---|---|---|
| 5 | Yellow Oil | 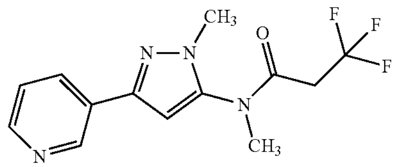 [SMILES: CN(C(=O)CC(F)(F)F)c1cc(-c2cccnc2)nn1C] |
| 6 | Yellow Gum | 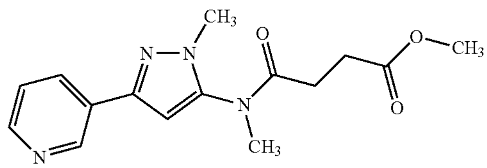 [SMILES: COC(=O)CCC(=O)N(C)c1cc(-c2cccnc2)nn1C] |
| 7 | Yellow Gum | 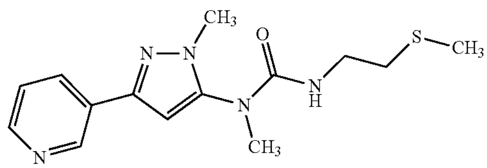 [SMILES: CSCCNC(=O)N(C)c1cc(-c2cccnc2)nn1C] |
| 8 | Yellow Gum | 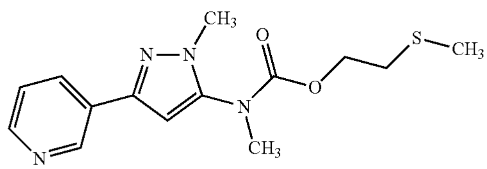 [SMILES: CSCCOC(=O)N(C)c1cc(-c2cccnc2)nn1C] |
| 9 | Beige Gum | 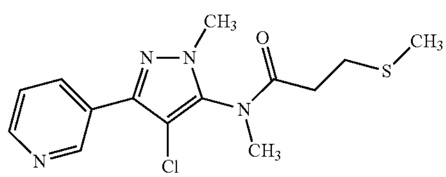 [SMILES: CSCCC(=O)N(C)c1c(Cl)c(-c2cccnc2)nn1C] |
| 10 | Colorless Gum | 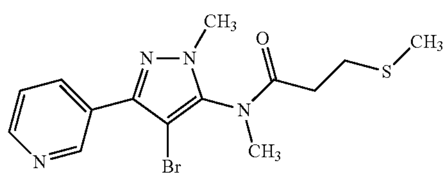 [SMILES: CSCCC(=O)N(C)c1c(Br)c(-c2cccnc2)nn1C] |
| 12 | Colorless Glass | 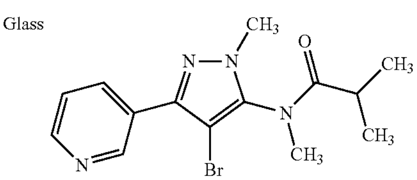 |
| 18 | Brown Oil | 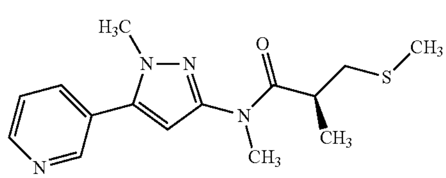 [SMILES: CSC[C@@H](C)C(=O)N(C)c1cc(-c2cccnc2)n(C)n1] |

TABLE 1-continued

| Compound No. | Appearance | Structure |
|---|---|---|
| 19 | Yellow Oil | 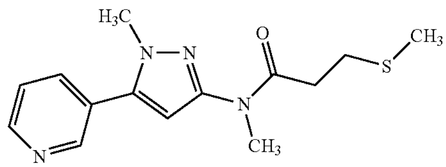 [SMILES: CSCCC(=O)N(C)c1cc(-c2cccnc2)n(C)n1] |
| 20 | Yellow Oil | 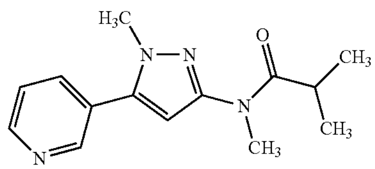 [SMILES: CC(C)C(=O)N(C)c1cc(-c2cccnc2)n(C)n1] |
| 21 | Yellow Oil | 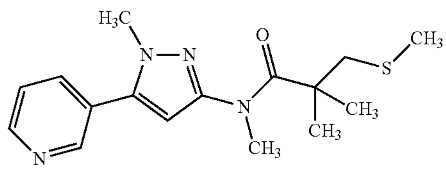 [SMILES: CSCC(C)(C)C(=O)N(C)c1cc(-c2cccnc2)n(C)n1] |
| 22 | Clear Oil | 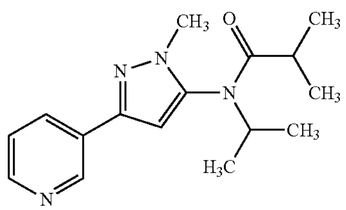 [SMILES: CC(C)C(=O)N(c1cc(-c2cccnc2)nn1C)C(C)C] |
| 23 | Clear Oil | 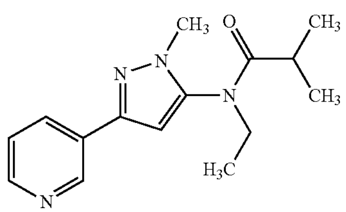 [SMILES: CCN(C(=O)C(C)C)c1cc(-c2cccnc2)nn1C] |
| 24 | | 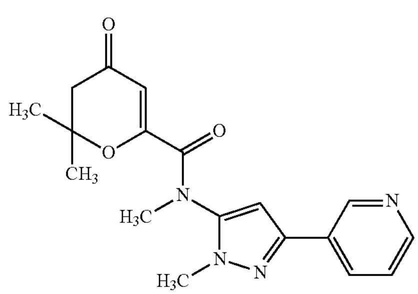 [SMILES: CN(C(=O)C1=CC(=O)CC(C)(C)O1)c1cc(-c2cccnc2)nn1C] |
| 25 | | 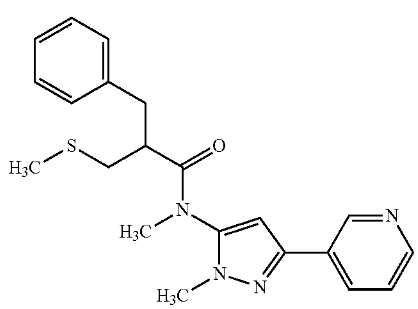 [SMILES: CSCC(Cc1ccccc1)C(=O)N(C)c1cc(-c2cccnc2)nn1C] |

TABLE 1-continued

Compound number, appearance, and structure

| Compound No. | Appearance | Structure |
|---|---|---|
| 26 | | (structure) |
| 27 | | (structure) |
| 28 | | (structure) |
| 29 | | (structure) |
| 30 | | (structure) |
| 31 | | (structure) |
| 32 | Gold Syrup | (structure) |

TABLE 1-continued
| Compound No. | Appearance | Structure |
|---|---|---|
| 33 | Brown Solid | 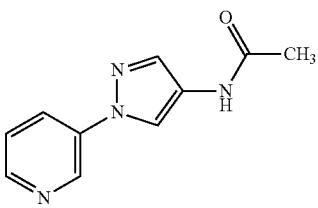 |
| 34 | Off White Solid | 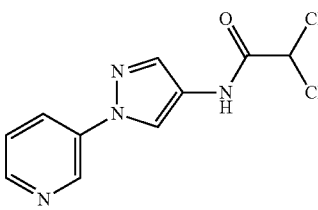 |
| 35 | Off White Solid | 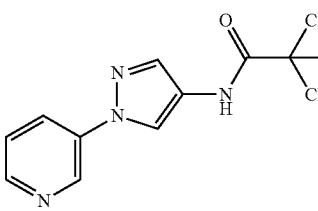 |
| 36 | Off White Solid | 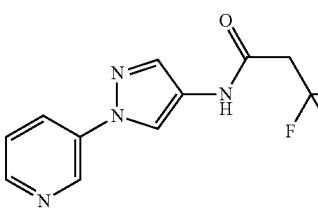 |
| 37 | White Solid | 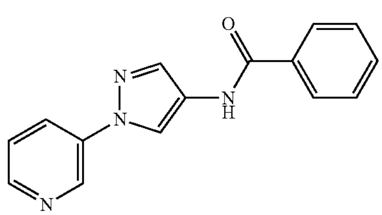 [SMILES: O=C(Nc1cnn(-c2cccnc2)c1)c1ccccc1] |
| 38 | Off White Solid | 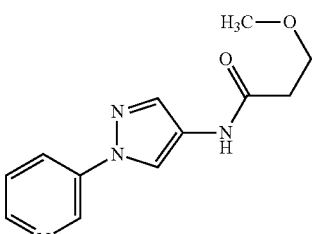 |

TABLE 1-continued
| Compound No. | Appearance | Structure |
|---|---|---|
| 39 | White Solid | 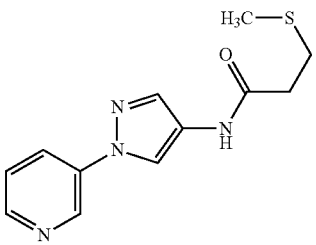 [SMILES: CSCCC(=O)Nc1cnn(-c2cccnc2)c1] |
| 40 | Pale Yellow Solid | 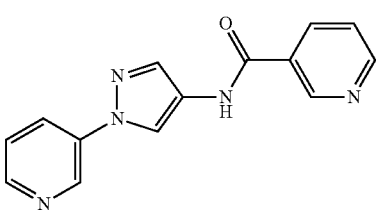 [SMILES: O=C(Nc1cnn(-c2cccnc2)c1)c1cccnc1] |
| 41 | Brown Thick Mass | 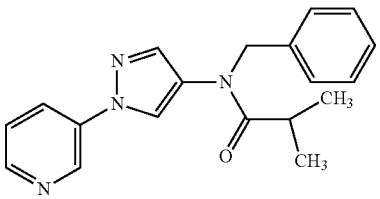 [SMILES: CC(C)C(=O)N(Cc1ccccc1)c1cnn(-c2cccnc2)c1] |
| 42 | Pale Yellow Semi Solid | 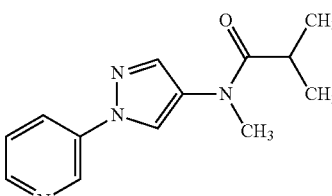 |
| 43 | Pale Yellow Solid | 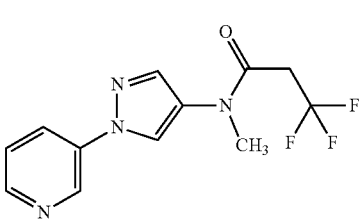 [SMILES: CN(C(=O)CC(F)(F)F)c1cnn(-c2cccnc2)c1] |
| 44 | White Solid | 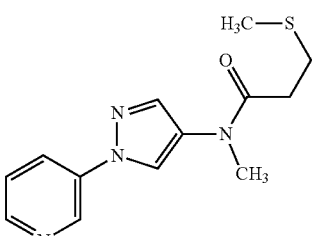 |

TABLE 1-continued
| Compound No. | Appearance | Structure |
|---|---|---|
| 45 | Brown Thick Mass | 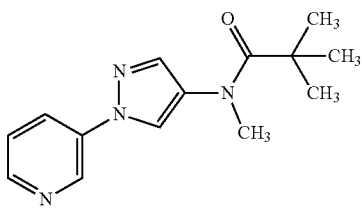 [SMILES: CN(C(=O)C(C)(C)C)c1cnn(-c2cccnc2)c1] |
| 46 | Pale Yellow Thick Mass | 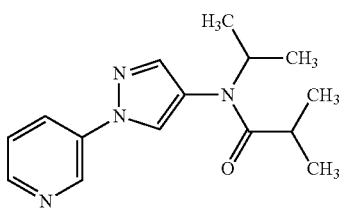 [SMILES: CC(C)C(=O)N(c1cnn(-c2cccnc2)c1)C(C)C] |
| 47 | Pale Yellow Thick Mass | 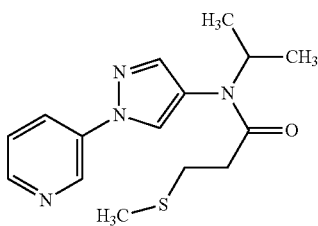 [SMILES: CSCCC(=O)N(c1cnn(-c2cccnc2)c1)C(C)C] |
| 48 | Pale Green Mass | 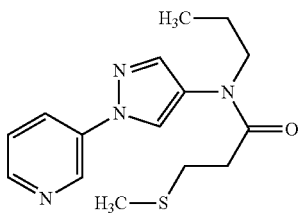 [SMILES: CCCN(C(=O)CCSC)c1cnn(-c2cccnc2)c1] |
| 49 | Pale Yellow Solid | 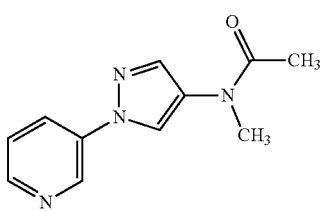 [SMILES: CC(=O)N(C)c1cnn(-c2cccnc2)c1] |
| 50 | Brown Thick Mass | 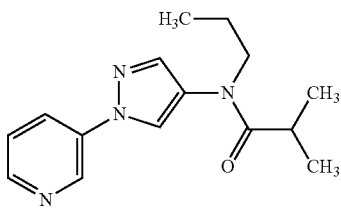 [SMILES: CCCN(C(=O)C(C)C)c1cnn(-c2cccnc2)c1] |

TABLE 1-continued
Compound number, appearance, and structure
| Compound No. | Appearance | Structure |
|---|---|---|
| 51 | Pale Yellow Thick Mass | 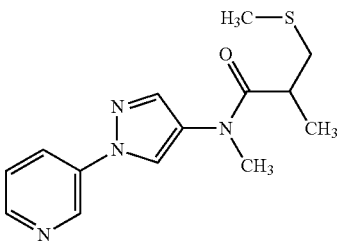 [SMILES: CSCC(C)C(=O)N(C)c1cnn(-c2cccnc2)c1] |
| 52 | Tan Solid | 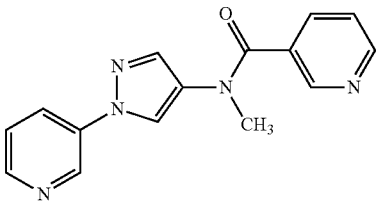 [SMILES: CN(C(=O)c1cccnc1)c1cnn(-c2cccnc2)c1] |
| 53 | White Solid | 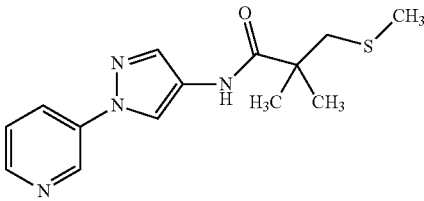 [SMILES: CSCC(C)(C)C(=O)Nc1cnn(-c2cccnc2)c1] |
| 54 | Clear Oil | 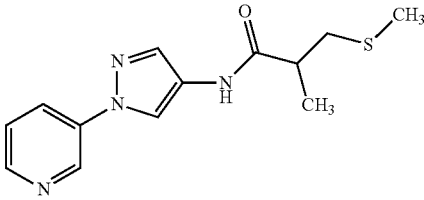 [SMILES: CSCC(C)C(=O)Nc1cnn(-c2cccnc2)c1] |
| 55 | White Semi Solid | 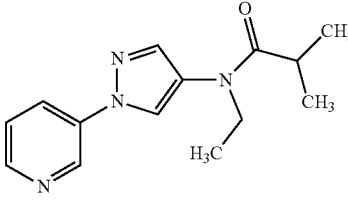 |
| 56 | Brown Solid | 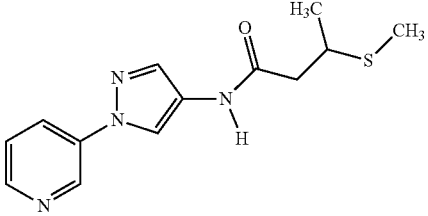 [SMILES: CSC(C)CC(=O)Nc1cnn(-c2cccnc2)c1] |
| 57 | White Solid | 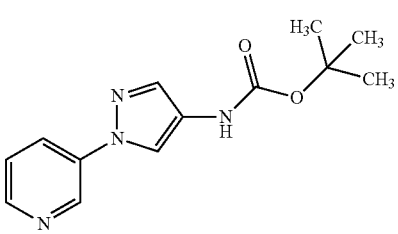 [SMILES: CC(C)(C)OC(=O)Nc1cnn(-c2cccnc2)c1] |

TABLE 1-continued
| Compound No. | Appearance | Structure |
|---|---|---|
| 58 | Clear Oil | 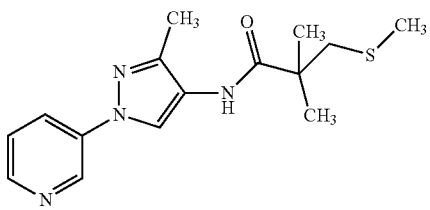 [SMILES: CSCC(C)(C)C(=O)Nc1cn(-c2cccnc2)nc1C] |
| 59 | White Solid | 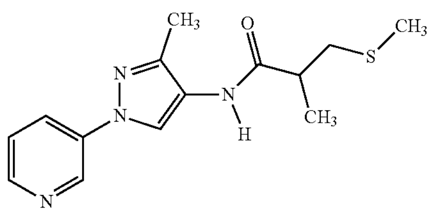 [SMILES: CSCC(C)C(=O)Nc1cn(-c2cccnc2)nc1C] |
| 60 | White Solid | 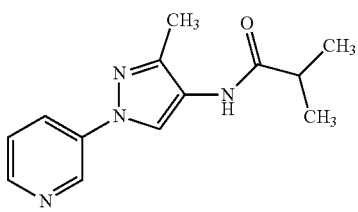 [SMILES: Cc1nn(-c2cccnc2)cc1NC(=O)C(C)C] |
| 61 | Light Yellow Solid | 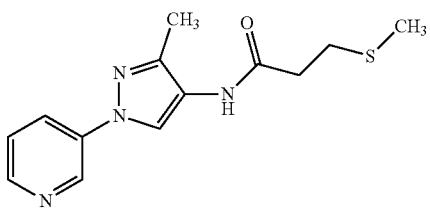 [SMILES: CSCCC(=O)Nc1cn(-c2cccnc2)nc1C] |
| 62 | Clear Oil | 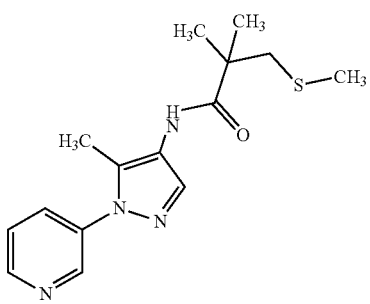 [SMILES: CSCC(C)(C)C(=O)Nc1cnn(-c2cccnc2)c1C] |
| 63 | Light Yellow Solid | 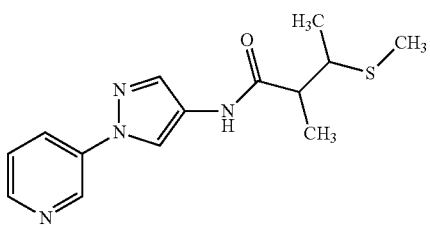 [SMILES: CSC(C)C(C)C(=O)Nc1cnn(-c2cccnc2)c1] |

TABLE 1-continued

| Compound No. | Appearance | Structure |
|---|---|---|
| 64 | White Solid | 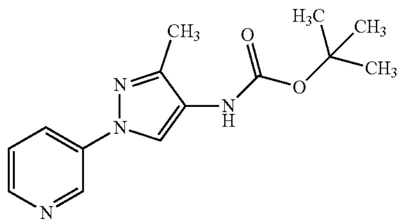 [SMILES: Cc1nn(-c2cccnc2)cc1NC(=O)OC(C)(C)C] |
| 65 | White Solid | 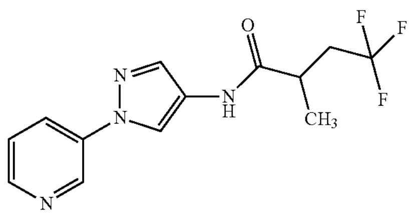 [SMILES: CC(CC(F)(F)F)C(=O)Nc1cnn(-c2cccnc2)c1] |
| 66 | White Semi Solid | 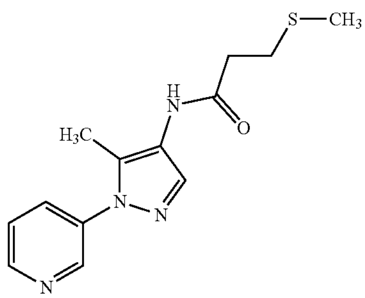 [SMILES: CSCCC(=O)Nc1cnn(-c2cccnc2)c1C] |
| 67 | Yellow Semi Solid | 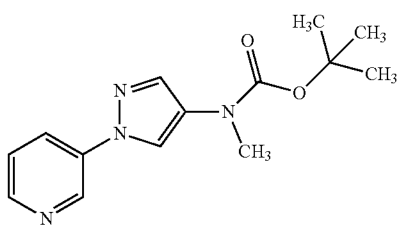 [SMILES: CN(C(=O)OC(C)(C)C)c1cnn(-c2cccnc2)c1] |
| 68 | Clear Oil | 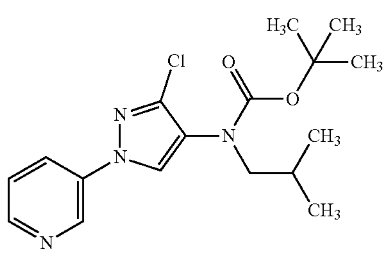 [SMILES: CC(C)CN(C(=O)OC(C)(C)C)c1cn(-c2cccnc2)nc1Cl] |
| 69 | Dark Brown Oil | 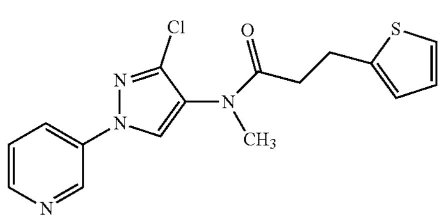 [SMILES: CN(C(=O)CCc1cccs1)c1cn(-c2cccnc2)nc1Cl] |

TABLE 1-continued
| Compound No. | Appearance | Structure |
|---|---|---|
| 70 | Viscous Pale Yellow Oil | 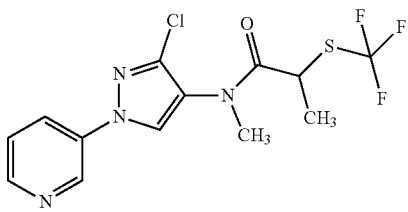 [SMILES: CC(SC(F)(F)F)C(=O)N(C)c1cn(-c2cccnc2)nc1Cl] |
| 71 | White Solid | 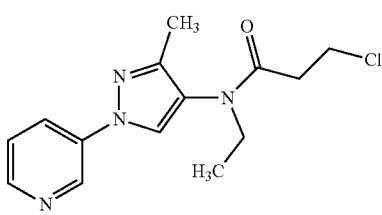 [SMILES: CCN(C(=O)CCCl)c1cn(-c2cccnc2)nc1C] |
| 72 | White Semi Solid | 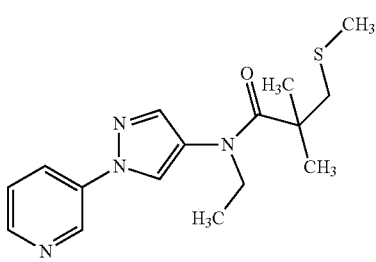 [SMILES: CCN(C(=O)C(C)(C)CSC)c1cnn(-c2cccnc2)c1] |
| 73 | White Semi Solid | 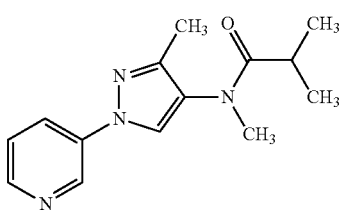 [SMILES: Cc1nn(-c2cccnc2)cc1N(C)C(=O)C(C)C] |
| 74 | Clear Oil | 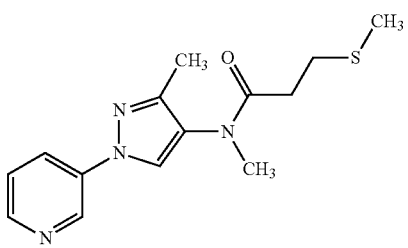 [SMILES: CSCCC(=O)N(C)c1cn(-c2cccnc2)nc1C] |
| 75 | White Semi Solid | 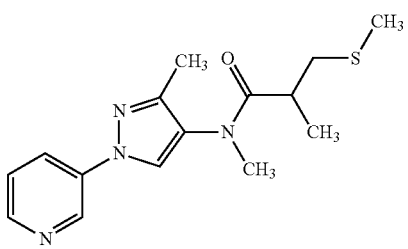 [SMILES: CSCC(C)C(=O)N(C)c1cn(-c2cccnc2)nc1C] |

TABLE 1-continued

Compound number, appearance, and structure

| Compound No. | Appearance | Structure |
|---|---|---|
| 76 | Clear Oil | 3-methyl-1-(pyridin-3-yl)-1H-pyrazol-4-yl, N-methyl, 2,2-dimethyl-3-(methylthio)propanamide |
| 77 | White Solid | 3-chloro-1-(pyridin-3-yl)-1H-pyrazol-4-yl, isobutyramide |
| 78 | White Solid | 3-chloro-1-(pyridin-3-yl)-1H-pyrazol-4-yl, 3-(methylthio)propanamide |
| 79 | White Solid | 3-chloro-1-(pyridin-3-yl)-1H-pyrazol-4-yl, 2-methyl-3-(methylthio)propanamide |
| 80 | White Solid | 3-chloro-1-(pyridin-3-yl)-1H-pyrazol-4-yl, 2-methyl-3-(methylthio)butanamide |
| 81 | White Solid | 3-chloro-1-(pyridin-3-yl)-1H-pyrazol-4-yl, 5,5,5-trifluoropentanamide |

TABLE 1-continued

Compound number, appearance, and structure

| Compound No. | Appearance | Structure |
|---|---|---|
| 82 | White Solid | |
| 83 | White Solid | |
| 84 | White Solid | |
| 85 | Off White Solid | |
| 86 | Yellow Solid | |
| 87 | Yellow Solid | |

TABLE 1-continued

| Compound No. | Appearance | Structure |
|---|---|---|
| 88 | White Solid | 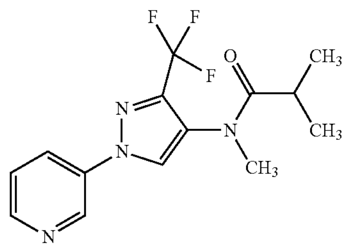 [SMILES: CC(C)C(=O)N(C)c1cn(-c2cccnc2)nc1C(F)(F)F] |
| 89 | White Solid | 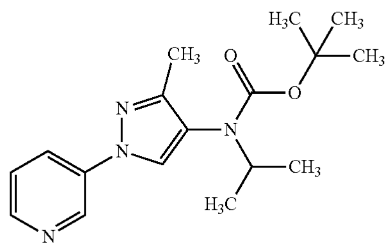 [SMILES: Cc1nn(-c2cccnc2)cc1N(C(=O)OC(C)(C)C)C(C)C] |
| 90 | Clear Oil | 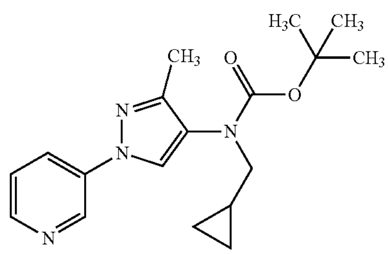 [SMILES: Cc1nn(-c2cccnc2)cc1N(CC1CC1)C(=O)OC(C)(C)C] |
| 91 | Faint Yellow Oil | 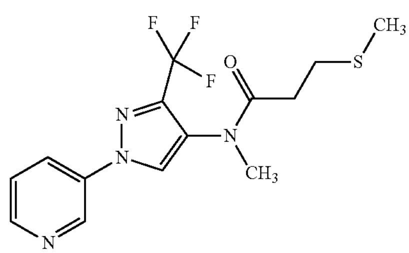 [SMILES: CSCCC(=O)N(C)c1cn(-c2cccnc2)nc1C(F)(F)F] |
| 92 | Faint Yellow Oil | 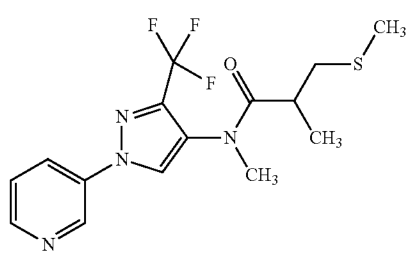 [SMILES: CSCC(C)C(=O)N(C)c1cn(-c2cccnc2)nc1C(F)(F)F] |
| 93 | White Solid | 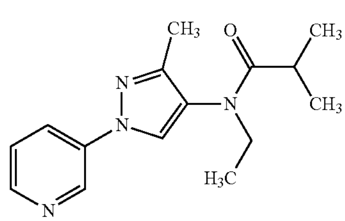 [SMILES: CCN(C(=O)C(C)C)c1cn(-c2cccnc2)nc1C] |

TABLE 1-continued
Compound number, appearance, and structure
| Compound No. | Appearance | Structure |
|---|---|---|
| 94 | Clear Oil | 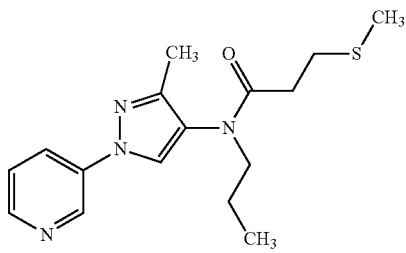 [SMILES: CCCN(C(=O)CCSC)c1cn(-c2cccnc2)nc1C] |
| 95 | Clear Oil | 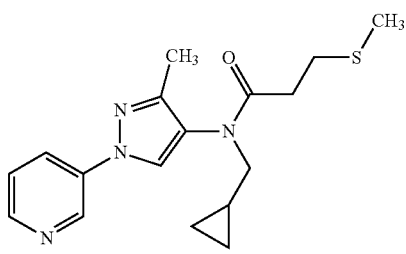 [SMILES: CSCCC(=O)N(CC1CC1)c1cn(-c2cccnc2)nc1C] |
| 96 | Yellow Solid | 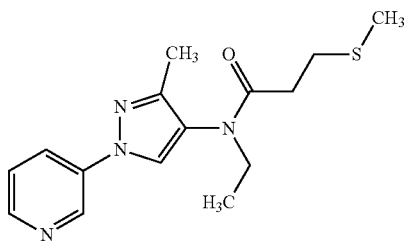 [SMILES: CCN(C(=O)CCSC)c1cn(-c2cccnc2)nc1C] |
| 97 | Yellow Oil | 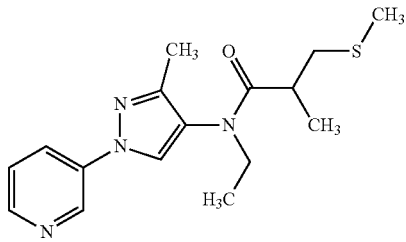 [SMILES: CCN(C(=O)C(C)CSC)c1cn(-c2cccnc2)nc1C] |
| 98 | Yellow Oil | 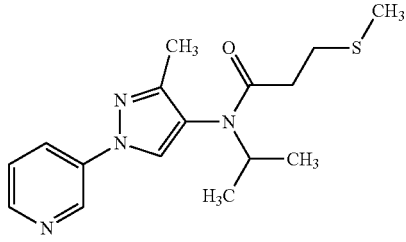 [SMILES: CSCCC(=O)N(c1cn(-c2cccnc2)nc1C)C(C)C] |
| 99 | Yellow Solid | 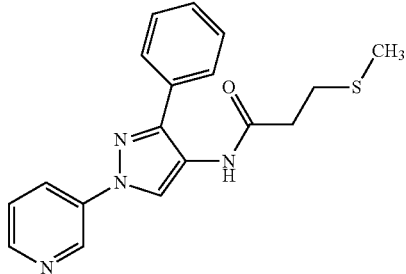 [SMILES: CSCCC(=O)Nc1cn(-c2cccnc2)nc1-c1ccccc1] |

TABLE 1-continued

Compound number, appearance, and structure

| Compound No. | Appearance | Structure |
|---|---|---|
| 100 | Clear Oil | 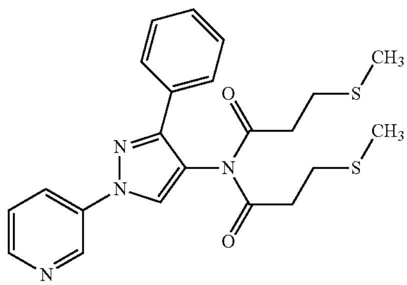 [SMILES: CSCCC(=O)N(C(=O)CCSC)c1cn(-c2cccnc2)nc1-c1ccccc1] |
| 101 | Clear Oil | 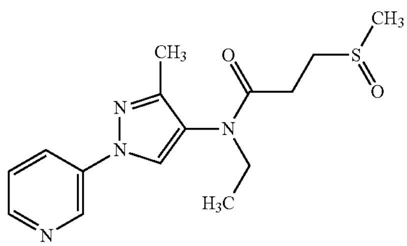 [SMILES: CCN(C(=O)CCS(C)=O)c1cn(-c2cccnc2)nc1C] |
| 102 | Clear Oil | 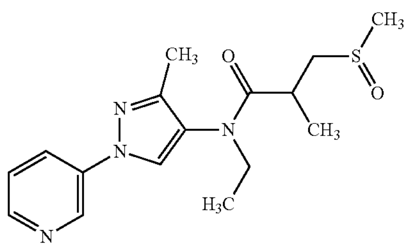 [SMILES: CCN(C(=O)C(C)CS(C)=O)c1cn(-c2cccnc2)nc1C] |
| 103 | Clear Oil | 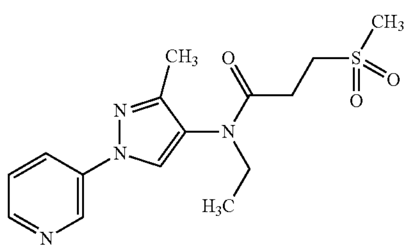 [SMILES: CCN(C(=O)CCS(C)(=O)=O)c1cn(-c2cccnc2)nc1C] |
| 104 | Faint Yellow Oil | 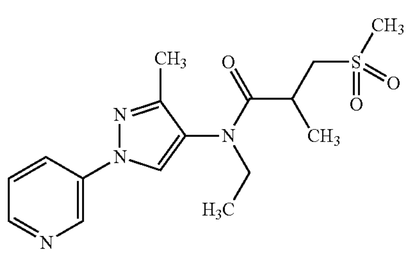 [SMILES: CCN(C(=O)C(C)CS(C)(=O)=O)c1cn(-c2cccnc2)nc1C] |
| 105 | Off White Solid | 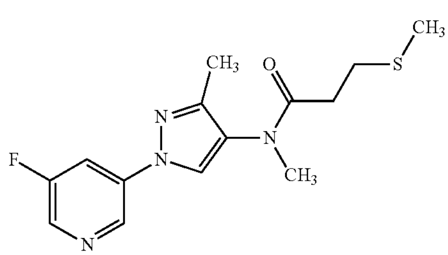 [SMILES: CSCCC(=O)N(C)c1cn(-c2cncc(F)c2)nc1C] |

TABLE 1-continued
Compound number, appearance, and structure
| Compound No. | Appearance | Structure |
|---|---|---|
| 106 | Faint Yellow Oil | 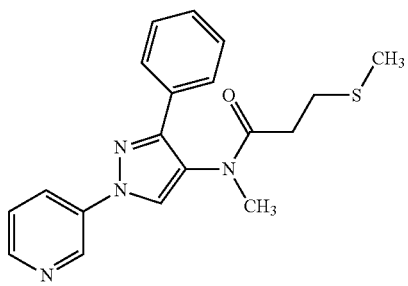 [SMILES: CSCCC(=O)N(C)c1cn(-c2cccnc2)nc1-c1ccccc1] |
| 107 | White Solid | 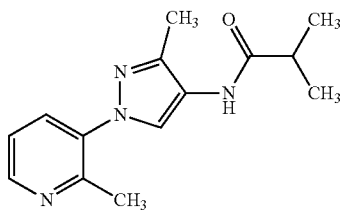 [SMILES: Cc1nn(-c2cccnc2C)cc1NC(=O)C(C)C] |
| 108 | Clear Oil | 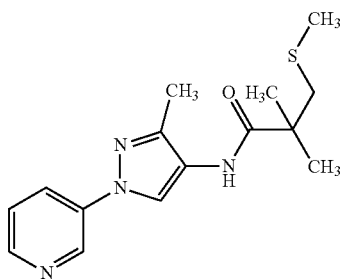 [SMILES: CSCC(C)(C)C(=O)Nc1cn(-c2cccnc2)nc1C] |
| 109 | Yellow Solid | 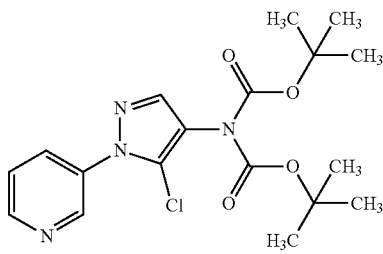 [SMILES: CC(C)(C)OC(=O)N(C(=O)OC(C)(C)C)c1cnn(-c2cccnc2)c1Cl] |
| 110 | Brown Oil | 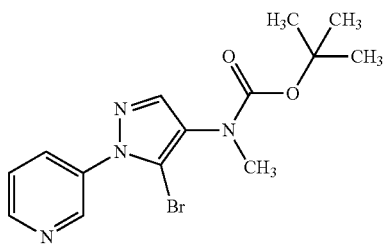 [SMILES: CN(C(=O)OC(C)(C)C)c1cnn(-c2cccnc2)c1Br] |

TABLE 1-continued
| Compound number, appearance, and structure |||
| --- | --- | --- |
| Compound No. | Appearance | Structure |
| 111 | Yellow Solid | 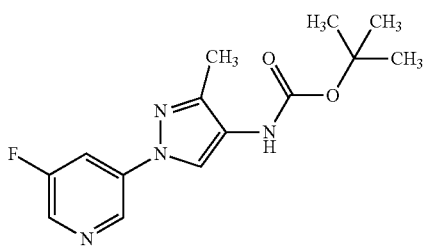 [SMILES: Cc1nn(-c2cncc(F)c2)cc1NC(=O)OC(C)(C)C] |
| 112 | Brown Oil | 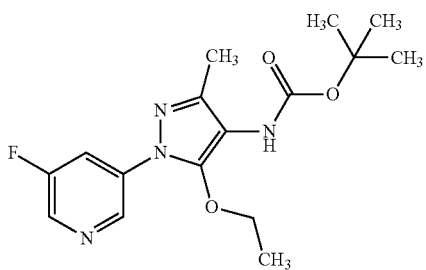 [SMILES: CCOc1c(NC(=O)OC(C)(C)C)c(C)nn1-c1cncc(F)c1] |
| 113 | Yellow Oil | 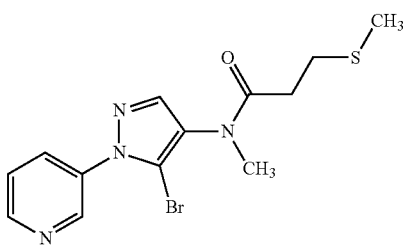 [SMILES: CSCCC(=O)N(C)c1cnn(-c2cccnc2)c1Br] |
| 114 | Brown Oil | 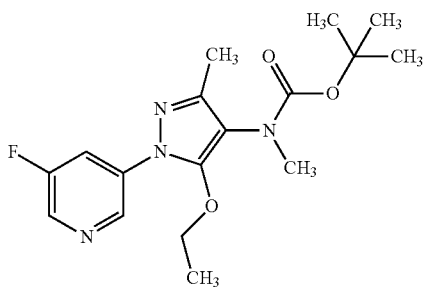 [SMILES: CCOc1c(N(C)C(=O)OC(C)(C)C)c(C)nn1-c1cncc(F)c1] |
| 115 | Light Brown Solid | 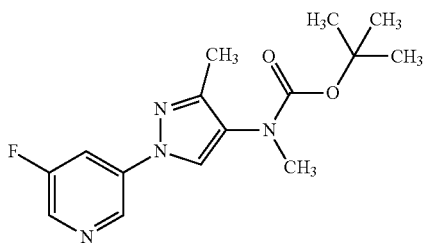 [SMILES: Cc1nn(-c2cncc(F)c2)cc1N(C)C(=O)OC(C)(C)C] |

TABLE 1-continued

Compound number, appearance, and structure

| Compound No. | Appearance | Structure |
|---|---|---|
| 116 | Yellow Solid | 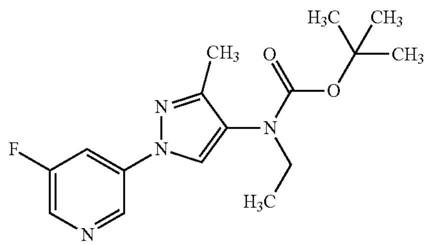 [SMILES: CCN(C(=O)OC(C)(C)C)c1cn(-c2cncc(F)c2)nc1C] |
| 117 | Yellow Oil | 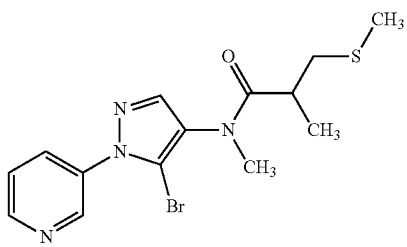 [SMILES: CSCC(C)C(=O)N(C)c1cnn(-c2cccnc2)c1Br] |
| 118 | Brown Oil | 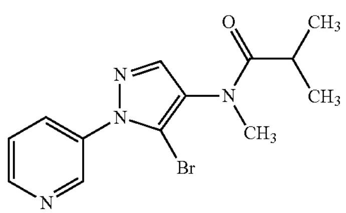 [SMILES: CC(C)C(=O)N(C)c1cnn(-c2cccnc2)c1Br] |
| 119 | Brown Oil | 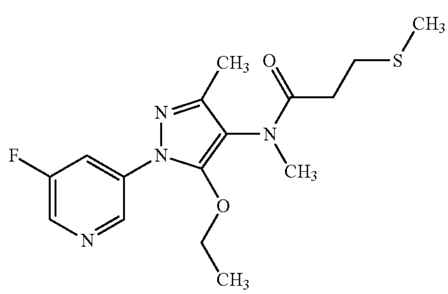 [SMILES: CCOc1c(N(C)C(=O)CCSC)c(C)nn1-c1cncc(F)c1] |
| 120 | Brown Oil | 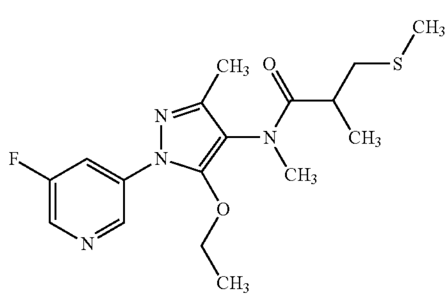 [SMILES: CCOc1c(N(C)C(=O)C(C)CSC)c(C)nn1-c1cncc(F)c1] |
| 121 | Off White Solid | 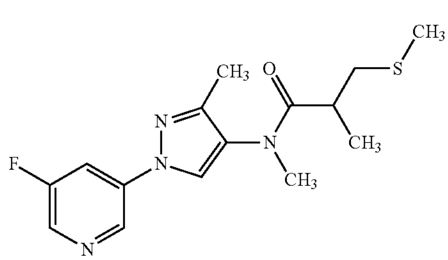 [SMILES: CSCC(C)C(=O)N(C)c1cn(-c2cncc(F)c2)nc1C] |

TABLE 1-continued
| Compound No. | Appearance | Structure |
|---|---|---|
| 122 | Faint Yellow Solid | 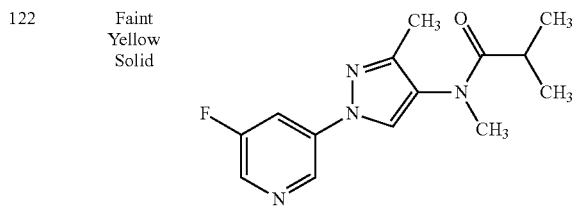 |
| 123 | Clear Oil | 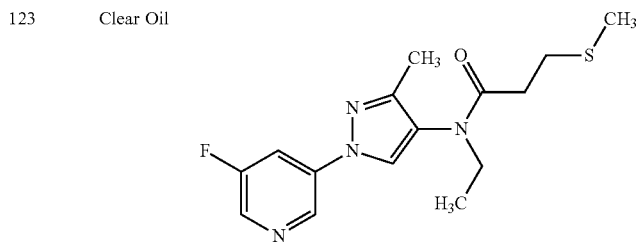 |
| 124 | Yellow Solid | 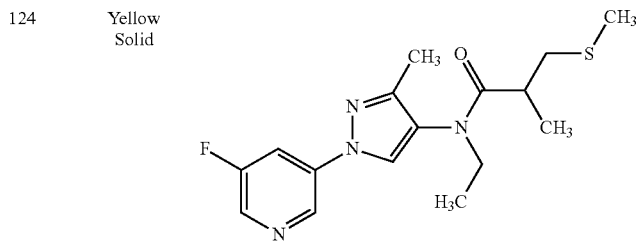 |
| 125 | White Solid | 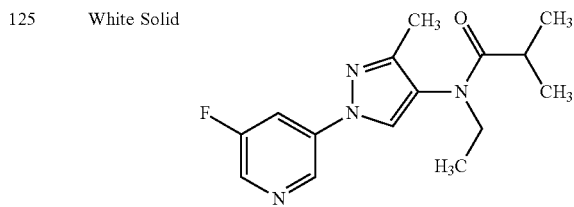 |
| 126 | Yellow Oil | 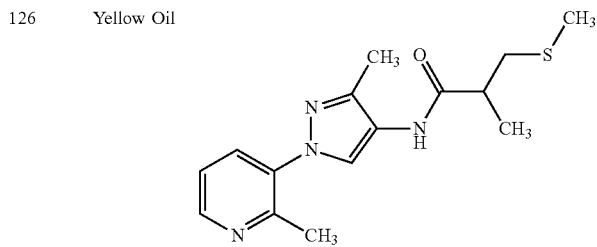 |
| 127 | Yellow Oil | 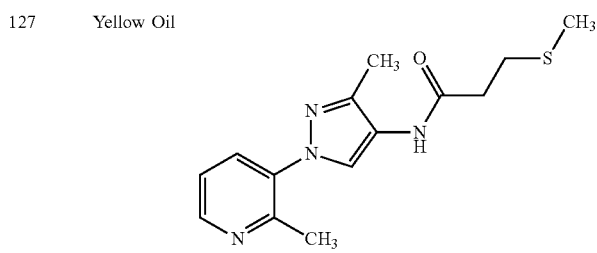 |

TABLE 1-continued
| Compound No. | Appearance | Structure |
|---|---|---|
| 128 | Neon Yellow Oil | 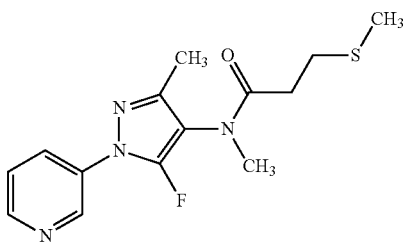 [SMILES: CSCCC(=O)N(C)c1c(C)nn(-c2cccnc2)c1F] |
| 129 | Neon Yellow Oil | 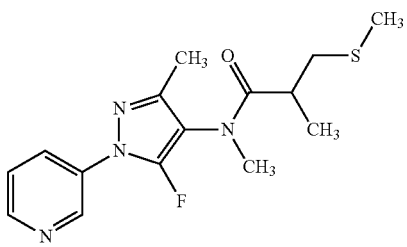 |
| 130 | Pink Solid | 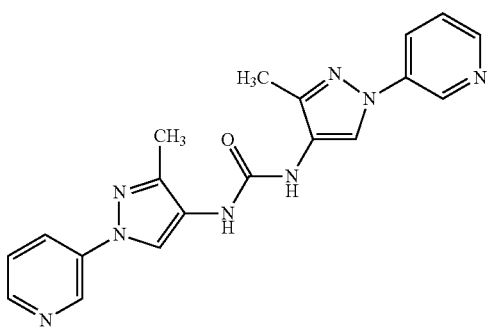 [SMILES: Cc1nn(-c2cccnc2)cc1NC(=O)Nc1cn(-c2cccnc2)nc1C] |
| 131 | Red Oil | 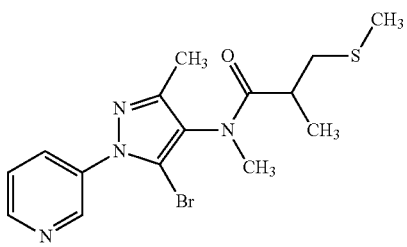 [SMILES: CSCC(C)C(=O)N(C)c1c(C)nn(-c2cccnc2)c1Br] |
| 132 | Yellow Oil | 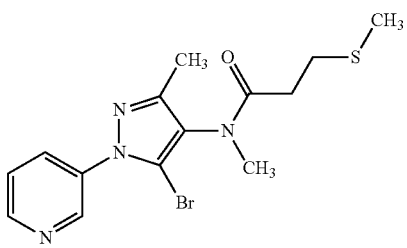 [SMILES: CSCCC(=O)N(C)c1c(C)nn(-c2cccnc2)c1Br] |

TABLE 1-continued
Compound number, appearance, and structure
| Compound No. | Appearance | Structure |
|---|---|---|
| 133 | Yellow Oil | 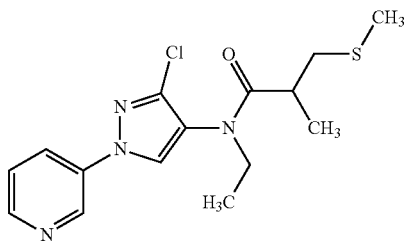 |
| 134 | Clear Oil | 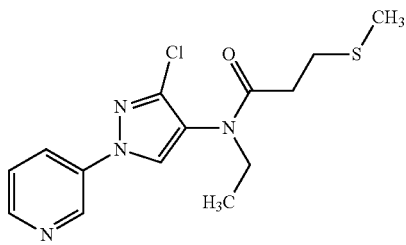 |
| 135 | Off White Solid | 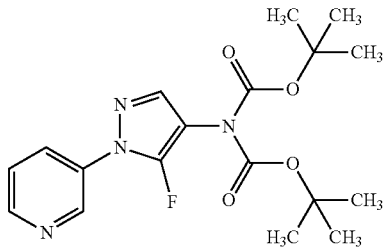 [SMILES: CC(C)(C)OC(=O)N(C(=O)OC(C)(C)C)c1cnn(-c2cccnc2)c1F] |
| 136 | Yellow Oil | 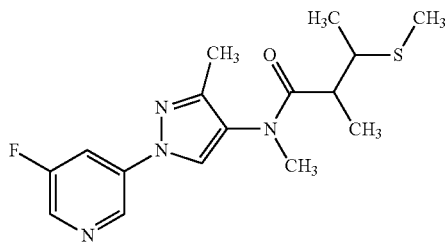 [SMILES: CSC(C)C(C)C(=O)N(C)c1cn(-c2cncc(F)c2)nc1C] |
| 137 | Yellow Oil | 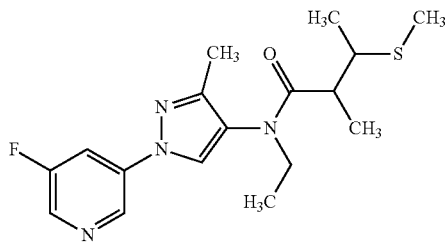 [SMILES: CCN(C(=O)C(C)C(C)SC)c1cn(-c2cncc(F)c2)nc1C] |
| 138 | Yellow Oil | 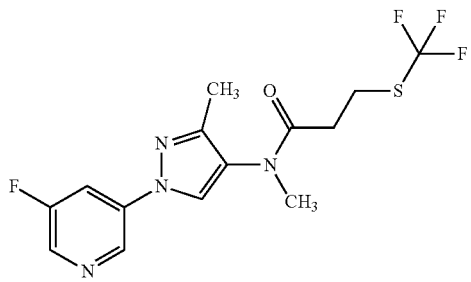 [SMILES: Cc1nn(-c2cncc(F)c2)cc1N(C)C(=O)CCSC(F)(F)F] |

TABLE 1-continued

Compound number, appearance, and structure

| Compound No. | Appearance | Structure |
|---|---|---|
| 139 | Faint Yellow Oil | 1-(pyridin-3-yl)-3-methyl-5-chloro-pyrazol-4-yl, N-methyl, N-C(O)CH₂CH₂SCH₃ |
| 140 | Faint Yellow | 1-(pyridin-3-yl)-3-methyl-5-chloro-pyrazol-4-yl, N-methyl, N-C(O)CH(CH₃)CH₂SCH₃ |
| 141 | Light Yellow Solid | 1-(pyridin-3-yl)-3-methyl-pyrazol-4-yl, N-allyl, N-C(O)O-C(CH₃)₃ |
| 142 | Clear Oil | 1-(pyridin-3-yl)-3-methyl-pyrazol-4-yl, N-allyl, N-C(O)O-C(CH₃)₃ |
| 143 | Colorless Oil | 1-(pyridin-3-yl)-3-methyl-pyrazol-4-yl, N-allyl, N-C(O)CH₂CH₂SCH₃ |
| 144 | Colorless Oil | 1-(pyridin-3-yl)-3-methyl-pyrazol-4-yl, N-allyl, N-C(O)CH(CH₃)CH₂SCH₃ |

TABLE 1-continued
| Compound number, appearance, and structure | | |
|---|---|---|
| Compound No. | Appearance | Structure |
| 145 | White Solid | 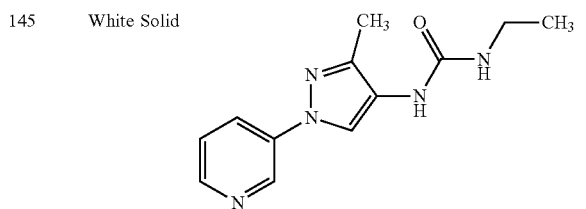 |
| 146 | Gray Oil | 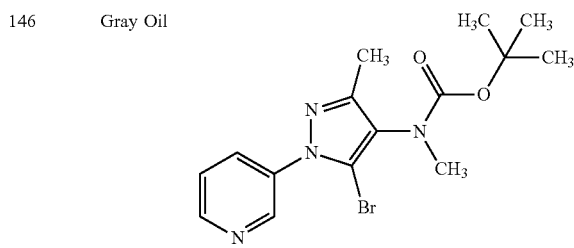 |
| 147 | Colorless Oil | 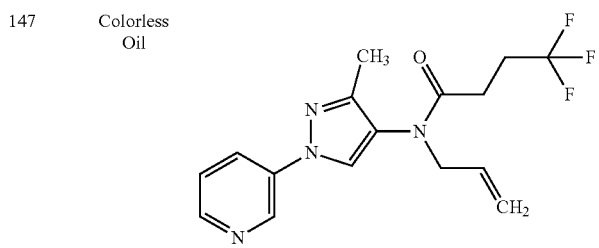 |
| 148 | White Solid | 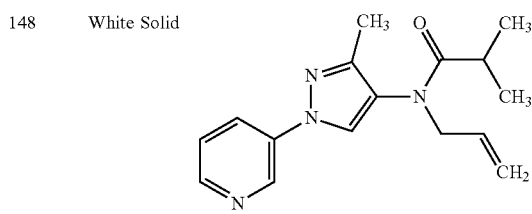 |
| 149 | Yellow Solid | 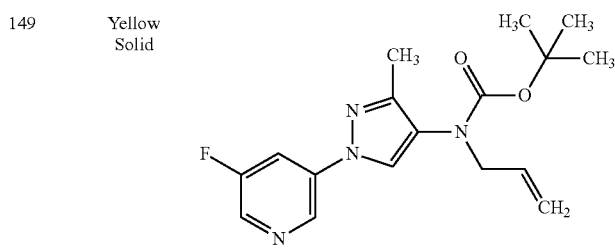 |
| 150 | White Solid | 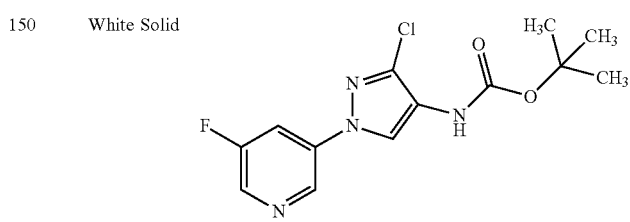 |

TABLE 1-continued
| Compound No. | Appearance | Structure |
|---|---|---|
| 151 | Clear Oil | 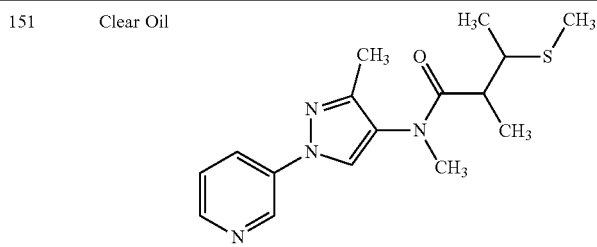 |
| 152 | Clear Oil | 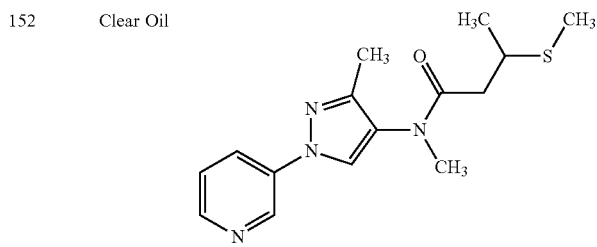 |
| 153 | White Solid | 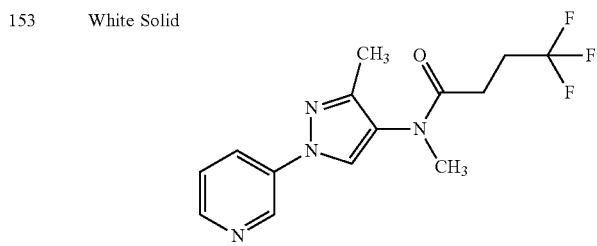 |
| 154 | Faint Orange Oil | 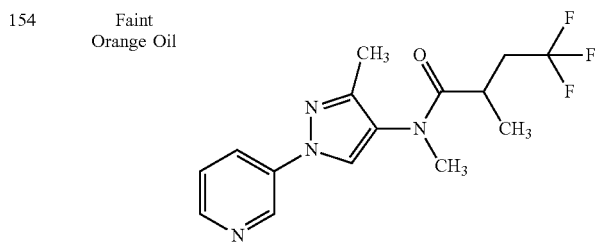 |
| 155 | Clear Oil | 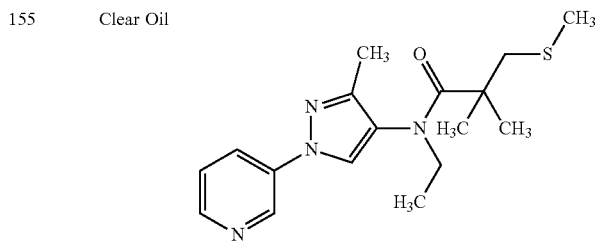 |
| 156 | Clear Oil | 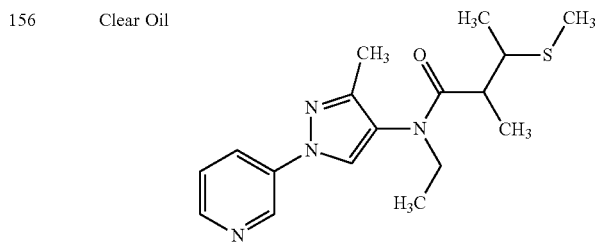 |

TABLE 1-continued
Compound number, appearance, and structure
| Compound No. | Appearance | Structure |
|---|---|---|
| 157 | Clear Oil | 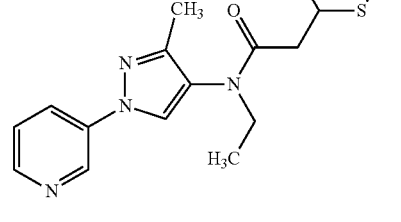 |
| 158 | Clear Oil | 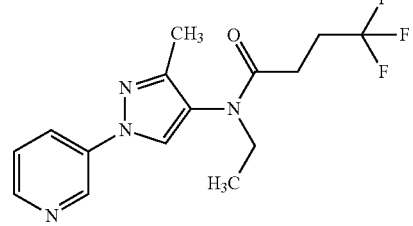 |
| 159 | Clear Oil | 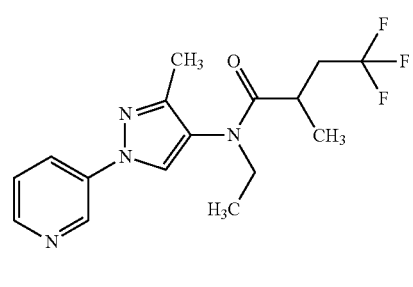 [SMILES: CCN(C(=O)C(C)CC(F)(F)F)c1cn(-c2cccnc2)nc1C] |
| 160 | White Solid | 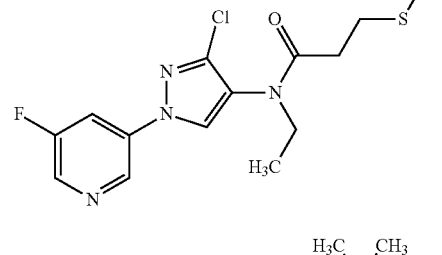 |
| 161 | Brown Oil | 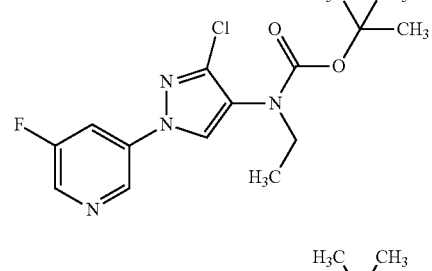 |
| 162 | Light Brown Solid | 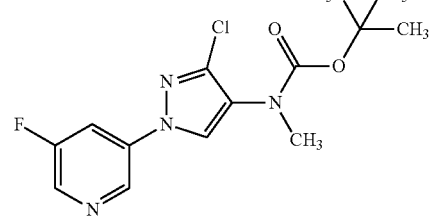 |

TABLE 1-continued

Compound number, appearance, and structure

| Compound No. | Appearance | Structure |
|---|---|---|
| 163 | White Solid | 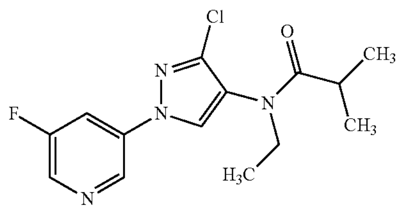 [SMILES: CCN(C(=O)C(C)C)c1cn(-c2cncc(F)c2)nc1Cl] |
| 164 | White Solid | 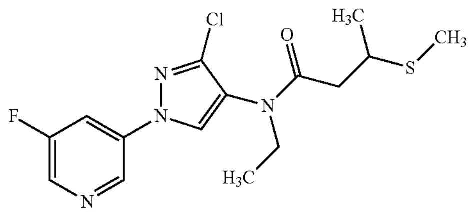 [SMILES: CCN(C(=O)CC(C)SC)c1cn(-c2cncc(F)c2)nc1Cl] |
| 165 | White Solid | 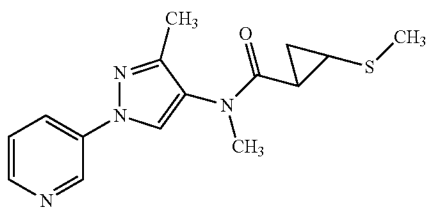 [SMILES: CSC1CC1C(=O)N(C)c1cn(-c2cccnc2)nc1C] |
| 166 | Yellow Oil | 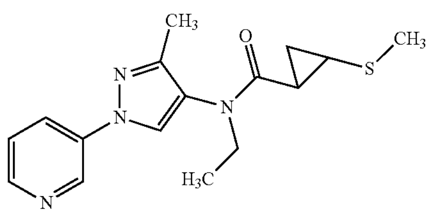 [SMILES: CCN(C(=O)C1CC1SC)c1cn(-c2cccnc2)nc1C] |
| 167 | Grey Oil | 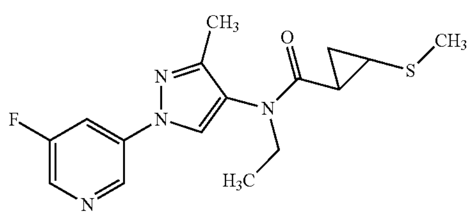 [SMILES: CCN(C(=O)C1CC1SC)c1cn(-c2cncc(F)c2)nc1C] |
| 168 | Faint Purple Oil | 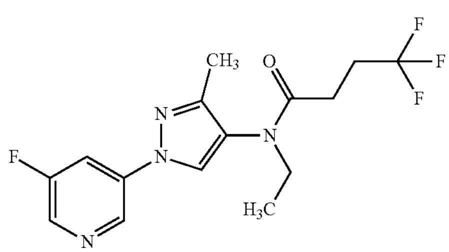 [SMILES: CCN(C(=O)CCC(F)(F)F)c1cn(-c2cncc(F)c2)nc1C] |
| 169 | White Solid | 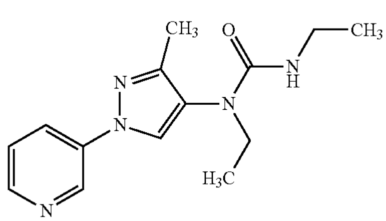 [SMILES: CCNC(=O)N(CC)c1cn(-c2cccnc2)nc1C] |

TABLE 1-continued
| Compound number, appearance, and structure |||
| --- | --- | --- |
| Compound No. | Appearance | Structure |
| 170 | White Solid | 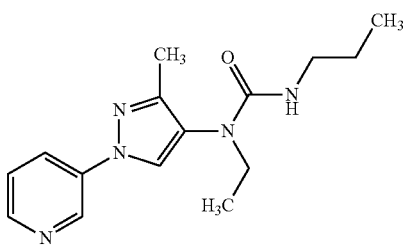 [SMILES: CCCNC(=O)N(CC)c1cn(-c2cccnc2)nc1C] |
| 171 | White Solid | 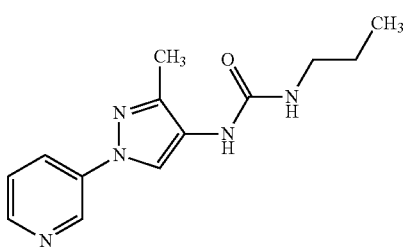 [SMILES: CCCNC(=O)Nc1cn(-c2cccnc2)nc1C] |
| 172 | White Solid | 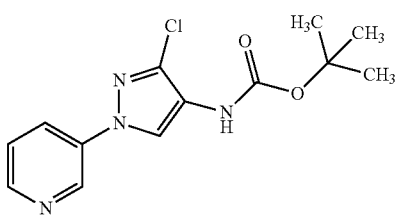 [SMILES: CC(C)(C)OC(=O)Nc1cn(-c2cccnc2)nc1Cl] |
| 173 | White Solid | 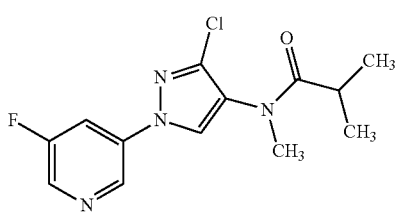 [SMILES: CC(C)C(=O)N(C)c1cn(-c2cncc(F)c2)nc1Cl] |
| 174 | Clear Oil | 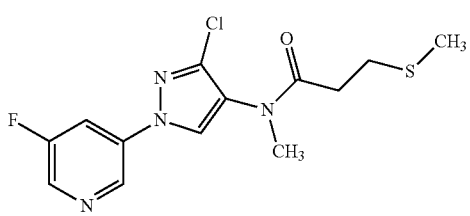 [SMILES: CSCCC(=O)N(C)c1cn(-c2cncc(F)c2)nc1Cl] |
| 175 | White Solid | 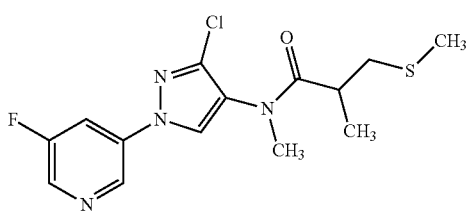 [SMILES: CSCC(C)C(=O)N(C)c1cn(-c2cncc(F)c2)nc1Cl] |

TABLE 1-continued
Compound number, appearance, and structure
| Compound No. | Appearance | Structure |
|---|---|---|
| 176 | Yellow Oil | 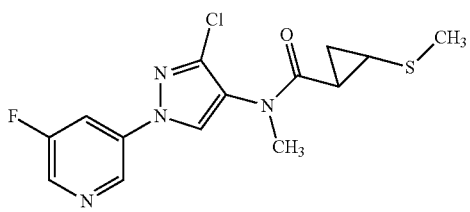 [SMILES: CSC1CC1C(=O)N(C)c1cn(-c2cncc(F)c2)nc1Cl] |
| 177 | White Solid | 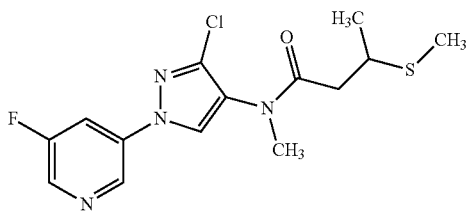 [SMILES: CSC(C)CC(=O)N(C)c1cn(-c2cncc(F)c2)nc1Cl] |
| 178 | Yellow Oil | 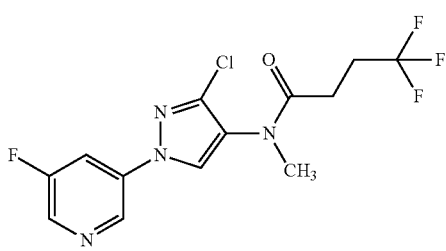 [SMILES: CN(C(=O)CCC(F)(F)F)c1cn(-c2cncc(F)c2)nc1Cl] |
| 179 | White Solid | 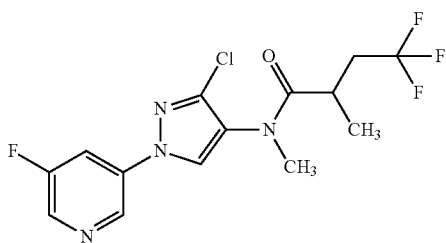 [SMILES: CC(CC(F)(F)F)C(=O)N(C)c1cn(-c2cncc(F)c2)nc1Cl] |
| 180 | Yellow Solid | 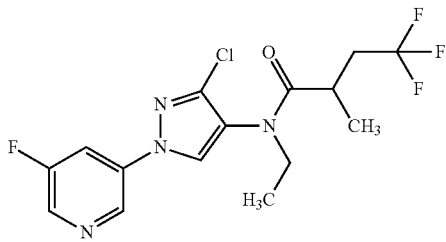 |
| 181 | Faint Yellow Oil | 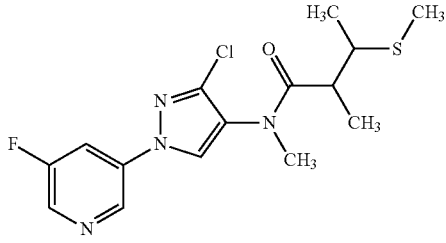 [SMILES: CSC(C)C(C)C(=O)N(C)c1cn(-c2cncc(F)c2)nc1Cl] |

TABLE 1-continued

| Compound No. | Appearance | Structure |
|---|---|---|
| 182 | Faint Yellow Oil | 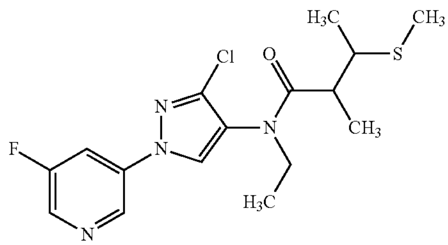 [SMILES: CCN(C(=O)C(C)C(C)SC)c1cn(-c2cncc(F)c2)nc1Cl] |
| 183 | Yellow Oil | 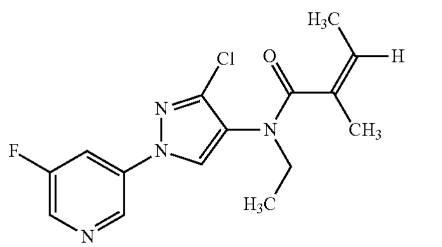 [SMILES: C/C=C(/C)C(=O)N(CC)c1cn(-c2cncc(F)c2)nc1Cl] |
| 184 | Colorless Oil | 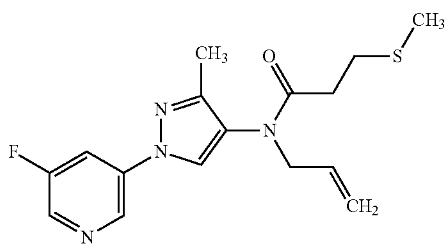 [SMILES: C=CCN(C(=O)CCSC)c1cn(-c2cncc(F)c2)nc1C] |
| 185 | White Solid | 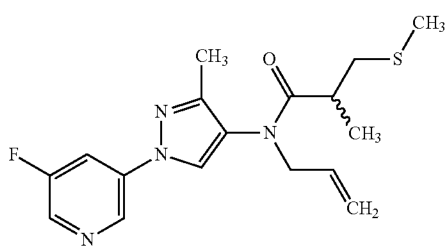 [SMILES: C=CCN(C(=O)C(C)CSC)c1cn(-c2cncc(F)c2)nc1C] |
| 186 | White Solid | 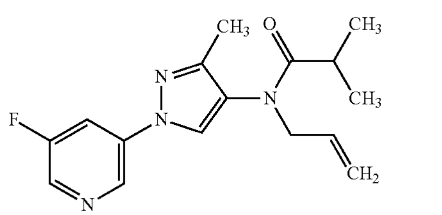 [SMILES: C=CCN(C(=O)C(C)C)c1cn(-c2cncc(F)c2)nc1C] |
| 187 | Solid Yellow | 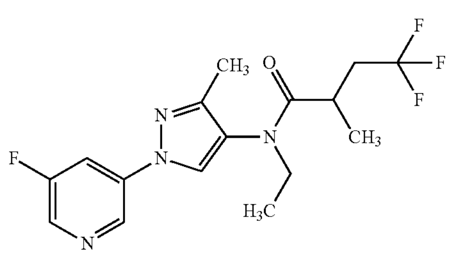 [SMILES: CCN(C(=O)C(C)CC(F)(F)F)c1cn(-c2cncc(F)c2)nc1C] |

TABLE 1-continued

| Compound No. | Appearance | Structure |
|---|---|---|
| 188 | Yellow Oil | 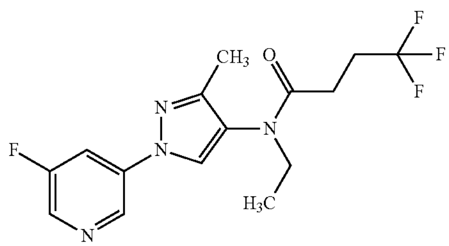 [SMILES: CCN(C(=O)CCC(F)(F)F)c1cn(-c2cncc(F)c2)nc1C] |
| 189 | Yellow Oil | 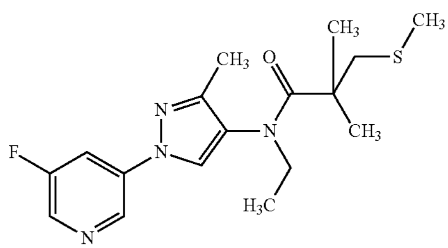 [SMILES: CCN(C(=O)C(C)(C)CSC)c1cn(-c2cncc(F)c2)nc1C] |
| 190 | Yellow Oil | 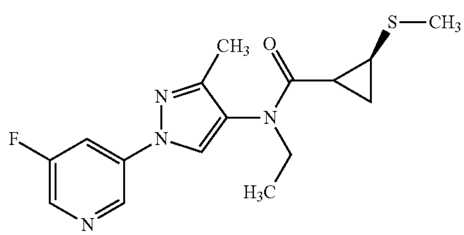 [SMILES: CCN(C(=O)C1C[C@@H]1SC)c1cn(-c2cncc(F)c2)nc1C] |
| 191 | Yellow Oil | 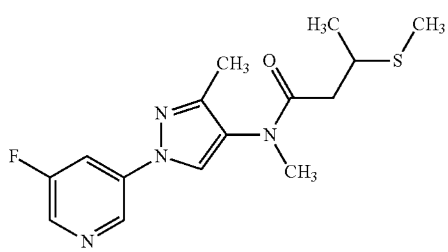 [SMILES: CSC(C)CC(=O)N(C)c1cn(-c2cncc(F)c2)nc1C] |
| 192 | Yellow Oil | 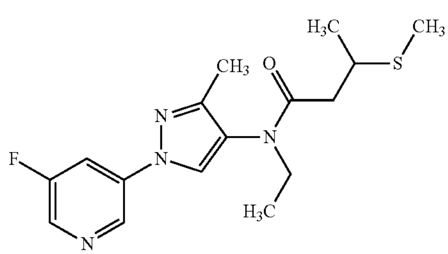 [SMILES: CCN(C(=O)CC(C)SC)c1cn(-c2cncc(F)c2)nc1C] |
| 193 | Yellow Solid | 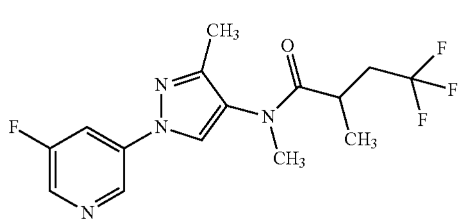 [SMILES: Cc1nn(-c2cncc(F)c2)cc1N(C)C(=O)C(C)CC(F)(F)F] |

TABLE 1-continued

Compound number, appearance, and structure

| Compound No. | Appearance | Structure |
|---|---|---|
| 194 | White Solid | 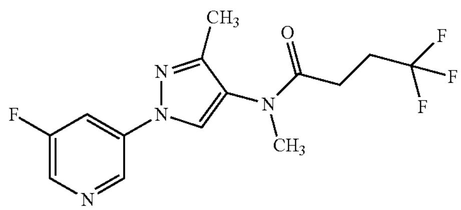 [SMILES: Cc1nn(-c2cncc(F)c2)cc1N(C)C(=O)CCC(F)(F)F] |
| 195 | White Solid | 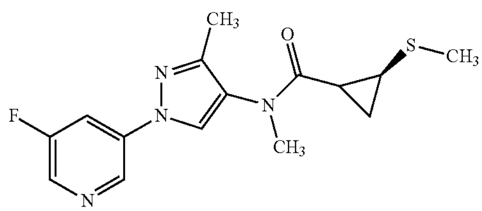 [SMILES: CS[C@H]1CC1C(=O)N(C)c1cn(-c2cncc(F)c2)nc1C] |
| 196 | Tan Solid | 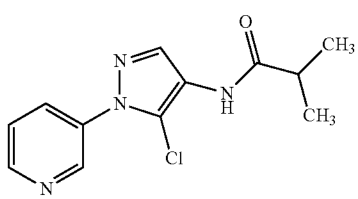 [SMILES: CC(C)C(=O)Nc1cnn(-c2cccnc2)c1Cl] |
| 197 | White Solid | 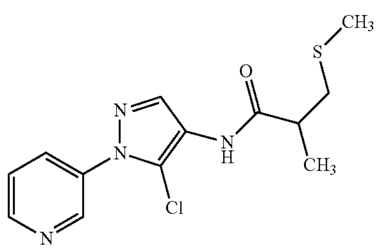 [SMILES: CSCC(C)C(=O)Nc1cnn(-c2cccnc2)c1Cl] |
| 198 | Tan Solid | 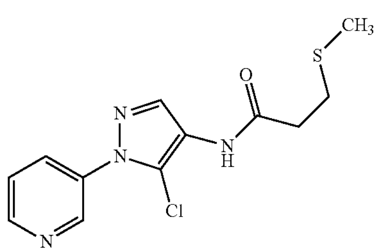 [SMILES: CSCCC(=O)Nc1cnn(-c2cccnc2)c1Cl] |
| 199 | Gold Solid | 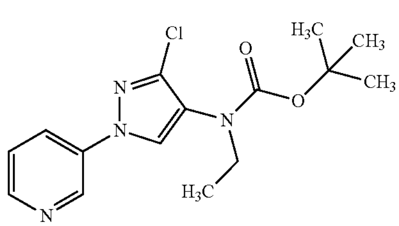 [SMILES: CCN(C(=O)OC(C)(C)C)c1cn(-c2cccnc2)nc1Cl] |

TABLE 1-continued

Compound number, appearance, and structure

| Compound No. | Appearance | Structure |
|---|---|---|
| 200 | Yellow Oil | |
| 201 | Gold Oil | |
| 202 | White Semi Solid | |
| 203 | Yellow Oil | |
| 204 | Yellow Oil | |
| 205 | Yellow Oil | AND Enantiomer |
| 206 | Yellow Oil | |

TABLE 1-continued
| Compound No. | Appearance | Structure |
|---|---|---|
| 207 | White Solid | 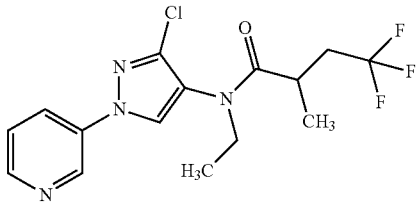 [SMILES: CCN(C(=O)C(C)CC(F)(F)F)c1cn(-c2cccnc2)nc1Cl] |
| 208 | White Solid | 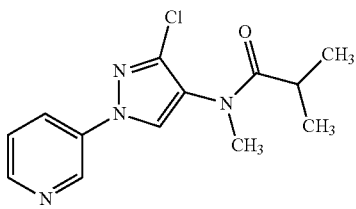 [SMILES: CC(C)C(=O)N(C)c1cn(-c2cccnc2)nc1Cl] |
| 209 | Yellow Oil | 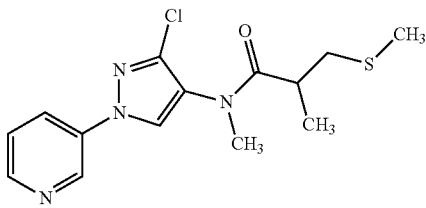 [SMILES: CSCC(C)C(=O)N(C)c1cn(-c2cccnc2)nc1Cl] |
| 210 | Yellow Oil | 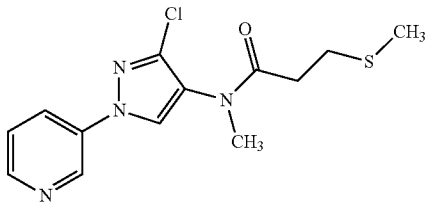 [SMILES: CSCCC(=O)N(C)c1cn(-c2cccnc2)nc1Cl] |
| 211 | Yellow Oil | 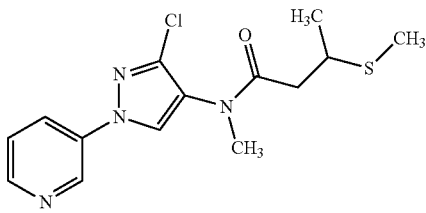 [SMILES: CSC(C)CC(=O)N(C)c1cn(-c2cccnc2)nc1Cl] |
| 212 | Yellow Oil | 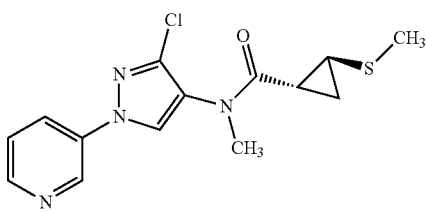 [SMILES: CS[C@H]1C[C@@H]1C(=O)N(C)c1cn(-c2cccnc2)nc1Cl] |
| 213 | Yellow Oil | 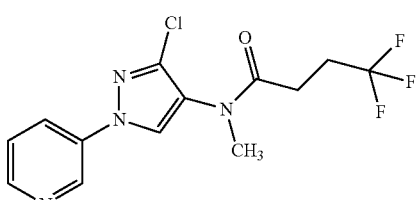 |

TABLE 1-continued

Compound number, appearance, and structure

| Compound No. | Appearance | Structure |
|---|---|---|
| 214 | Yellow Oil | 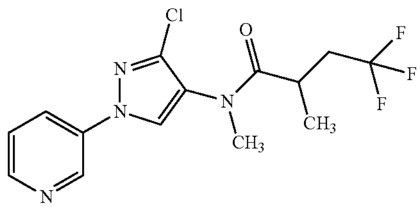 [SMILES: CC(CC(F)(F)F)C(=O)N(C)c1cn(-c2cccnc2)nc1Cl] |
| 215 | Clear Oil | 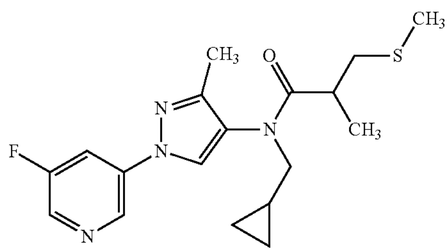 [SMILES: CSCC(C)C(=O)N(CC1CC1)c1cn(-c2cncc(F)c2)nc1C] |
| 216 | Cream Colored Solid | 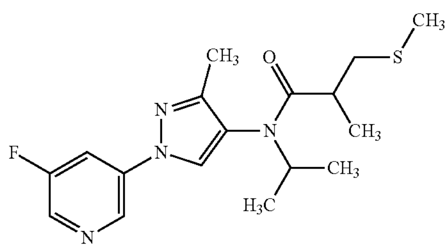 [SMILES: CSCC(C)C(=O)N(c1cn(-c2cncc(F)c2)nc1C)C(C)C] |
| 217 | Clear Oil | 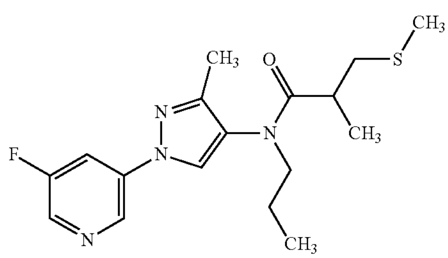 [SMILES: CCCN(C(=O)C(C)CSC)c1cn(-c2cncc(F)c2)nc1C] |
| 218 | Clear Oil | 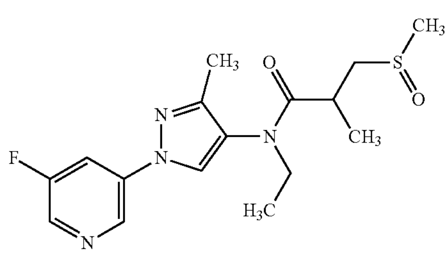 [SMILES: CCN(C(=O)C(C)CS(C)=O)c1cn(-c2cncc(F)c2)nc1C] |
| 219 | Clear Oil | 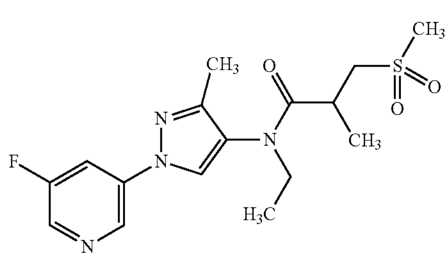 [SMILES: CCN(C(=O)C(C)CS(C)(=O)=O)c1cn(-c2cncc(F)c2)nc1C] |

TABLE 1-continued

Compound number, appearance, and structure

| Compound No. | Appearance | Structure |
|---|---|---|
| 220 | Yellow Oil | 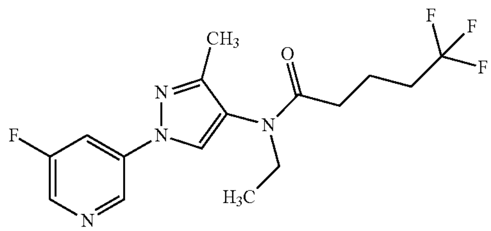 [SMILES: CCN(C(=O)CCCC(F)(F)F)c1cn(-c2cncc(F)c2)nc1C] |
| 221 | White Solid | 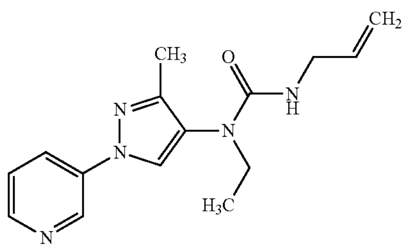 [SMILES: C=CCNC(=O)N(CC)c1cn(-c2cccnc2)nc1C] |
| 222 | White Solid | 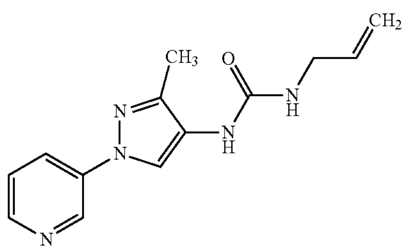 [SMILES: C=CCNC(=O)Nc1cn(-c2cccnc2)nc1C] |
| 223 | White Solid | 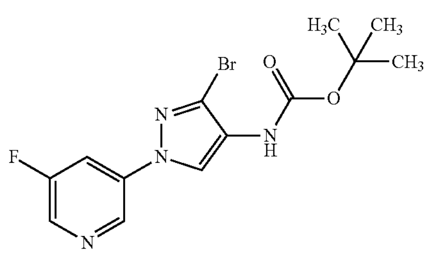 [SMILES: CC(C)(C)OC(=O)Nc1cn(-c2cncc(F)c2)nc1Br] |
| 224 | Colorless Oil | 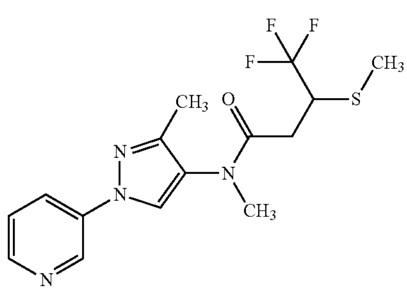 [SMILES: CSC(CC(=O)N(C)c1cn(-c2cccnc2)nc1C)C(F)(F)F] |
| 225 | Light Yellow Oil | 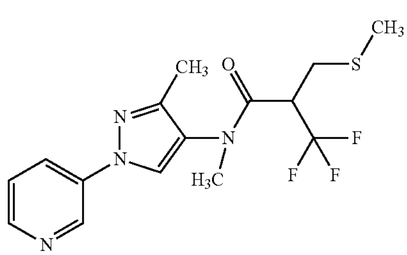 [SMILES: CSCC(C(=O)N(C)c1cn(-c2cccnc2)nc1C)C(F)(F)F] |

TABLE 1-continued
Compound number, appearance, and structure
| Compound No. | Appearance | Structure |
|---|---|---|
| 226 | White Solid | 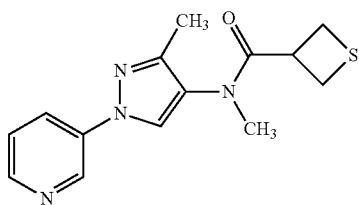 [SMILES: Cc1nn(-c2cccnc2)cc1N(C)C(=O)C1CSC1] |
| 227 | White Solid | 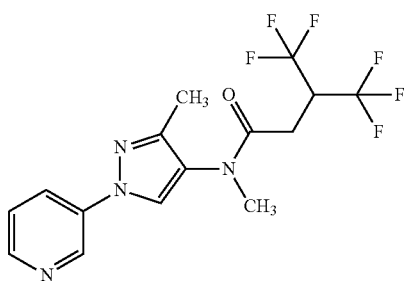 [SMILES: Cc1nn(-c2cccnc2)cc1N(C)C(=O)CC(C(F)(F)F)C(F)(F)F] |
| 228 | Colorless Oil | 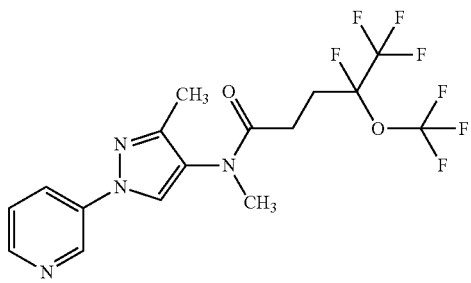 [SMILES: Cc1nn(-c2cccnc2)cc1N(C)C(=O)CCC(F)(OC(F)(F)F)C(F)(F)F] |
| 229 | Colorless Oil | 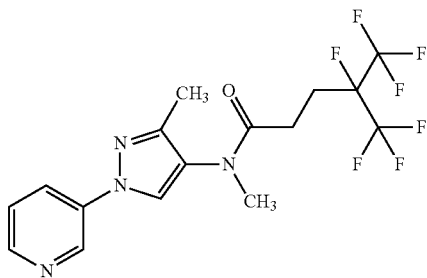 [SMILES: Cc1nn(-c2cccnc2)cc1N(C)C(=O)CCC(F)(C(F)(F)F)C(F)(F)F] |
| 230 | Colorless Oil | 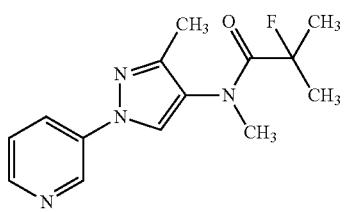 [SMILES: Cc1nn(-c2cccnc2)cc1N(C)C(=O)C(C)(C)F] |

TABLE 1-continued

| Compound No. | Appearance | Structure |
|---|---|---|
| 231 | Colorless Oil | (structure) |
| 232 | White Solid | (structure) |
| 233 | White Solid | (structure) |
| 234 | White Solid | (structure) |
| 235 | Colorless Oil | (structure) |
| 236 | Colorless Oil | (structure) |

TABLE 1-continued

| Compound No. | Appearance | Structure |
|---|---|---|
| 237 | White Solid | 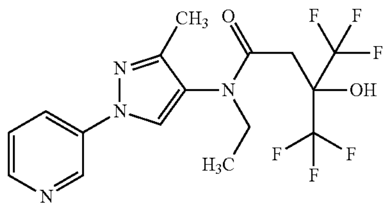 [SMILES: CCN(C(=O)CC(O)(C(F)(F)F)C(F)(F)F)c1cn(-c2cccnc2)nc1C] |
| 238 | Colorless Oil | 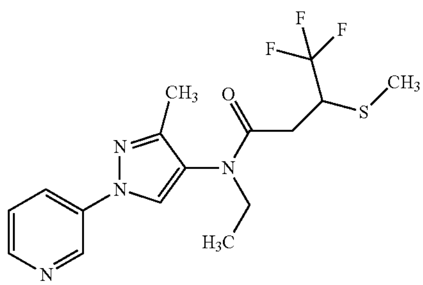 [SMILES: CCN(C(=O)CC(SC)C(F)(F)F)c1cn(-c2cccnc2)nc1C] |
| 239 | Colorless Oil | 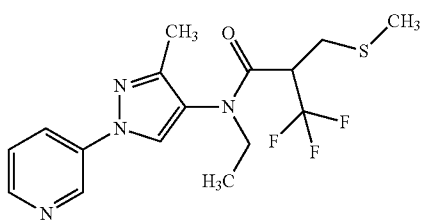 [SMILES: CCN(C(=O)C(CSC)C(F)(F)F)c1cn(-c2cccnc2)nc1C] |
| 240 | White Solid | 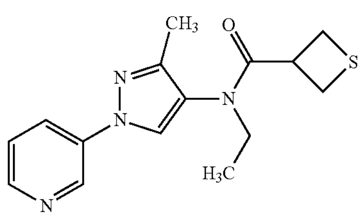 [SMILES: CCN(C(=O)C1CSC1)c1cn(-c2cccnc2)nc1C] |
| 241 | Colorless Oil | 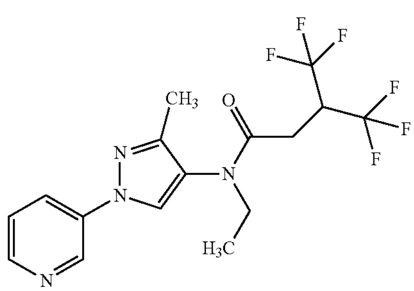 [SMILES: CCN(C(=O)CC(C(F)(F)F)C(F)(F)F)c1cn(-c2cccnc2)nc1C] |
| 242 | Colorless Oil | 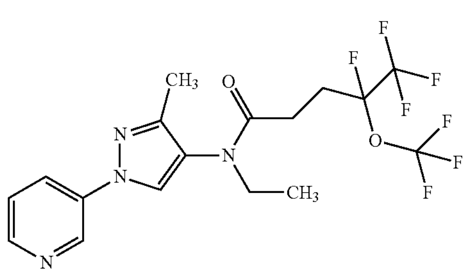 [SMILES: CCN(C(=O)CCC(F)(OC(F)(F)F)C(F)(F)F)c1cn(-c2cccnc2)nc1C] |

TABLE 1-continued

Compound number, appearance, and structure

| Compound No. | Appearance | Structure |
|---|---|---|
| 243 | Colorless Oil | 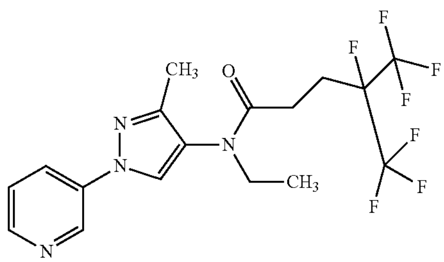 [SMILES: CCN(C(=O)CCC(F)(C(F)(F)F)C(F)(F)F)c1cn(-c2cccnc2)nc1C] |
| 244 | White Solid | 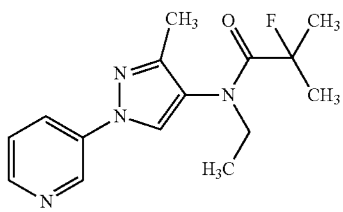 [SMILES: CCN(C(=O)C(C)(C)F)c1cn(-c2cccnc2)nc1C] |
| 245 | White Solid | 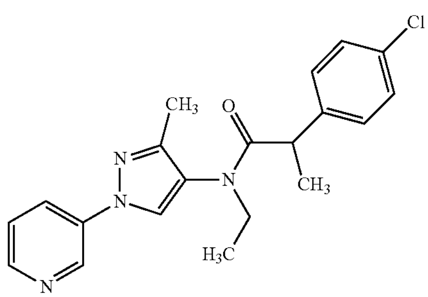 [SMILES: CCN(C(=O)C(C)c1ccc(Cl)cc1)c1cn(-c2cccnc2)nc1C] |
| 246 | Colorless Oil | 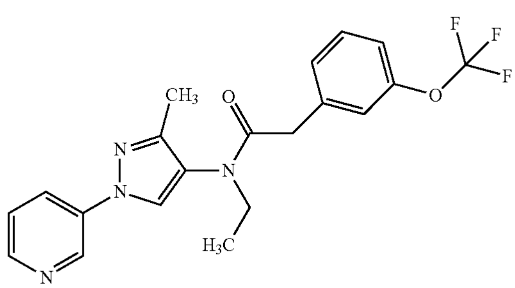 [SMILES: CCN(C(=O)Cc1cccc(OC(F)(F)F)c1)c1cn(-c2cccnc2)nc1C] |
| 247 | White Solid | 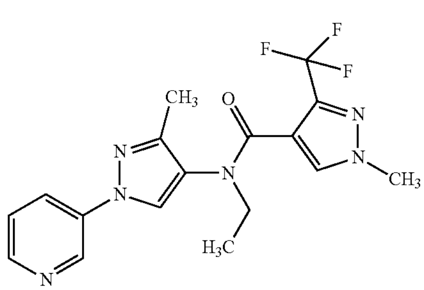 [SMILES: CCN(C(=O)c1cn(C)nc1C(F)(F)F)c1cn(-c2cccnc2)nc1C] |

TABLE 1-continued

Compound number, appearance, and structure

| Compound No. | Appearance | Structure |
|---|---|---|
| 248 | Colorless Oil | 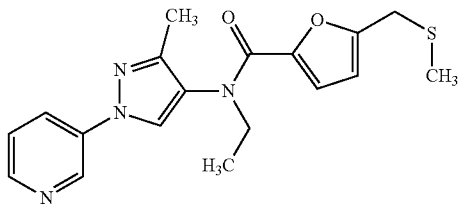 [SMILES: CCN(C(=O)c1ccc(CSC)o1)c1cn(-c2cccnc2)nc1C] |
| 249 | White Solid | 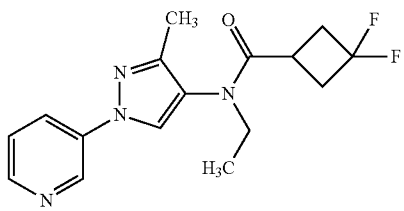 [SMILES: CCN(C(=O)C1CC(F)(F)C1)c1cn(-c2cccnc2)nc1C] |
| 250 | Clear Oil | 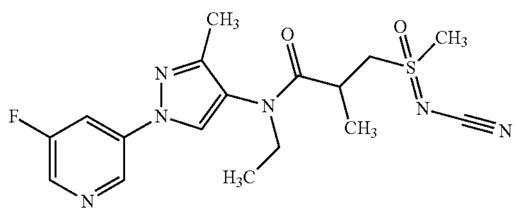 [SMILES: CCN(C(=O)C(C)CS(C)(=O)=NC#N)c1cn(-c2cncc(F)c2)nc1C] |
| 251 | Brown Oil | 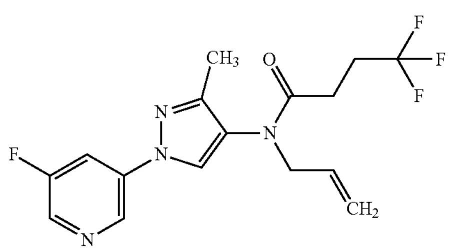 [SMILES: C=CCN(C(=O)CCC(F)(F)F)c1cn(-c2cncc(F)c2)nc1C] |
| 252 | Off White Solid | 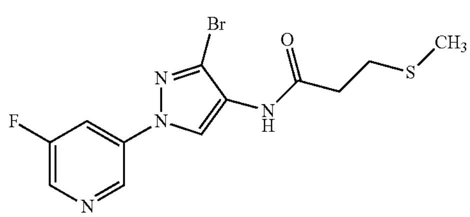 [SMILES: CSCCC(=O)Nc1cn(-c2cncc(F)c2)nc1Br] |
| 253 | Off White Solid | 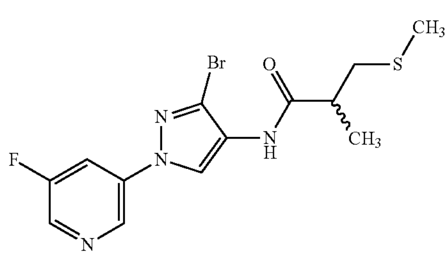 [SMILES: CSCC(C)C(=O)Nc1cn(-c2cncc(F)c2)nc1Br] |

TABLE 1-continued
| Compound No. | Appearance | Structure |
|---|---|---|
| 254 | Brown Solid | 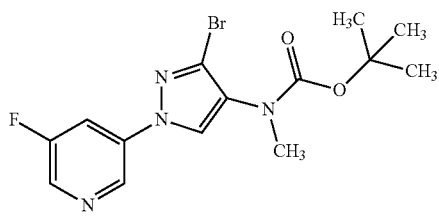 [SMILES: CN(C(=O)OC(C)(C)C)c1cn(-c2cncc(F)c2)nc1Br] |
| 255 | White Solid | 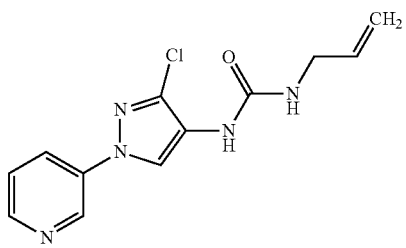 [SMILES: C=CCNC(=O)Nc1cn(-c2cccnc2)nc1Cl] |
| 256 | White Solid | 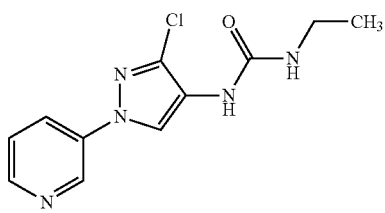 [SMILES: CCNC(=O)Nc1cn(-c2cccnc2)nc1Cl] |
| 257 | White Solid | 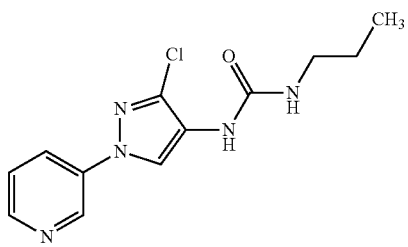 [SMILES: CCCNC(=O)Nc1cn(-c2cccnc2)nc1Cl] |
| 258 | Brown Oil | 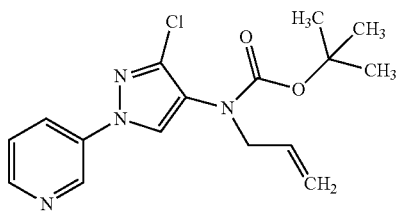 [SMILES: C=CCN(C(=O)OC(C)(C)C)c1cn(-c2cccnc2)nc1Cl] |
| 259 | White Solid | 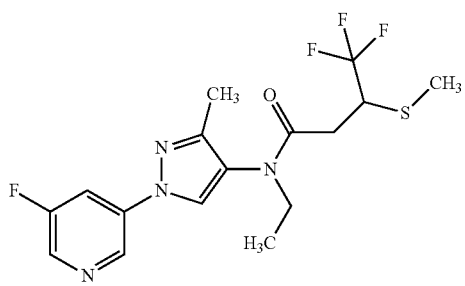 [SMILES: CCN(C(=O)CC(SC)C(F)(F)F)c1cn(-c2cncc(F)c2)nc1C] |

TABLE 1-continued

| Compound No. | Appearance | Structure |
|---|---|---|
| 260 | Colorless Oil | 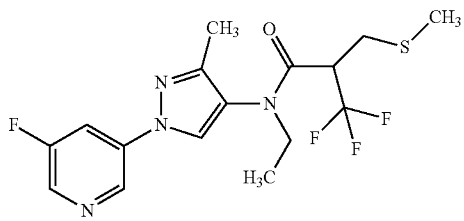 [SMILES: CCN(C(=O)C(CSC)C(F)(F)F)c1cn(-c2cncc(F)c2)nc1C] |
| 261 | White Solid | 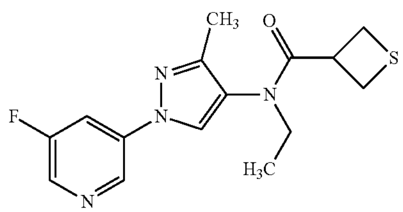 [SMILES: CCN(C(=O)C1CSC1)c1cn(-c2cncc(F)c2)nc1C] |
| 262 | White Solid | 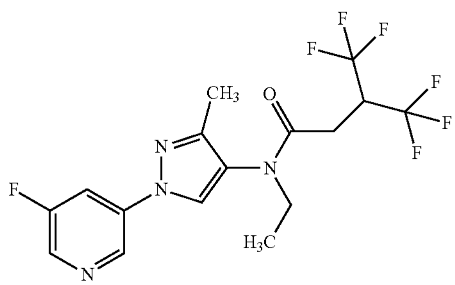 [SMILES: CCN(C(=O)CC(C(F)(F)F)C(F)(F)F)c1cn(-c2cncc(F)c2)nc1C] |
| 263 | Colorless Oil | 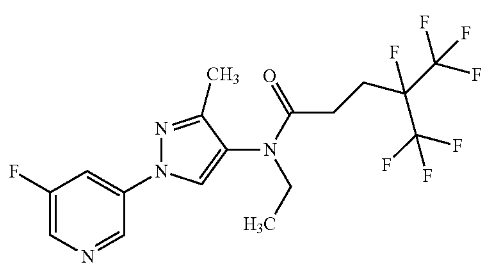 [SMILES: CCN(C(=O)CCC(F)(C(F)(F)F)C(F)(F)F)c1cn(-c2cncc(F)c2)nc1C] |
| 264 | Colorless Oil | 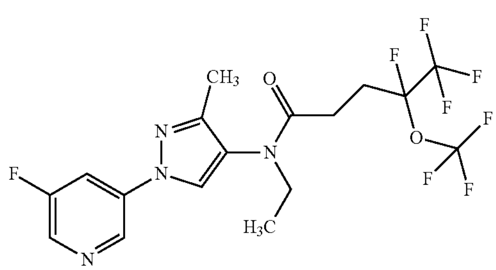 [SMILES: CCN(C(=O)CCC(F)(OC(F)(F)F)C(F)(F)F)c1cn(-c2cncc(F)c2)nc1C] |
| 265 | White Solid | 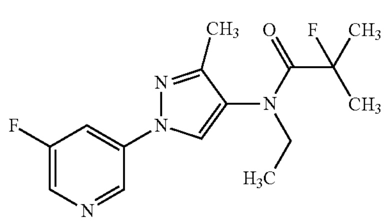 [SMILES: CCN(C(=O)C(C)(C)F)c1cn(-c2cncc(F)c2)nc1C] |

TABLE 1-continued

Compound number, appearance, and structure

| Compound No. | Appearance | Structure |
|---|---|---|
| 266 | Colorless Semi-Solid | 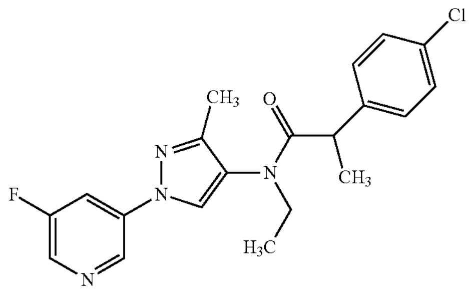 [SMILES: CCN(C(=O)C(C)c1ccc(Cl)cc1)c1cn(-c2cncc(F)c2)nc1C] |
| 267 | Colorless Oil | 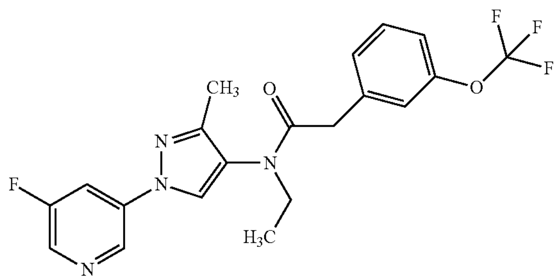 [SMILES: CCN(C(=O)Cc1cccc(OC(F)(F)F)c1)c1cn(-c2cncc(F)c2)nc1C] |
| 268 | White Solid | 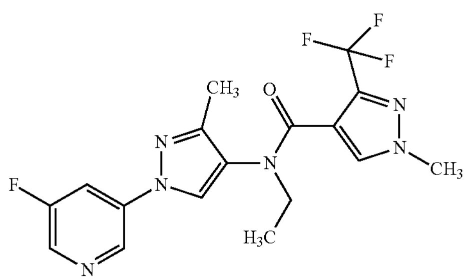 [SMILES: CCN(C(=O)c1cn(C)nc1C(F)(F)F)c1cn(-c2cncc(F)c2)nc1C] |
| 269 | White Solid | 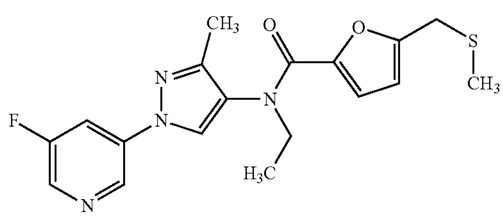 [SMILES: CCN(C(=O)c1ccc(CSC)o1)c1cn(-c2cncc(F)c2)nc1C] |
| 270 | White Solid | 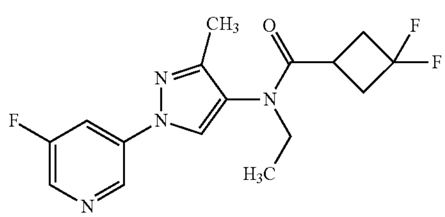 [SMILES: CCN(C(=O)C1CC(F)(F)C1)c1cn(-c2cncc(F)c2)nc1C] |
| 271 | Colorless Oil | 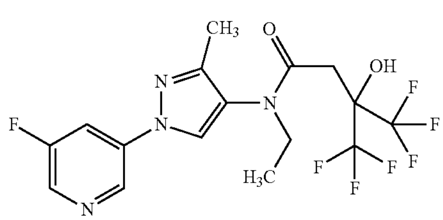 [SMILES: CCN(C(=O)CC(O)(C(F)(F)F)C(F)(F)F)c1cn(-c2cncc(F)c2)nc1C] |

TABLE 1-continued

Compound number, appearance, and structure

| Compound No. | Appearance | Structure |
|---|---|---|
| 272 | White Solid | 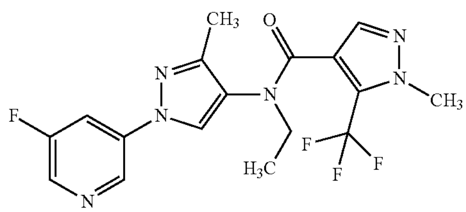 [SMILES: CCN(C(=O)c1cnn(C)c1C(F)(F)F)c1cn(-c2cncc(F)c2)nc1C] |
| 273 | Colorless Oil | 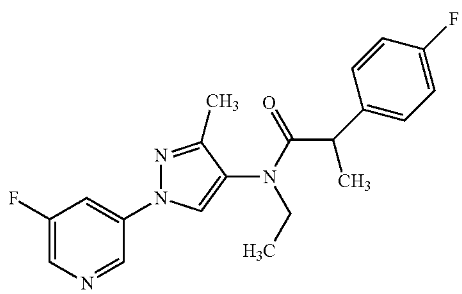 [SMILES: CCN(C(=O)C(C)c1ccc(F)cc1)c1cn(-c2cncc(F)c2)nc1C] |
| 274 | Colorless Oil | 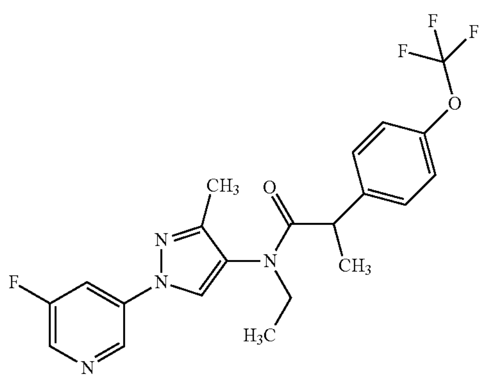 [SMILES: CCN(C(=O)C(C)c1ccc(OC(F)(F)F)cc1)c1cn(-c2cncc(F)c2)nc1C] |
| 275 | White Solid | 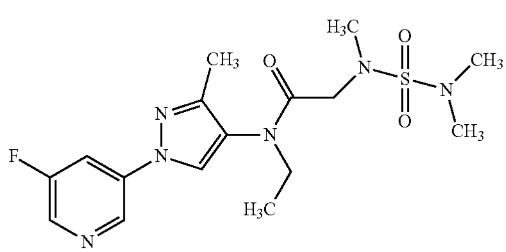 [SMILES: CCN(C(=O)CN(C)S(=O)(=O)N(C)C)c1cn(-c2cncc(F)c2)nc1C] |
| 276 | White Solid | 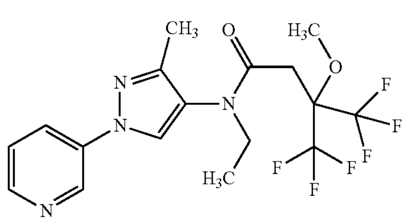 [SMILES: CCN(C(=O)CC(OC)(C(F)(F)F)C(F)(F)F)c1cn(-c2cccnc2)nc1C] |

TABLE 1-continued

Compound number, appearance, and structure

| Compound No. | Appearance | Structure |
|---|---|---|
| 277 | Brown Amorphous Solid | 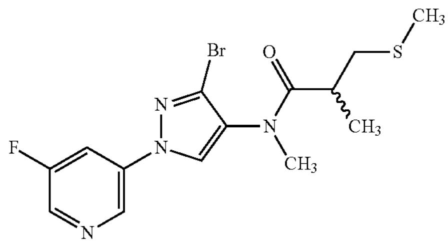 [SMILES: CSCC(C)C(=O)N(C)c1cn(-c2cncc(F)c2)nc1Br] |
| 278 | White Solid | 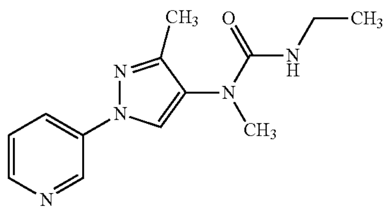 [SMILES: CCNC(=O)N(C)c1cn(-c2cccnc2)nc1C] |
| 279 | White Solid | 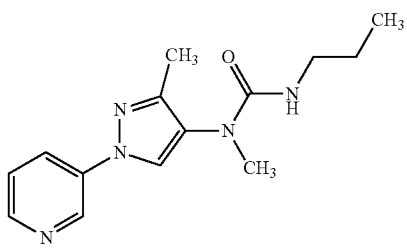 [SMILES: CCCNC(=O)N(C)c1cn(-c2cccnc2)nc1C] |
| 280 | White Solid | 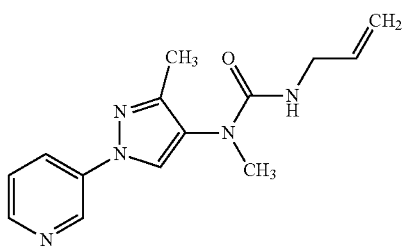 [SMILES: C=CCNC(=O)N(C)c1cn(-c2cccnc2)nc1C] |
| 281 | Orange Foam | 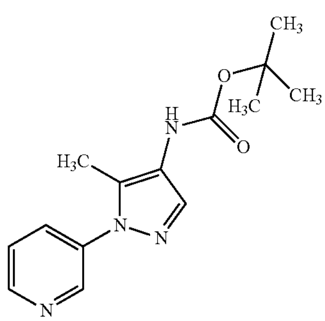 [SMILES: Cc1c(NC(=O)OC(C)(C)C)cnn1-c1cccnc1] |
| 282 | Colorless Oil | 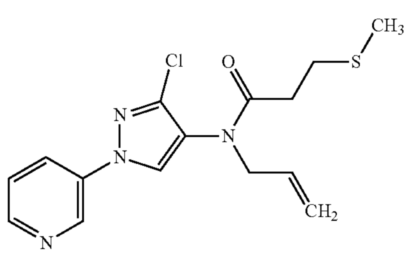 [SMILES: C=CCN(C(=O)CCSC)c1cn(-c2cccnc2)nc1Cl] |

TABLE 1-continued

Compound number, appearance, and structure

| Compound No. | Appearance | Structure |
|---|---|---|
| 283 | Colorless Oil | 3-chloro-1-(pyridin-3-yl)-pyrazol-4-yl with N-allyl-N-(2-(methylthiomethyl)propanoyl) substituent |
| 284 | Colorless Oil | 3-chloro-1-(pyridin-3-yl)-pyrazol-4-yl with N-allyl-N-isobutyryl substituent |
| 285 | Clear Oil | 3-methyl-1-(pyridin-3-yl)-pyrazol-4-yl with N-(3-(methylthio)propyl)-N-acetyl substituent |
| 286 | Yellow Oil | 3-methyl-1-(5-fluoropyridin-3-yl)-pyrazol-4-yl with N-ethyl-N-(3-(trifluoromethylthio)propanoyl) substituent |
| 287 | Yellow Oil | 3-methyl-1-(pyridin-3-yl)-pyrazol-4-yl with N-(3-(methylthio)propyl)-N-isobutyryl substituent |
| 288 | Yellow Oil | 3-methyl-1-(pyridin-3-yl)-pyrazol-4-yl with N-(3-(methylthio)propyl)-N-(ethoxycarbonyl) substituent |

TABLE 1-continued
Compound number, appearance, and structure
| Compound No. | Appearance | Structure |
|---|---|---|
| 289 | Dark Yellow Oil | 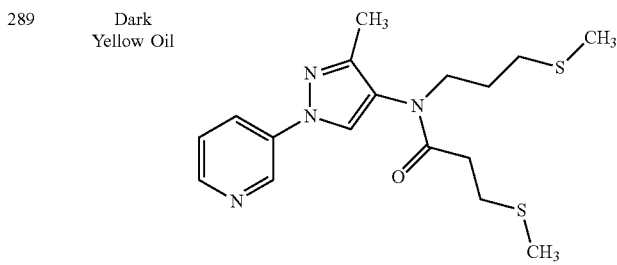 |
| 290 | Yellow Oil | 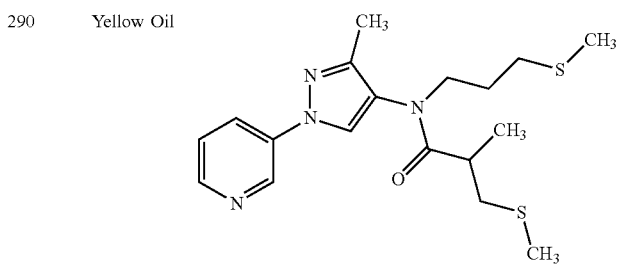 |
| 291 | Clear Oil | 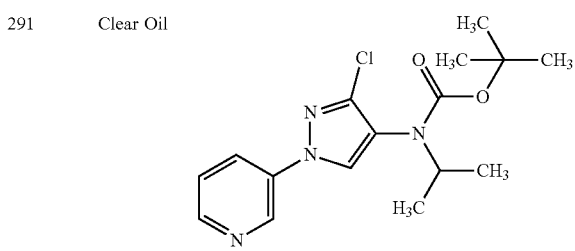 |
| 292 | Tan Solid | 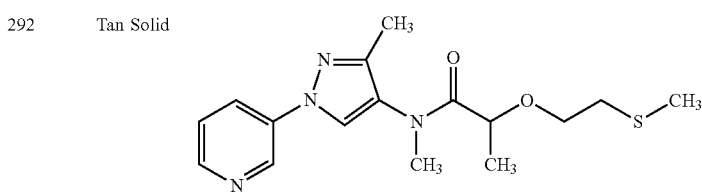 |
| 293 | Clear Oil | 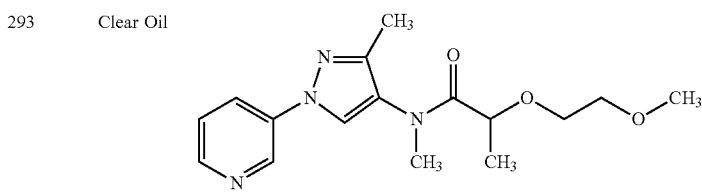 |
| 294 | Yellow Oil | 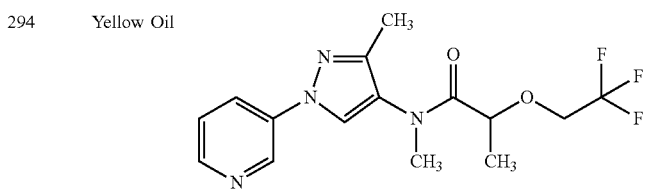 |

TABLE 1-continued
| Compound No. | Appearance | Structure |
|---|---|---|
| 295 | White Semi Solid | 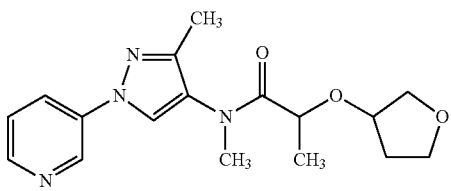 [SMILES: Cc1nn(-c2cccnc2)cc1N(C)C(=O)C(C)OC1CCOC1] |
| 296 | Colorless Oil | 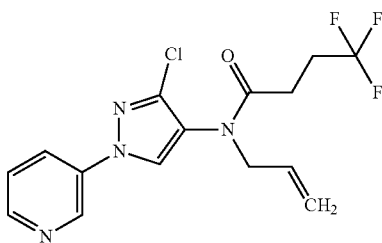 [SMILES: C=CCN(C(=O)CCC(F)(F)F)c1cn(-c2cccnc2)nc1Cl] |
| 297 | White Solid | 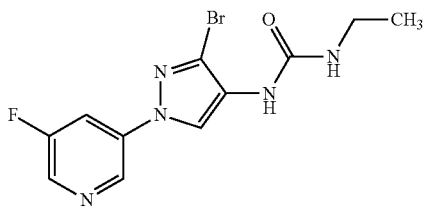 |
| 298 | White Solid | 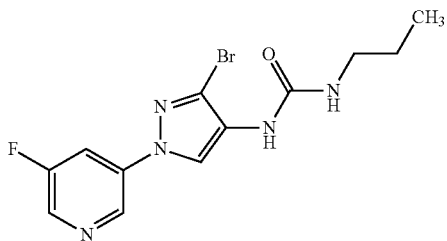 [SMILES: CCCNC(=O)Nc1cn(-c2cncc(F)c2)nc1Br] |
| 299 | White Solid | 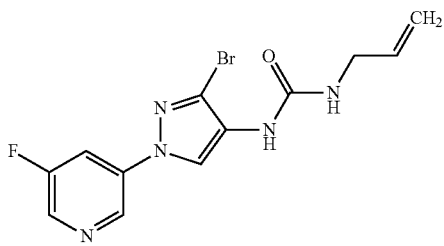 [SMILES: C=CCNC(=O)Nc1cn(-c2cncc(F)c2)nc1Br] |
| 300 | White Solid | 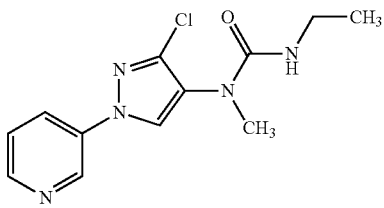 [SMILES: CCNC(=O)N(C)c1cn(-c2cccnc2)nc1Cl] |

TABLE 1-continued
Compound number, appearance, and structure
| Compound No. | Appearance | Structure |
|---|---|---|
| 301 | White Solid | 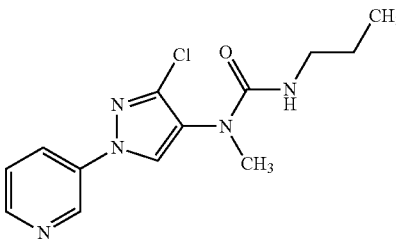 |
| 302 | White Solid | 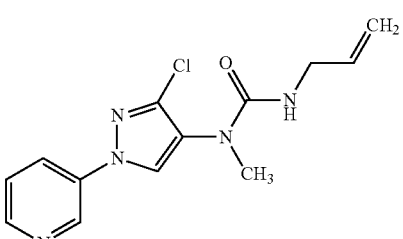 |
| 303 | Colorless Oil | 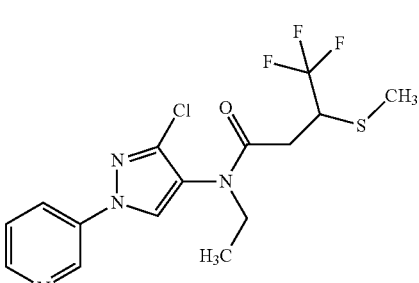 |
| 304 | Light Yellow Oil | 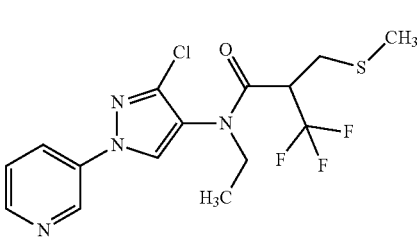 [SMILES: CCN(C(=O)C(CSC)C(F)(F)F)c1cn(-c2cccnc2)nc1Cl] |
| 305 | White Solid | 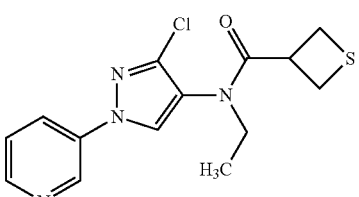 |
| 306 | Grey Solid | 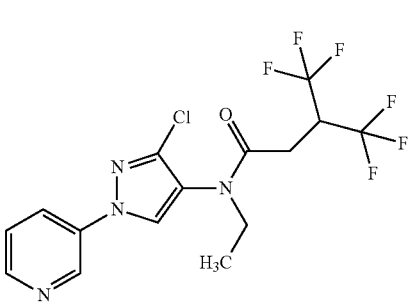 [SMILES: CCN(C(=O)CC(C(F)(F)F)C(F)(F)F)c1cn(-c2cccnc2)nc1Cl] |

TABLE 1-continued
Compound number, appearance, and structure
| Compound No. | Appearance | Structure |
|---|---|---|
| 307 | Colorless Oil | 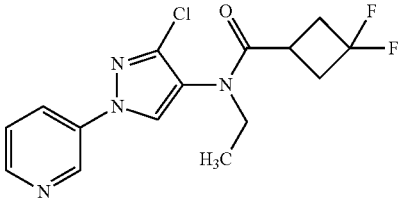 [SMILES: CCN(C(=O)C1CC(F)(F)C1)c1cn(-c2cccnc2)nc1Cl] |
| 308 | Colorless Oil | 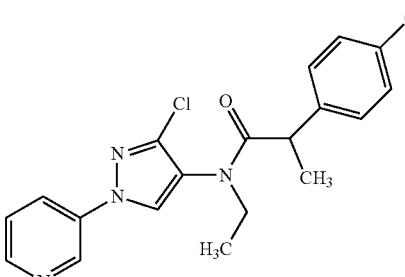 |
| 309 | Colorless Oil | 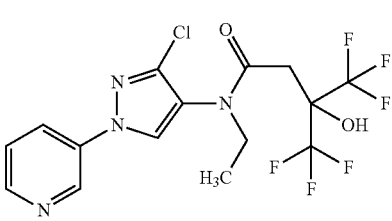 [SMILES: CCN(C(=O)CC(O)(C(F)(F)F)C(F)(F)F)c1cn(-c2cccnc2)nc1Cl] |
| 310 | Light Yellow Semi-Solid | 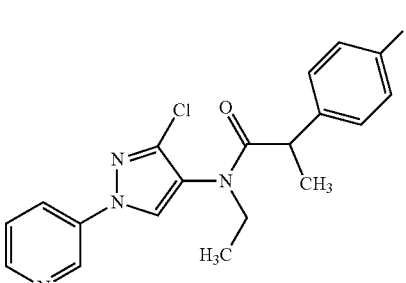 |
| 311 | Colorless Oil | 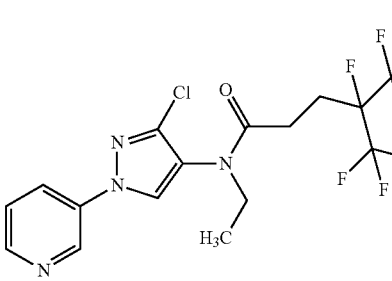 |
| 312 | White Solid | 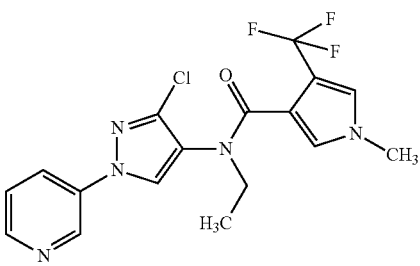 [SMILES: CCN(C(=O)c1cn(C)cc1C(F)(F)F)c1cn(-c2cccnc2)nc1Cl] |

TABLE 1-continued

Compound number, appearance, and structure

| Compound No. | Appearance | Structure |
|---|---|---|
| 313 | Light Yellow Solid | 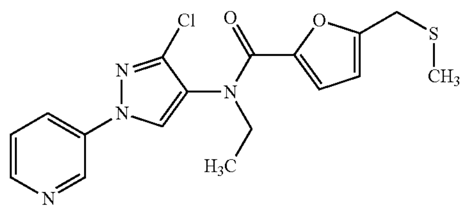 [SMILES: CCN(C(=O)c1ccc(CSC)o1)c1cn(-c2cccnc2)nc1Cl] |
| 314 | Faint Yellow Oil | 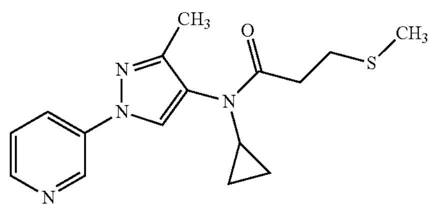 [SMILES: CSCCC(=O)N(c1cn(-c2cccnc2)nc1C)C1CC1] |
| 315 | Faint Yellow Oil | 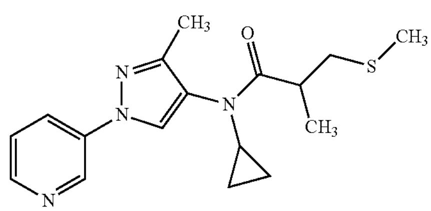 [SMILES: CSCC(C)C(=O)N(c1cn(-c2cccnc2)nc1C)C1CC1] |
| 316 | Faint Yellow Solid | 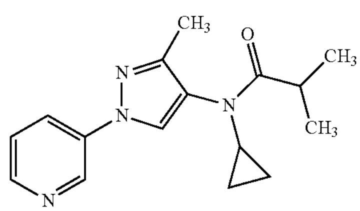 [SMILES: Cc1nn(-c2cccnc2)cc1N(C(=O)C(C)C)C1CC1] |
| 317 | White Solid | 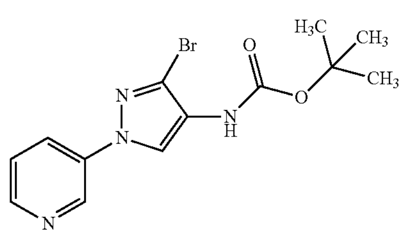 [SMILES: CC(C)(C)OC(=O)Nc1cn(-c2cccnc2)nc1Br] |
| 318 | Brown Solid | 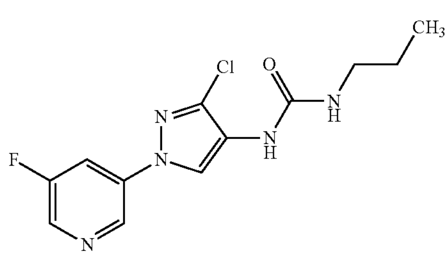 [SMILES: CCCNC(=O)Nc1cn(-c2cncc(F)c2)nc1Cl] |

TABLE 1-continued
| Compound No. | Appearance | Structure |
|---|---|---|
| 319 | Brown Solid | 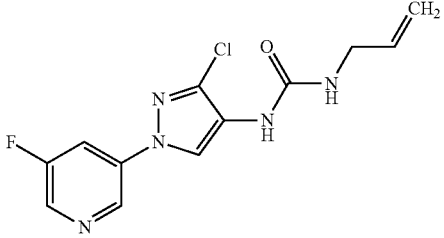 |
| 320 | Yellow Solid | 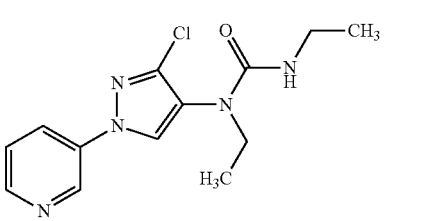 [SMILES: CCNC(=O)N(CC)c1cn(-c2cccnc2)nc1Cl] |
| 321 | Yellow Solid | 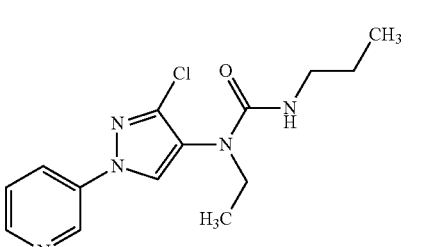 |
| 322 | Yellow Solid | 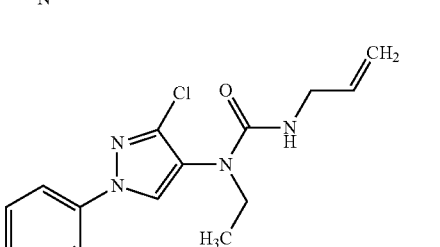 |
| 323 | Colorless Oil | 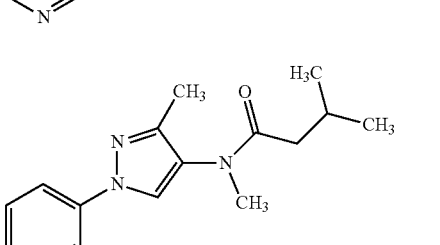 |
| 324 | White Solid | 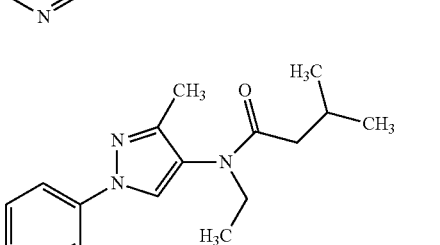 |

TABLE 1-continued

Compound number, appearance, and structure

| Compound No. | Appearance | Structure |
|---|---|---|
| 325 | White Solid | 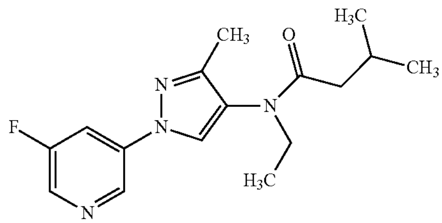 [SMILES: CCN(C(=O)CC(C)C)c1cn(-c2cncc(F)c2)nc1C] |
| 326 | Colorless Oil | 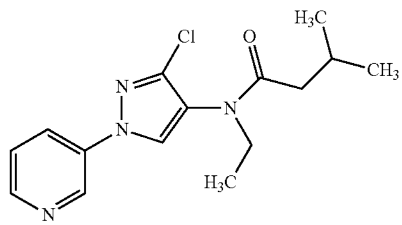 [SMILES: CCN(C(=O)CC(C)C)c1cn(-c2cccnc2)nc1Cl] |
| 327 | White Solid | 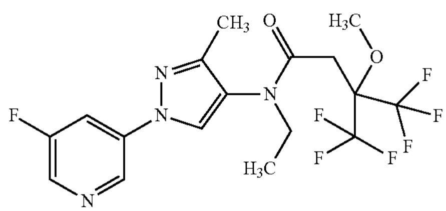 [SMILES: CCN(C(=O)CC(OC)(C(F)(F)F)C(F)(F)F)c1cn(-c2cncc(F)c2)nc1C] |
| 328 | White Foam | 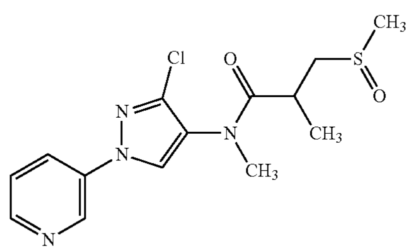 [SMILES: CC(CS(C)=O)C(=O)N(C)c1cn(-c2cccnc2)nc1Cl] |
| 329 | White Foam | 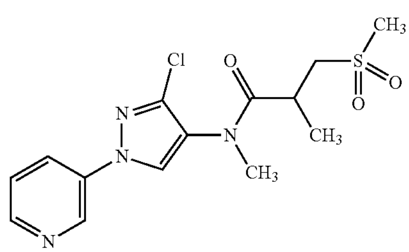 [SMILES: CC(CS(C)(=O)=O)C(=O)N(C)c1cn(-c2cccnc2)nc1Cl] |
| 330 | White Foam | 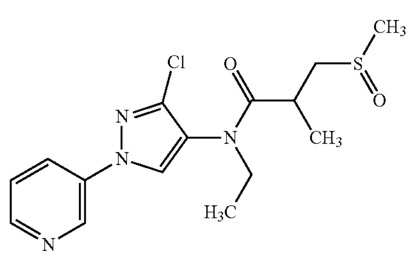 [SMILES: CCN(C(=O)C(C)CS(C)=O)c1cn(-c2cccnc2)nc1Cl] |

TABLE 1-continued
| Compound No. | Appearance | Structure |
|---|---|---|
| 331 | White Foam | 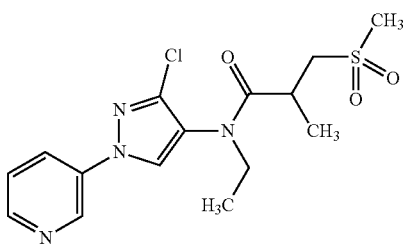 [SMILES: CCN(C(=O)C(C)CS(C)(=O)=O)c1cn(-c2cccnc2)nc1Cl] |
| 332 | Clear Yellow Oil | 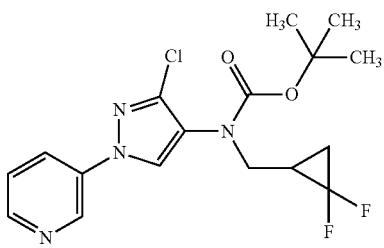 [SMILES: CC(C)(C)OC(=O)N(CC1CC1(F)F)c1cn(-c2cccnc2)nc1Cl] |
| 333 | Clear Oil | 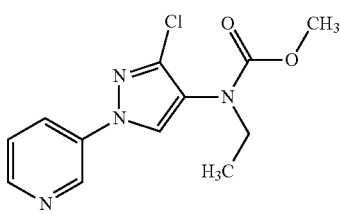 [SMILES: CCN(C(=O)OC)c1cn(-c2cccnc2)nc1Cl] |
| 334 | Light Brown Solid | 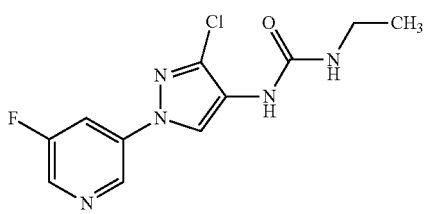 |
| 335 | White Solid | 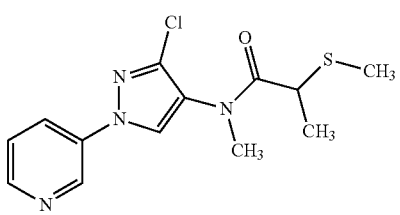 [SMILES: CSC(C)C(=O)N(C)c1cn(-c2cccnc2)nc1Cl] |
| 336 | White Solid | 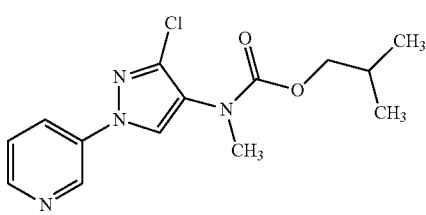 [SMILES: CC(C)COC(=O)N(C)c1cn(-c2cccnc2)nc1Cl] |

TABLE 1-continued
Compound number, appearance, and structure
| Compound No. | Appearance | Structure |
|---|---|---|
| 337 | Pale Yellow Oil | 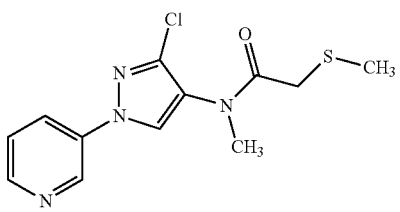 [SMILES: CSCC(=O)N(C)c1cn(-c2cccnc2)nc1Cl] |
| 338 | Clear Oil | 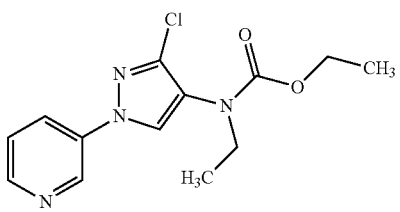 [SMILES: CCOC(=O)N(CC)c1cn(-c2cccnc2)nc1Cl] |
| 339 | Clear Oil | 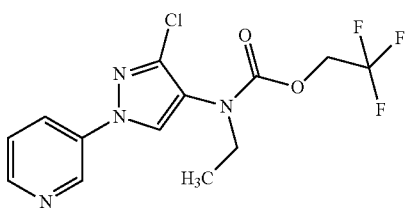 [SMILES: CCN(C(=O)OCC(F)(F)F)c1cn(-c2cccnc2)nc1Cl] |
| 340 | White Solid | 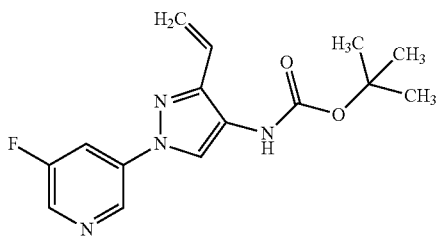 [SMILES: C=Cc1nn(-c2cncc(F)c2)cc1NC(=O)OC(C)(C)C] |
| 341 | Yellow Oil | 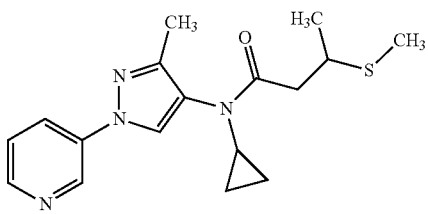 [SMILES: CSC(C)CC(=O)N(c1cn(-c2cccnc2)nc1C)C1CC1] |
| 342 | Yellow Oil | 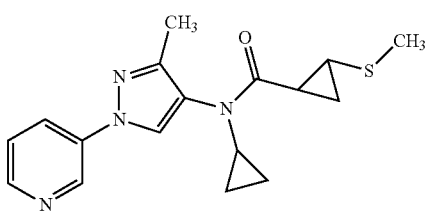 [SMILES: CSC1CC1C(=O)N(c1cn(-c2cccnc2)nc1C)C1CC1] |

TABLE 1-continued
| Compound No. | Appearance | Structure |
|---|---|---|
| 343 | Yellow Oil | 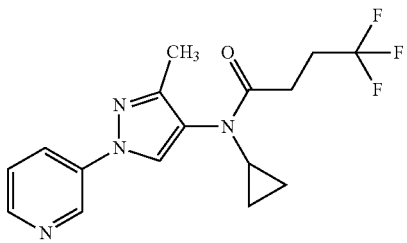 [SMILES: Cc1nn(-c2cccnc2)cc1N(C(=O)CCC(F)(F)F)C1CC1] |
| 344 | Yellow Oil | 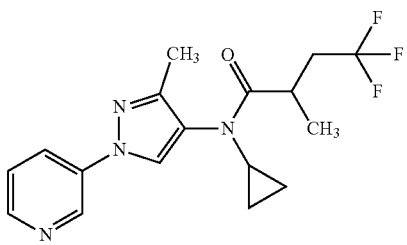 [SMILES: Cc1nn(-c2cccnc2)cc1N(C(=O)C(C)CC(F)(F)F)C1CC1] |
| 345 | Yellow Solid | 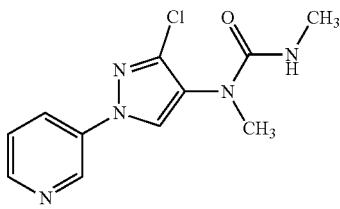 [SMILES: CNC(=O)N(C)c1cn(-c2cccnc2)nc1Cl] |
| 346 | White Solid | 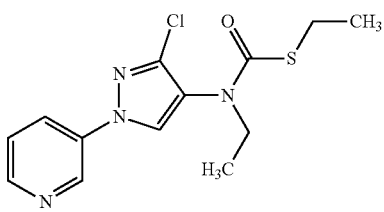 [SMILES: CCSC(=O)N(CC)c1cn(-c2cccnc2)nc1Cl] |
| 347 | Pale Yellow Oil | 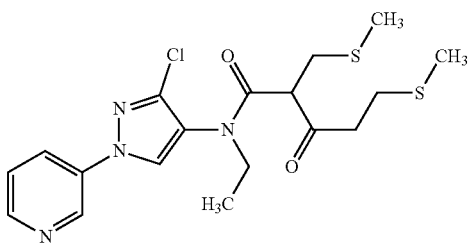 [SMILES: CCN(C(=O)C(CSC)C(=O)CCSC)c1cn(-c2cccnc2)nc1Cl] |
| 348 | Brown Solid | 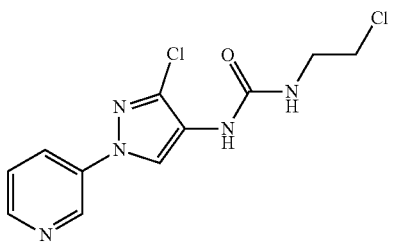 [SMILES: O=C(NCCCl)Nc1cn(-c2cccnc2)nc1Cl] |

TABLE 1-continued
| Compound No. | Appearance | Structure |
|---|---|---|
| 349 | Beige Solid | 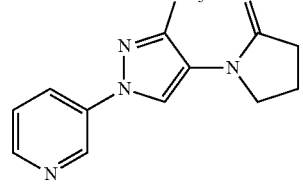 |
| 350 | Colorless Oil | 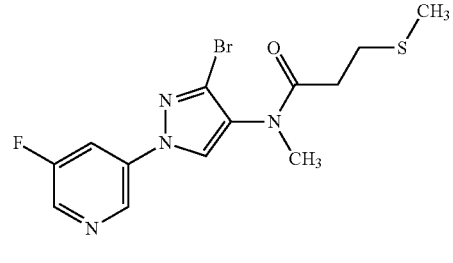 [SMILES: CSCCC(=O)N(C)c1cn(-c2cncc(F)c2)nc1Br] |
| 351 | White Solid | 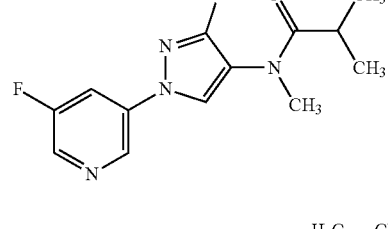 |
| 352 | Yellow Solid | 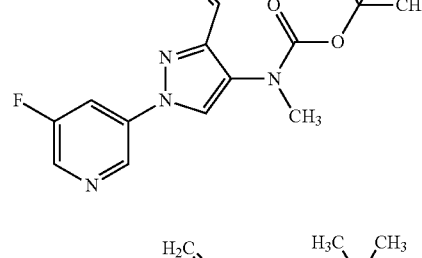 |
| 353 | Yellow Oil | 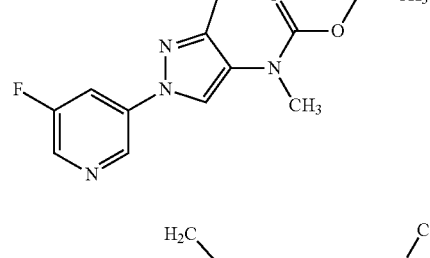 |
| 354 | Yellow Oil | 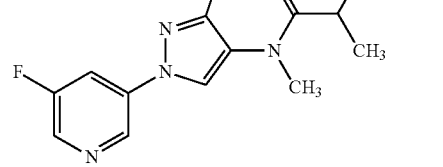 |

TABLE 1-continued

| Compound No. | Appearance | Structure |
|---|---|---|
| 355 | Yellow Solid | 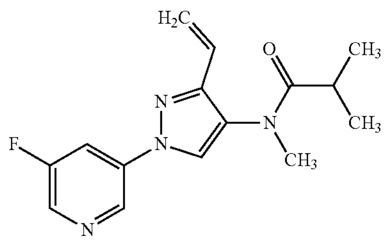 [SMILES: C=Cc1nn(-c2cncc(F)c2)cc1N(C)C(=O)C(C)C] |
| 356 | Yellow Oil | 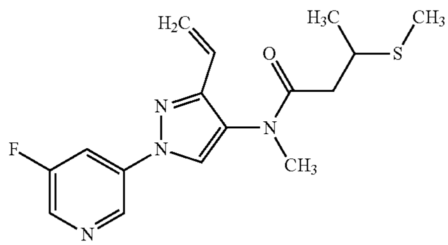 [SMILES: C=Cc1nn(-c2cncc(F)c2)cc1N(C)C(=O)CC(C)SC] |
| 357 | Yellow Oil | 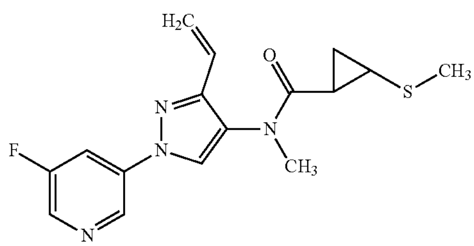 [SMILES: C=Cc1nn(-c2cncc(F)c2)cc1N(C)C(=O)C1CC1SC] |
| 358 | Off White Solid | 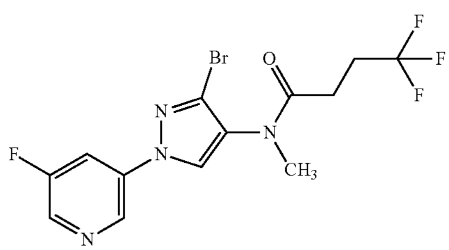 [SMILES: CN(C(=O)CCC(F)(F)F)c1cn(-c2cncc(F)c2)nc1Br] |
| 359 | Off White Solid | 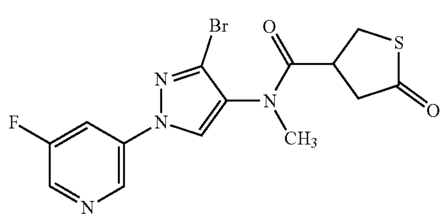 [SMILES: CN(C(=O)C1CSC(=O)C1)c1cn(-c2cncc(F)c2)nc1Br] |
| 360 | White Solid | 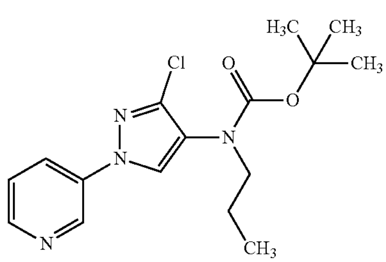 [SMILES: CCCN(C(=O)OC(C)(C)C)c1cn(-c2cccnc2)nc1Cl] |

TABLE 1-continued

Compound number, appearance, and structure

| Compound No. | Appearance | Structure |
|---|---|---|
| 361 | Tan Solid | 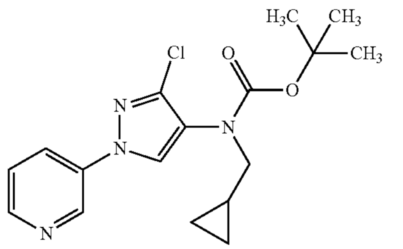 [SMILES: CC(C)(C)OC(=O)N(CC1CC1)c1cn(-c2cccnc2)nc1Cl] |
| 362 | Clear Oil | 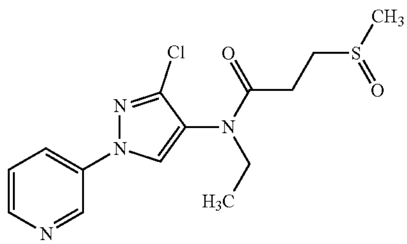 [SMILES: CCN(C(=O)CCS(C)=O)c1cn(-c2cccnc2)nc1Cl] |
| 363 | Clear Oil | 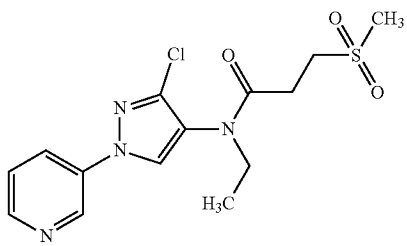 [SMILES: CCN(C(=O)CCS(C)(=O)=O)c1cn(-c2cccnc2)nc1Cl] |
| 364 | Yellow Oil | 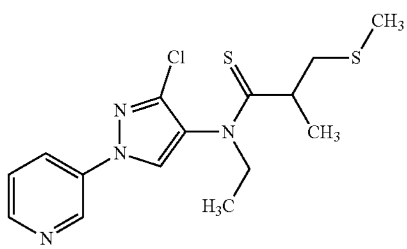 [SMILES: CCN(C(=S)C(C)CSC)c1cn(-c2cccnc2)nc1Cl] |
| 365 | Yellow Oil | 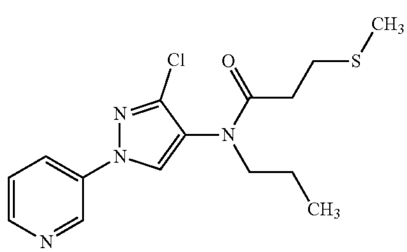 [SMILES: CCCN(C(=O)CCSC)c1cn(-c2cccnc2)nc1Cl] |
| 366 | Yellow Oil | 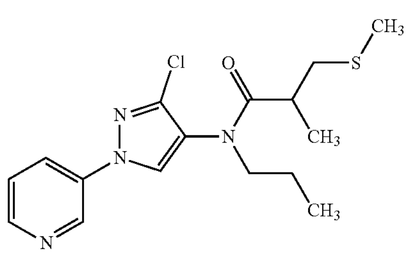 [SMILES: CCCN(C(=O)C(C)CSC)c1cn(-c2cccnc2)nc1Cl] |

TABLE 1-continued
| Compound No. | Appearance | Structure |
|---|---|---|
| 367 | Clear Oil | 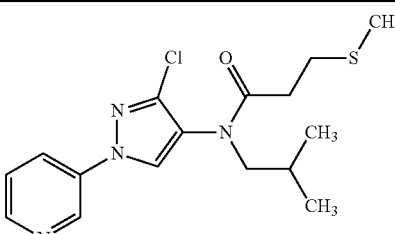 |
| 368 | White Solid | 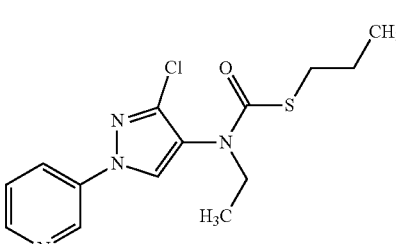 |
| 369 | Light Brown Oil | 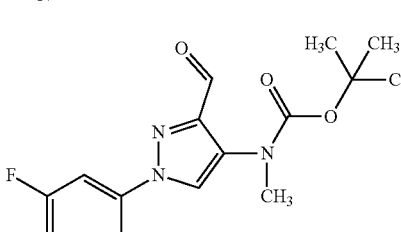 |
| 370 | Colorless Gum | 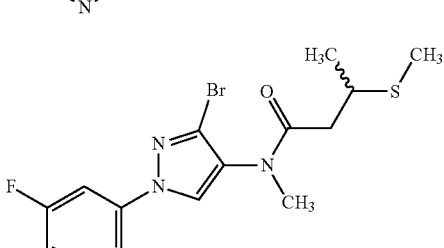 |
| 371 | Colorless Gum | 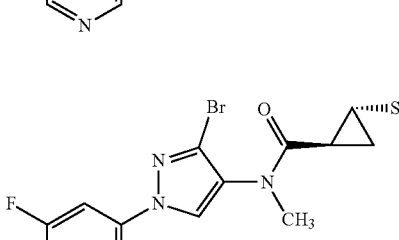 |
| 372 | Yellow Oil | 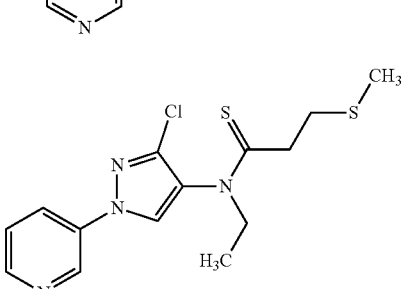 |

TABLE 1-continued
Compound number, appearance, and structure
| Compound No. | Appearance | Structure |
|---|---|---|
| 373 | White Solid | 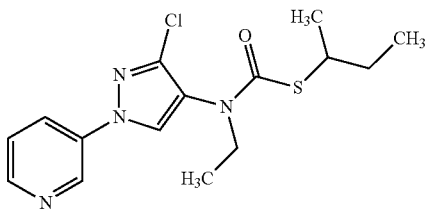 [SMILES: CCC(C)SC(=O)N(CC)c1cn(-c2cccnc2)nc1Cl] |
| 374 | Beige Solid | 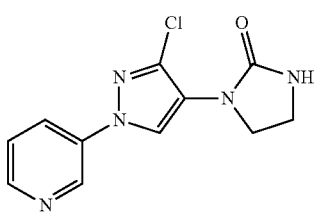 [SMILES: O=C1NCCN1c1cn(-c2cccnc2)nc1Cl] |
| 375 | White Solid | 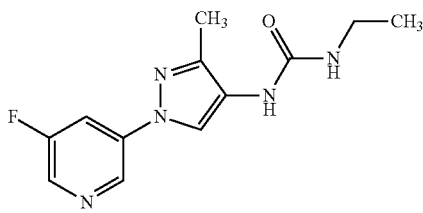 [SMILES: CCNC(=O)Nc1cn(-c2cncc(F)c2)nc1C] |
| 376 | White Solid | 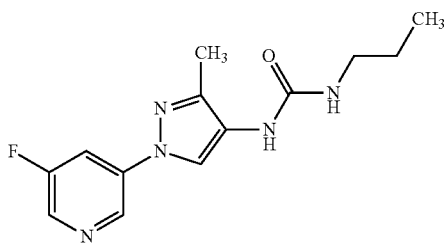 [SMILES: CCCNC(=O)Nc1cn(-c2cncc(F)c2)nc1C] |
| 377 | White Solid | 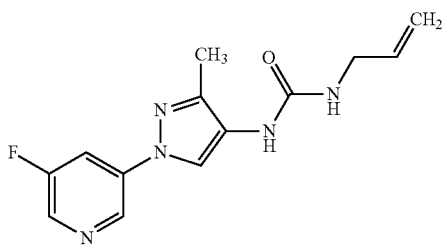 [SMILES: C=CCNC(=O)Nc1cn(-c2cncc(F)c2)nc1C] |
| 378 | White Solid | 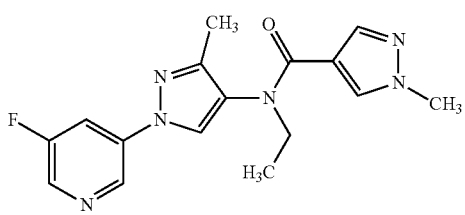 [SMILES: CCN(C(=O)c1cnn(C)c1)c1cn(-c2cncc(F)c2)nc1C] |

TABLE 1-continued

| Compound No. | Appearance | Structure |
|---|---|---|
| 379 | White Solid | 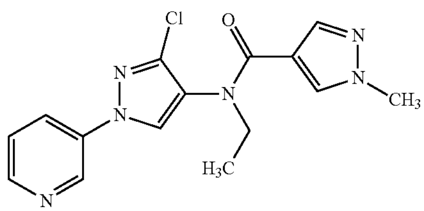 [SMILES: CCN(C(=O)c1cnn(C)c1)c1cn(-c2cccnc2)nc1Cl] |
| 380 | White Solid | 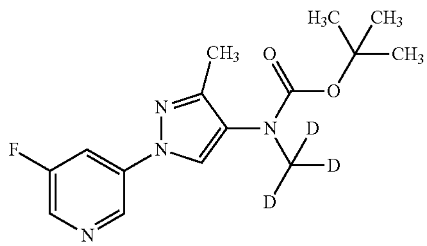 [SMILES: [2H]C([2H])([2H])N(C(=O)OC(C)(C)C)c1cn(-c2cncc(F)c2)nc1C] |
| 381 | White Solid | 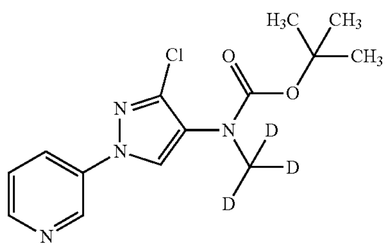 [SMILES: [2H]C([2H])([2H])N(C(=O)OC(C)(C)C)c1cn(-c2cccnc2)nc1Cl] |
| 382 | Clear Oil | 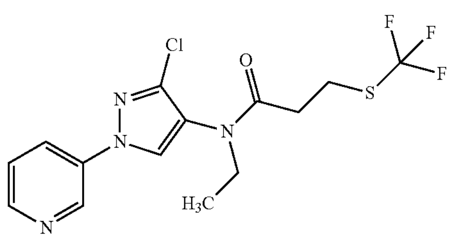 [SMILES: CCN(C(=O)CCSC(F)(F)F)c1cn(-c2cccnc2)nc1Cl] |
| 383 | Pale Yellow Oil | 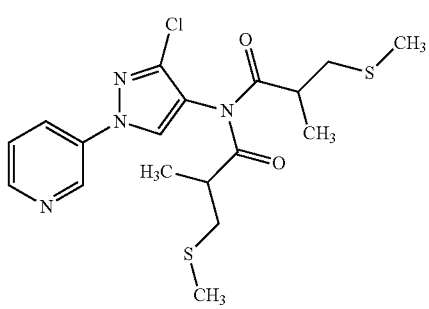 [SMILES: CSCC(C)C(=O)N(C(=O)C(C)CSC)c1cn(-c2cccnc2)nc1Cl] |
| 384 | Colorless Oil | 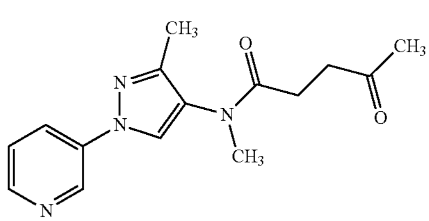 [SMILES: CC(=O)CCC(=O)N(C)c1cn(-c2cccnc2)nc1C] |

TABLE 1-continued
| Compound No. | Appearance | Structure |
|---|---|---|
| 385 | White Solid | 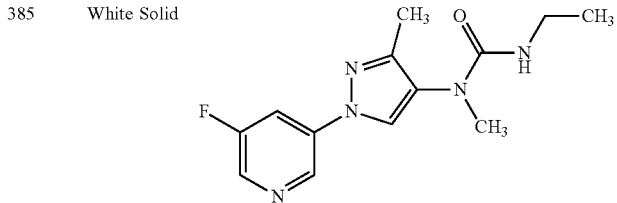 |
| 386 | White Solid | 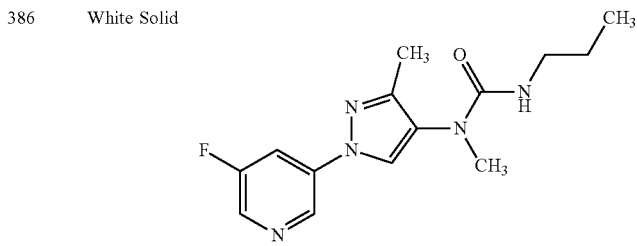 |
| 387 | White Solid | 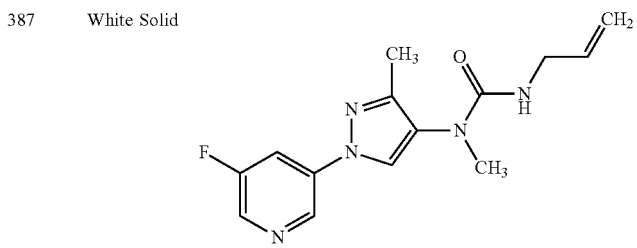 |
| 388 | White Solid | 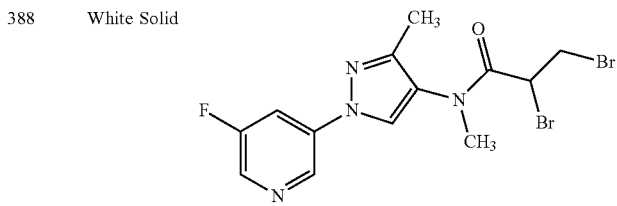 |
| 389 | Colorless Oil | 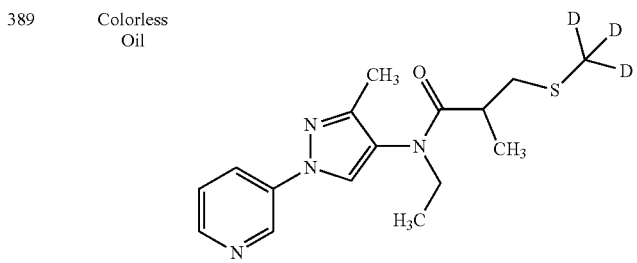 |
| 390 | Off-White Solid | 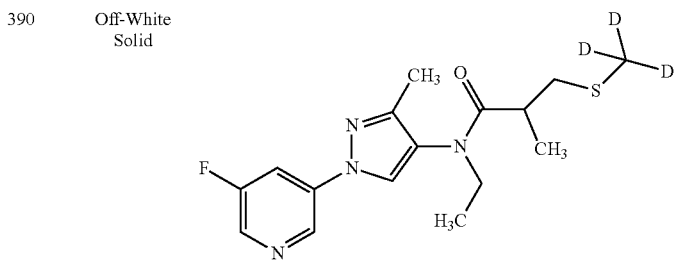 |

TABLE 1-continued
| Compound No. | Appearance | Structure |
|---|---|---|
| 391 | Colorless Oil | 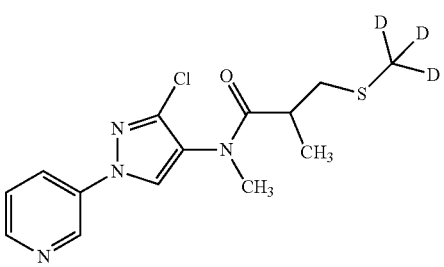 [SMILES: [2H]C([2H])([2H])SCC(C)C(=O)N(C)c1cn(-c2cccnc2)nc1Cl] |
| 392 | Colorless Oil | 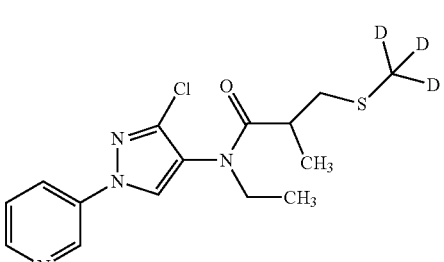 |
| 393 | Colorless Oil | 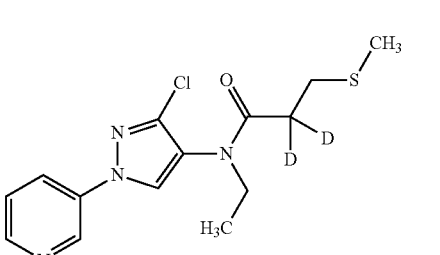 |
| 394 | Colorless Oil | 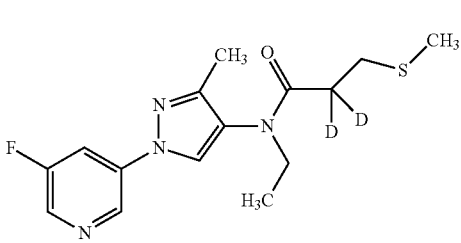 [SMILES: [2H]C([2H])(CSC)C(=O)N(CC)c1cn(-c2cncc(F)c2)nc1C] |
| 395 | Pink Solid | 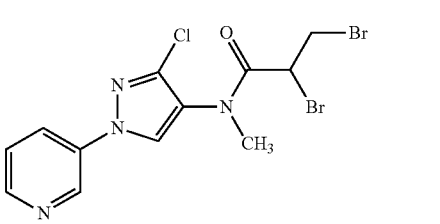 [SMILES: CN(C(=O)C(Br)CBr)c1cn(-c2cccnc2)nc1Cl] |
| 396 | Colorless Oil | 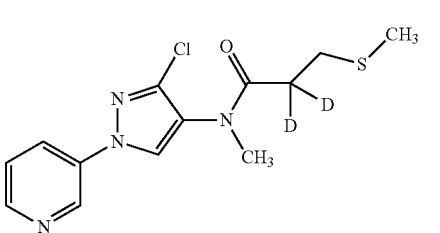 [SMILES: [2H]C([2H])(CSC)C(=O)N(C)c1cn(-c2cccnc2)nc1Cl] |

TABLE 1-continued
| Compound No. | Appearance | Structure |
|---|---|---|
| 397 | Colorless Oil | 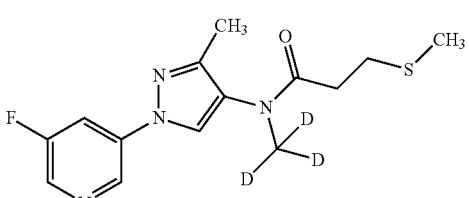 |
| 398 | White Solid | 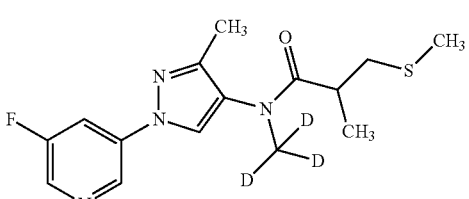 |
| 399 | White Solid | 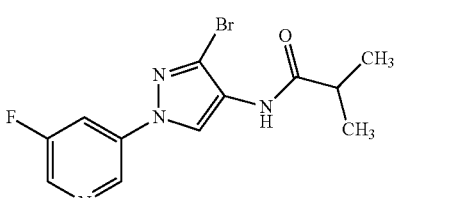 |
| 400 | Yellow Oil | 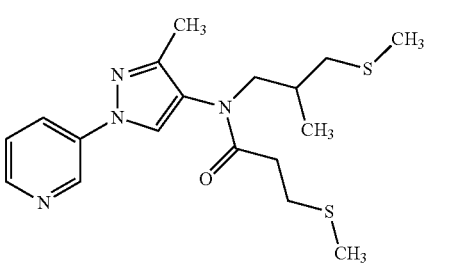 [SMILES: CSCCC(=O)N(CC(C)CSC)c1cn(-c2cccnc2)nc1C] |
| 401 | Yellow Oil | 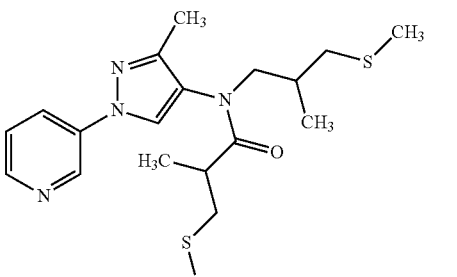 |
| 402 | Yellow Oil | 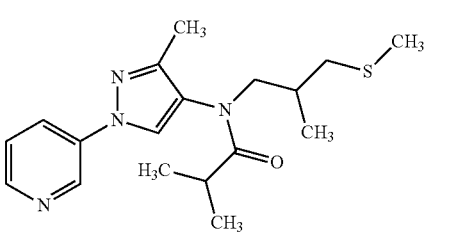 [SMILES: CSCC(C)CN(C(=O)C(C)C)c1cn(-c2cccnc2)nc1C] |

TABLE 1-continued
| Compound No. | Appearance | Structure |
|---|---|---|
| 403 | Yellow Oil | 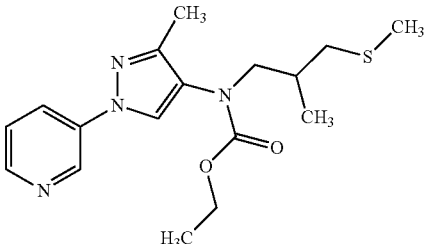 |
| 404 | Yellow Solid | 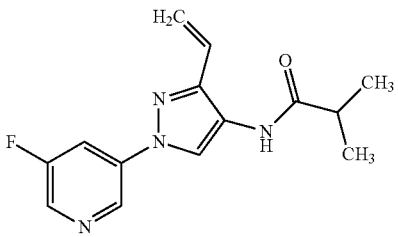 [SMILES: C=Cc1nn(-c2cncc(F)c2)cc1NC(=O)C(C)C] |
| 405 | Colorless Oil | 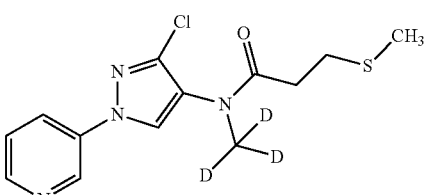 |
| 406 | Colorless Oil | 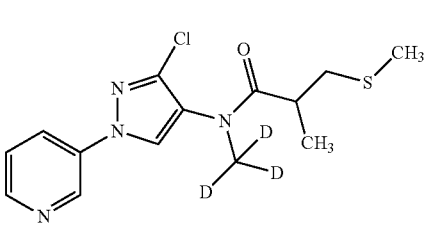 [SMILES: [2H]C([2H])([2H])N(C(=O)C(C)CSC)c1cn(-c2cccnc2)nc1Cl] |
| 407 | Pale Yellow Oil | 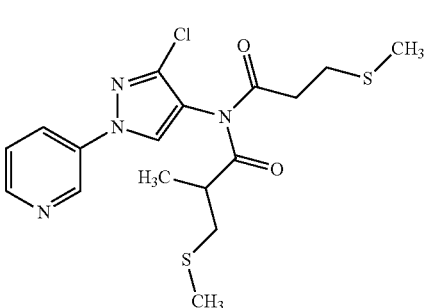 [SMILES: CSCCC(=O)N(C(=O)C(C)CSC)c1cn(-c2cccnc2)nc1Cl] |
| 408 | Yellow Oil | 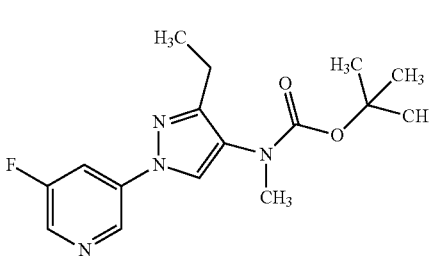 |

TABLE 1-continued
Compound number, appearance, and structure
| Compound No. | Appearance | Structure |
|---|---|---|
| 409 | White Solid | 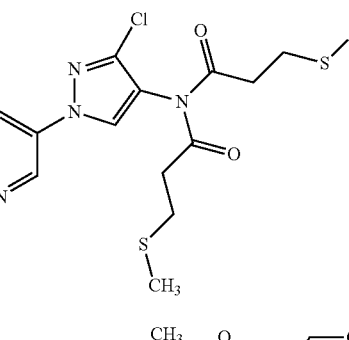 |
| 410 | Orange Oil | 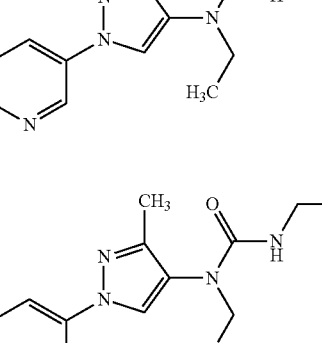 |
| 411 | Beige Solid | 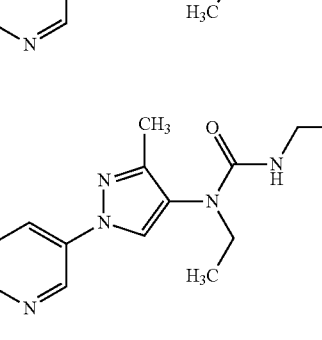 |
| 412 | White Solid | 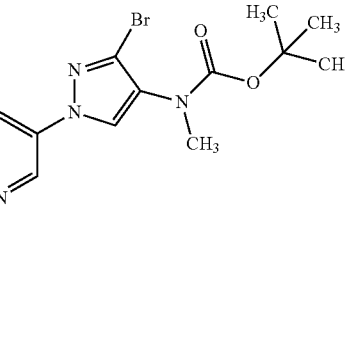 |
| 413 | White Solid | 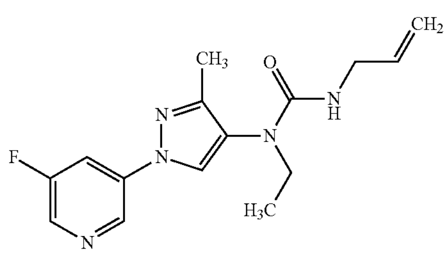 [SMILES: C=CCNC(=O)N(CC)c1cn(-c2cncc(F)c2)nc1C] |
| 414 | Yellow Oil | 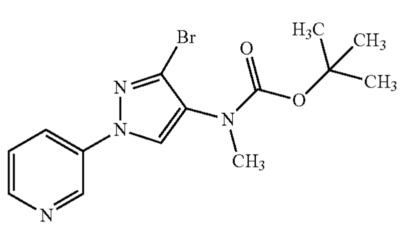 [SMILES: CN(C(=O)OC(C)(C)C)c1cn(-c2cccnc2)nc1Br] |

TABLE 1-continued
| Compound No. | Appearance | Structure |
|---|---|---|
| 415 | Off White Solid | 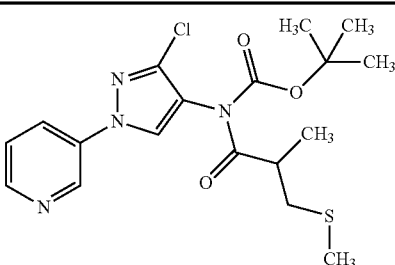 |
| 416 | Yellow Oil | 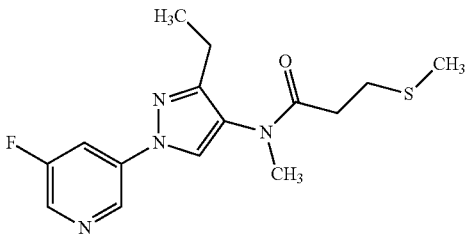 [SMILES: CCc1nn(-c2cncc(F)c2)cc1N(C)C(=O)CCSC] |
| 417 | Yellow Oil | 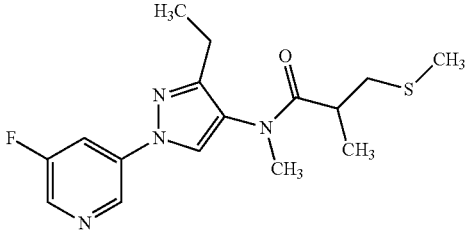 [SMILES: CCc1nn(-c2cncc(F)c2)cc1N(C)C(=O)C(C)CSC] |
| 418 | Yellow Solid | 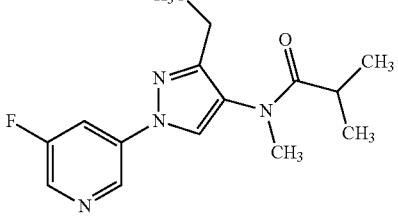 |
| 419 | Yellow Oil | 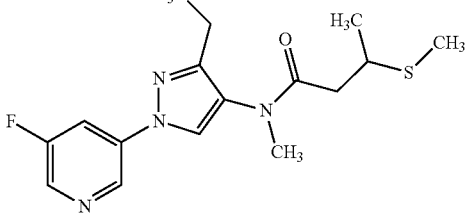 |
| 420 | Yellow Oil | 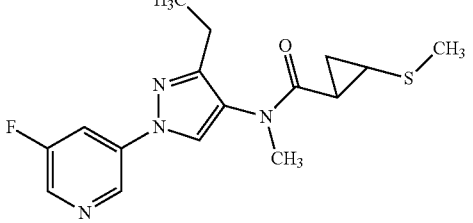 |

TABLE 1-continued

| Compound No. | Appearance | Structure |
|---|---|---|
| 421 | Light Yellow Oil | 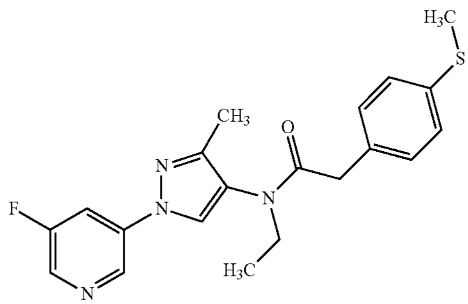 [SMILES: CCN(C(=O)Cc1ccc(SC)cc1)c1cn(-c2cncc(F)c2)nc1C] |
| 422 | Light Yellow Oil | 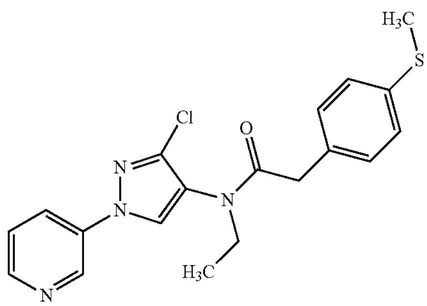 [SMILES: CCN(C(=O)Cc1ccc(SC)cc1)c1cn(-c2cccnc2)nc1Cl] |
| 423 | Light Yellow Oil | 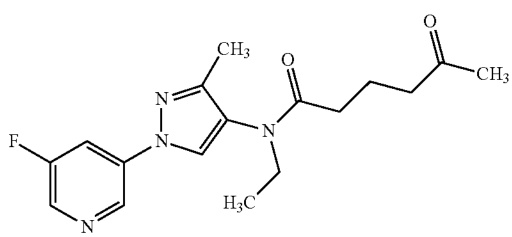 [SMILES: CCN(C(=O)CCCC(C)=O)c1cn(-c2cncc(F)c2)nc1C] |
| 424 | Tan Solid | 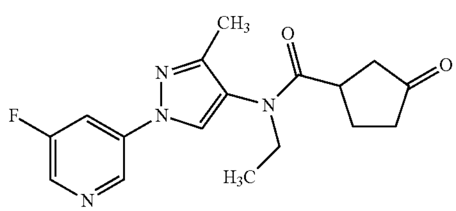 [SMILES: CCN(C(=O)C1CCC(=O)C1)c1cn(-c2cncc(F)c2)nc1C] |
| 425 | Colorless Oil | 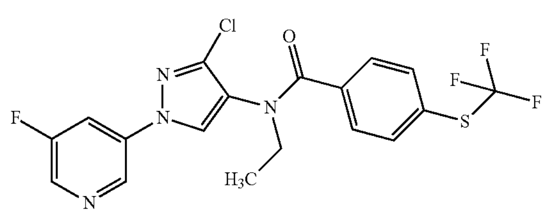 [SMILES: CCN(C(=O)c1ccc(SC(F)(F)F)cc1)c1cn(-c2cncc(F)c2)nc1Cl] |
| 426 | Colorless Oil | 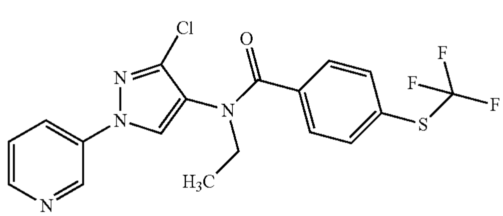 [SMILES: CCN(C(=O)c1ccc(SC(F)(F)F)cc1)c1cn(-c2cccnc2)nc1Cl] |

TABLE 1-continued
Compound number, appearance, and structure
| Compound No. | Appearance | Structure |
|---|---|---|
| 427 | Yellow Oil | 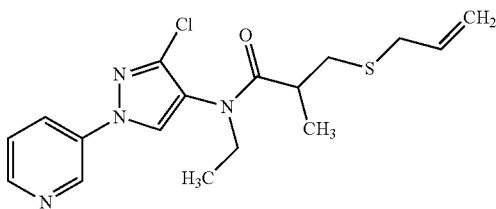 [SMILES: C=CCSCC(C)C(=O)N(CC)c1cn(-c2cccnc2)nc1Cl] |
| 428 | Yellow Oil | 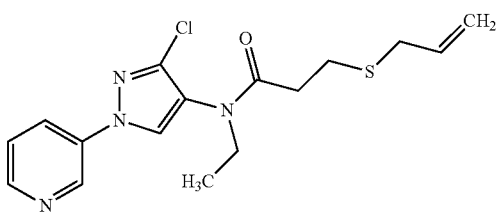 [SMILES: C=CCSCCC(=O)N(CC)c1cn(-c2cccnc2)nc1Cl] |
| 429 | Yellow Oil | 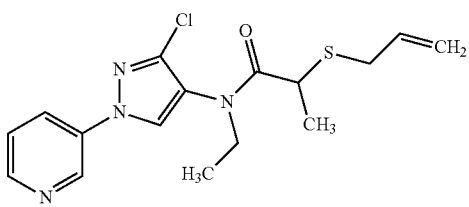 [SMILES: C=CCSC(C)C(=O)N(CC)c1cn(-c2cccnc2)nc1Cl] |
| 430 | Light Yellow Oil | 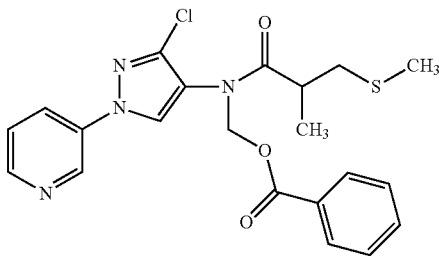 [SMILES: CSCC(C)C(=O)N(COC(=O)c1ccccc1)c1cn(-c2cccnc2)nc1Cl] |
| 431 | White Solid | 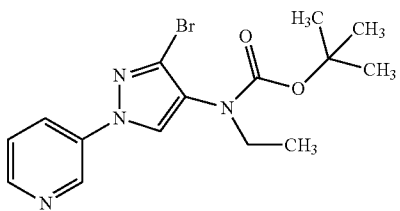 [SMILES: CCN(C(=O)OC(C)(C)C)c1cn(-c2cccnc2)nc1Br] |
| 432 | Yellow Oil | 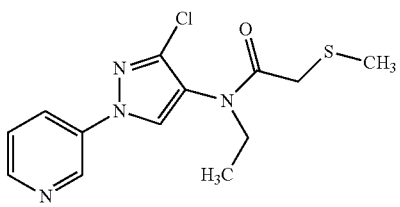 [SMILES: CCN(C(=O)CSC)c1cn(-c2cccnc2)nc1Cl] |

TABLE 1-continued
Compound number, appearance, and structure
| Compound No. | Appearance | Structure |
|---|---|---|
| 433 | Yellow Oil | 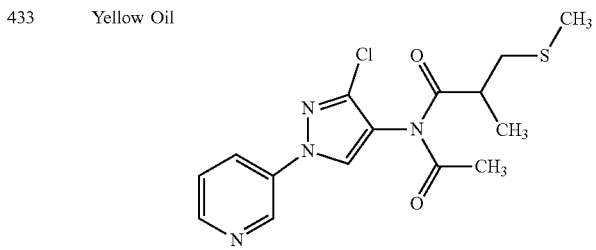 |
| 434 | White Solid | 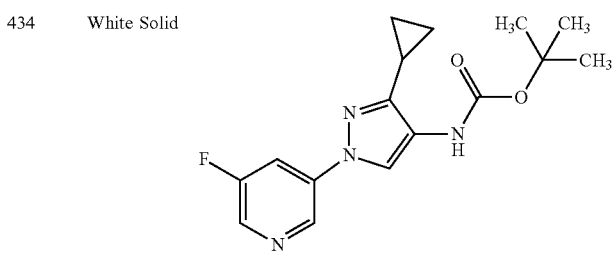 |
| 435 | White Solid | 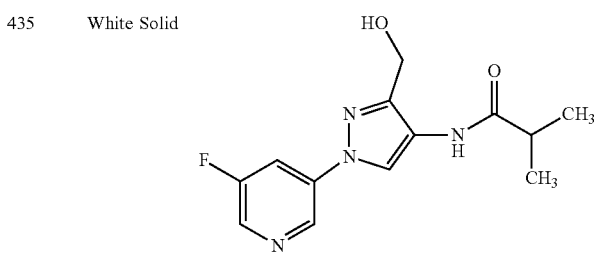 |
| 436 | White Solid | 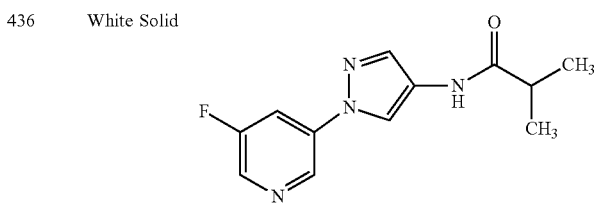 |
| 437 | Yellow Oil | 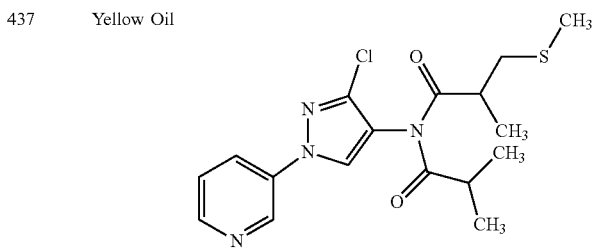 |
| 438 | Yellow Oil | 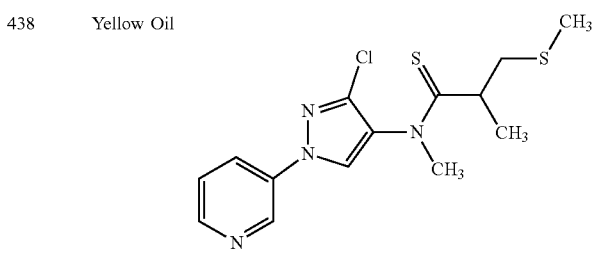 |

TABLE 1-continued
Compound number, appearance, and structure
| Compound No. | Appearance | Structure |
|---|---|---|
| 439 | White Solid | 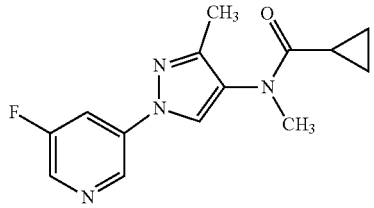 [SMILES: Cc1nn(-c2cncc(F)c2)cc1N(C)C(=O)C1CC1] |
| 440 | White Solid | 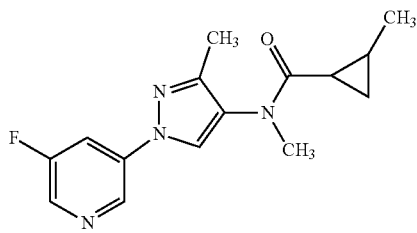 [SMILES: Cc1nn(-c2cncc(F)c2)cc1N(C)C(=O)C1CC1C] |
| 441 | Yellow Solid | 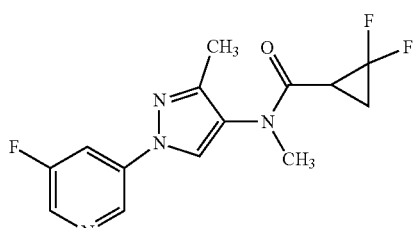 |
| 442 | White Solid | 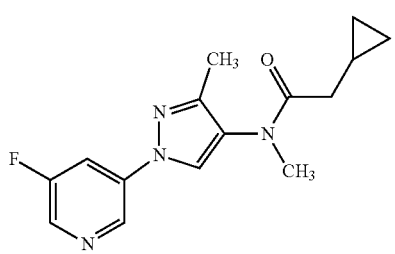 [SMILES: Cc1nn(-c2cncc(F)c2)cc1N(C)C(=O)CC1CC1] |
| 443 | White Solid | 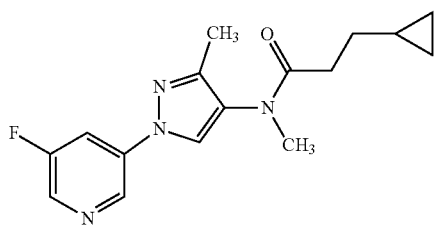 [SMILES: Cc1nn(-c2cncc(F)c2)cc1N(C)C(=O)CCC1CC1] |
| 444 | Brown Solid | 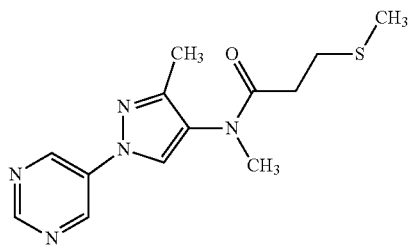 [SMILES: CSCCC(=O)N(C)c1cn(-c2cncnc2)nc1C] |

TABLE 1-continued
| Compound number, appearance, and structure | | |
|---|---|---|
| Compound No. | Appearance | Structure |
| 445 | Brown Solid | 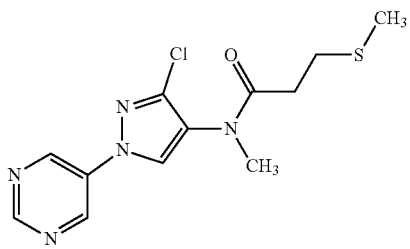 [SMILES: CSCCC(=O)N(C)c1cn(-c2cncnc2)nc1Cl] |
| 446 | Yellow Solid | 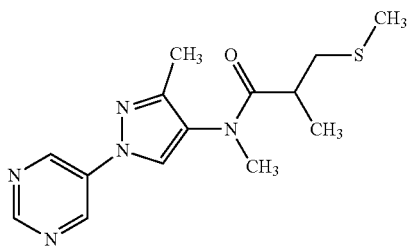 [SMILES: CSCC(C)C(=O)N(C)c1cn(-c2cncnc2)nc1C] |
| 447 | Dark Oil | 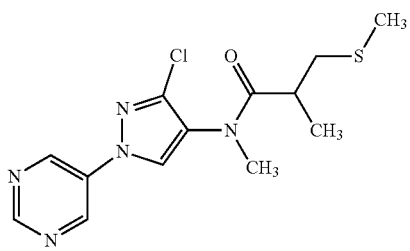 [SMILES: CSCC(C)C(=O)N(C)c1cn(-c2cncnc2)nc1Cl] |
| 448 | Brown Solid | 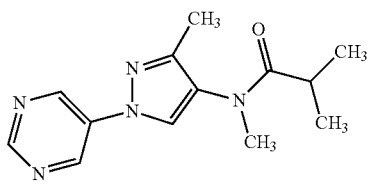 [SMILES: CC(C)C(=O)N(C)c1cn(-c2cncnc2)nc1Cl] |
| 449 | Tan Solid | 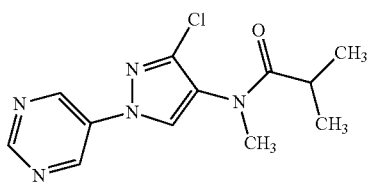 |
| 450 | White Oil | 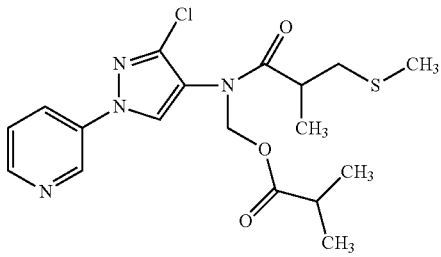 [SMILES: CSCC(C)C(=O)N(COC(=O)C(C)C)c1cn(-c2cccnc2)nc1Cl] |

TABLE 1-continued
| Compound No. | Appearance | Structure |
|---|---|---|
| 451 | Yellow Oil | 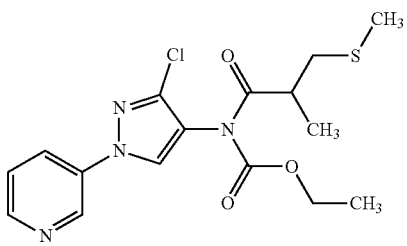 [SMILES: CCOC(=O)N(C(=O)C(C)CSC)c1cn(-c2cccnc2)nc1Cl] |
| 452 | Colorless Oil | 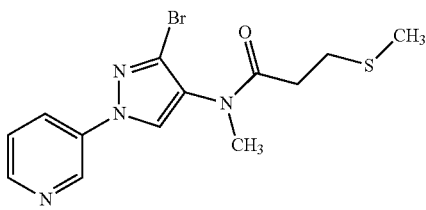 [SMILES: CSCCC(=O)N(C)c1cn(-c2cccnc2)nc1Br] |
| 453 | White Solid | 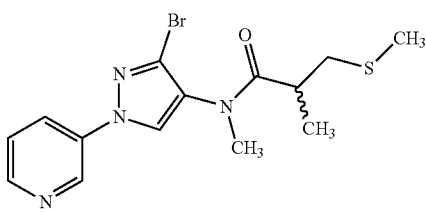 [SMILES: CSCC(C)C(=O)N(C)c1cn(-c2cccnc2)nc1Br] |
| 454 | White Solid | 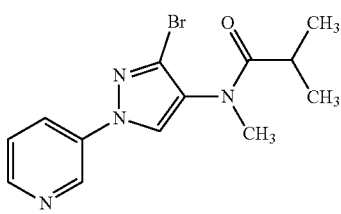 [SMILES: CC(C)C(=O)N(C)c1cn(-c2cccnc2)nc1Br] |
| 455 | Colorless Gum | 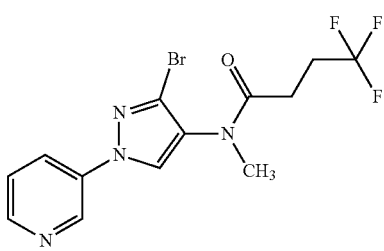 [SMILES: CN(C(=O)CCC(F)(F)F)c1cn(-c2cccnc2)nc1Br] |
| 456 | Yellow Oil | 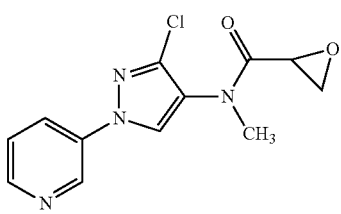 [SMILES: CN(C(=O)C1CO1)c1cn(-c2cccnc2)nc1Cl] |

TABLE 1-continued
| Compound No. | Appearance | Structure |
|---|---|---|
| 457 | White Oil | 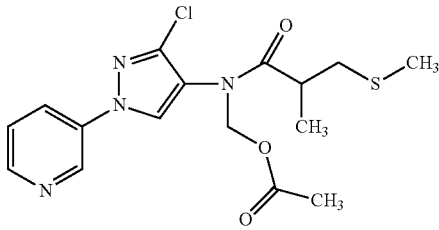 [SMILES: CSCC(C)C(=O)N(COC(C)=O)c1cn(-c2cccnc2)nc1Cl] |
| 458 | White Solid | AND Enantiomer 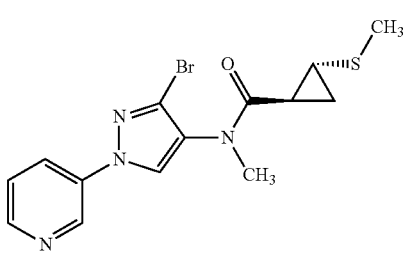 |
| 459 | Colorless Oil | 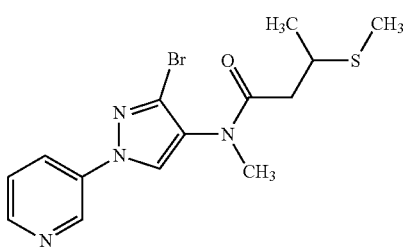 [SMILES: CSC(C)CC(=O)N(C)c1cn(-c2cccnc2)nc1Br] |
| 460 | White Solid | 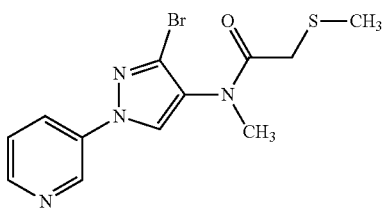 [SMILES: CSCC(=O)N(C)c1cn(-c2cccnc2)nc1Br] |
| 461 | Colorless Gum | 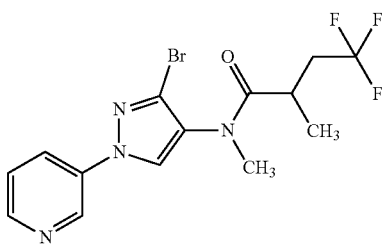 [SMILES: CC(CC(F)(F)F)C(=O)N(C)c1cn(-c2cccnc2)nc1Br] |
| 462 | White Solid | 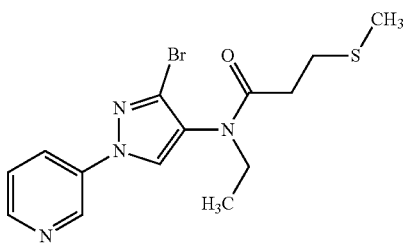 |

TABLE 1-continued
| Compound number, appearance, and structure | | |
|---|---|---|
| Compound No. | Appearance | Structure |
| 463 | White Solid | 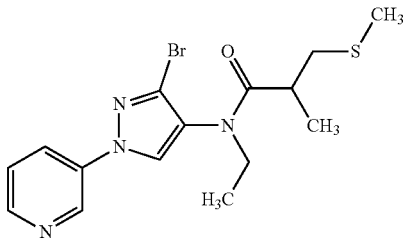 |
| 464 | Colorless Gum | 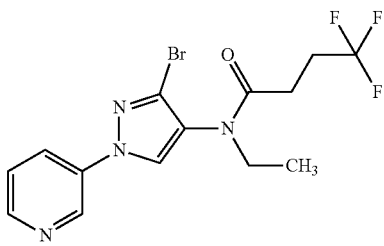 [SMILES: CCN(C(=O)CCC(F)(F)F)c1cn(-c2cccnc2)nc1Br] |
| 465 | White Solid | 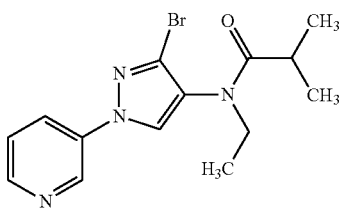 [SMILES: CCN(C(=O)C(C)C)c1cn(-c2cccnc2)nc1Br] |
| 466 | White Solid | 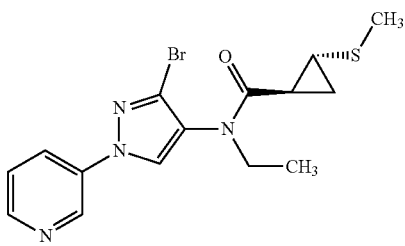 [SMILES: CCN(C(=O)[C@@H]1C[C@H]1SC)c1cn(-c2cccnc2)nc1Br] |
| 467 | Colorless Gum | 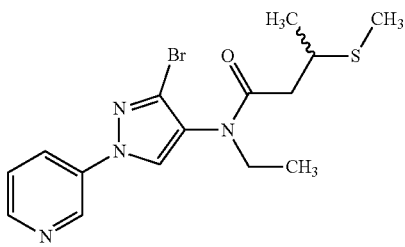 [SMILES: CCN(C(=O)CC(C)SC)c1cn(-c2cccnc2)nc1Br] |
| 468 | Light Yellow Solid | 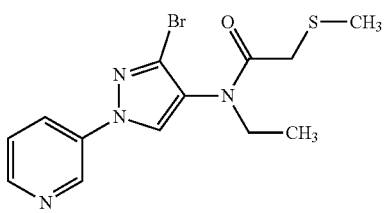 [SMILES: CCN(C(=O)CSC)c1cn(-c2cccnc2)nc1Br] |

TABLE 1-continued
| Compound No. | Appearance | Structure |
|---|---|---|
| 469 | White Solid | 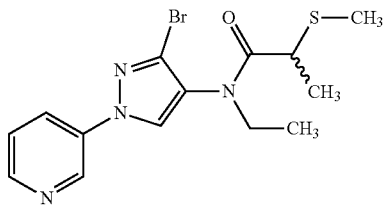 [SMILES: CCN(C(=O)C(C)SC)c1cn(-c2cccnc2)nc1Br] |
| 470 | Light Yellow Oil | 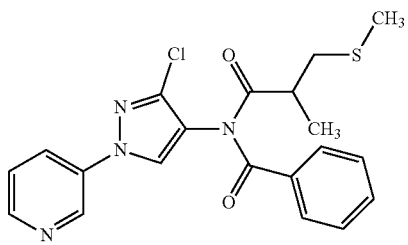 [SMILES: CSCC(C)C(=O)N(C(=O)c1ccccc1)c1cn(-c2cccnc2)nc1Cl] |
| 471 | Light Yellow Oil | 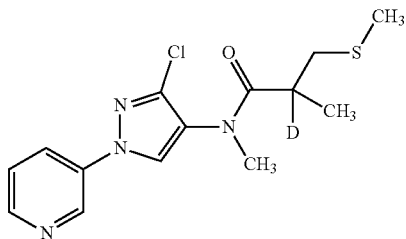 [SMILES: [2H]C(C)(CSC)C(=O)N(C)c1cn(-c2cccnc2)nc1Cl] |
| 472 | Light Yellow Oil | 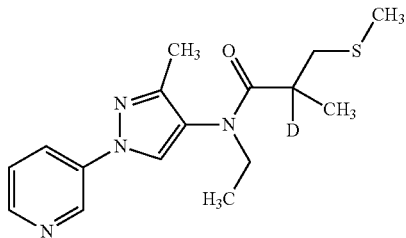 [SMILES: [2H]C(C)(CSC)C(=O)N(CC)c1cn(-c2cccnc2)nc1C] |
| 473 | Light Purple Solid | 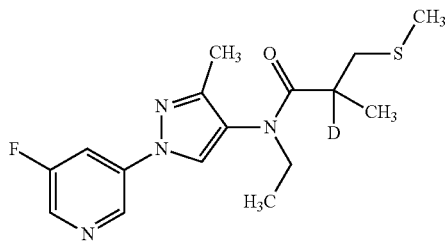 [SMILES: [2H]C(C)(CSC)C(=O)N(CC)c1cn(-c2cncc(F)c2)nc1C] |
| 474 | Yellow Oil | 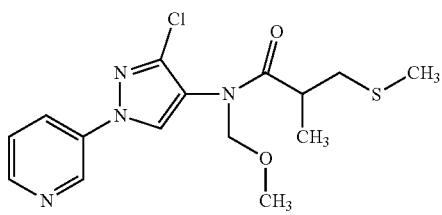 [SMILES: COCN(C(=O)C(C)CSC)c1cn(-c2cccnc2)nc1Cl] |

TABLE 1-continued
Compound number, appearance, and structure
| Compound No. | Appearance | Structure |
|---|---|---|
| 475 | Light Yellow Oil | 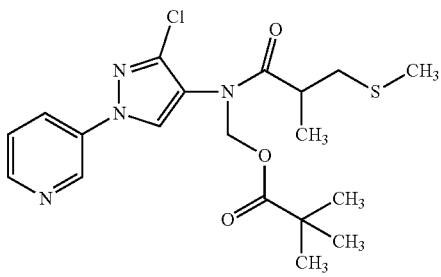 [SMILES: CSCC(C)C(=O)N(COC(=O)C(C)(C)C)c1cn(-c2cccnc2)nc1Cl] |
| 476 | White Solid | 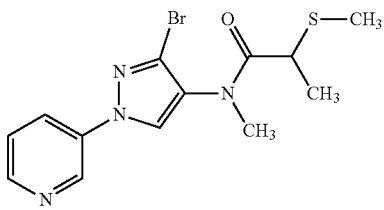 [SMILES: CSC(C)C(=O)N(C)c1cn(-c2cccnc2)nc1Br] |
| 477 | Off White Solid | 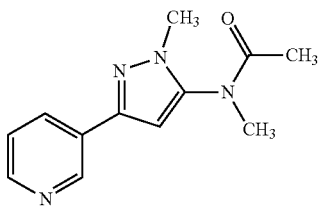 [SMILES: CC(=O)N(C)c1cc(-c2cccnc2)nn1C] |
| 478 | Clear Oil | 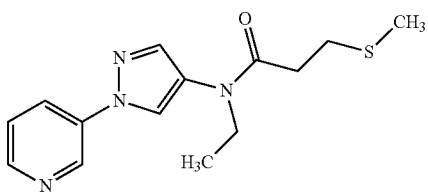 [SMILES: CCN(C(=O)CCSC)c1cnn(-c2cccnc2)c1] |
| 479 | Beige Solid | 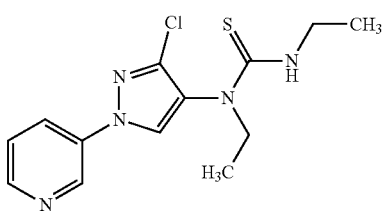 |
| 480 | White Solid | 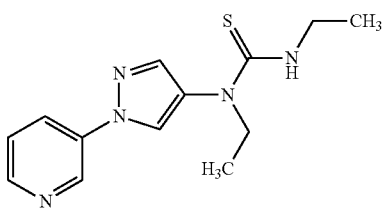 [SMILES: CCNC(=S)N(CC)c1cnn(-c2cccnc2)c1] |

TABLE 1-continued
| Compound number, appearance, and structure |||
| --- | --- | --- |
| Compound No. | Appearance | Structure |
| 481 | Light Yellow Oil | 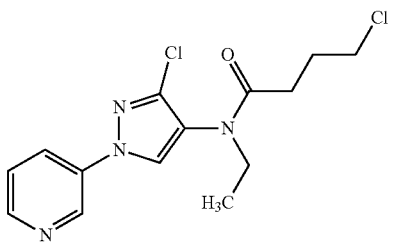 [SMILES: CCN(C(=O)CCCCl)c1cn(-c2cccnc2)nc1Cl] |
| 482 | Beige Solid | 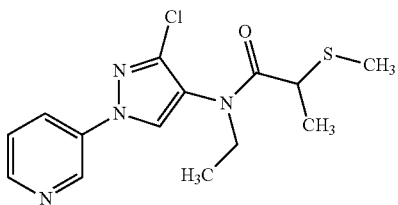 [SMILES: CCN(C(=O)C(C)SC)c1cn(-c2cccnc2)nc1Cl] |
| 483 | Clear Viscous Oil | 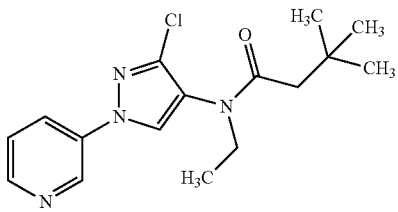 [SMILES: CCN(C(=O)CC(C)(C)C)c1cn(-c2cccnc2)nc1Cl] |
| 484 | Clear Viscous Oil | 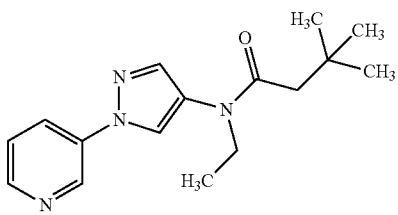 [SMILES: CCN(C(=O)CC(C)(C)C)c1cnn(-c2cccnc2)c1] |
| 485 | White Oil | 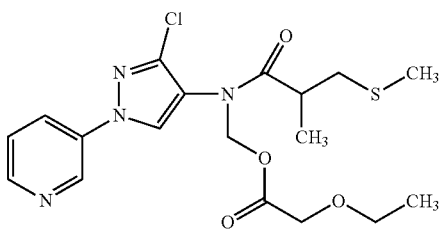 [SMILES: CCOCC(=O)OCN(C(=O)C(C)CSC)c1cn(-c2cccnc2)nc1Cl] |
| 486 | Off White Solid | 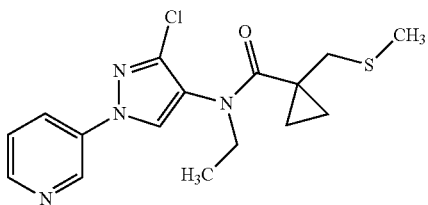 [SMILES: CCN(C(=O)C1(CSC)CC1)c1cn(-c2cccnc2)nc1Cl] |

TABLE 1-continued

| Compound No. | Appearance | Structure |
|---|---|---|
| 487 | Off White Gum | 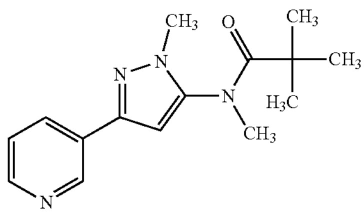 [SMILES: CN(C(=O)C(C)(C)C)c1cc(-c2cccnc2)nn1C] |
| 488 | Light Yellow Solid | 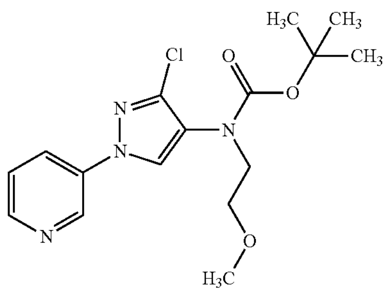 [SMILES: COCCN(C(=O)OC(C)(C)C)c1cn(-c2cccnc2)nc1Cl] |
| 489 | Yellow Solid | 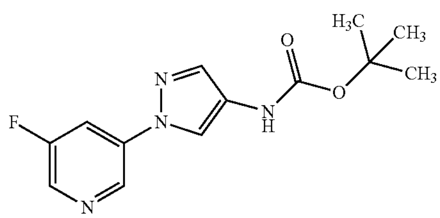 [SMILES: CC(C)(C)OC(=O)Nc1cnn(-c2cncc(F)c2)c1] |
| 490 | Light Yellow Oil | 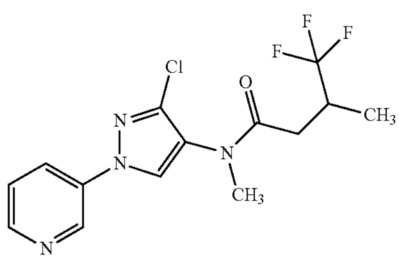 [SMILES: CC(CC(=O)N(C)c1cn(-c2cccnc2)nc1Cl)C(F)(F)F] |
| 491 | Light Yellow Oil | 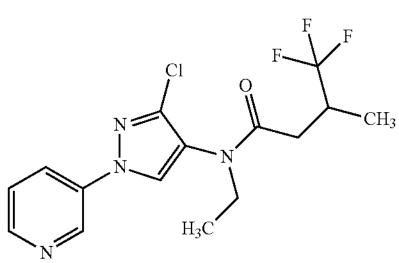 [SMILES: CCN(C(=O)CC(C)C(F)(F)F)c1cn(-c2cccnc2)nc1Cl] |
| 492 | White Solid | 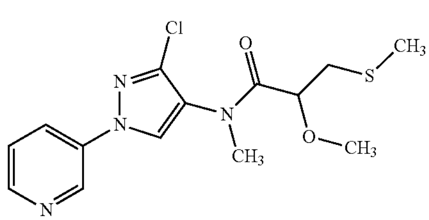 [SMILES: COC(CSC)C(=O)N(C)c1cn(-c2cccnc2)nc1Cl] |

TABLE 1-continued

Compound number, appearance, and structure

| Compound No. | Appearance | Structure |
|---|---|---|
| 493 | Light Orange Oil | 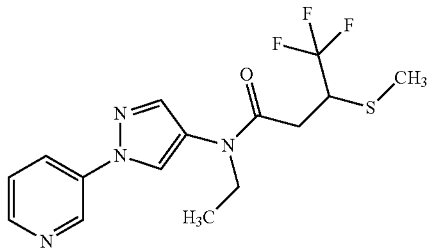 [SMILES: CCN(C(=O)CC(SC)C(F)(F)F)c1cnn(-c2cccnc2)c1] |
| 494 | Yellow Oil | 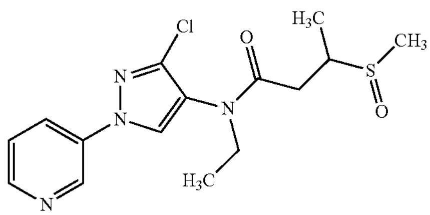 [SMILES: CCN(C(=O)CC(C)S(C)=O)c1cn(-c2cccnc2)nc1Cl] |
| 495 | Clear Oil | 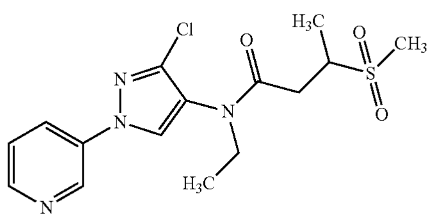 [SMILES: CCN(C(=O)CC(C)S(C)(=O)=O)c1cn(-c2cccnc2)nc1Cl] |
| 496 | Light Yellow Oil | 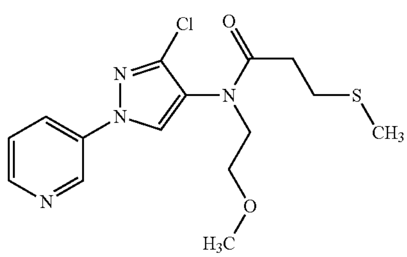 [SMILES: COCCN(C(=O)CCSC)c1cn(-c2cccnc2)nc1Cl] |
| 497 | Light Yellow Oil | 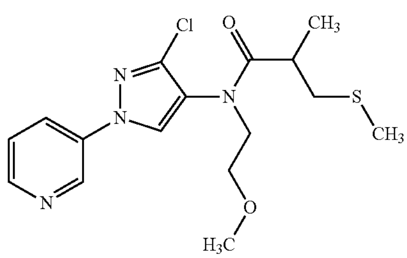 [SMILES: COCCN(C(=O)C(C)CSC)c1cn(-c2cccnc2)nc1Cl] |
| 498 | Light Yellow Oil | 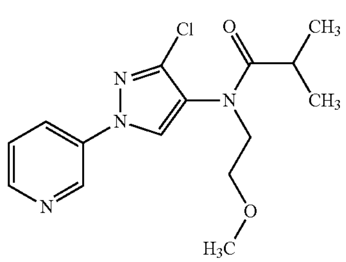 [SMILES: COCCN(C(=O)C(C)C)c1cn(-c2cccnc2)nc1Cl] |

TABLE 1-continued
Compound number, appearance, and structure
| Compound No. | Appearance | Structure |
|---|---|---|
| 499 | Colorless Oil | 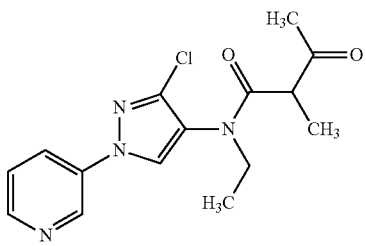 [SMILES: CCN(C(=O)C(C)C(C)=O)c1cn(-c2cccnc2)nc1Cl] |
| 500 | Beige Solid | 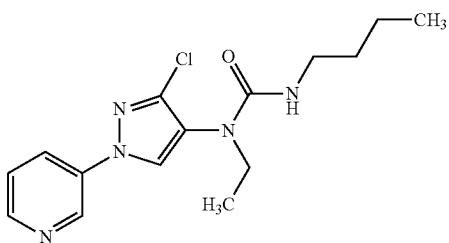 [SMILES: CCCCNC(=O)N(CC)c1cn(-c2cccnc2)nc1Cl] |
| 501 | White Solid | 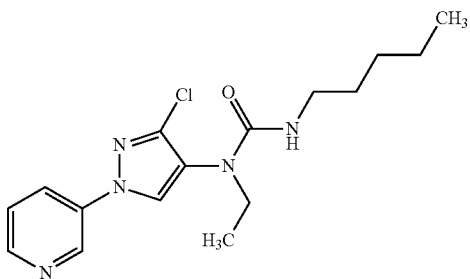 [SMILES: CCCCCNC(=O)N(CC)c1cn(-c2cccnc2)nc1Cl] |
| 502 | Thick Yellow Oil | 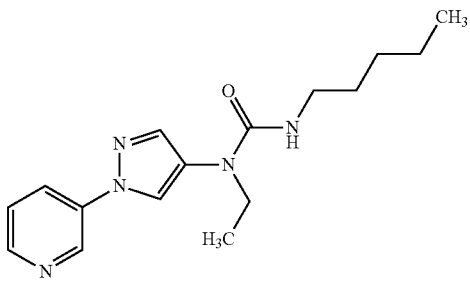 [SMILES: CCCCCNC(=O)N(CC)c1cnn(-c2cccnc2)c1] |
| 503 | Beige Solid | 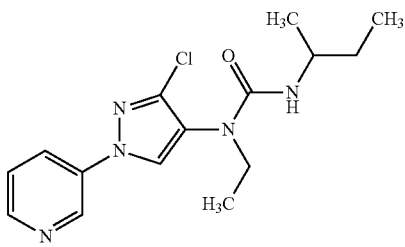 [SMILES: CCC(C)NC(=O)N(CC)c1cn(-c2cccnc2)nc1Cl] |

TABLE 1-continued

| Compound No. | Appearance | Structure |
|---|---|---|
| 504 | Beige Solid | 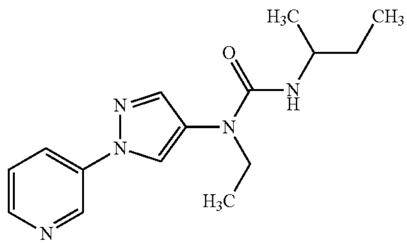 [SMILES: CCC(C)NC(=O)N(CC)c1cnn(-c2cccnc2)c1] |
| 505 | Colorless Gum | 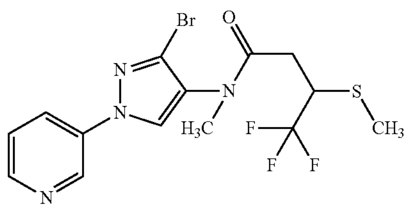 [SMILES: CSC(CC(=O)N(C)c1cn(-c2cccnc2)nc1Br)C(F)(F)F] |
| 506 | Clear Colorless Oil | 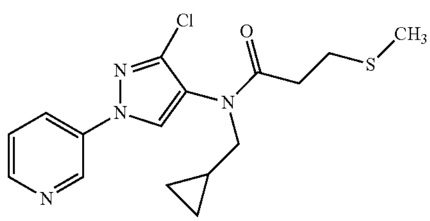 [SMILES: CSCCC(=O)N(CC1CC1)c1cn(-c2cccnc2)nc1Cl] |
| 507 | Clear Colorless Oil | 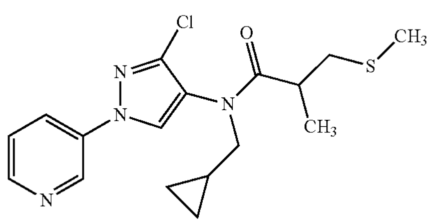 [SMILES: CSCC(C)C(=O)N(CC1CC1)c1cn(-c2cccnc2)nc1Cl] |
| 508 | Clear Colorless Oil | 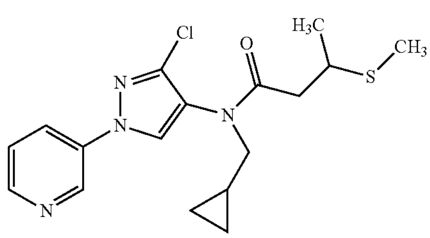 [SMILES: CSC(C)CC(=O)N(CC1CC1)c1cn(-c2cccnc2)nc1Cl] |
| 509 | Pale Yellow Gum | 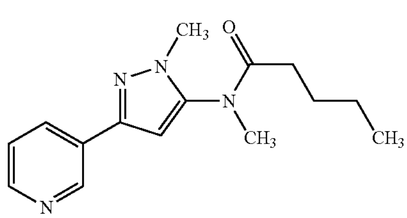 [SMILES: CCCCC(=O)N(C)c1cc(-c2cccnc2)nn1C] |

US 9,655,365 B2
TABLE 1-continued
Compound number, appearance, and structure
| Compound No. | Appearance | Structure |
|---|---|---|
| 510 | Yellow Oil | 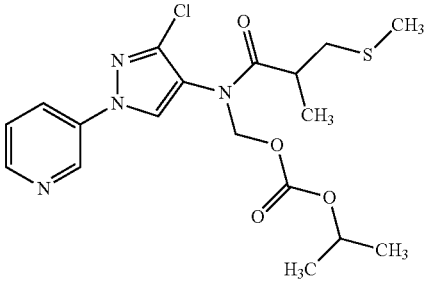 [SMILES: CSCC(C)C(=O)N(COC(=O)OC(C)C)c1cn(-c2cccnc2)nc1Cl] |
| 511 | White Oil | 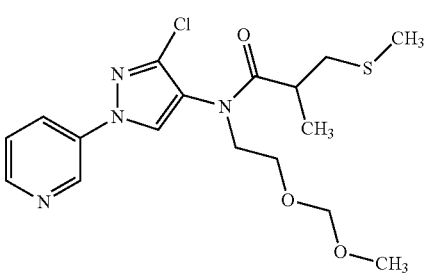 [SMILES: COCOCCN(C(=O)C(C)CSC)c1cn(-c2cccnc2)nc1Cl] |
| 512 | Pale Yellow Oil | 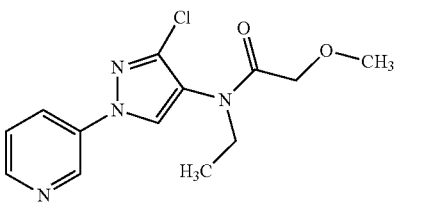 [SMILES: CCN(C(=O)COC)c1cn(-c2cccnc2)nc1Cl] |
| 513 | Thick Clear Oil | 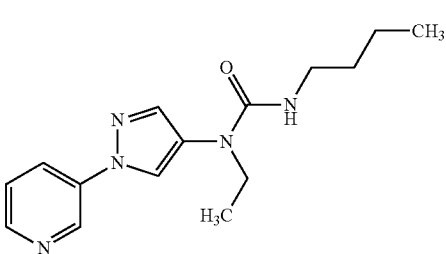 [SMILES: CCCCNC(=O)N(CC)c1cnn(-c2cccnc2)c1] |
| 514 | White Solid | 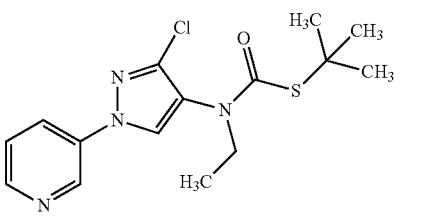 [SMILES: CCN(C(=O)SC(C)(C)C)c1cn(-c2cccnc2)nc1Cl] |
| 515 | White Oil | 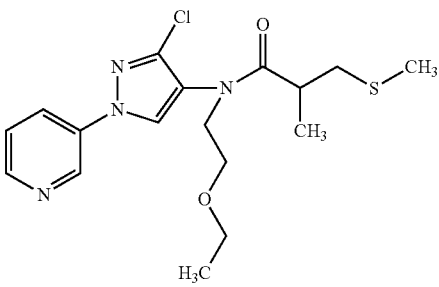 [SMILES: CCOCCN(C(=O)C(C)CSC)c1cn(-c2cccnc2)nc1Cl] |

TABLE 1-continued
| Compound No. | Appearance | Structure |
|---|---|---|
| 516 | Dark Brown Oil | 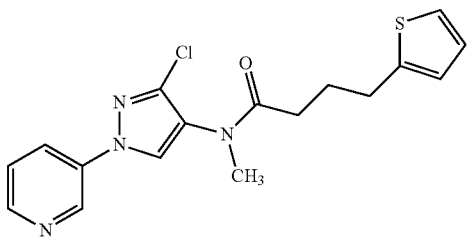 [SMILES: CN(C(=O)CCCc1cccs1)c1cn(-c2cccnc2)nc1Cl] |
| 517 | White Solid | 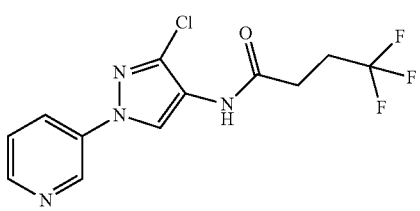 [SMILES: O=C(CCC(F)(F)F)Nc1cn(-c2cccnc2)nc1Cl] |
| 518 | White Solid | 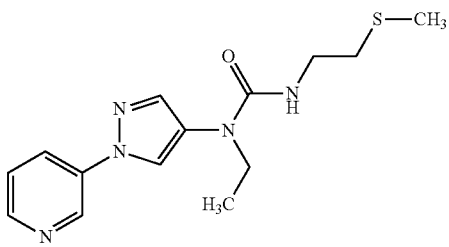 [SMILES: CCN(C(=O)NCCSC)c1cnn(-c2cccnc2)c1] |
| 519 | White Solid | 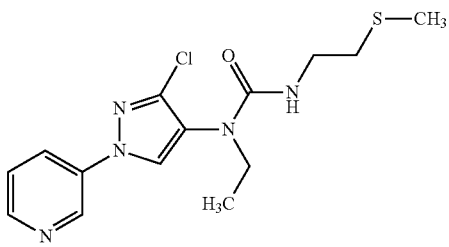 [SMILES: CCN(C(=O)NCCSC)c1cn(-c2cccnc2)nc1Cl] |
| 520 | Brown Gum | 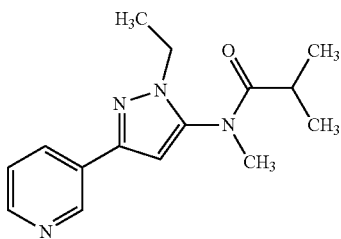 [SMILES: CCn1nc(-c2cccnc2)cc1N(C)C(=O)C(C)C] |
| 521 | Beige Solid | 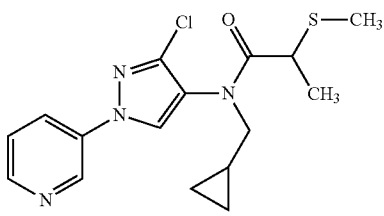 [SMILES: CSC(C)C(=O)N(CC1CC1)c1cn(-c2cccnc2)nc1Cl] |

TABLE 1-continued
| Compound No. | Appearance | Structure |
|---|---|---|
| 522 | White Solid | 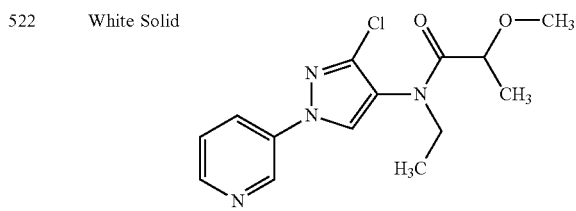 |
| 523 | Yellow Solid | 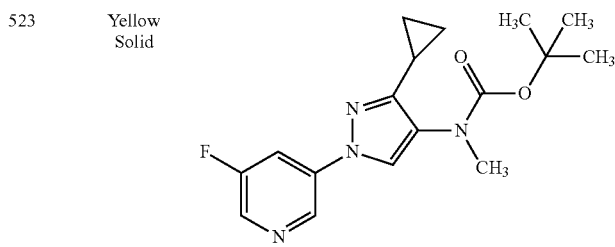 |
| 524 | Light Brown Solid | 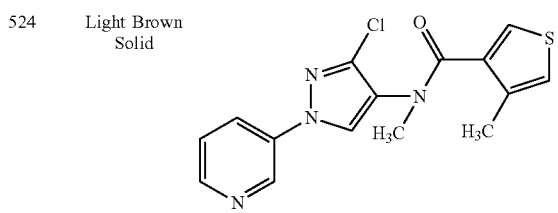 |
| 525 | Faint Yellow Solid | 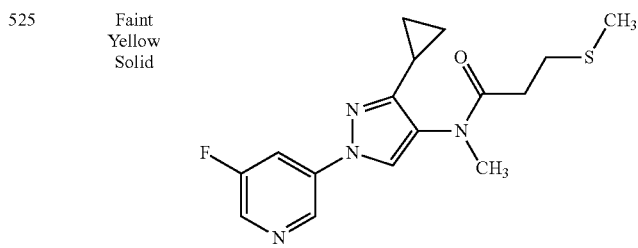 |
| 526 | Faint Yellow Solid | 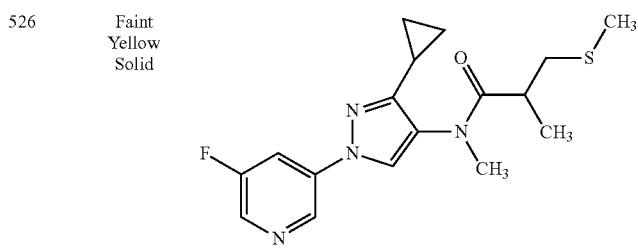 |
| 527 | Yellow Oil | 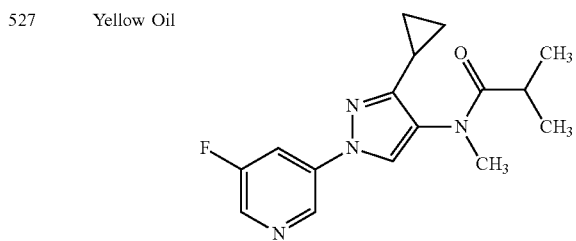 |

TABLE 1-continued
| Compound number, appearance, and structure |
| Compound No. | Appearance | Structure |
|---|---|---|
| 528 | Light Brown Oil | 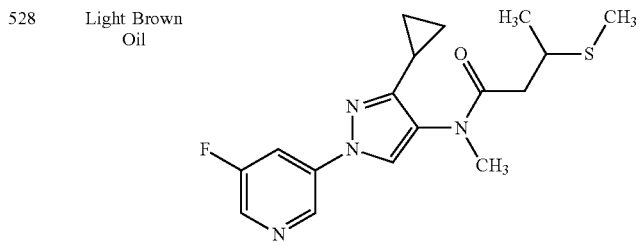 |
| 529 | Faint Yellow Solid | 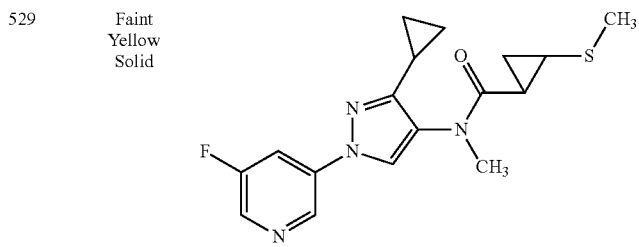 |
| 530 | Clear Oil | 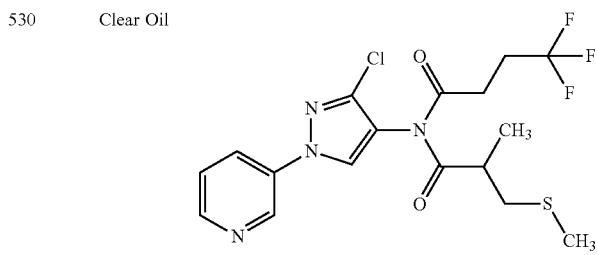 |
| 531 | Yellow Oil | 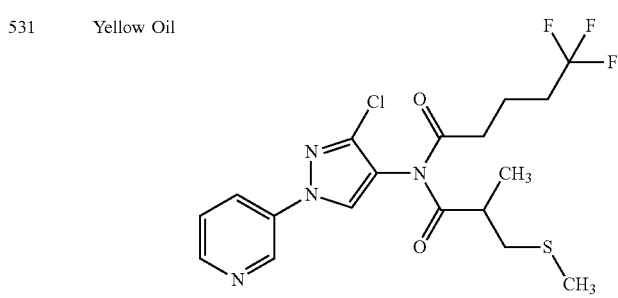 |
| 532 | White Solid | 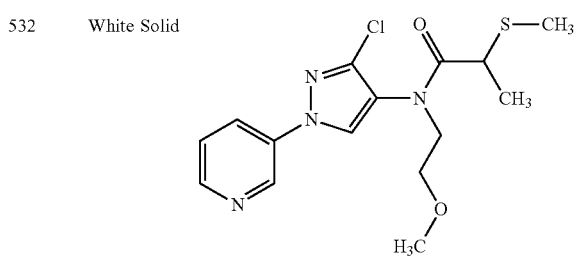 |

TABLE 1-continued
| Compound No. | Appearance | Structure |
|---|---|---|
| 533 | Orange Oil | 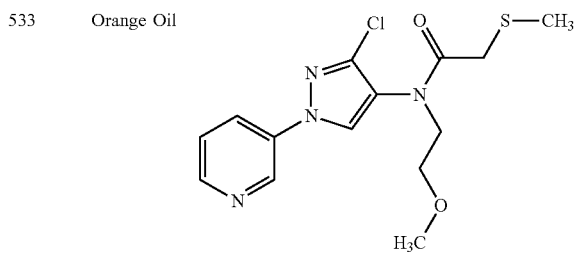 |
| 534 | Red Oil | 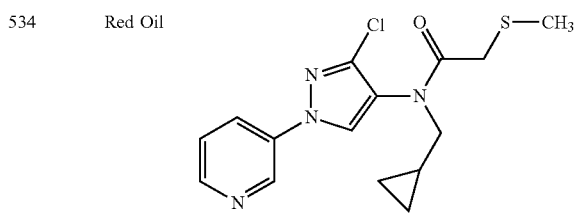 |
| 535 | White Oil | 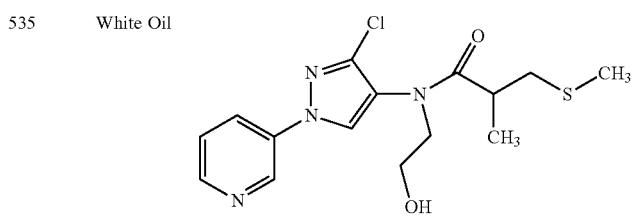 |
| 536 | White Solid | 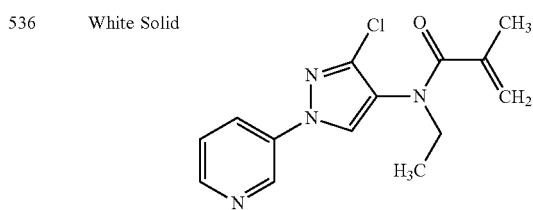 |
| 537 | Clear Oil | 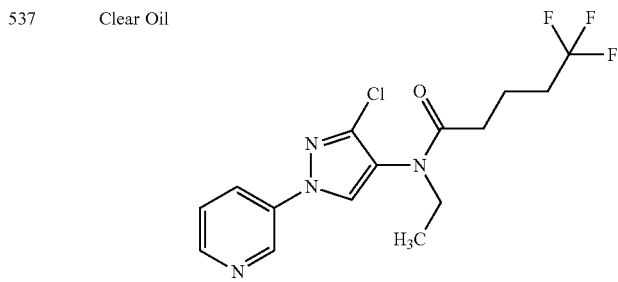 |
| 538 | White Solid | 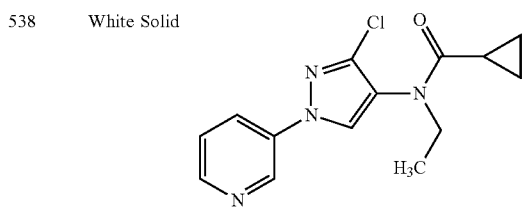 |

TABLE 1-continued
Compound number, appearance, and structure
| Compound No. | Appearance | Structure |
|---|---|---|
| 539 | Clear Oil | 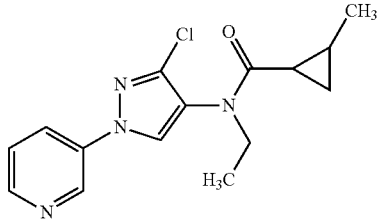 [SMILES: CCN(C(=O)C1CC1C)c1cn(-c2cccnc2)nc1Cl] |
| 540 | Clear Oil | 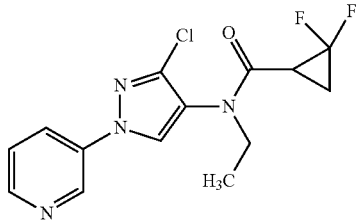 [SMILES: CCN(C(=O)C1CC1(F)F)c1cn(-c2cccnc2)nc1Cl] |
| 541 | Light Yellow Oil | 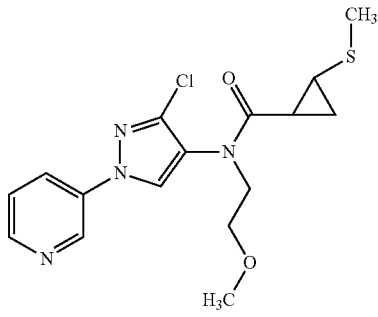 [SMILES: COCCN(C(=O)C1CC1SC)c1cn(-c2cccnc2)nc1Cl] |
| 542 | Colorless Oil | 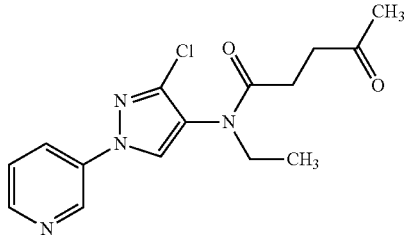 |
| 543 | White Solid | 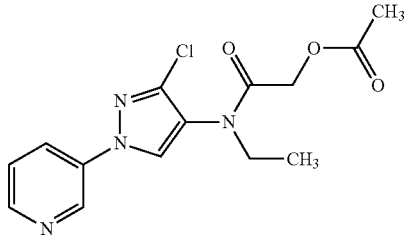 [SMILES: CCN(C(=O)COC(C)=O)c1cn(-c2cccnc2)nc1Cl] |
| 544 | White Solid | 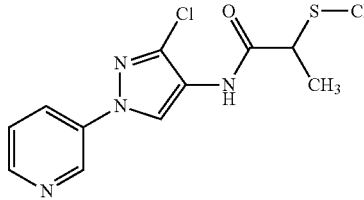 |

TABLE 1-continued
| Compound No. | Appearance | Structure |
|---|---|---|
| 545 | White Fluffy Solid | 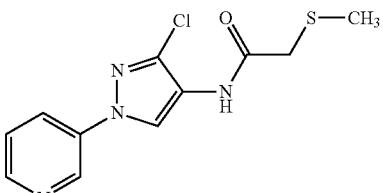 |
| 546 | Brown Solid | 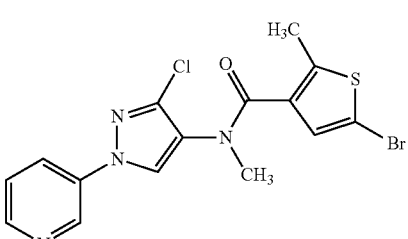 |
| 547 | Yellow Oil | 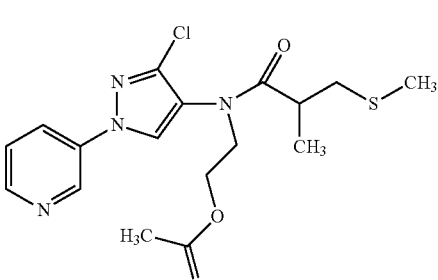 |
| 548 | White Yellow Oil | 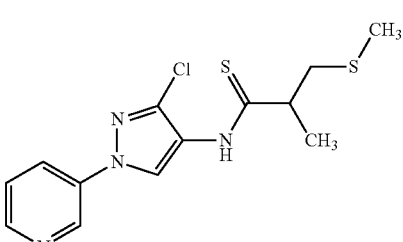 |
| 549 | Colorless Oil | 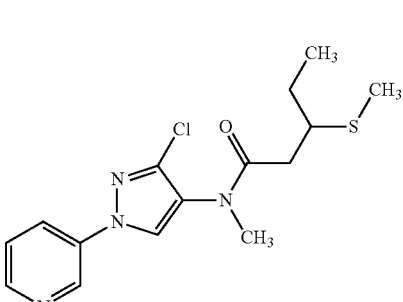 |

TABLE 1-continued

Compound number, appearance, and structure

| Compound No. | Appearance | Structure |
|---|---|---|
| 550 | Colorless Oil | 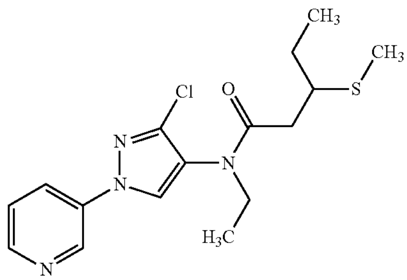 [SMILES: CCC(CC(=O)N(CC)c1cn(-c2cccnc2)nc1Cl)SC] |
| 551 | Colorless Oil | 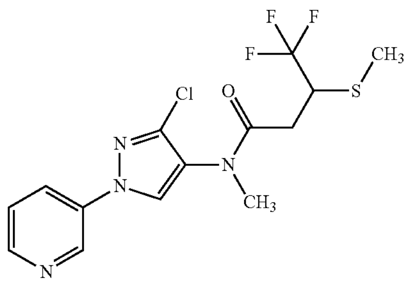 [SMILES: CSC(CC(=O)N(C)c1cn(-c2cccnc2)nc1Cl)C(F)(F)F] |
| 552 | Colorless Oil | 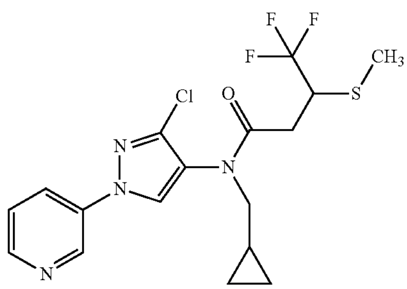 [SMILES: CSC(CC(=O)N(CC1CC1)c1cn(-c2cccnc2)nc1Cl)C(F)(F)F] |
| 553 | Colorless Oil | 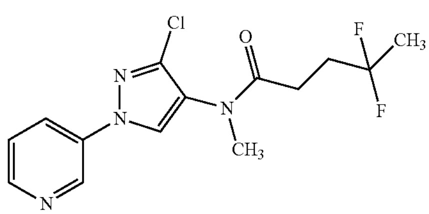 [SMILES: CN(C(=O)CCC(C)(F)F)c1cn(-c2cccnc2)nc1Cl] |
| 554 | Colorless Oil | 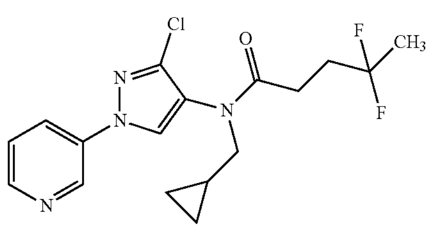 [SMILES: CC(F)(F)CCC(=O)N(CC1CC1)c1cn(-c2cccnc2)nc1Cl] |
| 555 | Yellow Oil | 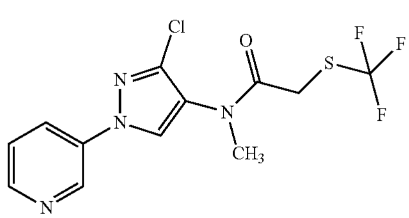 [SMILES: CN(C(=O)CSC(F)(F)F)c1cn(-c2cccnc2)nc1Cl] |

TABLE 1-continued
Compound number, appearance, and structure
| Compound No. | Appearance | Structure |
|---|---|---|
| 556 | Pale Yellow Gum | 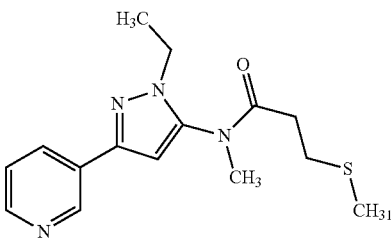 |
| 557 | Pale Yellow Gum | 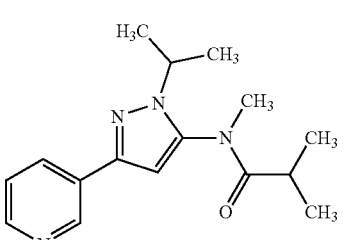 |
| 558 | Faint Yellow Oil | 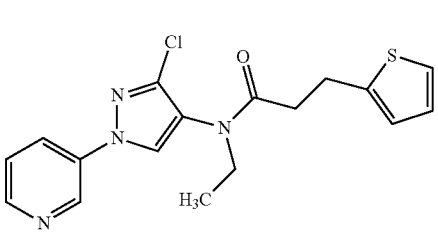 [SMILES: CCN(C(=O)CCc1cccs1)c1cn(-c2cccnc2)nc1Cl] |
| 559 | Faint Yellow Oil | 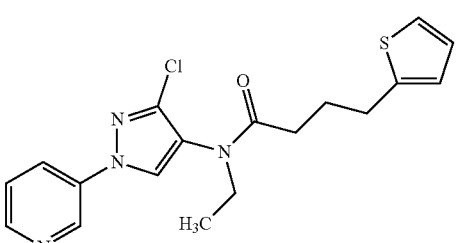 |
| 560 | Yellow Solid | 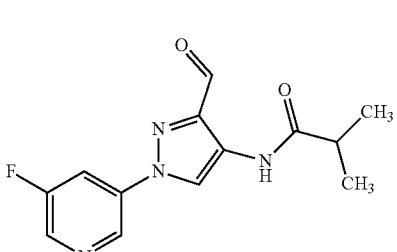 |
| 561 | White Solid | 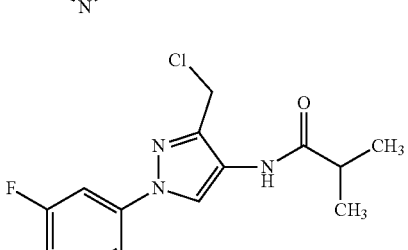 |

295
296
TABLE 1-continued
Compound number, appearance, and structure
| Compound No. | Appearance | Structure |
|---|---|---|
| 562 | Brown Gum | 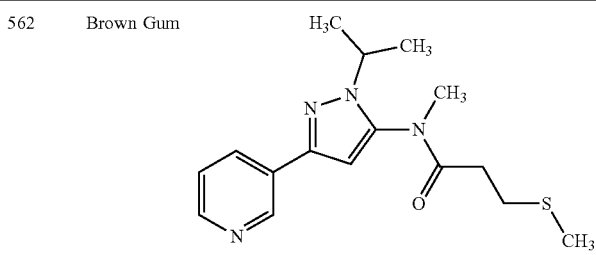 |
| 563 | Pale Yellow Gum | 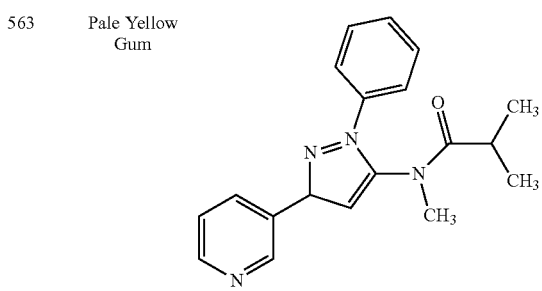 |
| 564 | Pale Yellow Gum | 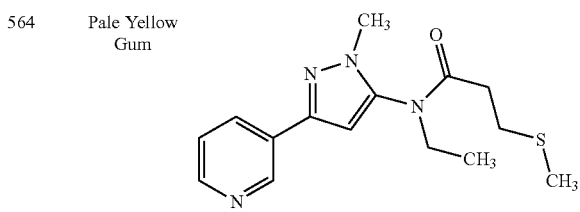 |
| 565 | Pale Yellow Gum | 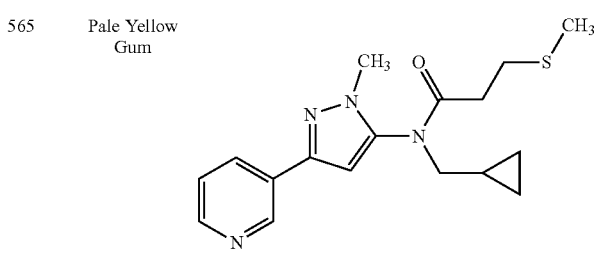 |
| 566 | Pale Yellow Gum | 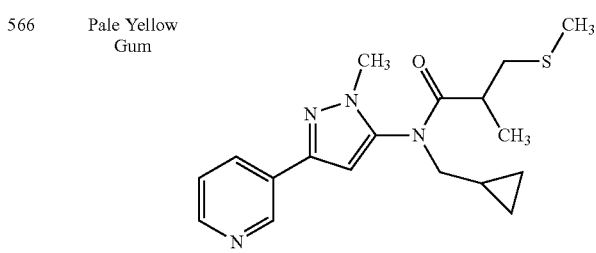 |
| 567 | Off White Solid | 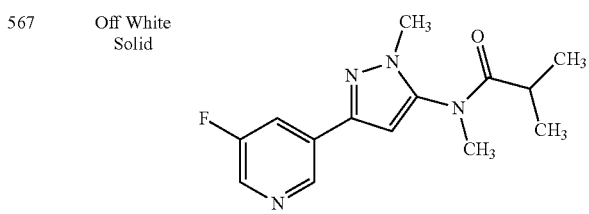 |

TABLE 1-continued

| Compound No. | Appearance | Structure |
|---|---|---|
| 568 | Pale Yellow Gum | 5-fluoropyridin-3-yl substituted 1-methylpyrazol-5-yl with N-methyl-N-(2-(methylthio)ethyl)carboxamide |
| 569 | Colorless Oil | 3-chloro-1-(pyridin-3-yl)pyrazol-4-yl with N-ethyl-4,4-difluoro-4-methylbutanamide (N-ethyl) |
| 570 | White Semi Solid | 3-chloro-1-(pyridin-3-yl)pyrazol-4-yl with N-ethyl-4,4,4-trifluoro-3-(methylsulfinyl)butanamide |
| 571 | White Semi Solid | 3-chloro-1-(pyridin-3-yl)pyrazol-4-yl with N-ethyl-2-(methylsulfinylmethyl)-3,3,3-trifluoropropanamide |
| 572 | Colorless Oil | 3-chloro-1-(pyridin-3-yl)pyrazol-4-yl with N-methyl-4,4,5,5,5-pentafluoropentanamide |
| 573 | Colorless Oil | 3-chloro-1-(pyridin-3-yl)pyrazol-4-yl with N-ethyl-4,4,5,5,5-pentafluoropentanamide |

TABLE 1-continued
Compound number, appearance, and structure
| Compound No. | Appearance | Structure |
|---|---|---|
| 574 | Colorless Oil | 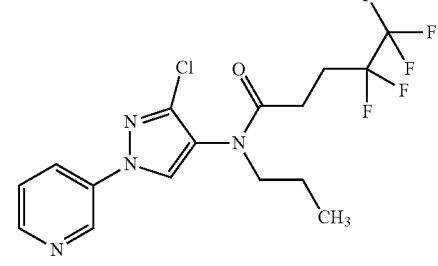 |
| 575 | Colorless Oil | 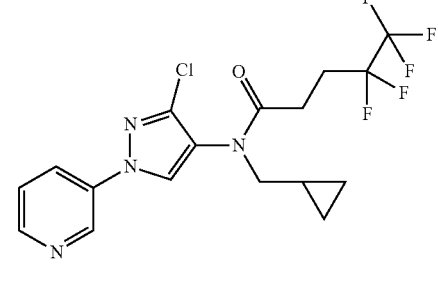 |
| 576 | Colorless Oil | 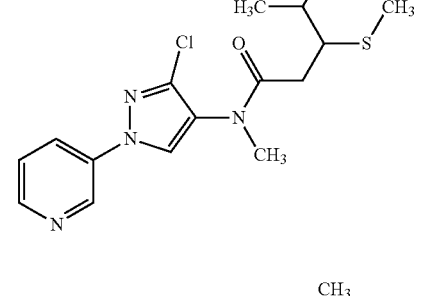 |
| 577 | Colorless Oil | 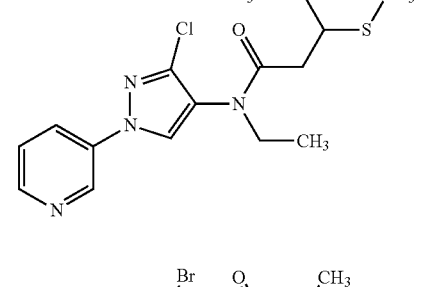 |
| 578 | Colorless Oil | 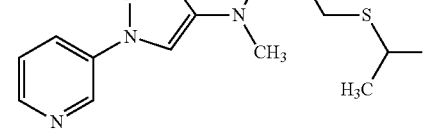 |

TABLE 1-continued
Compound number, appearance, and structure
| Compound No. | Appearance | Structure |
|---|---|---|
| 579 | Colorless Oil | 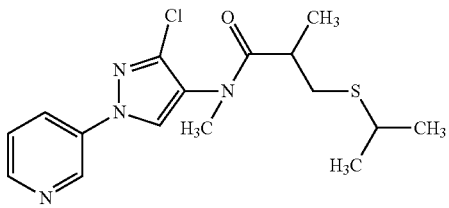 [SMILES: CC(C)SCC(C)C(=O)N(C)c1cn(-c2cccnc2)nc1Cl] |
| 580 | Colorless Oil | 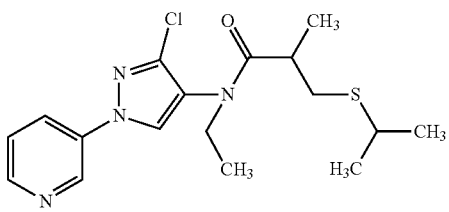 [SMILES: CCN(C(=O)C(C)CSC(C)C)c1cn(-c2cccnc2)nc1Cl] |
| 581 | Colorless Solid | 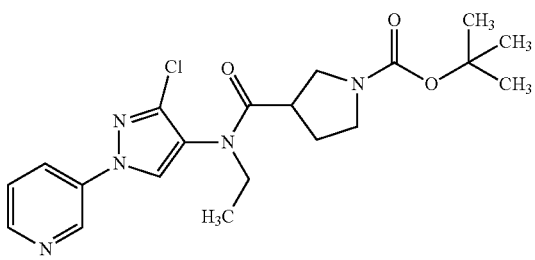 [SMILES: CCN(C(=O)C1CCN(C(=O)OC(C)(C)C)C1)c1cn(-c2cccnc2)nc1Cl] |
| 582 | Clear Oil | 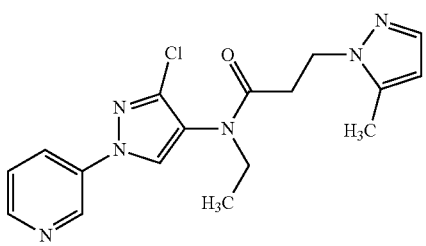 [SMILES: CCN(C(=O)CCn1nccc1C)c1cn(-c2cccnc2)nc1Cl] |
| 583 | Brown Oil | 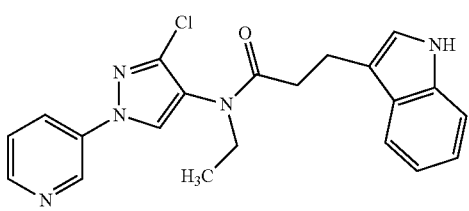 [SMILES: CCN(C(=O)CCc1c[nH]c2ccccc12)c1cn(-c2cccnc2)nc1Cl] |
| 584 | Dark Yellow Oil | 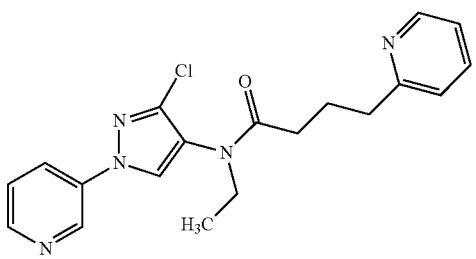 [SMILES: CCN(C(=O)CCCc1ccccn1)c1cn(-c2cccnc2)nc1Cl] |

TABLE 1-continued
| Compound No. | Appearance | Structure |
|---|---|---|
| 585 | White Solid | 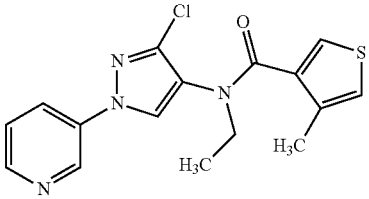 [SMILES: CCN(C(=O)c1cscc1C)c1cn(-c2cccnc2)nc1Cl] |
| 586 | Yellow Solid | 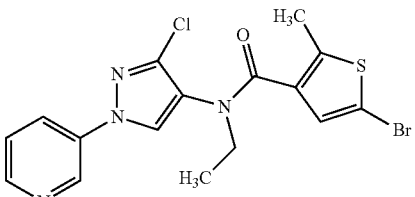 |
| 587 | Purple Solid | 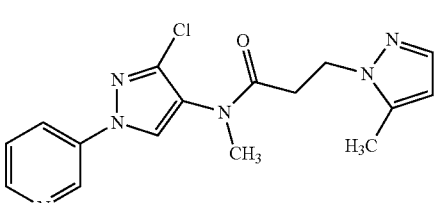 |
| 588 | Dark Yellow Oil | 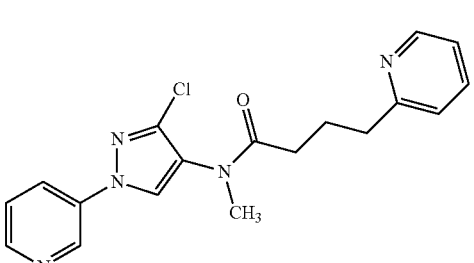 |
| 589 | Colorless Solid | 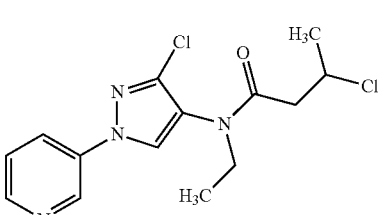 |
| 590 | Brown Solid | 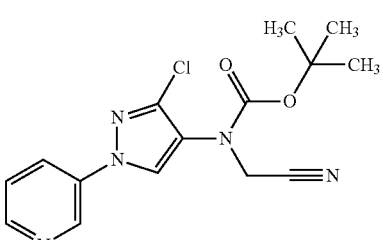 |

TABLE 1-continued
| Compound number, appearance, and structure | | |
|---|---|---|
| Compound No. | Appearance | Structure |
| 591 | Light Yellow Solid | 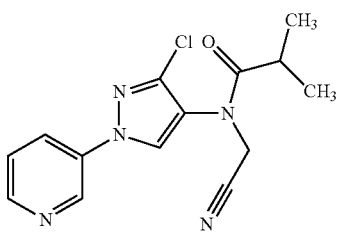 [SMILES: CC(C)C(=O)N(CC#N)c1cn(-c2cccnc2)nc1Cl] |
| 592 | Brown Oil | 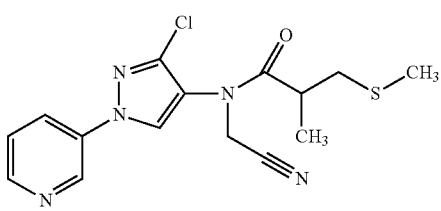 [SMILES: CSCC(C)C(=O)N(CC#N)c1cn(-c2cccnc2)nc1Cl] |
| 593 | Brown Oil | 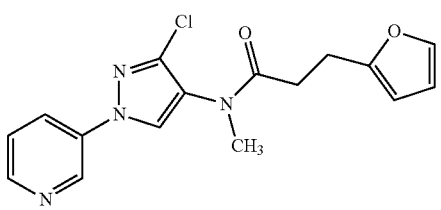 [SMILES: CN(C(=O)CCc1ccco1)c1cn(-c2cccnc2)nc1Cl] |
| 594 | Faint Yellow Solid | 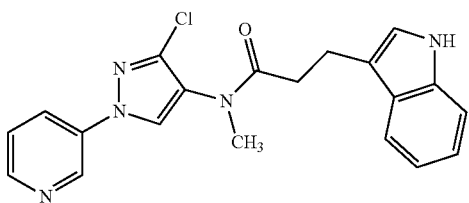 [SMILES: CN(C(=O)CCc1c[nH]c2ccccc12)c1cn(-c2cccnc2)nc1Cl] |
| 595 | White Solid | 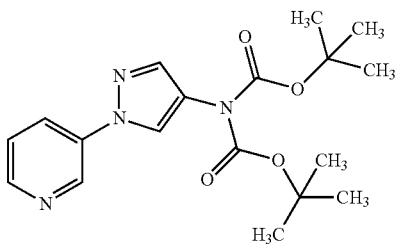 [SMILES: CC(C)(C)OC(=O)N(C(=O)OC(C)(C)C)c1cnn(-c2cccnc2)c1] |
| 596 | Brown Solid | 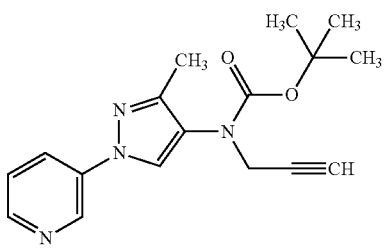 [SMILES: C#CCN(C(=O)OC(C)(C)C)c1cn(-c2cccnc2)nc1C] |

TABLE 1-continued

Compound number, appearance, and structure

| Compound No. | Appearance | Structure |
|---|---|---|
| 597 | Colorless Oil | (3-methyl-1-(pyridin-3-yl)-1H-pyrazol-4-yl)-N-(prop-2-yn-1-yl)-4,4,4-trifluorobutanamide |
| 598 | Colorless Oil | N-(3-methyl-1-(pyridin-3-yl)-1H-pyrazol-4-yl)-3-(methylthio)-N-(prop-2-yn-1-yl)propanamide |
| 599 | Colorless Oil | N-(3-methyl-1-(pyridin-3-yl)-1H-pyrazol-4-yl)-2-methyl-3-(methylthio)-N-(prop-2-yn-1-yl)propanamide |
| 600 | White Solid | N-(3-methyl-1-(pyridin-3-yl)-1H-pyrazol-4-yl)-2-methyl-N-(prop-2-yn-1-yl)propanamide |
| 601 | Yellow Solid | tert-butyl (1-(5-fluoropyridin-3-yl)-3-methyl-1H-pyrazol-4-yl)(prop-2-yn-1-yl)carbamate |
| 602 | Colorless Oil | N-(1-(5-fluoropyridin-3-yl)-3-methyl-1H-pyrazol-4-yl)-2-methyl-3-(methylthio)-N-(prop-2-yn-1-yl)propanamide |

TABLE 1-continued
| Compound No. | Appearance | Structure |
|---|---|---|
| 603 | Light Brown Solid | 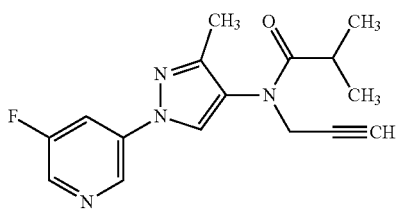 [SMILES: C#CCN(C(=O)C(C)C)c1cn(-c2cncc(F)c2)nc1C] |
| 604 | Brown Gum | 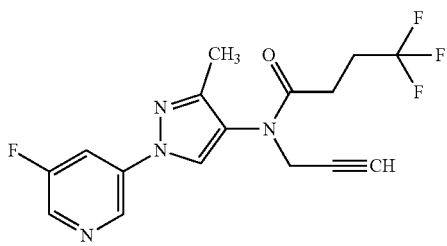 [SMILES: C#CCN(C(=O)CCC(F)(F)F)c1cn(-c2cncc(F)c2)nc1C] |
| 605 | Light Brown Oil | 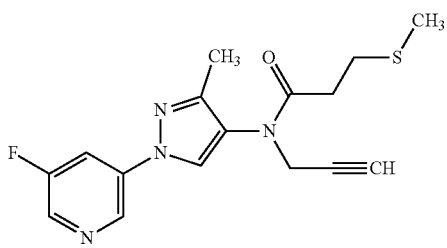 [SMILES: C#CCN(C(=O)CCSC)c1cn(-c2cncc(F)c2)nc1C] |
| 606 | Light Brown Oil | 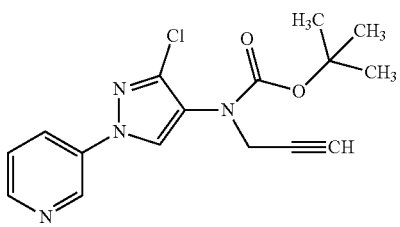 [SMILES: C#CCN(C(=O)OC(C)(C)C)c1cn(-c2cccnc2)nc1Cl] |
| 607 | Colorless Oil | 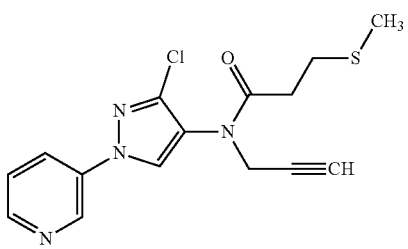 [SMILES: C#CCN(C(=O)CCSC)c1cn(-c2cccnc2)nc1Cl] |
| 608 | Colorless Oil | 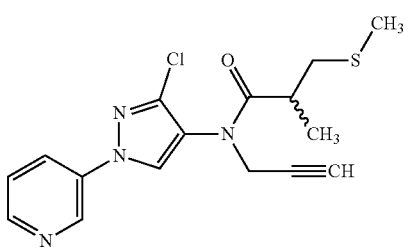 [SMILES: C#CCN(C(=O)C(C)CSC)c1cn(-c2cccnc2)nc1Cl] |

TABLE 1-continued
| Compound No. | Appearance | Structure |
|---|---|---|
| 609 | Colorless Oil | 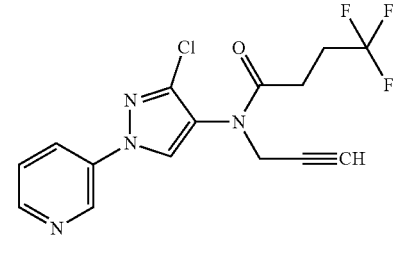 [SMILES: C#CCN(C(=O)CCC(F)(F)F)c1cn(-c2cccnc2)nc1Cl] |
| 610 | Yellow Solid | 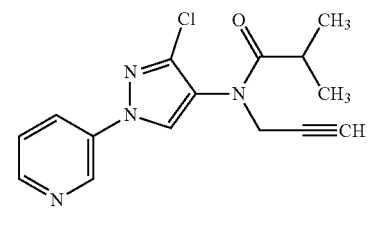 [SMILES: C#CCN(C(=O)C(C)C)c1cn(-c2cccnc2)nc1Cl] |
| 611 | Yellow Oil | 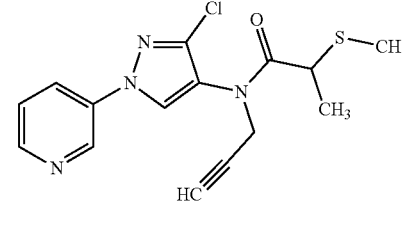 |
| 612 | Beige Solid | 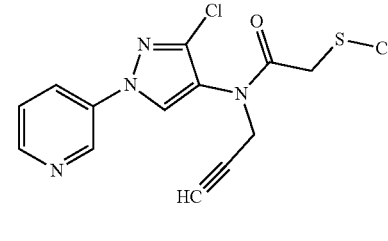 |
| 613 | Brown Oil | 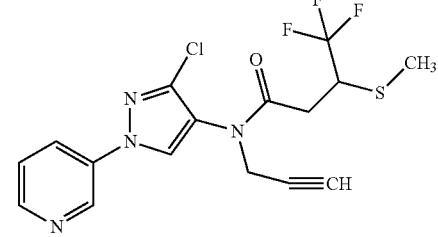 |
| 614 | Colorless Oil | 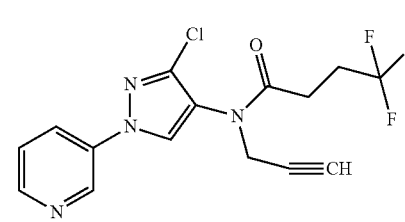 |

TABLE 1-continued

| Compound No. | Appearance | Structure |
|---|---|---|
| 615 | Colorless Oil | (structure) |
| 616 | White Solid | (structure) |
| 617 | Off White Foam | (structure) |
| 618 | Yellow Foam | (structure) |
| 619 | White Solid | (structure) |
| 620 | Pale Yellow Oil | (structure) |

TABLE 1-continued

| Compound No. | Appearance | Structure |
|---|---|---|
| 621 | Pale Yellow Oil | 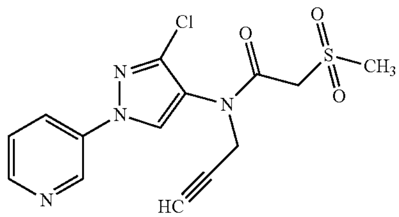 [SMILES: C#CCN(C(=O)CS(C)(=O)=O)c1cn(-c2cccnc2)nc1Cl] |
| 622 | Yellow Oil | 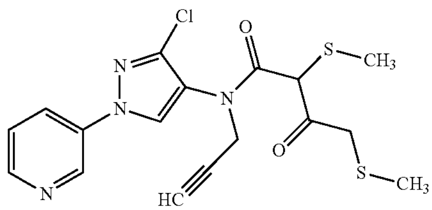 [SMILES: C#CCN(C(=O)C(SC)C(=O)CSC)c1cn(-c2cccnc2)nc1Cl] |
| 623 | Yellow Solid | 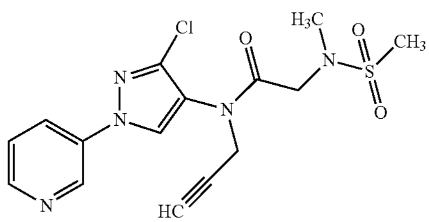 [SMILES: C#CCN(C(=O)CN(C)S(C)(=O)=O)c1cn(-c2cccnc2)nc1Cl] |
| 624 | White Solid | 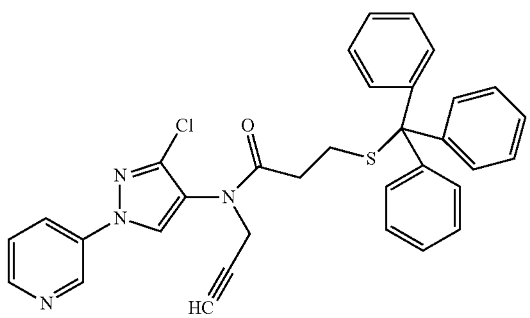 [SMILES: C#CCN(C(=O)CCSC(c1ccccc1)(c1ccccc1)c1ccccc1)c1cn(-c2cccnc2)nc1Cl] |
| 625 | Colorless Oil | 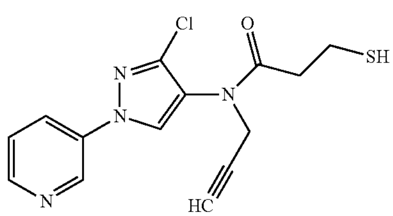 [SMILES: C#CCN(C(=O)CCS)c1cn(-c2cccnc2)nc1Cl] |
| 626 | Light Yellow Oil | 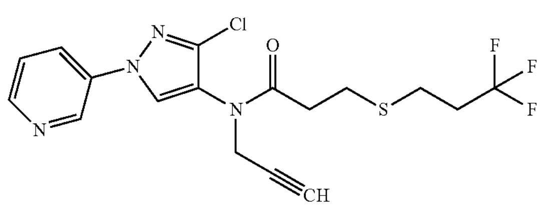 [SMILES: C#CCN(C(=O)CCSCCC(F)(F)F)c1cn(-c2cccnc2)nc1Cl] |

TABLE 1-continued

Compound number, appearance, and structure

| Compound No. | Appearance | Structure |
|---|---|---|
| 627 | Yellow Viscous Oil | (structure: 1-(pyridin-3-yl)-3-methyl-1H-pyrazol-4-yl with N-propargyl amide linked to -CH₂CH₂-S-CH₂CH₂-CF₃) |

TABLE 2

Compound number and analytical data

| Compound No. | MP[a] | IR[b] | Mass | ¹H NMR | ¹³C NMR |
|---|---|---|---|---|---|
| 596 | 73-75 | | ESIMS m/z 312.2 ([M + 1]⁺) | ¹H NMR (300 MHz, DMSO-d₆) δ 9.04 (d, J = 2.4 Hz, 1H), 8.60 (s, 1H), 8.49 (dd, J = 4.7, 1.4 Hz, 1H), 8.17 (ddd, J = 8.4, 2.7, 1.4 Hz, 1H), 7.52 (ddd, J = 8.4, 4.7, 0.6 Hz, 1H), 4.30 (d, J = 2.1 Hz, 2H), 3.23 (s, 1H), 2.18 (s, 3H), 1.39 (s, 6H). | |
| 597 | | | ESIMS m/z 337 ([M + H]⁺) | ¹H NMR (400 MHz, CDCl₃) δ 8.97(d, J = 2.5 Hz, 1H), 8.59 (dd, J = 4.7, 1.3 Hz, 1H), 8.05 (ddd, J = 8.3, 2.7, 1.5 Hz, 1H), 8.01 (s, 1H), 7.44 (ddd, J = 8.3, 4.8, 0.4 Hz, 1H), 4.44 (s, 2H), 2.61-2.43 (m, 2H), 2.43-2.33 (m, 2H), 2.30 (s, 3H), 2.26 (t, J = 2.5 Hz, 1H). | ¹³C NMR (101 MHz, CDCl₃) δ 170.37, 148.49, 148.04, 140.21, 136.04, 126.23, 125.26, 124.16, 124.01, 78.59, 72.69, 38.69, 29.57, 29.26, 26.69, 11.14 |
| 598 | | | ESIMS m/z 315.1 ([M + H]⁺) | ¹H NMR (400 MHz, CDCl3) δ 8.96 (d, J = 2.4 Hz, 1H), 8.58 (dd, J = 4.7, 1.4 Hz, 1H), 8.04 (ddd, J = 8.3, 2.7, 1.5 Hz, 1H), 8.01 (s, 1H), 7.43 (ddd, J= 8.3, 4.8, 0.5 Hz, 1H), 4.45 (s, 2H), 2.79 (t, J = 7.3 Hz, 2H), 2.45 (t, J = 7.3 Hz, 2H), 2.31 (s, 3H), 2.24 (t, J = 2.5 Hz, 1H), 2.06 (s, 3H). | 13C NMR (101 MHz, CDCl3) δ 171.73, 148.71, 147.93, 140.17, 136.09, 126.15, 125.41, 124.55, 123.99, 78.85, 72.51, 38.35, 33.80, 29.57, 15.96, 11.20 |
| 599 | | | ESIMS m/z 283 ([M-SMe + H]⁺) | ¹H NMR (400 MHz, CDCl3) δ 8.96(d, J = 2.5 Hz, 1H), 8.58 (dd, J = 4.7, 1.4 Hz, 1H), 8.04 (ddd, J = 6.9, 2.7, 1.5 Hz, 2H), 7.48-7.38 (m, 1H), 4.47 (bs, 2H), 2.88 (dd, J = 12.7, 9.2 Hz, 1H), 2.77 (s, 1H), 2.44 (dd, J = 12.8, 5.1 Hz, 1H), 2.34 (s, 3H), 2.24 (s, 1H), 2.01 (s, 3H), 1.14 (d, J = 6.7 Hz, 3H). | |
| 600 | 89-90 | | ESIMS m/z 283.5 ([M + H]⁺) | ¹H NMR (400 MHz, CDCl₃) δ 8.96 (d, J = 2.5 Hz, 1H), 8.57 (dd, J = 4.7, 1.3 Hz, 1H), 8.04 (ddd, J = 8.3, 2.7, 1.5 Hz, 1H), 8.00 (s, 1H), 7.43 (dd, J = 8.3, 4.8 Hz, 1H), 4.43 (bs, 2H), 2.60 (dt, J = 13.5, 6.8 Hz, 1H), 2.29 (s, 3H), 2.23 (t, J = 2.5 Hz, 1H), 1.08 (d, J = 6.7 Hz, 6H). | ¹³C NMR (101 MHz, CDCl₃) δ 177.64, 148.89, 148.85, 147.83, 140.13, 136.13, 126.06, 125.08, 125.02, 123.97, 79.12, 72.41, 38.23, 31.05, 19.52, 11.16. |
| 601 | 81-82 | | ESIMS m/z 329.8 ([M + H]⁺) | ¹H NMR (400 MHz, CDCl₃) δ 8.73 (s, 1H), 8.37 (d, J = 2.5 Hz, 1H), 7.99 (s, 1H), 7.83 (dt, J = 9.5, 2.2 Hz, 1H), 4.31 (s, 2H), 2.29 (t, J = 2.4 Hz, 1H), 2.27 (s, 3H), 1.45 (s, 9H). | |
| 602 | | | ESIMS m/z 347.5 ([M + H]⁺) | ¹H NMR (400 MHz, CDCl₃) δ 8.77 (d, J = 1.7 Hz, 1H), 8.43 (d, J = 2.5 Hz, 1H), 8.05 (s, 1H), 7.86 (dt, J = 9.4, 2.3 Hz, 1H), 4.49 (s, 2H), 2.88 (dd, J = 12.8, 9.4 Hz, 1H), 2.74 (s, 1H), 2.45 (dd, J = 12.9, 5.0 Hz,1H), 2.34 (s, 3H), 2.24 (t, J = 2.5 Hz, 1H), 2.02 (s, 3H), 1.14 (d, J = 6.8 Hz, 3H). | |
| 603 | 99-100 | | ESIMS m/z 299.5 ([M + H]⁺) | ¹H NMR (400 MHz, CDCl₃) δ 8.77 (d, J = 1.5 Hz, | |

TABLE 2-continued

Compound number and analytical data

| Compound No. | MP[a] | IR[b] | Mass | ¹H NMR | ¹³C NMR |
|---|---|---|---|---|---|
| | | | | 1H), 8.43 (d, J = 2.5 Hz, 1H), 8.01 (s, 1H), 7.86 (dt, J = 9.4, 2.3 Hz, 1H), 4.43 (s, 2H), 2.57 (dt, J = 13.5, 6.7 Hz, 1H), 2.29 (s, 3H), 2.23 (t, J = 2.5 Hz, 1H), 1.08 (d, J = 6.7 Hz, 6H). | |
| 604 | | | ESIMS m/z 353.8 ([M]⁺) | ¹H NMR (400 MHz, CDCl3) δ 8.77 (d, J = 1.9 Hz, 1H), 8.44 (t, J = 4.4 Hz, 1H), 8.03 (s, 1H), 7.87 (dt, J = 9.3, 2.4 Hz, 1H), 4.44 (s, 2H), 2.56-2.42 (m, 2H), 2.36 (dd, J = 12.7, 5.5 Hz, 2H), 2.30 (s, 3H), 2.27 (s, 1H). | ¹³C NMR (101 MHz, CDCl₃) δ 170.26, 149.03, 136.33, 136.28, 136.05, 135.42, 135.29, 126.49, 125.48, 124.59, 113.48, 78.51, 72.81, 38.62, 26.73, 11.13. |
| 605 | | | ESIMS m/z 333.69 ([M + H]⁺) | ¹H NMR (400 MHz, CDCl3) δ 8.76 (d, J = 1.6 Hz, 1H), 8.44 (d, J = 2.5 Hz, 1H), 8.05 (s, 1H), 7.86 (dt, J = 9.3, 2.3 Hz, 1H), 4.45 (s, 2H), 2.79 (t, J = 7.3 Hz, 2H) 2.43 (t, J = 7.3 Hz, 2H), 2.30 (s, 3H), 2.25 (t, J = 2.5 Hz, 1H), 2.06 (s, 3H) | |
| 606 | | | ESIMS m/z 276.8 ([M-t-Bu]⁺) | ¹H NMR (400 MHz, CDCl3) δ 8.94 (d, J = 2.5 Hz, 1H), 8.58 (dd, J = 4.7, 1.3 Hz, 1H), 8.07 (s, 1H), 8.05-7.92 (m, 1H), 7.42 (dd, J = 8.3, 4.8 Hz, 1H), 4.36 (s, 2H), 2.29 (t, J = 2.4 Hz, 1H), 1.46 (s, 9H). | ¹³C NMR (101 MHz, CDCl₃) δ 170.97, 154.09, 148.02, 139.81, 136.83, 135.90, 133.69, 133.53, 126.02, 124.26, 123.96, 81.33, 60.31, 28.08. |
| 607 | | | ESIMS m/z 335.1 ([M + H]⁺) | ¹H NMR (400 MHz, CDCl₃) δ 8.96 (d, J = 2.5 Hz, 1H), 8.64 (dd, J = 4.7, 1.3 Hz, 1H), 8.12 (s, 1H), 8.06 (ddd, J = 8.4, 2.7, 1.4 Hz, 1H), 7.47 (dd, J = 8.3, 4.8 Hz, 1H), 4.48 (s, 2H), 2.81 (t, J = 7.4 Hz, 2H), 2.50 (t, J = 7.4 Hz, 2H), 2.27 (t, J = 2.5 Hz, 1H), 2.08 (s, 3H). | ¹³C NMR (101 MHz, CDCl₃) δ 175.54, 148.75, 140.82, 140.16, 135.66, 126.41, 124.12, 122.68, 78.61, 77.33, 77.02, 76.70, 72.86, 37.83, 37.22, 18.11, 16.54. |
| 608 | | | ESIMS m/z 349.1 ([M + H]⁺) | ¹H NMR (400 MHz, CDCl3) δ 8.97 (d, J = 2.5 Hz, 1H), 8.64 (dd, J = 4.7, 1.3 Hz, 1H), 8.16 (s, 1H), 8.05 (ddd, J = 8.3, 2.7, 1.4 Hz, 1H), 7.47 (dd, J = 8.3, 4.8 Hz, 1H), 5.30 (s, 2H), 2.87 (dd, J = 12.8, 8.8 Hz, 1H), 2.75 (d, J = 6.3 Hz, 1H), 2.49 (dd, J = 12.9, 5.4 Hz, 1H), 2.26 (t, J = 2.5 Hz, 1H), 2.03 (s, 3H), 1.18 (d, J = 6.7 Hz, 3H). | ¹³C NMR (101 MHz, CDCl₃) δ 171.42, 148.77, 140.68, 140.10, 135.65, 127.00, 126.48, 124.14, 122.73, 78.58, 72.91, 37.82, 33.86, 29.41, 15.92. |
| 609 | | | ESIMS m/z 357.1 ([M + H]⁺) | ¹H NMR (400 MHz, CDCl3) δ 8.97 (d, J = 2.5 Hz, 1H), 8.65 (dd, J = 4.7, 1.3 Hz, 1H), 8.22 (s, 1H) 8.12 (s, 1H), 7.48 (dd, J = 7.5, 3.9 Hz, 1H), 4.46 (s, 2H), 2.61-2.35 (m, 4H), 2.29 (dd, J = 4.7, 2.4 Hz, 1H). | ¹³C NMR (101 MHz, CDCl₃) δ 170.10, 148.90, 140.16, 139.27, 126.82, 126.57, 124.14, 123.89, 122.29, 78.32, 73.09, 72.50, 38.13, 36.29, 26.71. |
| 610 | 98-99 | | ESIMS m/z 303.1 ([M + H]⁺) | ¹H NMR (400 MHz, CDCl3) δ 8.96(d, J = 2.6 Hz, 1H), 8.63 (dd, J = 4.7, 1.2 Hz, 1H), 8.09 (s, 1H), 8.06 (ddd, J = 8.3, 2.7, 1.5 Hz, 1H), 7.46 (dd, J = 8.4, 4.8 Hz, 1H), 4.40 (m, 2H), 2.76-2.44 (m, 1H), 2.24 (t, J = 2.4 Hz, 1H), 1.57 (s, 1H), 1.11 (d, J = 6.7 Hz, 6H). | |
| 611 | | | ESIMS m/z 335 ([M + H]⁺) | ¹H NMR (400 MHz, CDCl3) δ 8.97(d, J = 2.5 Hz, 1H), 8.66-8.60 (m, 1H), 8.25 (s, 1H), 8.08-8.01 (m, 1H), 7.49-7.42 (m, 1H), 4.86 (s, 1H), 4.29-3.97 (m, 1H), 3.31 (d, J = 6.5 Hz, 1H), 2.30-2.24 (m, 1H), 2.09 (s, 3H), 1.46 (d, J = 6.9 Hz, 3H). | ¹³C NMR (101 MHz, CDCl₃) δ 171.30, 148.66, 140.71, 140.18, 135.71, 127.87, 126.35, 124.11, 122.12, 78.53, 72.92, 53.39, 37.97, 16.42, 11.07. |
| 612 | 65-68 | | ESIMS m/z 321 ([M + H]⁺) | ¹H NMR (400 MHz, CDCl3) δ 8.96 (s, 1H), 8.63 (d, J = 4.2 Hz, 1H), 8.21 (s, 1H), 8.09-8.00 (m, 1H), 7.50-7.43 (m, 1H), 4.53 (br s, 2H), 3.12 (s, 2H), 2.28 (t, J = 2.5 Hz, 1H), 2.23 (s, 3H). | ¹³C NMR (101 MHz, CDCl₃) δ 169.20, 148.57, 140.58, 140.10, 127.82, 126.47, 122.27, 99.98, 78.37, 77.23, 73.07, 37.90, 35.01, 15.96. |
| 613 | | 1674 | ESIMS m/z 403 ([M + H]⁺) | ¹H NMR (400 MHz, CDCl3) δ 8.97(d, J = 2.6 Hz, 1H), 8.64 (dd, J = 4.7, 1.3 Hz, 1H), 8.13 (s, 1H), 8.07 (ddd, J = 8.3, 2.7, 1.5 Hz, 1H), 7.48 (ddd, J = 8.3, 4.8, 0.5 Hz, 1H), 4.39 (s, 2H), 3.76 (dqd, | |

TABLE 2-continued

Compound number and analytical data

| Compound No. | MP[a] | IR[b] | Mass | ¹H NMR | ¹³C NMR |
|---|---|---|---|---|---|
| | | | | J = 17.2, 8.6, 3.6 Hz, 1H), 2.67 (dd, J = 16.6, 3.6 Hz, 1H), 2.46 (dd, J = 16.5, 9.9 Hz, 1H), 2.29 (d, J = 2.5 Hz, 4H). | |
| 614 | | 1671 | ESIMS m/z 353 ([M + H]⁺) | ¹H NMR (400 MHz, CDCl₃) δ 8.97 (d, J = 2.5 Hz, 1H), 8.64 (dd, J = 4.7, 1.4 Hz, 1H), 8.12 (s, 1H), 8.07 (ddd, J = 8.3, 2.7, 1.4 Hz, 1H), 7.47 (ddd, J = 8.3, 4.8, 0.4 Hz, 1H), 4.47 (s, 2H), 2.48-2.35 (m, 2H), 2.35-2.16 (m, 3H), 1.60 (t, J = 18.4 Hz, 3H). | |
| 615 | | 1676 | ESIMS m/z 407 ([M + H]⁺) | ¹H NMR (400 MHz, CDCl₃) δ 8.97(d, J = 2.5 Hz, 1H), 8.65 (dd, J = 4.7, 1.2 Hz, 1H), 8.13 (s, 1H), 8.07 (ddd, J = 8.3, 2.7, 1.5 Hz, 1H), 7.48 (dd, J = 8.3, 4.7 Hz, 1H), 4.47 (s, 2H), 2.58-2.39 (m, 4H), 2.29 (t, J = 2.5 Hz, 1H). | |
| 616 | | 1662 | ESIMS m/z 377 ([M + H]⁺) | ¹H NMR (400 MHz, CDCl₃) δ 8.97(d, J = 2.5 Hz, 1H), 8.64 (dd, J = 4.7, 1.1 Hz, 1H), 8.17 (s, 1H), 8.06 (ddd, J = 8.3, 2.7, 1.4 Hz, 1H), 7.47 (dd, J = 8.3, 4.7 Hz, 1H). 4.92-4.10 (m, 7.7, 6.2, 4.3 Hz, 1H), 2.45 (s, 1H), 2.44 (d, J = 2.4 Hz, 1H), 2.27 (t, J = 2.5 Hz, 1H), 2.11 (s, 3H), 1.97-1.85 (m, 1H), 0.96 (d, J = 6.7 Hz, 3H), 0.88 (d, J = 6.8 Hz, 3H). | |
| 617 | | | ESIMS m/z 351 ([M + H]⁺) | ¹H NMR (400 MHz, CDCl₃) δ 8.98 (s, 1H), 8.65 (d, J = 4.6 Hz, 1H), 8.23 (s, 1H), 8.11-7.97 (m, 1H), 7.51-7.41 (m, 1H), 4.88 (hr s, 1H), 4.14 (hr s, 1H), 2.64 (s, 1.2H), 2.55 (s, 1.8H), 2.33-2.27 (m, 1H), 1.47 (d, J = 6.8 Hz, 3H), 1,42 (br s). | ¹³C NMR (101 MHz, CDCl₃) δ 168.11, 148.95, 148.78, 140.45, 140.33, 140.20, 135.56, 126.54, 124.10, 121.68, 121.58, 121.48, 77.69, 73.49, 38.60. |
| 618 | | | ESIMS m/z 367 ([M + H]⁺) | ¹H NMR (400 MHz, CDCl₃) δ 9.00 (s, 1H), 8.65 (s, 1H), 8.29 (s, 1H), 8.03 (d, J = 8.0 Hz, 1H), 7.54- | ¹³C NMR (101 MHz, CDCl₃) δ 166.97, 166.90, 148.77, 140.43, 140.24, 135.58, 129.36, 126.64, |
| | | | | 7.39 (m, 1H), 4.89 (d, J = 16.9 Hz, 1H), 4.20-4.08 (m, 1H), 4.07-3.92 (m, 1H), 3.01 (s, 3H), 2.34-2.29 (m, 1H), 1.67 (d, J = 7.0 Hz, 3H). | 124.14, 121.34, 73.80, 60.91, 38.78, 36.29, 13.97. |
| 619 | 109-112 | 1665 | ESIMS m/z 375.5 ([M + H]⁺) | ¹H NMR (400 MHz, CDCl₃) δ 8.97 (s, 1H), 8.64 (d, J = 4.2 Hz, 1H), 8.14 (s, 1H), 8.07 (ddd, J = 8.3, 2.6, 1.4 Hz, 1H), 7.47 (dd, J = 8.3, 4.7 Hz, 1H), 4.45 (s, 2H), 2.63-2.46 (m, 3H), 2.27 (t, J = 2.5 Hz, 1H), 2.14 (s, 3H), 0.90-0.73 (m, 1H), 0.66-0.57 (m, 1H), 0.57-0.44 (m, 1H), 0.42-0.35 (m, 1H), 0.35-0.23 (m, 1H). | |
| 620 | | 1673 | ESIMS m/z 337 ([M + H]⁺) | ¹H NMR (300 MHz, CDCl3) δ 8.97 (d, J = 2.6 Hz, 1H), 8.64 (dd, J = 4.8, 1.4 Hz, 1H), 8.23 (s, 1H), 8.03 (ddd, J = 8.4, 2.7, 1.5 Hz, 1H), 7.46 (dd, J = 8.4, 4.7 Hz, 1H), 4.52 (br s, 2H), 3.68 (br s, 2H), 2.78 (s, 3H), 2.29 (t, J = 2.5 Hz, 1H). | |
| 621 | | 1667 | ESIMS m/z 353 ([M + H]⁺) | ¹H NMR (300 MHz, CDCl3) δ 8.98 (d, J = 2.7 Hz, 1H), 8.64 (d, J = 4.8 Hz, 1H), 8.28 (d, J = 1.0 Hz, 1H), 8.03 (dt, J = 8.4, 1.3 Hz, 1H), 7.46 (dd, J = 8.3, 4.8 Hz, 1H), 4.88 (br S, 2H), 3.97 (br s, 2H), 3.20 (s, 3H), 2.31 (dt, J = 2.4, 1.3 Hz, 1H). | |
| 622 | | 1749, 1666 | ESIMS m/z 409 ([M + H]⁺) | ¹H NMR (300 MHz, CDCl3) δ 9.01 (s, 1H), 8.61 (s, 1H), 8.28 (s, 1H), 8.12-8.05 (m, 1H), 7.48-7.41 (m, 1H), 6.09 (s, 0.5H), 4.10 (s, 1H), 3.58 (s, 0.5H), 3.37 (s, 0.5H), 3.27 (s, 1.5H), 2.30 (d, J = 1.4 Hz, 1H), 2.24 (s, 3H), 2.20 (s, 3H), 1.61 (s, 1H) | |
| 623 | | 1678 | ESIMS m/z 382 ([M + H]⁺) | ¹H NMR (400 MHz, CDCl₃) δ 8.97 (d, J = 2.6 Hz, 1H), 8.65 (dd, J = 4.8, 1.3 Hz, 1H), 8..15 (s, 1H), 8.04 (ddd, J = 8.3, 2.7, | |

TABLE 2-continued

Compound number and analytical data

| Compound No. | MP[a] | IR[b] | Mass | ¹H NMR | ¹³C NMR |
|---|---|---|---|---|---|
| | | | | 1.4 Hz, 1H), 7.48 (dd, J = 8.4, 4.7 Hz, 1H), 3.77 (hept, J = 6.9 Hz, 2H), 3.05 (s, 2H), 3.01 (s, 3H), 2.87 (s, 3H), 2.31 (t, J = 2.5 Hz, 1H). | |
| 624 | 68-70 | | ESIMS m/z 563.2 ([M + 1]⁺) | ¹H NMR (400 MHz, CDCl₃) δ 8.94 (dd, J = 4.9, 2.7 Hz, 1H), 8.65 (dd, J = 4.8, 1.5 Hz, 1H), 8.07-7.98 (m, 1H), 7.94 (s, 1H), 7.2-7.5 (m, 16H), 4.44(m, 2H), 2.64 (t, J = 7.1 Hz, 2H), 2.52 (t, J = 7.3 Hz, 2H), 2.22 (s, 1H). | |
| 625 | | 3254, 3039, 2555, 1685 | ESIMS m/z 321.1 ([M + 1]⁺) 319.1 ([M − 1]⁺) | ¹H NMR (400 MHz, CDCl₃) δ 9.01-8.92 (m, 1H), 8.64 (d, J = 5.9 Hz, 1H), 8.11 (s, 1H), 8.06 (ddd, J = 8.3, 2.7, 1.5 Hz, 1H), 7.47 (dd, J = 8.3, 4.8 Hz, 1H), 4.56 (m, 1H), 2.93 (dt, J = 8.5, 6.6 Hz, 2H), 2.54 (t, J = 6.7 Hz, 2H), 2.27 (t, J = 2.5 Hz, 1H), 1.71 (dt, J = 11.6, 8.4 Hz, 2H). | |
| 626 | | 3299, 1672 | ESIMS m/z 417.2 ([M + H]⁺) HRMS-FAB (m/z) [M + H]⁺ calcd for C₁₇H₁₇ClF₃N₄OS 417.0758; found, 417.0754 | ¹H NMR (400 MHz, CDCl₃) δ 8.96 (d, J = 2.7 Hz, 1H), 8.64 (dd, J = 4.8, 1.4 Hz, 1H), 8.12 (s, 1H), 8.06 (ddd, J = 8.3, 2.7, 1.5 Hz, 1H), 7.47 (dd, J = 8.5, 4.8 Hz, 1H), 4.47 (s, 2H), 2.86 (t, J = 7.2 Hz, 2H), 2.74-2.61 (m, 2H), 2.50 (t, J = 7.2 Hz, 2H), 2.45-2.29 (m, 2H), 2.28 (t, J = 2.5 Hz, 1H). | |
| 627 | | 3293, 1663 | ESIMS m/z 397.3 ([M + H]⁺) HRMS-FAB (m/z) [M + H]⁺ calcd for C₁₈H₂₀F₃N₄OS 397.1304; found, 397.1322 | ¹H NMR (400 MHz, CDCl₃) δ 8.96 (d, J = 2.6 Hz, 1H), 8.58 (dd, J = 4.8, 1.5 Hz, 1H), 8.04 (ddd, J = 8.3, 2.7, 1.5 Hz, 1H), 8.01 (s, 1H), 7.44 (dd, J = 8.3, 4.9 Hz, 1H), 4.45 (s, 2H), 2.84 (t, J = 7.1 Hz, 2H), 2.72-2.60 (m, 2H), 2.44 (t, J = 7.1 Hz, 2H), 2.41-2.32 (m, 2H), 2.31 (s, 3H), 2.26 (t, J = 2.4 Hz, 1H). | |

[a](° C.)
[b](Thin Film; cm⁻¹)

TABLE 3

GPA (MYZUPE) and sweetpotato whitefly-crawler (BEMITA) Rating Table

| % Control (or Mortality) | Rating |
|---|---|
| 80-100 | A |
| More than 0-Less than 80 | B |
| Not Tested | C |
| No activity noticed in this bioassay | D |

TABLE 4

Biological Data for GPA (MYZUPE) and sweetpotato whitefly-crawler (BEMITA)

| Compound No. | MYZUPE % Ctrl @ 200 ppm | BEMITA % Ctrl @ 200 ppm |
|---|---|---|
| 596 | A | A |
| 597 | A | B |
| 598 | A | B |
| 599 | A | B |
| 600 | A | B |
| 601 | A | A |
| 602 | A | A |
| 603 | A | A |
| 604 | A | A |
| 605 | A | A |
| 606 | A | A |
| 607 | A | A |
| 608 | A | A |
| 609 | A | A |
| 610 | A | A |
| 611 | A | A |
| 612 | A | A |
| 613 | A | A |
| 614 | A | A |
| 615 | B | A |
| 616 | C | C |
| 617 | C | C |
| 618 | C | C |
| 619 | A | A |
| 620 | A | A |
| 621 | A | A |
| 622 | A | A |
| 623 | A | A |
| 624 | C | C |
| 625 | C | C |
| 626 | A | A |
| 627 | A | A |

We claim:

1. A formulation comprising a carrier and a molecule according to

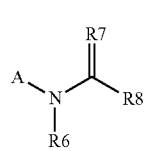

"Formula One"

wherein (a) A is

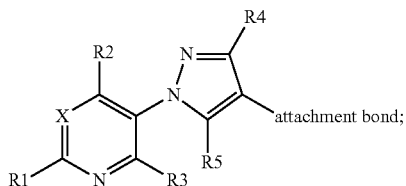

attachment bond;

(b) R1 is H, F, Cl, Br, I, or substituted or unsubstituted $C_1$-$C_6$ alkyl, wherein each said R1, which is substituted, has one or more substituents selected from F, Cl, Br, or I;

(c) R2 is H, F, Cl, Br, I, or substituted or unsubstituted $C_1$-$C_6$ alkyl, wherein each said R2, which is substituted, has one or more substituents selected from F, Cl, Br, or I;

(d) R3 is H, F, Cl, Br, I, or substituted or unsubstituted $C_1$-$C_6$ alkyl, wherein each said R3, which is substituted, has one or more substituents selected from F, Cl, Br, or I;

(e) R4 is H, F, Cl, Br, I, or substituted or unsubstituted $C_1$-$C_6$ alkyl, wherein each said R4, which is substituted, has one or more substituents selected from F, Cl, Br, or I;

(f) R5 is H;

(g) R6 is R11;

(h) R7 is O or S;

(i) R8 is (substituted or unsubstituted $C_1$-$C_6$ alkyl)-S(O)$_n$-(substituted or unsubstituted $C_1$-$C_6$ alkyl) wherein said substituents on said substituted alkyls are selected from F, Cl, Br, or I;

(j) R9 is unsubstituted $C_1$-$C_6$ alkyl;

(k) n is 0, 1, or 2;

(l) X is $CR_{n1}$ where $R_{n1}$ is H, F, Cl, Br, I, CN, $NO_2$, or substituted or unsubstituted $C_1$-$C_6$ alkyl, wherein each said $R_{n1}$ which is substituted, has one or more substituents selected from F, Cl, Br, or I;

(p) R11 is $Q_1$(C≡C)R12, wherein $Q_1$ is an unsubstituted $C_1$-$C_6$ alkyl; and (q) R12 is R9.

2. A formulation according to claim 1 wherein said molecule has one of the following structures

598

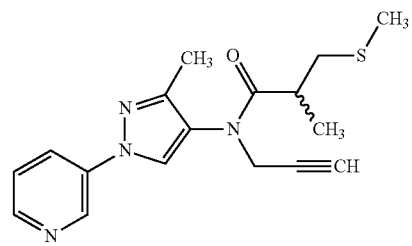

599

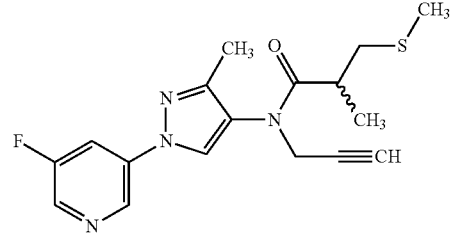

602

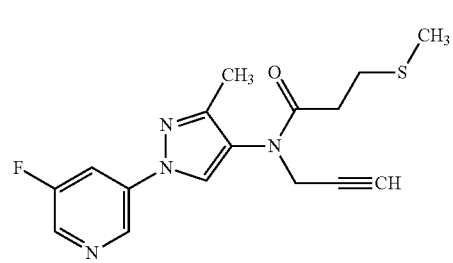

605

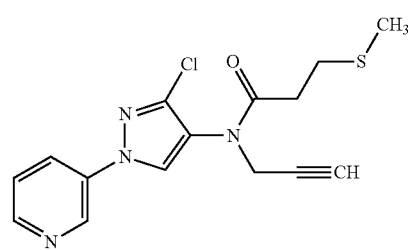

607

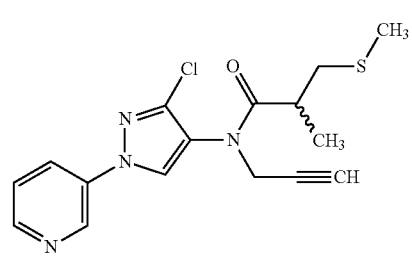

608

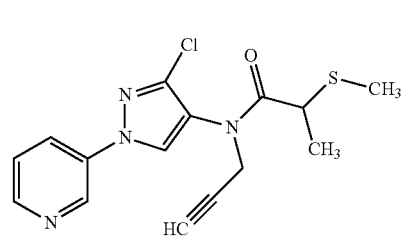

611

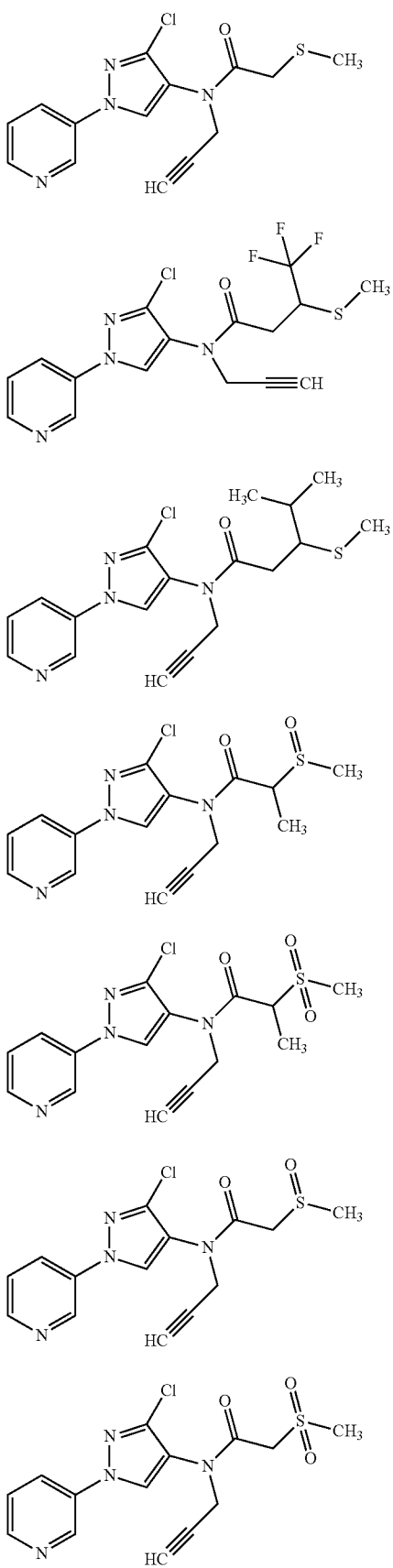

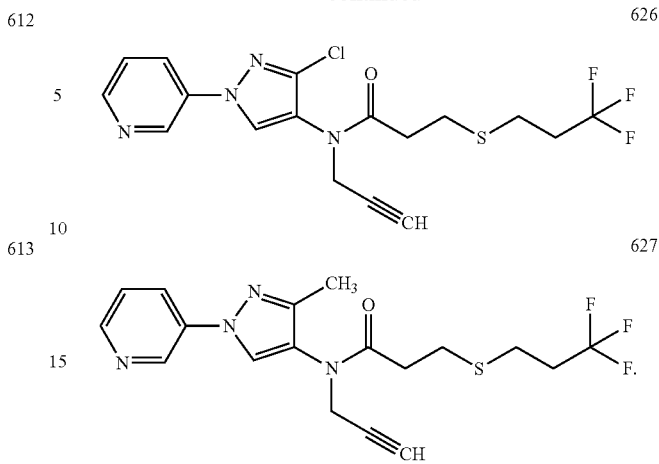

3. A formulation according to claim 1 wherein said molecule said R1 is H.

4. A formulation according to claim 1 wherein said molecule said R2 is H.

5. A formulation according to claim 1 wherein said molecule said R3 is selected from H, or substituted or unsubstituted $C_1$-$C_6$ alkyl.

6. A formulation according to claim 1 wherein said molecule said R3 is selected from H or $CH_3$.

7. A formulation according to claim 1 wherein said molecule said R4 is selected from Cl, or unsubstituted $C_1$-$C_6$ alkyl.

8. A formulation according to claim 1 wherein said molecule R4 is Cl or $CH_3$.

9. A formulation according to claim 1 wherein said molecule said R4 is Cl.

10. A formulation according to claim 1 wherein said molecule said R11 is $CH_2C\equiv CH$ and R8 is (unsubstituted $C_1$-$C_6$ alkyl)-$S(O)_n$-(unsubstituted $C_1$-$C_6$ alkyl).

11. A formulation according to claim 1 wherein said molecule said R11 is $CH_2C\equiv CH$ and R8 is (unsubstituted $C_1$-$C_6$ alkyl)-$S(O)_n$-(unsubstituted $C_1$-$C_6$ alkyl).

12. A formulation according to claim 1 wherein said molecule said R11 is $CH_2C\equiv CH$ and R8 is (unsubstituted $C_1$-$C_2$ alkyl)-$S(O)_n$-(unsubstituted $C_1$-$C_3$ alkyl).

13. A formulation according to claim 1 wherein said molecule said R11 is unsubstituted $C_1$-$C_3$ alkyl$C\equiv CH$.

14. A formulation according to claim 1 wherein said molecule said R11 is unsubstituted $C_1$-$C_2$ alkyl$C\equiv CH$.

15. A formulation according to claim 1 wherein said molecule said R11 is $CH_2C\equiv CH$.

16. A formulation according to claim 1 wherein said molecule said R7 is O.

17. A formulation according to claim 1 wherein said molecule said R8 is $CH(CH_3)CH_2SCH_3$, $C(CH_3)_2$, $CH_2SCH_3$, $CH_2CH_2SCH_3$, $CH_2CH(CH_3)SCH_3$, $C(CH_3)_2CH_2SCH_3$, $CH(CH_3)CH(CH_3)SCH_3$, $CH(CH_3)SCF_3$, $CH_2CH_2S(=O)CH_3$, $CH(CH_3)CH_2S(=O)CH_3$, $CH_2CH_2S(=O)_2CH_3$, $CH(CH_3)CH_2S(=O)_2CH_3$, $CH_2CH(CF_3)SCH_3$, $CH(CF_3)CH_2SCH_3$, $CH(CH_3)SCH_3$, $CH_2SCH_3$, $CH_2CH_2SCH_2CH_2CF_3$, $CH_2S(O)CH_3$, or $CH(CH_3)CH_2SCD_3$.

18. A formulation according to claim 1 wherein said molecule said X is $CR_{n1}$ where $R_{n1}$ is H or halo.

19. A formulation according to claim 1 wherein said molecule said X is $CR_{n1}$ where $R_{n1}$ is H or F.

20. A formulation according to one of claim 1 or 2 wherein said carrier is an agriculturally acceptable carrier.

21. A formulation according to claim 1 wherein said formulation is encapsulated inside, or placed on the surface of, a capsule, wherein said capsule has a diameter of about 100-900 nanometers.

22. A formulation according to claim 1 wherein said formulation is encapsulated inside, or placed on the surface of, a capsule, wherein said capsule has a diameter of about 10-900 microns.

23. A formulation according to one of claims 1 and 2 further comprising:
(a) one or more compounds having acaricidal, algicidal, avicidal, bactericidal, fungicidal, herbicidal, insecticidal, molluscicidal, nematicidal, rodenticidal, or virucidal properties; or
(b) one or more compounds that are antifeedants, bird repellents, chemosterilants, herbicide safeners, insect attractants, insect repellents, mammal repellents, mating disrupters, plant activators, plant growth regulators, or synergists; or
(c) both (a) and (b).

24. A formulation according to one of claims 1 and 2 further comprising one or more compounds selected from the group consisting of: (3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluoron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlomidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cyclopropthrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfuram, disulfoton, disulsodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfenethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, fluorochloridone, fluoroxypyr, fluoroxypyr-butomethyl, fluoroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexylure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, musculare, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nomicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluoron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluoron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclostrobin, pyraflufen, pyraflufen-ethyl, pyrafluprole, pyramat, pyrametostrobin, pyraoxystrobin,pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfuram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluoron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluoron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

25. A formulation according to claim 1 wherein said molecule is in the form of a pesticidally acceptable acid addition salt.

26. A formulation according to claim 1 wherein said molecule is in the form of a salt derivative.

27. A formulation according to claim 1 wherein said molecule is in the form a hydrate.

28. A formulation according to claim 1 wherein said molecule is in the form of a resolved stereoisomer.

29. A formulation according to claim 1 wherein said molecule is in the form of a crystal polymorph.

30. A formulation according to claim 1 wherein said molecule has a $^2H$ in place of $^1H$.

31. A formulation according to claim 1 wherein said molecule has a $^{14}C$ in place of a $^{12}C$.

32. A formulation according to claim 1 further comprising a biopesticide.

33. A formulation according to claim 1 further comprising one or more of the following compounds:
    (a) 3-(4-chloro-2,6-dimethylphenyl)-4-hydroxy-8-oxa-1-azaspiro[4,5]dec-3-en-2-one;
    (b) 3-(4'-chloro-2,4-dimethyl[1,1'-biphenyl]-3-yl)-4-hydroxy-8-oxa-1-azaspiro[4,5]dec-3-en-2-one;
    (c) 4-[[(6-chloro-3-pyridinyl)methyl]methylamino]-2(5H)-furanone;
    (d) 4-[[(6-chloro-3-pyridinyl)methyl]cyclopropylamino]-2(5H)-furanone;
    (e) 3-chloro-N2[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
    (f) 2-cyano-N-ethyl-4-fluoro-3-methoxy-benenesulfonamide;
    (g) 2-cyano-N-ethyl-3-methoxy-benzenesulfonamide;
    (h) 2-cyano-3-difluoromethoxy-N-ethyl-4-fluoro-benzenesulfonamide;
    (i) 2-cyano-3-fluoromethoxy-N-ethyl-benzenesulfonamide;
    (j) 2-cyano-6-fluoro-3-methoxy-N,N-dimethyl-benzenesulfonamide;
    (k) 2-cyano-N-ethyl-6-fluoro-3-methoxy-N-methyl-benzenesulfonamide;
    (l) 2-cyano-3-difluoromethoxy-N,N-dimethylbenzenesulfonamide;
    (m) 3-(difluoromethyl)-N-[2-(3,3-dimethylbutyl)phenyl]-1-methyl-1H-pyrazole-4-carboxamide;
    (n) N-ethyl-2,2-dimethylpropionamide-2-(2,6-dichloro-α,α,α-trifluoro-p-tolyl) hydrazone;
    (o) N-ethyl-2,2-dichloro-1-methylcyclopropane-carboxamide-2-(2,6-dichloro-α,α,α-trifluoro-p-tolyl) hydrazone nicotine;
    (p) O-{(E-)-[2-(4-chloro-phenyl)-2-cyano-1-(2-trifluoromethylphenyl)-vinyl]}S-methyl thiocarbonate;
    (q) (E)-N1-[(2-chloro-1,3-thiazol-5-ylmethyl)]-N2-cyano-N1-methylacetamidine;
    (r) 1-(6-chloropyridin-3-ylmethyl)-7-methyl-8-nitro-1,2,3,5,6,7-hexahydro-imidazo[1,2-a]pyridin-5-ol;
    (s) 4-[4-chlorophenyl-(2-butylidine-hydrazono)methyl)] phenyl mesylate; and
    (t) N-Ethyl-2,2-dichloro-1-methylcyclopropanecarboxamide-2-(2,6-dichloro-alpha,alpha,alpha-trifluoro-p-tolyl)hydrazone.

34. A formulation according to claim 1 further comprising a compound having one or more of the following modes of action: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs).

35. A formulation according to claim 1 further comprising a seed.

36. A formulation according to claim 1 further comprising a seed that has been genetically modified to express one or more specialized traits.

37. A formulation according to claim 1 wherein said composition is encapsulated inside, or placed on the surface of, a capsule.

38. A process to control a pest comprising applying a formulation according to one of claims 1 and 2, to an area to control a pest, in an amount sufficient to control such pest.

39. A process according to claim 38 wherein said pest is selected from beetles, earwigs, cockroaches, flies, aphids, scales, whiteflies, leafhoppers, ants, wasps, termites, moths, butterflies, lice, grasshoppers, locusts, crickets, fleas, thrips, bristletails, mites, ticks, nematodes, and symphylans.

40. A process according to claim 38 wherein said pest is from the phyla Nematoda or Arthropoda.

41. A process according to claim 38 wherein said pest is from the subphyla Chelicerata, Myriapoda, or Hexapoda.

42. A process according to claim 38 wherein said pest is from the class of Arachnida, Symphyla, or Insecta.

43. A process according to claim 38 wherein said pest is from the order Anoplura, order Coleoptera, order Dermaptera, order Blattaria, order Diptera, order Hemiptera, order Hymenoptera, order Isoptera, order Lepidoptera, order Mallophaga, order Orthoptera, order Siphonaptera, order Thysanoptera, order Thysanura, order Acarina, or order Symphyla.

44. A process according to claim 38 wherein said pest is *Myzus persicae* (MYZUPE) or *Bemisia tabaci* (BEMITA).

45. A process according to claim 38 wherein said amount is from about 0.01 grams per hectare to about 5000 grams per hectare.

46. A process according to claim 38 wherein said amount is from about 0.1 grams per hectare to about 500 grams per hectare.

47. A process according to claim 38 wherein said amount is from about 1 gram per hectare to about 50 grams per hectare.

48. A process according to claim 38 wherein said area is an area where apples, corn, cotton, soybeans, canola, wheat, rice, sorghum, barley, oats, potatoes, oranges, alfalfa, lettuce, strawberries, tomatoes, peppers, crucifers, pears, tobacco, almonds, sugar beets, or beans, are growing, or the seeds thereof are going to be planted.

49. A process according to claim 38 further comprising applying said composition to a genetically modified plant that has been genetically modified to express one or more specialized traits.

50. A formulation according to claim 1 where said formulation further comprises ammonium sulfate.

51. A process to control endoparasites, ectoparasites, or both comprising: orally administering; or topically applying; a formulation according to claim 2, to a non-human animal.

52. A process to enhance plant health, yield, vigor, quality, or tolerance comprising applying a composition according to claim 2 to a plant at a time when pest activity is low.

* * * * *